United States Patent
Di Lucrezia et al.

(10) Patent No.: US 12,281,079 B2
(45) Date of Patent: Apr. 22, 2025

(54) QUINOLINE DERIVATIVES, PROCESSES FOR THEIR PREPARATION AND USES THEREOF FOR THE TREATMENT OF CANCER

(71) Applicant: Lead Discovery Center GmbH, Dortmund (DE)

(72) Inventors: Raffaella Di Lucrezia, Wuppertal (DE); Tim Bergbrede, Dortmund (DE); Peter Nussbaumer, Dortmund (DE); Peter Schröder, Dortmund (DE)

(73) Assignee: Lead Discovery Center GmbH, Dortmund (DE)

( * ) Notice: Subject to any disclaimer, the term of this patent is extended or adjusted under 35 U.S.C. 154(b) by 779 days.

(21) Appl. No.: 17/440,468

(22) PCT Filed: Mar. 19, 2020

(86) PCT No.: PCT/EP2020/057663
§ 371 (c)(1),
(2) Date: Sep. 17, 2021

(87) PCT Pub. No.: WO2020/188049
PCT Pub. Date: Sep. 24, 2020

(65) Prior Publication Data
US 2022/0169616 A1 Jun. 2, 2022

(30) Foreign Application Priority Data
Mar. 20, 2019 (EP) .................................. 19163976

(51) Int. Cl.
| | | |
|---|---|---|
| *C07D 215/20* | (2006.01) | |
| *A61K 31/4375* | (2006.01) | |
| *A61K 31/438* | (2006.01) | |
| *A61K 31/4545* | (2006.01) | |
| *A61K 31/47* | (2006.01) | |
| *A61K 31/4709* | (2006.01) | |
| *A61K 31/496* | (2006.01) | |
| *A61K 31/5377* | (2006.01) | |
| *A61K 45/06* | (2006.01) | |
| *A61P 35/00* | (2006.01) | |
| *C07D 401/12* | (2006.01) | |
| *C07D 409/14* | (2006.01) | |
| *C07D 471/04* | (2006.01) | |
| *C07D 471/10* | (2006.01) | |
(Continued)

(52) U.S. Cl.
CPC ........ *C07D 215/20* (2013.01); *A61K 31/4375* (2013.01); *A61K 31/438* (2013.01); *A61K 31/47* (2013.01); *A61K 31/4709* (2013.01); *A61K 31/5377* (2013.01); *A61K 45/06* (2013.01); *A61P 35/00* (2018.01); *C07D 401/12* (2013.01); *C07D 471/04* (2013.01); *C07D 471/10* (2013.01); *C07D 491/107* (2013.01); *C07D 519/00* (2013.01)

(58) Field of Classification Search
CPC .. C07D 471/04; C07D 471/10; C07D 215/20; C07D 401/12; C07D 491/07; C07D 519/00; C07D 409/14; A61P 35/00; A61K 31/4375; A61K 31/438; A61K 31/47; A61K 31/4709; A61K 31/5377; A61K 31/4545; A61K 31/496; A61K 45/06
See application file for complete search history.

(56) References Cited

U.S. PATENT DOCUMENTS

2024/0252454 A1* 8/2024 Bergbrede ........... A61K 31/437

FOREIGN PATENT DOCUMENTS

WO 2017155991 A1 9/2017

OTHER PUBLICATIONS

International Search Report and Written Opinion for International Application No. PCT/EP2020/057663, mailed Jul. 27, 2020, (14 pages).

(Continued)

*Primary Examiner* — Sun Jae Yoo
(74) *Attorney, Agent, or Firm* — Kagan Binder, PLLC

(57) ABSTRACT

The present invention relates to compounds of the general formula (I): (I), wherein V, W, M, R, R and Y have the designations cited below, or a pharmaceutically or veterinary acceptable salt, hydrate or solvate thereof, and to processes for the preparation of compounds of the general formula (I) or a pharmaceutically or veterinary acceptable salt, hydrate or solvate thereof. The invention also relates to compounds of the general formula (I) or a pharmaceutically or veterinary acceptable salt, hydrate or solvate thereof for use as a medicament. Further, the invention relates to compounds of the general formula (I) or a pharmaceutically or veterinary acceptable salt, hydrate or solvate thereof for use in the treatment of cancer. Moreover, the invention relates to compounds of the general formula (I) or a pharmaceutically or veterinary acceptable salt, hydrate or solvate thereof for treating cancer in simultaneous, alternating or subsequent combination with another cancer therapy.

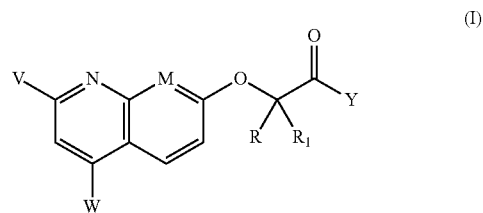

20 Claims, 5 Drawing Sheets
Specification includes a Sequence Listing.

(51) Int. Cl.
*C07D 491/107* (2006.01)
*C07D 519/00* (2006.01)

(56) References Cited

OTHER PUBLICATIONS

Weinberg et al., "Targeting mitochondria metabolism for cancer therapy", Nat Chem Biol., vol. 11, No. 1, pp. 9-15, 2015, (18 pages).
Fulda et al., "Targeting mitochondria for cancer therapy", Nature Reviews Drug Discovery, vol. 9, No. 6, pp. 447-464, 2010, (12 pages).

* cited by examiner

QUINOLINE DERIVATIVES, PROCESSES FOR THEIR PREPARATION AND USES THEREOF FOR THE TREATMENT OF CANCER

CROSS-REFERENCE TO RELATED APPLICATIONS

This application claims priority to International Application No. PCT/EP2020/057663, filed Mar. 19, 2020 and titled "QUINOLINE DERIVATIVES, PROCESSES FOR THEIR PREPARATION AND USES THEREOF FOR THE TREATMENT OF CANCER," which in turn claims priority from a European Patent Application having serial number 19163976.4, filed Mar. 20, 2019, titled "QUINOLINE DERIVATIVES, PROCESSES FOR THEIR PREPARATION AND USES THEREOF FOR THE TREATMENT OF CANCER," both of which are incorporated herein by reference in their entireties.

REFERENCE TO SEQUENCE LISTING

This application contains a Sequence Listing submitted via EFS-Web. The entire contents of the sequence listing in ASCII text file is entitled "IBH0004US_Sequence_Listing.txt," created on Sep. 17, 2021 and is 1 kilobyte in size and is incorporated herein by reference in its entirety.

FIELD OF THE INVENTION

The present invention relates to compounds of the general formula (I)

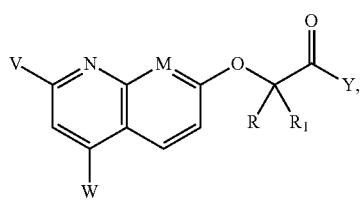

wherein V, W, M, R, $R_1$ and Y have the designations cited below, or a pharmaceutically or veterinary acceptable salt, hydrate or solvate thereof, and to processes for the preparation of compounds of the general formula (I) or a pharmaceutically or veterinary acceptable salt, hydrate or solvate thereof. The invention also relates to compounds of the general formula (I) or a pharmaceutically or veterinary acceptable salt, hydrate or solvate thereof for use as a medicament. Further, the invention relates to compounds of the general formula (I) or a pharmaceutically or veterinary acceptable salt, hydrate or solvate thereof for use in the treatment of cancer. Moreover, the invention relates to compounds of the general formula (I) or a pharmaceutically or veterinary acceptable salt, hydrate or solvate thereof for treating cancer in simultaneous, alternating or subsequent combination with another cancer therapy.

BACKGROUND OF THE INVENTION

Despite enormous research efforts during the last decades and advanced cancer treatments, cancer remains a major public health problem worldwide and is the second leading cause of death in the United States. In the US population, incidence and death rates are even increasing for several cancer types, including liver and pancreas—two of the most fatal cancers (Siegel et al., 2016). Thus, there is still an urgent need to obtain additional and improved treatment options for fighting cancer besides the established chemotherapies, radiation and upcoming immunotherapies.

Interfering with the cancer metabolism is another principle to tackle tumor growth. In contrast to normal differentiated cells, which rely primarily on mitochondrial oxidative phosphorylation to generate energy, most cancer cells instead rely on aerobic glycolysis, a phenomenon termed "the Warburg effect" (Vander Heiden et al., 2009). Aerobic glycolysis in the cytoplasm leads to pyruvate generated from glucose, which is not transported into mitochondria for total oxidation for yielding more energy but is converted to lactate, originally described by Warburg (Hsu and Sabatini, 2008). Lactate is transferred to the liver, where the carbon skeleton is used to synthesize glucose known as the "neoplastic or pathological Cori cycle" contributing to the clinical metabolic state of Cachexia, a condition existing in neoplastic patients who suffer massive loss of normal body mass as the neoplasm continues its growth (Tisdale, 2002). Consequently, inhibiting aerobic glycolysis (Warburg effect) and/or neoplastic anabolism (pathological Cori cycle) may be another effective way to interfere with cancer metabolism and effectively treat cancer patients. The inhibition of glycolysis in connection with the Warburg effect for cancer treatment has been described by Pelicano, H. et al. (2006) and Scatena et al. (2008).

However, the relevance of mitochondrial respiration in tumors is varied depending on tumor type. An oxidative class of tumors and tumors with dual capacity for glycolytic and oxidative metabolism is evident and the importance of mitochondria in tumor cell survival and proliferation, including utilization of alternative oxidizable substrates such as glutamine and fatty acids, has been increasingly appreciated. The diversity of carbon substrate utilization pathways in tumors is indicative of metabolic heterogeneity that may not only be relevant across different types of cancer but also manifest within a group of tumors that otherwise share a common diagnosis (Caro et al., 2012). Accordingly, tumors show heterogeneity in fuel utilization even within the same disease entity with some having a significant mitochondrial component, marked by elevated oxidative phosphorylation (OXPHOS), increased contribution of mitochondria to total cellular energy budget, greater incorporation of fatty acid- and glucose-derived carbons into the TCA cycle, and increased lipogenesis from these carbon substrates (Caro et al., 2012).

Indeed, recent evidence supports the hypothesis that acquired resistance to therapy is accompanied by a metabolic shift from aerobic glycolysis toward respiratory metabolism, suggesting that metabolic plasticity can have a role in survival of cells responsible for tumor relapse, suggesting that metabolic plasticity can have a role in survival of cells responsible for tumor relapse. For example, it has been observed that several drug-resistant tumor cells show a higher respiratory activity than parental cells. The metabolic adaptation allows OXPHOS-addicted cancer cells to easily survive drug treatments, but leaves cells susceptible to inhibitors of OXPHOS (Denise et al., 2015).

Cancer cell mitochondria are structurally and functionally different from their normal counter parts. Moreover, tumor cells exhibit an extensive metabolic reprogramming that renders them more susceptible to mitochondrial perturbations than non-immortalized cells. Based on these premises, mitochondrially-targeted agents emerge as a means to selectively target tumors. The correction of cancer-associated mitochondrial dysfunctions and the (re)activation of cell death programs by pharmacological agents that induce or facilitate mitochondrial membrane permeabilization represent attractive strategies for cancer therapy. Further, autophagy in the tumor stroma and oxidative mitochondrial metabolism (OXPHOS) in cancer cells can both dramatically promote tumor growth, independently of tumor angiogenesis (Salem et al., 2012) and that cancer-associated fibroblasts undergo aerobic glycolysis, thereby producing lactate, which is utilized as a metabolic substrate by adjacent cancer cells. In this model, "energy transfer" or "metabolic-coupling" between the tumor stroma and epithelial cancer cells "fuels" tumor growth and metastasis, via oxidative mitochondrial metabolism in anabolic cancer cells, the "reverse Warburg effect" (Whitaker-Menezes et al., 2011).

Accordingly, these findings provide a rationale and for novel strategies for anti-cancer therapies by employing inhibitors of OXPHOS and mitochondrial functions. Mitochondrial targeted anti-cancer drugs are reviewed by Fulda et al. (2010) and Weinberg and Chandel (2015) including inhibitors of mitochondrial complex 1, inhibitors of the electron transfer chain (ETC) complex, inhibitors of mitochondrial ribosomal machinery, inhibitors of the translation of ETC subunits, inhibitors of mitochondrial chaperone proteins, inhibitors of glutaminases, aminotransferases or glutamate dehydrogenases, short term inhibition of autophagy, mitochondrial-targeted antioxidants.

Recently, mitochondrial RNA polymerase (POLRMT, also known as h-mtRNAP) has been proposed as a new target in acute myeloid leukemia (Bralha et al., 2015). POLRMT is responsible for the transcription of the 13 subunits of the OXPHOS complexes, two rRNAs and 22 tRNAs required for mitochondrial translation and acts as the RNA primase for mitochondrial DNA replication (Wanrooij and Falkenberg, 2010, Scarpulla, 2008). Therefore, this enzyme is of fundamental importance for both expression and replication of the human mitochondrial genome (Arnold et al., 2012).

A number of nucleoside analogues used as antiviral agents to target viral RNA polymerases demonstrate off-target inhibition of POLRMT (Arnold et al., 2012); POLRMT is distantly related to bacteriophage 17 class of single-subunit RNAPs. The finding that treatment with 2-C-methyladenosine, identified as an inhibitor of the RNA-dependent RNA polymerase of hepatitis C virus (Carroll et al., 2003), triggers the death of AML cells allegedly through rather unspecific inhibition of mitochondrial transcription confirms this rational (Bralha et al., 2015).

Thus, there is a need for alternative novel compounds, which specifically inhibit POLRMT and are suitable for use as a medicament. In particular, a need exists for novel compounds that can be used in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer. Furthermore, POLRMT inhibitors are of interest, which can be used in a method for treating cancer in simultaneous, alternating or subsequent combination with another cancer therapy.

Accordingly, the present invention provides specific POLRMT inhibitors for the treatment of cancer.

SUMMARY OF THE INVENTION

The present invention, in one aspect, relates to a compound of the general formula (I)

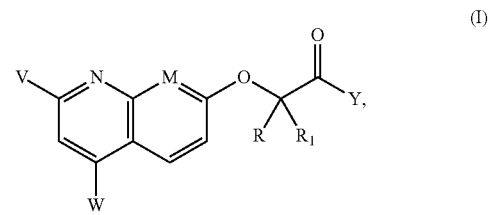

wherein
R is —H, or —$C_1$-$C_4$-alkyl, preferably —H, -methyl or -ethyl, in particular -methyl;
$R_1$ is —H, or -methyl, preferably —H;
M is CH or N, preferably CH;
V is —H, —OH, —Cl, —F, or —$C_1$-$C_4$-alkyl, preferably —H, —Cl, —F, or -methyl;
W is

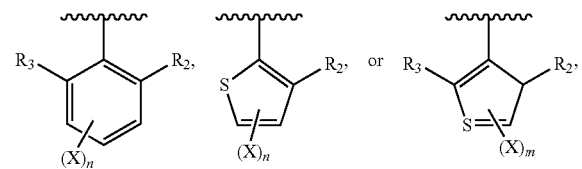

with
$R_2$ and $R_3$ are identical or different and are —H, —$C_1$-$C_4$-alkyl, halogen-$C_1$-$C_4$-alkyl, —$C_1$-$C_4$-alkoxy, —$C_1$-$C_4$-dialkylamino, —$C_2$-$C_6$-alkenyl, —$C_2$-$C_6$-alkynyl, -halogen, —CN or —CO—$NH_2$; preferably —H, —$C_1$-$C_4$-alkyl, —$CF_3$, —$OCH_3$, —$NHCH_3$, —$N(CH_3)_2$, —F, or —C;
X is -halogen, or —CN, preferably —F, with n=1 or 2 or with m=1
n=0, 1, or 2, preferably 0 or 1;
m=0 or 1, preferably 0;
Y is —$NR_4R_5$ with
$R_4$ is —H, or —$C_1$-$C_4$-alkyl, preferably —H or -methyl, and
$R_5$ is —H, —$C_1$-$C_4$-alkyl, an unsubstituted or substituted —$C_3$-$C_6$-cycloalkyl, preferably -methyl, -ethyl, -isopropyl, or -cyclopropyl; or
an unsubstituted or substituted pyridine residue; or
an unsubstituted or substituted phenyl residue, preferably substituted at the pa re position;
Y is —$NR_4R_5$ with N, $R_4$ and $R_5$ forming an unsubstituted or substituted 4-, 5- or 6-membered saturated heterocycle, preferably an unsubstituted or substituted azetidine, an unsubstituted or substituted piperidine, an unsubstituted or substituted pyrrolidine, an unsubstituted or substituted piperazine, or an unsubstituted or substituted tetrahydropyridine residue; or
Y is —$OR_6$, with $R_6$ is —H or —$C_1$-$C_4$-alkyl, preferably —H, -methyl, -ethyl, -isopropyl, or -tert-butyl;
or a pharmaceutically or veterinary acceptable salt, hydrate or solvate thereof.
In one embodiment, the invention relates to a compound of the general formula (I) as de fined above, wherein W is

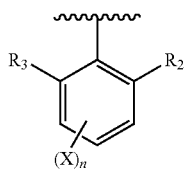

R₃ is —H, —C₁-C₄-alkyl, —CF₃, —OCH₃, —N(CH₃)₂, acetylenyl, —F, —Cl, —Br, —CN, or —CO—NH₂;

R₂ is —H, -methyl, -ethyl, isopropyl, —CF₃, —F, or —C; and

X is —F with n=1; preferably, wherein X is at the para-position of the phenyl ring; or n=0.

In another embodiment, the invention relates to a compound of the general formula (I) as defined above, wherein W is

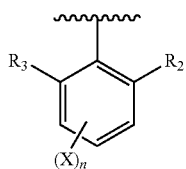

R₂ is —H, -methyl, -ethyl, isopropyl, —Cl, preferably -methyl or —C;

R₃ is —H, -methyl or —C; preferably R₂ is -methyl and R₃ is -methyl, or R₂ is —Cl and R₃ is —C; and n=0.

In another embodiment, the invention relates to a compound of the general formula (I) as defined above, wherein Y is —NR₄R₃ with R₄ is —H, or —C₁-C₄-alkyl, preferably —H or -methyl, and R₅ is —H, —C₁-C₄-alkyl, unsubstituted —C₃-C₄-cycloalkyl, —C₄-cycloalkyl substituted with —COO—CH₃, preferably -methyl, -ethyl, -isopropyl, or -cyclopropyl.

In another embodiment, the invention relates to a compound of the general formula (I) as defined above, wherein Y is —NR₄R₃ with R₄ is —H, or —C₁-C₄-alkyl, preferably —H or -methyl, and R₅ is an unsubstituted pyridine residue; or an unsubstituted or substituted phenyl residue, preferably unsubstituted or substituted with one substituent at the para position; wherein the substituents are selected from the group consisting of:

—C₁-C₄-alkyl, —C₁-C₄-alkoxy, —(CH₂)₂—OH, —COOH, or —CO—O—(C₁-C₄-alkyl).

In another embodiment, the invention relates to a compound of the general formula (I) as defined above, wherein Y is —NR₄R₃ with N, R₄ and R₅ forming an unsubstituted or substituted azetidine residue, an unsubstituted or substituted piperidine, an unsubstituted or substituted piperazine, an unsubstituted or substituted pyrrolidine residue, an unsubstituted or substituted morpholine residue, or an unsubstituted or substituted tetrahydropyridine residue, preferably an unsubstituted or substituted piperidine residue, each optionally and independently substituted with one or more, preferably with one of the following residues:

—C₁-C₄-alkyl;

—C(OH)-cyclopropyl; —C(COOH)-cyclopropyl;

unsubstituted or substituted —C₃-C₆-cycloalkyl; preferably hydroxycyclopropyl or carboxycyclopropyl;

—(CH₂)ₒ—COOR₇ with

R₇ is —H, —C₁-C₈-alkyl, preferably —H, -methyl, -ethyl, -isopropyl, or -tert-butyl, and o=0, 1 or 2; preferably 0 or 1;

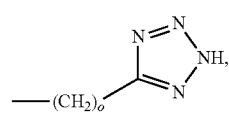

and o is as defined above;

—(CH₂)ₚCONR₈R₉ with

R₈ and R₉ independently are —H, —OH, —CN, or —C₁-C₄-alkyl, preferably —H or -methyl, and p=0, 1 or 2; preferably 0 or 1;

—C(CH₃)₂—COOH;

=O or —OH;

—CO-cyclopropyl;

CO—(C₁-C₄-alkyl), preferably —CO—CH₂—CH₃;

—CO—(CH₂)_q—NR₁₂R₁₃ with R₁₂ and R₁₃ independently are —H, —C₁-C₄-alkyl or —CN, preferably —CO—(CH₂)_q—NH₂, more preferably —CO—CH₂—NH₂, and q=0, 1 or 2, preferably 0 or 1;

—NH₂, —NH—CO-cyclopropyl, —NH—CO—CH₂—Cl, —NH—CO—CH₂—CH₃, —NH—CO—NH—C(CH₃)₃, —NH—SO₂CH₃, —NH—CO-phenyl, —NOH—CO—CH₃;

—F; —CN;

R₁₄ and R₁₅ forming a pyrrolidinone ring, a cyclopropanecarboxlic acid ring, an oxetane ring, or a —CH₂— group; or —(CH₂)ᵣSO₂NR₁₀R₁₁ with R₁₀ and R₁₁ independently are —H, or —C₁-C₄-alkyl, preferably —H or -methyl, preferably —CH₂SO₂NH₂ and r=0, 1 or 2, preferably 0 or 1.

In another embodiment, the invention relates to a compound of the general formula (I) as defined above, wherein Y is —NR₄R₅ with N, R₄ and R₅ forming an unsubstituted or substituted piperidine residue, an unsubstituted or substituted piperazine, an unsubstituted or substituted pyrrolidine residue or an unsubstituted or substituted morpholine, each optionally and independently substituted with one or more, preferably with one of the following residues:

—C₁-C₄-alkyl;

—C(OH)cyclopropyl;

hydroxycyclopropyl or carboxycyclopropyl;

—(CH₂)ₒ—COOR₇ with

R₇ is —H, —C₁-C₈-alkyl, preferably —H, -methyl, -ethyl, -isopropyl, or -tert-butyl, and o=0, 1 or 2;

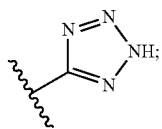

—(CH$_2$)$_p$CONR$_8$R$_9$ with
R$_8$ and R$_9$ independently are —H, —OH, —CN, -methyl or tert-butyl, and p=0; —C(CH$_3$)$_2$—COOH;
=O or —OH;
—CO-cyclopropyl;
—CO—CH$_2$—CH$_3$;
—CO-tert-butyl;
—NH$_2$,
—CO—CH$_2$—NH$_2$;
—NH—CO—CH$_2$—CH$_3$, —NH—CO—NH—C(CH$_3$)$_3$, —NH—SO$_2$CH$_3$, —NH—CO-phenyl, —NOH—CO—CH$_3$;
—CN;
R$_{14}$ and R$_{15}$ forming a pyrrolidinone ring; a cyclopropanecarboxlic acid ring, an oxetane ring, or a —CH$_2$— group;
—SO$_2$NR$_{10}$R$_{11}$ with R$_{10}$ and R$_{11}$ independently are —H or -methyl; or
—CH$_2$SO$_2$NH$_2$.

In another embodiment, the invention relates to a compound of the general formula (I) as defined above, wherein Y is —NR$_4$R$_5$ with
N, R$_4$ and R$_5$ forming an unsubstituted or substituted piperidine residue, optionally and independently substituted with one or more, preferably with one of the following residues:
—COOH, —COOCH$_3$, —COOC$_2$H$_5$, —CH$_2$COOH, —C(CH$_3$)$_2$—COOH, —CH$_2$COOCH$_3$, —CH$_2$COOCH$_2$CH$_3$, —CONH$_2$, —CONHCH$_3$, —CON(CH$_3$)$_2$, —SO$_2$NH$_2$ or —CH$_2$SO$_2$NH$_2$.

In another embodiment, the invention relates to a compound of the general formula (I) as defined above, wherein Y is —OR$_6$, with R$_6$ is —H, -methyl, -ethyl, -isopropyl, or -tert-butyl, preferably -ethyl.

In another embodiment, the invention relates to a compound of the general formula (I) as defined above, wherein V is —H, —Cl, —F, or -methyl, preferably —H.

In another embodiment, the invention relates to a compound of the general formula (I) as defined above, wherein R is -methyl, preferably —(R)-methyl; and
R$_1$ is —H.

In another embodiment, the invention relates to a compound of the general formula (I) as defined above, wherein X is at the para-position of the phenyl ring.

In another embodiment, the invention relates to a compound of the general formula (I) as defined above, selected from
(3S)-1-[(2R)-2-[[4-(o-tolyl)-7-quinolyl]oxy]propanoyl]piperidine-3-carboxylic acid,
(3S)-1-[(2R)-2-[[4-(2,6-dimethylphenyl)-7-quinolyl]oxy]propanoyl]piperidine-3-carboxylic acid,
2-[(3R)-1-[(2R)-2-[[4-(2,6-dimethylphenyl)-7-quinolyl]oxy]propanoyl]-3-piperidyl]acetic acid,
ethyl (3S)-1-[(2R)-2-[[4-(2,6-dimethylphenyl)-7-quinolyl]oxy]propanoyl]piperidine-3-carboxylate,
2-[(3S)-1-[(2R)-2-[[4-(2,6-dimethylphenyl)-7-quinolyl]oxy]propanoyl]-3-piperidyl]acetic acid,
ethyl 2-[(3R)-1-[(2R)-2-[[4-(2,6-dimethylphenyl)-7-quinolyl]oxy]propanoyl]-3-piperidyl]acetate,
(3R)-1-[(2R)-2-[[4-(2-chlorophenyl)-7-quinolyl]oxy]propanoyl]piperidine-3-carboxylic acid,
ethyl 2-[(3R)-1-[(2R)-2-[[4-(o-tolyl)-7-quinolyl]oxy]propanoyl]-3-piperidyl]acetate,
(3S)-1-[(2R)-2-[[4-(2-chlorophenyl)-7-quinolyl]oxy]propanoyl]piperidine-3-carboxylic acid,
(3S)-1-[(2R)-2-[[4-(2-chloro-4-fluoro-phenyl)-7-quinolyl]oxy]propanoyl]piperidine-3-carboxylic acid,
(2R)-2-[[4-(2-chloro-4-fluoro-phenyl)-7-quinolyl]oxy]-1-[(3S)-3-(2H-tetrazol-5-yl)-1-piperidyl]propan-1-one,
(3S)-1-[(2R)-2-[[4-(2-chlorophenyl)-2-fluoro-7-quinolyl]oxy]propanoyl]piperidine-3-carboxylic acid,
2-[(3R)-1-[(2R)-2-[[4-(o-tolyl)-7-quinolyl]oxy]propanoyl]-3-piperidyl]acetic acid,
ethyl (3S)-1-[(2R)-2-[[4-(o-tolyl)-7-quinolyl]oxy]propanoyl]piperidine-3-carboxylate,
ethyl 2-[(3R)-1-[(2R)-2-[[4-(2-chloro-4-fluoro-phenyl)-7-quinolyl]oxy]propanoyl]-3-piperidyl]acetate,
2-[(3R)-1-[(2R)-2-[[4-(2-chlorophenyl)-7-quinolyl]oxy]propanoyl]-3-piperidyl]acetic acid
(3R)-1-[(2R)-2-[[4-(2-chloro-4-fluoro-phenyl)-7-quinolyl]oxy]propanoyl]piperidine-3-carboxylic acid,
2-[(3R)-1-[(2R)-2-[[4-(2-chloro-4-fluoro-phenyl)-7-quinolyl]oxy]propanoyl]-3-piperidyl]acetic acid,
(3S)-1-[(2R)-2-[[4-(2-chloro-4-fluoro-phenyl)-7-quinolyl]oxy]propanoyl]pyrrolidine-3-carboxylic acid,
(2R)-2-[[4-(2-chloro-4-fluoro-phenyl)-7-quinolyl]oxy]-1-(1-piperidyl)propan-1-one,
2-[(3R)-1-[(2R)-2-[[2-chloro-4-(o-tolyl)-7-quinolyl]oxy]propanoyl]-3-piperidyl]acetic acid,
2-[(3S)-1-[(2R)-2-[[4-(2-chloro-4-fluoro-phenyl)-7-quinolyl]oxy]propanoyl]-3-piperidyl]acetic acid,
rac-(3S)-1-[2-[[4-(2-chlorophenyl)-7-quinolyl]oxy]propanoyl]piperidine-3-carboxylic acid,
1-[(2R)-2-[[4-(2-chloro-4-fluoro-phenyl)-7-quinolyl]oxy]propanoyl]piperidine-4-carboxylic acid,
(3S)-1-[rac-(2R)-2-[[2-chloro-4-(o-tolyl)-7-quinolyl]oxy]propanoyl]piperidine-3-carboxylic acid,
3-[[(2R)-2-[[4-(2-chloro-4-fluoro-phenyl)-7-quinolyl]oxy]propanoyl]amino]benzoic acid
ethyl (3S)-1-[(2R)-2-[[4-(2-chloro-4-fluoro-phenyl)-7-quinolyl]oxy]propanoyl]piperidine-3-carboxylate,
(2R)-2-[[4-(2-chloro-4-fluoro-phenyl)-7-quinolyl]oxy]-1-(4-propanoylpiperazin-1-yl)propan-1-one,
tert-butyl (2R)-2-[[4-(2-chlorophenyl)-7-quinolyl]oxy]propanoate,
(3S)-1-[(2R)-2-[[4-(2-chloro-4-fluoro-phenyl)-7-quinolyl]oxy]propanoyl]piperidine-3-carbonitrile,
(3S)-1-[(2R)-2-[[2-methyl-4-(o-tolyl)-7-quinolyl]oxy]propanoyl]piperidine-3-carboxylic acid,
(2R)-2-[[4-(2-chlorophenyl)-7-quinolyl]oxy]-N-isopropyl-N-methyl-propanamide,
1-[rac-(2R)-2-[[4-(2-chloro-4-fluoro-phenyl)-7-quinolyl]oxy]propanoyl]piperidine-3-sulfonamide,
(3S)-1-[(2R)-2-[[2-chloro-4-(2-chlorophenyl)-7-quinolyl]oxy]propanoyl]piperidine-3-carboxylic acid,
(3S)-1-[(2R)-2-[[2-chloro-4-(4-fluoro-2-methyl-phenyl)-7-quinolyl]oxy]propanoyl]piperidine-3-carboxylic acid,
isopropyl (2R)-2-[[4-(2-chlorophenyl)-7-quinolyl]oxy]propanoate,
methyl 2-[(3R)-1-[(2R)-2-[[4-(2-chloro-4-fluoro-phenyl)-7-quinolyl]oxy]propanoyl]pyrrolidin-3-yl]acetate,
(3S)-1-[(2R)-2-[[4-(2-chloro-4-fluoro-phenyl)-7-quinolyl]oxy]propanoyl]-N-methyl-piperidine-3-carboxamide,
2-[(3S)-1-[(2R)-2-[[4-(2-chloro-4-fluoro-phenyl)-7-quinolyl]oxy]propanoyl]pyrrolidin-3-yl]acetic acid, 2-[(3R)-1-[(2R)-2-[[4-(2-chloro-4-fluoro-phenyl)-7-quinolyl]oxy]propanoyl]pyrrolidin-3-yl]acetic acid,
ethyl (3S)-1-[(2R)-2-[[4-(2-chlorophenyl)-2-fluoro-7-quinolyl]oxy]propanoyl]piperidine-3-carboxylate,
(2R)-2-[[4-(2-chloro-4-fluoro-phenyl)-7-quinolyl]oxy]-1-pyrrolidin-1-yl-propan-1-one,
(2R)-2-[[2-chloro-4-(o-tolyl)-7-quinolyl]oxy]propanoic acid,
(2R)-2-[[4-(2-chloro-4-fluoro-phenyl)-7-quinolyl]oxy]propanoic acid,
(2R)-2-[[4-(2-chloro-4-fluoro-phenyl)-7-quinolyl]oxy]-N,N-dimethyl-propanamide,
rac-(3S)-1-[2-[[4-(2-chlorophenyl)-7-quinolyl]oxy]acetyl]piperidine-3-carboxylic acid,
(2R)—N-tert-butyl-2-[[4-(2-chloro-4-fluoro-phenyl)-7-quinolyl]oxy]propanamide,
(2R)-2-[[4-(2-chlorophenyl)-7-quinolyl]oxy]-N-isopropyl-propanamide,
ethyl 2-[(3R)-1-[(2R)-2-[[2-methyl-4-(o-tolyl)-7-quinolyl]oxy]propanoyl]-3-piperidyl]acetate,
ethyl (2R)-2-[[4-(2-chlorophenyl)-7-quinolyl]oxy]propanoate,
ethyl 4-[[(2R)-2-[[4-(2-chloro-4-fluoro-phenyl)-7-quinolyl]oxy]propanoyl]amino]benzoate,
(3S)-1-[(2R)-2-[[2-chloro-4-(o-tolyl)-7-quinolyl]oxy]propanoyl]piperidine-3-carboxamide,
(2R)-2-[[4-(2-chlorophenyl)-7-quinolyl]oxy]-1-(1-piperidyl)propan-1-one,
methyl 3-[[(2R)-2-[[4-(2-chloro-4-fluoro-phenyl)-7-quinolyl]oxy]propanoyl]amino]cyclobutanecarboxylate,
(2R)-2-[[4-(2-chloro-4-fluoro-phenyl)-7-quinolyl]oxy]-1-piperazin-1-yl-propan-1-one,
2-[(3R)-1-[(2R)-2-[[2-chloro-4-(2-chloro-4-fluoro-phenyl)-7-quinolyl]oxy]propanoyl]-3-piperidyl]acetic acid,
2-[(3R)-1-[(2R)-2-[[2-chloro-4-(4-fluoro-2-methyl-phenyl)-7-quinolyl]oxy]propanoyl]-3-piperidyl]acetic acid,
ethyl 1-[(2R)-2-[[4-(2-chloro-4-fluoro-phenyl)-7-quinolyl]oxy]propanoyl]piperidine-4-carboxylate,
(3S)-1-[(2R)-2-[[4-(2-chloro-4-fluoro-phenyl)-2-methyl-7-quinolyl]oxy]propanoyl]piperidine-3-carboxylic acid,
4-[[(2R)-2-[[4-(2-chloro-4-fluoro-phenyl)-7-quinolyl]oxy]propanoyl]amino]benzoic acid,
(2R)-2-[[4-(2-chloro-4-fluoro-phenyl)-7-quinolyl]oxy]-N-isopropyl-propanamide,
(3S)-1-[2-[[5-(2-chloro-4-fluoro-phenyl)-1,8-naphthyridin-2-yl]oxy]propanoyl]piperidine-3-carboxylic acid,
4-[(2R)-2-[[4-(2-chloro-4-fluoro-phenyl)-7-quinolyl]oxy]propanoyl]piperazin-2-one,
(3S)-1-[(2R)-2-[[2-chloro-4-(2-chloro-4-fluoro-phenyl)-7-quinolyl]oxy]propanoyl]piperidine-3-carboxylic acid,
2-[(3R)-1-[(2R)-2-[[4-(2-chloro-3-fluoro-phenyl)-7-quinolyl]oxy]propanoyl]-3-piperidyl]acetic acid,
(3S)-1-[(2R)-2-[(4-phenyl-7-quinolyl)oxy]propanoyl]piperidine-3-carboxylic acid,
methyl 2-[(3S)-1-[(2R)-2-[[4-(2-chloro-4-fluoro-phenyl)-7-quinolyl]oxy]propanoyl]pyrrolidin-3-yl]acetate,
2-[(3R)-1-[(2R)-2-[[2-chloro-4-(2-chlorophenyl)-7-quinolyl]oxy]propanoyl]-3-piperidyl]-N-methyl-acetamide,
2-[(3R)-1-[(2R)-2-[[2-methyl-4-(o-tolyl)-7-quinolyl]oxy]propanoyl]-3-piperidyl]acetic acid,
(2R)-2-[[2-chloro-4-(2-chlorophenyl)-7-quinolyl]oxy]-1-[4-(cyclopropanecarbonyl)piperazin-1-yl]propan-1-one,
methyl (3R)-1-[(2R)-2-[[4-(2-chloro-4-fluoro-phenyl)-7-quinolyl]oxy]propanoyl]piperidine-3-carboxylate,
(2R)-2-[[2-chloro-4-(2-chlorophenyl)-7-quinolyl]oxy]-1-(4-propanoylpiperazin-1-yl)propan-1-one,
tert-butyl (2R)-2-[[2-chloro-4-(o-tolyl)-7-quinolyl]oxy]propanoate,
ethyl 2-[(3R)-1-[(2R)-2-[[4-(2-chloro-4-fluoro-phenyl)-2-methyl-7-quinolyl]oxy]propanoyl]-3-piperidyl]acetate,
ethyl (3S)-1-[(2R)-2-[[4-(2-chloro-4-fluoro-phenyl)-7-quinolyl]oxy]propanoyl]pyrrolidine-3-carboxylate,
(3S)-1-[(2R)-2-[[2-chloro-4-(2-chlorophenyl)-7-quinolyl]oxy]propanoyl]piperidine-3-carboxamide,
(2R)-2-[[4-(2-chloro-4-fluoro-phenyl)-7-quinolyl]oxy]-N-cyclopropyl-propanamide,
(3S)-1-[(2S)-2-[[4-(2-chlorophenyl)-7-quinolyl]oxy]propanoyl]piperidine-3-carboxylic acid,
2-[(3R)-1-[(2R)-2-[[4-(2-methyl-3-thienyl)-7-quinolyl]oxy]propanoyl]-3-piperidyl]acetic acid,
2-[rac-(3R)-1-[2-[[5-(2-chloro-4-fluoro-phenyl)-1,8-naphthyridin-2-yl]oxy]propanoyl]-3-piperidyl]acetic acid,
(3S)-1-[(2R)-2-[[2-chloro-4-(2-chloro-4-fluoro-phenyl)-7-quinolyl]oxy]propanoyl]piperidine-3-carboxamide,
isopropyl 2-[[4-(2-chlorophenyl)-7-quinolyl]oxy]acetate,
(3S)-1-[(2R)-2-[[4-(4-fluoro-2,6-dimethyl-phenyl)-7-quinolyl]oxy]propanoyl]piperidine-3-carboxylic acid,
(2R)-1-[4-(2-aminoacetyl)piperazin-1-yl]-2-[[2-chloro-4-(2-chlorophenyl)-7-quinolyl]oxy]propan-1-one,
2-[[4-(2-chlorophenyl)-7-quinolyl]oxy]-N,N-dimethyl-propanamide,
ethyl (3S)-1-[2-[[4-(2-chlorophenyl)-7-quinolyl]oxy]acetyl]piperidine-3-carboxylate,
(2R)-2-[[4-(2-chlorophenyl)-7-quinolyl]oxy]-N,N-dimethyl-propanamide,
ethyl 2-[(3S)-1-[(2R)-2-[[4-(2-chloro-4-fluoro-phenyl)-7-quinolyl]oxy]propanoyl]-3-piperidyl]acetate,
(2R)-2-[[4-(2-chlorophenyl)-2-fluoro-7-quinolyl]oxy]propanoic acid,
(2R)-2-[[2-chloro-4-(2-chloro-4-fluoro-phenyl)-7-quinolyl]oxy]propanoic acid,
ethyl 2-[(3R)-1-[(2R)-2-[[2-chloro-4-(2-chlorophenyl)-7-quinolyl]oxy]propanoyl]-3-piperidyl]acetate,
ethyl 2-[(3R)-1-[(2R)-2-[[2-chloro-4-(2-chloro-4-fluoro-phenyl)-7-quinolyl]oxy]propanoyl]-3-piperidyl]acetate,
ethyl (3S)-1-[(2R)-2-[[2-chloro-4-(4-fluoro-2-methyl-phenyl)-7-quinolyl]oxy]propanoyl]piperidine-3-carboxylate,
(2R)-2-[[4-(2-chloro-4-fluoro-phenyl)-7-quinolyl]oxy]-N-(4-pyridyl) propanamide,
(3S)-1-[(2R)-2-[[2-chloro-4-(2-chlorophenyl)-7-quinolyl]oxy]propanoyl]-N-methyl-piperidine-3-carboxamide,
methyl 3-[[(2R)-2-[[2-chloro-4-(2-chlorophenyl)-7-quinolyl]oxy]propanoyl]amino]cyclobutanecarboxylate,
2-[(3R)-1-[(2R)-2-[[2-chloro-4-(2-chloro-4-fluoro-phenyl)-7-quinolyl]oxy]propanoyl]-3-piperidyl]-N-methyl-acetamide,
(2R)-2-[[2-chloro-4-(2-chlorophenyl)-7-quinolyl]oxy]-1-(1-piperidyl)propan-1-one,
(3S)-1-[(2R)-2-[[2-chloro-4-(2-chlorophenyl)-7-quinolyl]oxy]propanoyl]-N,N-dimethylpiperidine-3-carboxamide,
2-[(3R)-1-[(2R)-2-[[4-(2-chloro-4-fluoro-phenyl)-2-methyl-7-quinolyl]oxy]propanoyl]-3-piperidyl]acetic acid,
(3R)-1-[(2S)-2-[[4-(2-chlorophenyl)-7-quinolyl]oxy]propanoyl]piperidine-3-carboxylic acid,
(2R)-2-[[4-(2-chlorophenyl)-7-quinolyl]oxy]propanoic acid,
(2R)-2-[[2-chloro-4-(2-chlorophenyl)-7-quinolyl]oxy]-1-piperazin-1-yl-propan-1-one,
(3S)—N-methyl-1-[(2R)-2-[[2-chloro-4-(2-chloro-4-fluoro-phenyl)-7-quinolyl]oxy]propanoyl]piperidine-3-carboxamide,
2-[[4-(o-tolyl)-7-quinolyl]oxy]acetamide, (2R)-2-[[2-chloro-4-(2-chloro-4-fluoro-phenyl)-7-quinolyl]oxy]-1-(1-piperidyl)propan-1-one,
ethyl 3-[[(2R)-2-[[4-(2-chloro-4-fluoro-phenyl)-7-quinolyl]oxy]propanoyl]amino]benzoate,
2-[[5-(2-chloro-4-fluoro-phenyl)-1,8-naphthyridin-2-yl]oxy]-N-isopropyl-propanamide,
2-[(3R)-1-[(2R)-2-[[4-(2-fluorophenyl)-7-quinolyl]oxy]propanoyl]-3-piperidyl]acetic acid,
tert-butyl (3S)-1-[(2R)-2-[[2-methyl-4-(o-tolyl)-7-quinolyl]oxy]propanoyl]piperidine-3-carboxylate,
2-[1-[(2R)-2-[[4-(2-chlorophenyl)-7-quinolyl]oxy]propanoyl]-4-piperidyl]acetic acid,
(3S)-1-[rac-(2R)-2-[[4-(2,6-dimethylphenyl)-2-methyl-7-quinolyl]oxy]propanoyl]piperidine-3-sulfonamide,
(3R)-1-[rac-(2R)-2-[[4-(2,6-dimethylphenyl)-2-methyl-7-quinolyl]oxy]propanoyl]piperidine-3-sulfonamide,
(3R)-1-[rac-(2R)-2-[[4-(2,6-dimethylphenyl)-2-methyl-7-quinolyl]oxy]propanoyl]piperidine-3-sulfonamide,
(3R)-1-[(2R)-2-[[4-(2-chloro-4-fluoro-phenyl)-2-methyl-7-quinolyl]oxy]propanoyl]piperidine-3-sulfonamide,
(3S)-1-[(2R)-2-[[4-(2-chloro-4-fluoro-phenyl)-7-quinolyl]oxy]propanoyl]piperidine-3-sulfonamide,
(3R)-1-[(2R)-2-[[4-(2-chloro-4-fluoro-phenyl)-7-quinolyl]oxy]propanoyl]piperidine-3-sulfonamide,
3-[1-[(2R)-2-[[4-(2-chlorophenyl)-7-quinolyl]oxy]propanoyl]-4-piperidyl]propanoic acid,
1-[rac-(2R)-2-[[4-(2,6-dimethylphenyl)-7-quinolyl]oxy]propanoyl]piperidine-3-sulfonamide,
2-[(3R)-1-[(2R)-2-[[4-(2,6-dichlorophenyl)-7-quinolyl]oxy]propanoyl]-3-piperidyl]acetic acid,
2-[(3R)-1-[(2R)-2-[[4-(2-ethylphenyl)-7-quinolyl]oxy]propanoyl]-3-piperidyl]acetic acid,
2-[(3R)-1-[(2R)-2-[[4-(2-isopropylphenyl)-7-quinolyl]oxy]propanoyl]-3-piperidyl]acetic acid,
[1-[rac-(2R)-2-[[4-(2-chloro-4-fluoro-phenyl)-7-quinolyl]oxy]propanoyl]-3-piperidyl]methanesulfonamide,
2-[(3R)-1-[(2R)-2-[[4-(2,6-dimethylphenyl)-2-methyl-7-quinolyl]oxy]propanoyl]-3-piperidyl]acetic acid,
(2R)-2-[[4-(2-chloro-4-fluoro-phenyl)-7-quinolyl]oxy]-N-[4-(2-hydroxyethyl)phenyl]propanamide,
(3S)-1-[(2R)-2-[[5-(2-chloro-4-fluoro-phenyl)-1,8-naphthyridin-2-yl]oxy]propanoyl]piperidine-3-carboxylic acid,
(3S)-1-[(2S)-2-[[5-(2-chloro-4-fluoro-phenyl)-1,8-naphthyridin-2-yl]oxy]propanoyl]piperidine-3-carboxylic acid,
(3S)-1-[(2S)-2-[[5-(2-chloro-4-fluoro-phenyl)-1,8-naphthyridin-2-yl]oxy]propanoyl]piperidine-3-carboxylic acid,
2-[(3R)-1-[(2R)-2-[[5-(2-chloro-4-fluoro-phenyl)-1,8-naphthyridin-2-yl]oxy]propanoyl]-3-piperidyl]acetic acid,
2-[(3R)-1-[(2R)-2-[[5-(2-chloro-4-fluoro-phenyl)-1,8-naphthyridin-2-yl]oxy]propanoyl]-3-piperidyl]acetic acid,
(3S)-1-[(2R)-2-[[4-(2,6-dichlorophenyl)-7-quinolyl]oxy]propanoyl]piperidine-3-carboxylic acid,
(2R)-2-[[4-(2-chloro-4-fluoro-phenyl)-7-quinolyl]oxy]-N-(2-pyridyl)propanamide,
(2R)-2-[[4-(2-chloro-4-fluoro-phenyl)-7-quinolyl]oxy]-N-ethyl-propanamide,
(3S)-1-[(2R)-2-[[4-(2,6-dichloro-4-fluoro-phenyl)-7-quinolyl]oxy]propanoyl]piperidine-3-carboxylic acid
2-[(3R)-1-[(2R)-2-[[4-(4-methyl-3-thienyl)-7-quinolyl]oxy]propanoyl]-3-piperidyl]acetic acid
2-[(3R)-1-[(2R)-2-[[4-(3-methyl-2-thienyl)-7-quinolyl]oxy]propanoyl]-3-piperidyl]acetic acid
2-[(3R)-1-[(2R)-2-[[4-(2-methoxyphenyl)-7-quinolyl]oxy]propanoyl]-3-piperidyl]acetic acid
2-[(3R)-1-[(2R)-2-[[4-[2-(trifluoromethyl)phenyl]-7-quinolyl]oxy]propanoyl]-3-piperidyl]acetic acid
2-[(3R)-1-[(2R)-2-[[4-[2-(trifluoromethoxy)phenyl]-7-quinolyl]oxy]propanoyl]-3-piperidyl]acetic acid,
(3S)-1-[(2R)-2-[[4-(2,6-dimethylphenyl)-7-quinolyl]oxy]propanoyl]piperidine-3-sulfonamide,
2-[(3R)-1-[2-[[4-(2-chlorophenyl)-7-quinolyl]oxy]-2-methyl-propanoyl]-3-piperidyl]acetic acid,
2-[rac-(3R)-1-[2-[[4-(2-chlorophenyl)-7-quinolyl]oxy]butanoyl]-3-piperidyl]acetic acid,
2-[(3R)-1-[(2R)-2-[[4-(2-chloro-6-methyl-phenyl)-7-quinolyl]oxy]propanoyl]-3-piperidyl]acetic acid,
2-[(3R)-1-[(2R)-2-[[4-(2-bromophenyl)-7-quinolyl]oxy]propanoyl]-3-piperidyl]acetic acid,
2-[(3R)-1-[(2R)-2-[[4-(2-cyanophenyl)-7-quinolyl]oxy]propanoyl]-3-piperidyl]acetic acid,
2-[(3R)-1-[(2R)-2-[[4-(2-ethynylphenyl)-7-quinolyl]oxy]propanoyl]-3-piperidyl]acetic acid,
2-[(3R)-1-[(2R)-2-[[4-[2-(dimethylamino)phenyl]-7-quinolyl]oxy]propanoyl]-3-piperidyl]acetic acid,
2-[(3R)-1-[(2R)-2-[[4-(2-carbamoylphenyl)-7-quinolyl]oxy]propanoyl]-3-piperidyl]acetic acid,
2-[(3R)-1-[(2R)-2-[[4-(2,6-difluorophenyl)-7-quinolyl]oxy]propanoyl]-3-piperidyl]acetic acid,
2-[(3R)-1-[(2R)-2-[[4-(2,4-dimethyl-3-thienyl)-7-quinolyl]oxy]propanoyl]-3-piperidyl]acetic acid,
2-[(3R)-1-[(2R)-2-[[4-[2-chloro-6-(trifluoromethyl)phenyl]-7-quinolyl]oxy]propanoyl]-3-piperidyl]acetic acid,
2-[(3R)-1-[(2R)-2-[[4-(2-bromo-6-chloro-phenyl)-7-quinolyl]oxy]propanoyl]-3-piperidyl]acetic acid,
2-[(3R)-1-[(2R)-2-[[4-[2,6-bis(trifluoromethyl)phenyl]-7-quinolyl]oxy]propanoyl]-3-piperidyl]acetic acid,
2-[(3R)-1-[(2R)-2-[[4-(2-chloro-6-methoxy-phenyl)-7-quinolyl]oxy]propanoyl]-3-piperidyl]acetic acid,
2-[(3R)-1-[(2R)-2-[[4-(2,6-diisopropylphenyl)-7-quinolyl]oxy]propanoyl]-3-piperidyl]acetic acid,
(2R)-1-[(3R)-3-amino-1-piperidyl]-2-[[4-(2,6-dimethylphenyl)-7-quinolyl]oxy]propan-1-one,
(2R)-1-[(3S)-3-amino-1-piperidyl]-2-[[4-(2,6-dimethylphenyl)-7-quinolyl]oxy]propan-1-one,
N-[(3S)-1-[(2R)-2-[[4-(2,6-dimethylphenyl)-7-quinolyl]oxy]propanoyl]-3-piperidyl]propanamide,
N-tert-butyl-4-[(2R)-2-[[4-(2,6-dimethylphenyl)-7-quinolyl]oxy]propanoyl]piperazine-1-carboxamide,
(2R)-2-[[4-(2,6-dimethylphenyl)-7-quinolyl]oxy]-1-[3-(1-hydroxycyclopropyl)-1-piperidyl]propan-1-one,
8-[(2R)-2-[[4-(2,6-dimethylphenyl)-7-quinolyl]oxy]propanoyl]-2,8-diazaspiro[4.5]decan-1-one,
(2R)-2-[[4-(2,6-dimethylphenyl)-7-quinolyl]oxy]-1-(3,5-dimethylpiperazin-1-yl)propan-1-one,
N-[(3S)-1-[(2R)-2-[[4-(2,6-dimethylphenyl)-7-quinolyl]oxy]propanoyl]-3-piperidyl]-N-hydroxyacetamide,
1-[4-[(2R)-2-[[4-(2,6-dimethylphenyl)-7-quinolyl]oxy]propanoyl]piperazin-1-yl]-2,2-dimethylpropan-1-one,
N-[(3S)-1-[(2R)-2-[[4-(2,6-dimethylphenyl)-7-quinolyl]oxy]propanoyl]-3-piperidyl]methanesulfonamide,
N-[(3S)-1-[(2R)-2-[[4-(2,6-dimethylphenyl)-7-quinolyl]oxy]propanoyl]-3-piperidyl]benzamide,
(3S)—N-cyano-1-[(2R)-2-[[4-(2,6-dimethylphenyl)-7-quinolyl]oxy]propanoyl]piperidine-3-carboxamide,
(3S)-1-[(2R)-2-[[4-(2,6-dimethylphenyl)-7-quinolyl]oxy]propanoyl]piperidine-3-carbohydroxamic acid,
2-[(3R)-1-[(2R)-2-[[4-(2,6-dimethylphenyl)-7-quinolyl]oxy]propanoyl]-3-piperidyl]ethanehydroxamic acid,
(2R)-1-(3-aminoazetidin-1-yl)-2-[[4-(2,6-dimethylphenyl)-7-quinolyl]oxy]propan-1-one,
(2R)-2-[[4-(2,6-dimethylphenyl)-7-quinolyl]oxy]-1-[3-(1H-tetrazol-5-yl)azetidin-1-yl]propan-1-one, 3-hydroxy-1-[(2R)-2-[[4-(2,6-dimethylphenyl)-7-quinolyl]oxy]propanoyl]piperidine-3-carboxylic acid,
5-[(2R)-2-[[4-(2,6-dimethylphenyl)-7-quinolyl]oxy]propanoyl]-5-azaspiro[2.5]octane-2-carboxylic acid,
(3R)-1-[(2R)-2-[[4-(2,6-dimethylphenyl)-7-quinolyl]oxy]propanoyl]piperidine-3-sulfonamide,
(3S)-1-[(2R)-2-[[4-(2,6-dichloro-4-fluoro-phenyl)-7-quinolyl]oxy]propanoyl]-3-methylpiperidine-3-carboxylic acid,
5-[rac-(2R)-2-[[4-(4-fluoro-2,6-dimethyl-phenyl)-7-quinolyl]oxy]propanoyl]-5-azaspiro[2.5]octane-2-carboxylic acid,
(3R)-1-[(2R)-2-[[4-(4-fluoro-2,6-dimethyl-phenyl)-7-quinolyl]oxy]propanoyl]-3-methylpiperidine-3-carboxylic acid,
(2R)-2-[[4-(4-fluoro-2,6-dimethyl-phenyl)-7-quinolyl]oxy]-1-[(2S)-2-methyl-1-piperidyl]propan-1-one,
5-[rac-(2R)-2-[[4-(2,6-dichloro-4-fluoro-phenyl)-7-quinolyl]oxy]propanoyl]-5-azaspiro[2.5]octane-2-carboxylic acid,
(2R)-2-[[4-(4-fluoro-2,6-dimethyl-phenyl)-7-quinolyl]oxy]-1-morpholino-propan-1-one,
(2R)-2-[[4-(4-fluoro-2,6-dimethyl-phenyl)-7-quinolyl]oxy]-1-(2-oxa-7-azaspiro[3.5]nonan-7-yl)propan-1-one,
rac-(2R)-2-[[4-(4-fluoro-2,6-dimethyl-phenyl)-7-quinolyl]oxy]-1-[3-(1-hydroxycyclopropyl)-1-piperidyl]propan-1-one,
8-[(2R)-2-[[4-(4-fluoro-2,6-dimethyl-phenyl)-7-quinolyl]oxy]propanoyl]-2,8-diazaspiro[4.5]decan-1-one,
1-[1-[rac-(2R)-2-[[4-(4-fluoro-2,6-dimethyl-phenyl)-7-quinolyl]oxy]propanoyl]-3-piperidyl]cyclopropanecarboxylic acid,
2-[(3R)-1-[(2R)-2-[[4-(4-fluoro-2,6-dimethyl-phenyl)-7-quinolyl]oxy]propanoyl]-3-piperidyl]acetic acid,
(3S)-1-[(2R)-2-[[4-(4-fluoro-2,6-dimethyl-phenyl)-7-quinolyl]oxy]propanoyl]-3-methylpiperidine-3-carboxylic acid,
N-[(3S)-1-[(2R)-2-[[4-(4-fluoro-2,6-dimethyl-phenyl)-7-quinolyl]oxy]propanoyl]-3-piperidyl]-N-hydroxy-acetamide,
2-methyl-2-[1-[rac-(2R)-2-[[4-(4-fluoro-2,6-dimethyl-phenyl)-7-quinolyl]oxy]propanoyl]-3-piperidyl]propanoic acid,
(2R)-2-[[4-(4-fluoro-2,6-dimethyl-phenyl)-7-quinolyl]oxy]-1-[(2R)-2-methyl-1-piperidyl]propan-1-one,
(3R)-1-[(2R)-2-[[4-(2,6-dichloro-4-fluoro-phenyl)-7-quinolyl]oxy]propanoyl]-3-methylpiperidine-3-carboxylic acid,
(3S)-1-[(2R)-2-[[4-(2-chloro-4-fluoro-phenyl)-7-quinolyl]oxy]propanoyl]-3-methyl-piperidine-3-carboxylic acid,
[1-[rac-(2R)-2-[[4-(2,6-dimethylphenyl)-7-quinolyl]oxy]propanoyl]-3-piperidyl]methanesulfonamide,
rac-(2R)-1-(2,6-dimethyl-1-piperidyl)-2-[[4-(4-fluoro-2,6-dimethyl-phenyl)-7-quinolyl]oxy]propan-1-one,
2-[(3R)-1-[(2R)-2-[[4-(2,6-dichloro-4-fluoro-phenyl)-7-quinolyl]oxy]propanoyl]-3-piperidyl]acetic acid,
5-[rac-(2R)-2-[[4-(2-chloro-4-fluoro-phenyl)-7-quinolyl]oxy]propanoyl]-5-azaspiro[2.5]octane-2-carboxylic acid,
1-[1-[rac-(2R)-2-[[4-(2-chloro-4-fluoro-phenyl)-7-quinolyl]oxy]propanoyl]-3-piperidyl]cyclopropanecarboxylic acid,
2-methyl-2-[1-[rac-(2R)-2-[[4-(2,6-dichloro-4-fluoro-phenyl)-7-quinolyl]oxy]propanoyl]-3-piperidyl]propanoic acid,
1-[1-[rac-(2R)-2-[[4-(2,6-dichloro-4-fluoro-phenyl)-7-quinolyl]oxy]propanoyl]-3-piperidyl]cyclopropanecarboxylic acid,
2-methyl-2-[1-[rac-(2R)-2-[[4-(2-chloro-4-fluoro-phenyl)-7-quinolyl]oxy]propanoyl]-3-piperidyl]propanoic acid,
(3R)-1-[(2R)-2-[[4-(2-chloro-4-fluoro-phenyl)-7-quinolyl]oxy]propanoyl]-3-methyl-piperidine-3-carboxylic acid,
(2R)-2-[[4-(2,6-dichloro-4-fluoro-phenyl)-7-quinolyl]oxy]-1-[(2S)-2-methyl-1-piperidyl]propan-1-one,
rac-(2R)-2-[[4-(2-chloro-4-fluoro-phenyl)-7-quinolyl]oxy]-1-(2-methyl-1-piperidyl)propan-1-one,
(2R)-2-[[4-(2,6-dichloro-4-fluoro-phenyl)-7-quinolyl]oxy]-1-morpholino-propan-1-one,
8-[(2R)-2-[[4-(2,6-dichloro-4-fluoro-phenyl)-7-quinolyl]oxy]propanoyl]-2,8-diazaspiro[4.5]decan-1one,
rac-(2R)-2-[[4-(2,6-dichloro-4-fluoro-phenyl)-7-quinolyl]oxy]-1-[3-(1-hydroxycyclopropyl)-1-piperidyl]propan-1-one,
(2R)-2-[[4-(2,6-dichloro-4-fluoro-phenyl)-7-quinolyl]oxy]-1-[(2R)-2-methyl-1-piperidyl]propan-1-one,
8-[(2R)-2-[[4-(2-chloro-4-fluoro-phenyl)-7-quinolyl]oxy]propanoyl]-2,8-diazaspiro[4.5]decan-1-one,
(2R)-2-[[4-(2-chloro-4-fluoro-phenyl)-7-quinolyl]oxy]-1-morpholino-propan-1-one,
(2R)-2-[[4-(2-chloro-4-fluoro-phenyl)-7-quinolyl]oxy]-1-[3-(1-hydroxycyclopropyl)-1-piperidyl]propan-1-one,
(2R)-2-[[4-(2,6-dichloro-4-fluoro-phenyl)-7-quinolyl]oxy]-1-(2-oxa-7-azaspiro[3.5]nonan-7-yl)propan-1-one,
N-hydroxy-N-[rac-(3S)-1-[rac-(2R)-2-[[4-(2-chloro-4-fluoro-phenyl)-7-quinolyl]oxy]propanoyl]-3-piperidyl]acetamide,
(2R)-2-[[4-(2-chloro-4-fluoro-phenyl)-7-quinolyl]oxy]-1-(2-oxa-7-azaspiro[3.5]nonan-7-yl)propan-1-one,
(2R)-2-[[4-(2-chloro-4-fluoro-phenyl)-7-quinolyl]oxy]-1-(2,6-dimethyl-1-piperidyl)propan-1-one,
(2R)-2-[[4-(2-chloro-4-fluoro-phenyl)-7-quinolyl]oxy]-1-(2-oxa-8-azaspiro[3.5]nonan-8-yl)propan-1-one,
(2R)-2-[[4-(2-chloro-4-fluoro-phenyl)-7-quinolyl]oxy]-1-(2-oxa-7-azaspiro[3.4]octan-7-yl)propan-1-one,
1-tert-butyl-3-[(3R)-1-[(2R)-2-[[4-(2-chloro-4-fluoro-phenyl)-7-quinolyl]oxy]propanoyl]pyrrolidin-3-yl]urea,
(2R)-2-[[4-(2-chloro-4-fluoro-phenyl)-7-quinolyl]oxy]-1-(3,3,5,5-tetramethylpiperazin-1-yl)propan-1-one,
(2R)-2-[[4-(2-chloro-4-fluoro-phenyl)-7-quinolyl]oxy]-1-(3,5-dimethylpiperazin-1-yl)propan-1-one,
(2R)-2-[[4-(2-chloro-4-fluoro-phenyl)-7-quinolyl]oxy]-1-[(1R)-2,5-diazabicyclo[2.2.1]heptan-2-yl]propan-1-one,
(2R)-2-[[4-(2-chloro-4-fluoro-phenyl)-7-quinolyl]oxy]-1-(2-oxa-6-azaspiro[3.3]heptan-6-yl)propan-1-one,
1-[(2R)-2-[[4-(2-chloro-4-fluoro-phenyl)-7-quinolyl]oxy]propanoyl]-3,6-dihydro-2H-pyridine-5-carboxylic acid,
2-[(3R)-1-[(2R)-2-[[5-(2,6-dichloro-4-fluoro-phenyl)-1,8-naphthyridin-2-yl]oxy]propanoyl]-3-piperidyl]acetic acid, and
2-[(3R)-1-[(2R)-2-[[5-(4-fluoro-2,6-dimethyl-phenyl)-1,8-naphthyridin-2-yl]oxy]propanoyl]-3-piperidyl]acetic acid, or a pharmaceutically or veterinary acceptable salt, hydrate or solvate thereof.

In another aspect, the invention relates to a process for manufacturing a compound of the general formula (I) as defined above, wherein V is —H, —OH, —Cl or —$C_1$-$C_4$-alkyl, comprising the step of:

(a) alkylating a compound of formulae ($D_1$ to $D_5$)

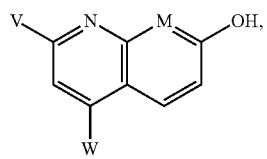

($D_1$ to $D_5$)

wherein
in $D_1$ V is —H, M is CH, and W is as defined herein,
in $D_2$ V is —OH, M is N, and W is as defined herein,
in $D_3$ V is —Cl, M is CH, and W is as defined herein,
in $D_4$ V is —H, M is CH, and W is as defined herein, and
in $D_3$ V is —$C_1$-$C_4$-alkyl, M is CH, and W is as defined herein,
with an alkylating agent, preferably with an alkylating agent of the formula Z—OH or
Z—Br, wherein Z is the group

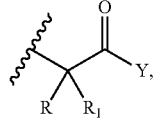

wherein R, $R_1$ and Y are as defined herein,
to obtain a compound of formulae ($E_1$ to $E_5$)

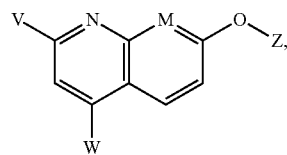

($E_1$ to $E_5$)

wherein
in $E_1$ V is —H, M is CH, and W and Z are as defined herein,
in $E_2$ V is —OH, M is CH, and W and Z are as defined herein,
in $E_3$ V is —Cl, M is CH, and W and Z are as defined herein,
in $E_4$ V is —H, M is N, and W and Z are as defined herein, and
in $E_5$ V is $C_1$-$C_4$-alkyl, M is N, and W and Z are as defined herein—

The compounds of formulae $E_1$ to $E_5$ correspond to the compounds of the general formula (I) as defined above, wherein V is —H, —OH, —Cl or $C_1$-$C_4$-alkyl.

In another aspect, the invention relates to a process for manufacturing a compound of the general formula (I) as defined herein, wherein V is —F, comprising the step of:
(b) reacting a compound of formula ($E_1$)

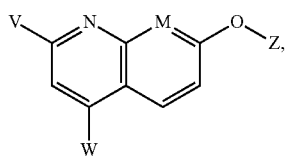

($E_1$)

wherein
in $E_1$ V is —H, M is CH, and W and Z are as defined herein,
with a fluorinating agent, preferably with $AgF_2$, to obtain a compound of formula $E_6$

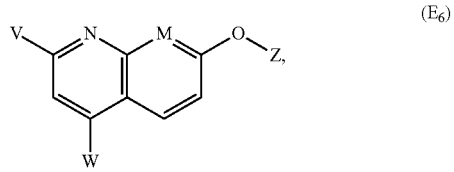

($E_6$)

wherein
V is —F, M is CH, and W and Z are as defined herein.

In another aspect, the invention relates to a compound of the general formula (I) as defined herein for use as a medicament.

In another aspect, the invention relates to a compound of the general formula (I) as defined herein for use in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

In another aspect, the invention relates to a compound of the general formula (I) as defined herein for use in a method for treating cancer in simultaneous, alternating or subsequent combination with another cancer therapy, preferably selected from chemotherapy, immunotherapy, hormone therapy, stem cell transplantation therapy, radiation therapy or surgery.

DETAILED DESCRIPTION OF THE INVENTION

Definitions, Abbreviations and Acronyms

"4, 5- or 6-membered saturated heterocycle" represents an unsubstituted or substituted saturated or partially unsaturated ring system containing 4, 5 or 6 ring atoms and containing in addition to C ring atoms one to three nitrogen atoms and/or an oxygen or sulfur atom or one or two oxygen and/or sulfur atoms. In a particular preferred embodiment the "4, 5- or 6-membered saturated heterocycle" represents an unsubstituted or substituted saturated ring system containing 4, 5 or 6 ring atoms and containing in addition to C ring atoms one to three nitrogen atoms and/or an oxygen or sulfur atom or one or two oxygen and/or sulfur atoms. In a preferred embodiment, the 4-, 5- or 6-membered saturated heterocycle contains in addition to C ring atoms one N and optionally one additional heteroatom. The additional heteroatoms are preferably selected from O, N or S. Especially preferred are heterocycles with only one N as a heteroatom. Preferably, these substituted heterocycles are single or two-fold substituted. The 4-, 5- or 6-membered saturated heterocycle may be substituted at the C atom(s), at the O atom(s), at the N atom(s) or at the S atom(s). Examples of 4-, 5- or 6-membered saturated heterocycle include, but are not limited to oxetanyl, azetidinyl, 1,3-diazetinyl, thietanyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4 thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1-piperazinyl, 2-piperazinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, preferably piperidin-1-yl, 2 piperidinyl, 3-piperidinyl, 4-piperidinyl, 1-piperazinyl, 2-piperazinyl, 2-pyrrolidinyl, and 3-pyrrolidinyl, tetrahydropyridinyl, preferably 1,2,3,6-tetrahydropyridinyl, 1,2-oxazinyl, 1,3-oxazinyl, and 1,4-oxazinyl, preferably tetrahydro-1,4-oxazinyl.

The 4-, 5- or 6-membered saturated heterocycle may be each optionally and independently substituted with one or more, preferably with one of the following residues:

—$C_1$-$C_4$-alkyl;
—C(OH)-cyclopropyl; —C(COOH)-cyclopropyl;
unsubstituted or substituted —$C_3$-$C_6$-cycloalkyl; preferably hydroxycyclopropyl or carboxycyclopropyl;
—$(CH_2)_o$—$COOR_7$ with
  $R_7$ is —H, —$C_1$-$C_8$-alkyl,
  preferably —H, -methyl, -ethyl, -isopropyl, or -tert-butyl, and
  o=0, 1 or 2; preferably 0 or 1;

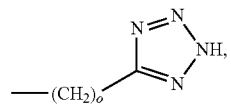

and o is as defined above;
—$(CH_2)_p CONR_8 R_9$ with
  $R_8$ and $R_9$ independently are —H, —OH, —CN, or —$C_1$-$C_4$-alkyl, preferably —H or -methyl, and
  p=0, 1 or 2; preferably 0 or 1;
—$C(CH_3)_2$—COOH;
=O or —OH;
—CO-cyclopropyl;

—CO—($C_1$-$C_4$-alkyl), preferably —CO—$CH_2$—$CH_3$;
—CO—$(CH_2)_q$—$NR_{12}R_{13}$ with $R_{12}$ and $R_{13}$ independently are —H, —$C_1$-$C_4$-alkyl or —CN, preferably —CO—$(CH_2)_q$—$NH_2$, more preferably —CO—$CH_2$—$NH_2$, and
q=0, 1 or 2, preferably 0 or 1;
—$NH_2$, —NH—CO-cyclopropyl, —NH—CO—$CH_2$—Cl, —NH—CO—$CH_2$—$CH_3$, —NH—CO—NH—C$(CH_3)_3$, —NH—$SO_2CH_3$, —NH—CO-phenyl, —NOH—CO—$CH_3$;
—F; —CN;
$R_{14}$ and $R_{15}$ forming a pyrrolidinone ring, a cyclopropanecarboxlic acid ring, an oxetane ring or a —$CH_2$— group;
or
—$(CH_2)_r SO_2 NR_{10}R_{11}$ with $R_{10}$ and $R_{11}$ independently are —H, or —$C_1$-$C_4$-alkyl, preferably —H or -methyl, preferably —$CH_2SO_2NH_2$ and
r=0, 1 or 2, preferably 0 or 1.

"$C_1$-$C_4$-alkyl" and "$C_1$-$C_8$-alkyl" represent a straight-chain or branched-chain alkyl group with 1 to 4 or 1 to 8 carbon atoms, respectively. Examples of straight-chain and branched groups include, but are not limited to, methyl, ethyl, propyl, isopropyl, butyl, isobutyl, and tert-butyl, preferably methyl and ethyl and most preferred methyl.

"halogen-$C_1$-$C_4$-alkyl" represents a straight-chain or branched alkyl group having 1 to 4 carbon atoms (as mentioned above), it being possible for the hydrogen atoms in these groups to be partly or completely replaced by halogen atoms as mentioned above, e.g. $C_1$-$C_2$-halogenalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2fluoroethyl, 2-chloro-2,2-difluoroethyl, 2,2-dichloro-2-fluoroethyl, 2,2,2-trichloroethyl and pentafluoroethyl;

"$C_1$-$C_4$-alkoxy" represents a straight-chain or branched-chain alkyl group with 1 to 4 or 1 to 8 carbon atoms, which are bonded to the structure via an oxygen atom (—O).

"$C_1$-$C_4$-dialkylamino" represents two straight-chain or branched alkyl groups having 1 to 4 carbon atoms (as mentioned above), which are independent of one another and are bonded to the structure via a nitrogen atom (—N:);

"$C_2$-$C_6$-alkenyl" represents a straight-chain or branched-chain hydrocarbon group comprising an olefinic bond in any desired position and 2 to 6, more preferably 2 to 4 carbon atoms. Examples of alkenyl groups include, but are not limited to, ethenyl, 1-propenyl, 2-propenyl, isopropenyl, 1-butenyl, 2-butenyl, 3-butenyl and isobutenyl. Preferred examples are 1 propenyl and 2-propenyl.

"$C_2$-$C_6$-alkynyl" represents a straight-chain or branched hydrocarbon group having 2 to 6 carbon atoms and a triple bond in any desired position, such as ethynyl, 1-propynyl, 2-propynyl, 1-butynyl, 2-butynyl, 3-butynyl, 1-methyl-2-propynyl, 1-pentynyl, 2-pentynyl, 3 pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

"$C_3$-$C_6$-cycloalkyl" represents a carbocyclic saturated ring system having 3 to 6 carbon atoms. Examples of $C_3$-$C_6$-cycloalkyl include, but are not limited cyclopropyl, cyclobutyl, cyclopentyl, or cyclohexyl, preferably cyclopentyl and cyclohexyl.

"Substitution" or "substituted" represents one or more substituents commonly known in the art, or as specifically defined herein.

"Halogen" represents fluoro, chloro, bromo or iodo, preferably represents fluoro and chloro.

"Stereoisomer(s)" as it relates to a compound of formula (I) and to its intermediate compounds represents any possible enantiomers or diastereomers of a compound of formula (I) and its salts or hydrates. In particular, the term "stereoisomer" means a single compound or a mixture of two or more compounds, wherein at least one chiral center is predominantly present in one definite isomeric form, in particular the S-enantiomer, the R-enantiomer and the racemate of a compound of formula (I). It is also possible that two or more stereogenic centers are predominantly present in one definite isomeric form of a derivative of a compound of formula (I) as defined above. In the sense of the present invention, "predominantly" has the meaning of at least 60%, preferably at least 70%, particularly preferably at least 80%, most preferably at least 90%. According to the present invention, also stereoisomers of a compound of formula (I) may be present as a salt or a hydrate.

The terms stereoisomer, salt, and hydrate may also be used in conjunction with one another. For example, a stereoisomer of a compound of formula (I) may have a salt. Combinations of these terms are considered to be within the scope of the invention.

References to compounds by number refer to the compounds as defined in Table 6.

Technical terms are used by their common sense. If a specific meaning is conveyed to certain terms, definitions of terms will be given in the following in the context of which the terms are used.

The below mentioned general or preferred residue definitions apply both to the end products of the formula (I) and to specific embodiments thereof, and also, correspondingly, to the starting materials or intermediates of formulae (A) to (J) required in each case for the preparation. These residue definitions can be combined with one another at will, i.e. including combinations between the given preferred residues. Further, individual definitions may not apply.

Novel POLRMT Inhibitors

As indicated above, there is a need for alternative novel compounds, which inhibit POLRMT and are suitable for use as a medicament. In particular, a need exists for novel compounds that can be used in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer. Further, POLRMT inhibitors are of interest, which can be used in a method for treating cancer in simultaneous, alternating or subsequent combination with another cancer therapy.

A problem of the present invention was therefore to provide novel alternative compounds having the above-mentioned desired characteristics.

In one aspect, according to the present invention there is provided a compound of the general formula (I)

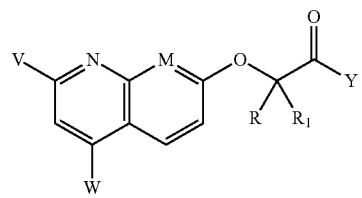

wherein
R is —H or —$C_1$-$C_4$-alkyl, preferably —H, -methyl or -ethyl, in particular -methyl;
$R_1$ is —H, or -methyl, preferably —H;
M is CH or N, preferably —H;
V is —H, —OH, —Cl, —F, or —$C_1$-$C_4$-alkyl, preferably —H, —Cl, —F, or -methyl;
W is

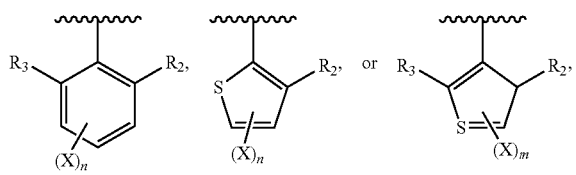

with
$R_2$ and $R_3$ are identical or different and are
—H, —$C_1$-$C_4$-alkyl, halogen-$C_1$-$C_4$-alkyl, —$C_1$-$C_4$-alkoxy, —$C_1$-$C_4$-dialkylamino, —$C_2$-$C_6$-alkenyl, —$C_2$-$C_6$-alkynyl, -halogen, —CN or —CO—NH$_2$;
preferably —H, —$C_1$-$C_4$-alkyl, —CF$_3$, —OCH$_3$, —NHCH$_3$, —N(CH$_3$)$_2$, —F, or —Cl;
X is -halogen, or —CN, preferably —F, with n=1 or 2 or m=1;
n=0, 1, or 2, preferably 0 or 1;
m=0 or 1;
Y is —NR$_4$R$_5$ with
R$_4$ is —H, or —$C_1$-$C_4$-alkyl, preferably —H or -methyl, and
R$_5$ is —H, —$C_1$-$C_4$-alkyl, an unsubstituted or substituted —$C_3$-$C_6$-cycloalkyl, preferably -methyl, -ethyl, -isopropyl, or -cyclopropyl; or
an unsubstituted or substituted pyridine residue; or
an unsubstituted or substituted phenyl residue, preferably substituted at the para position;
Y is —NR$_4$R$_5$ with N, R$_4$ and R$_5$ forming an unsubstituted or substituted 4-, 5- or 6-membered saturated heterocycle, preferably an unsubstituted or substituted azetidine, an unsubstituted or substituted piperidine, an unsubstituted or substituted pyrrolidine, an unsubstituted or substituted piperazine, or an unsubstituted or substituted tetrahydropyridine residue; or
Y is —OR$_6$, with R$_6$ is —H or —$C_1$-$C_4$-alkyl, preferably —H, -methyl, -ethyl, -isopropyl or -tert-butyl,
or a pharmaceutically or veterinary acceptable salt, hydrate or solvate thereof.

In a preferred embodiment, the compounds of the general formula (I) are quinoline derivatives, wherein M is CH.

Further included are pharmaceutically or veterinary acceptable salts, hydrates or solvates of the compounds of formula (I) or its intermediate compounds disclosed herein. A pharmaceutically or veterinary acceptable salt can be an anionic counterion, e.g. an acetate, a bromide, camsylate, chloride, citrate, formate, fumarate, lactate, maleate, mesylate, nitrate, oxalate, phosphate, sulfate, tartrate, thiocyanate, or tosylate, or preferably a cationic counterion, e.g. ammonium, arginine, diethylamine, ethylenediamine, piperazine, potassium, sodium, or any other counter ion disclosed in Haynes et al. (2005). Some compounds of the invention contain one or more chiral centers due to the presence of asymmetric carbon atoms, which gives rise to stereoisomers, for example to diastereoisomers with R or S stereochemistry at each chiral center. The invention includes all such stereoisomers and diastereoisomers and mixtures thereof.

As shown in the Examples, the inventors have now surprisingly and unexpectedly found that the compounds of general formula (I) or a pharmaceutically or veterinary acceptable salt, hydrate or solvate thereof, are useful as mitochondrial RNA polymerase (POLRMT) inhibitors and thereby inhibit mitochondrial DNA replication and/or mitochondrial transcription.

In the following, preferred groups of the compounds of general formula (I) of the present invention are described. The preferred groups constitute preferred embodiments of the compounds of general formula (I). Any combinations of the embodiments of the compounds of general formula (I) of the invention described herein are considered to be within the scope of the invention.

In a preferred embodiment, the invention relates to a compound of the general formula (I) as defined above, wherein
W is

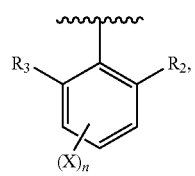

with
$R_3$ is —H, —$C_1$-$C_4$-alkyl, —$CF_3$, —$OCH_3$, —$NHCH_3$, —$N(CH_3)_2$, acetylenyl, —F, —Cl, —Br, CN, or $CONH_2$;
$R_2$ is —H, -methyl, -ethyl, isopropyl, —$CF_3$, —F, or —C; and
X is —F with n=1; preferably, wherein X is at the pare-position of the phenyl ring; or
n=0.

This preferred group of compounds corresponds to the compounds of formula (IA)

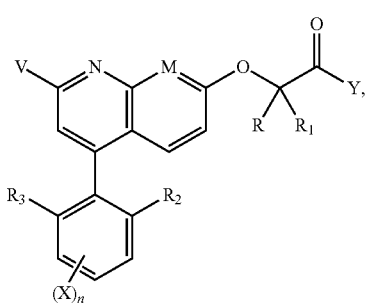

(IA)

wherein R, $R_1$, $R_2$, $R_3$, M, V, X, n and Y are as defined in the preferred group above.

A particular preferred group of compounds are compounds of formula (IB)

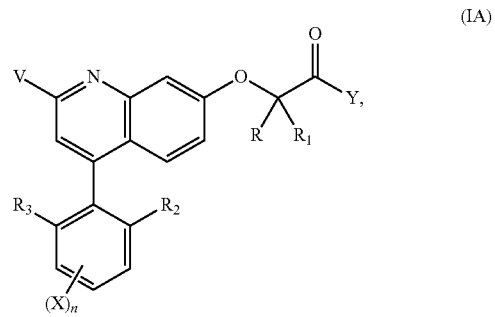

(IA)

wherein R, $R_1$, $R_2$, $R_3$, M, V, X, n and Y are as defined in the preferred group above.

In one embodiment, the invention relates to a compound of the general formula (I) as defined above, wherein
W is

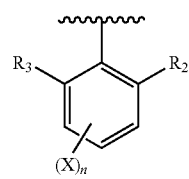

$R_2$ is —H, -methyl, -ethyl, isopropyl, —Cl, preferably -methyl or —C;
$R_3$ is —H, -methyl or —C; preferably $R_2$ is -methyl and $R_3$ is -methyl, or $R_2$ is —Cl and $R_3$ is —C; and
n=0.

In one embodiment, the invention relates to a compound of the general formula (I) as defined above, wherein
R is —$C_1$-$C_4$-alkyl, preferably -methyl or -ethyl, in particular -methyl;
$R_1$ is —H, or -methyl, preferably —H;
M is —CH;
V is as defined above;
W is

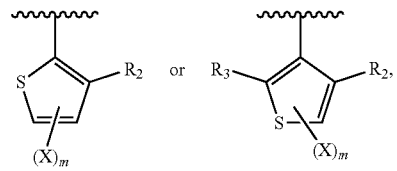

with
$R_2$ is —H, methyl, -halogen, —CN, preferably -methyl, —Cl, or —Br,
$R_3$ is —H, $C_1$-$C_4$-alkyl, -halogen, —CN, preferably -methyl, -ethyl, —Cl, or —Br,
X is -halogen, or —CN, preferably —Cl, —Br, or —F, in particular —F, with n=1 or 2;
n=0, 1, or 2, preferably 0 or 1;
m=0 or 1;
Y is —$NR_4R_5$ with
$R_4$ is —H, or —$C_1$-$C_4$-alkyl, preferably —H or -methyl, and $R_5$ is —$C_1$-$C_4$-alkyl or —$C_3$-$C_6$-cycloalkyl, preferably -methyl, -ethyl, -isopropyl, or -cyclopropyl; or an unsubstituted or substituted pyridine residue; or an unsubstituted or substituted phenyl residue, preferably substituted at the pare position;

Y is —$NR_4R_5$ with N, $R_4$ and $R_5$ form an unsubstituted or substituted 5- or 6-membered saturated heterocycle; or Y is —$OR_6$, with $R_6$ is —H or —$C_1$-$C_4$-alkyl, preferably —H, -methyl, -ethyl, or -isopropyl.

In one embodiment, the invention relates to a compound of the general formula (I) of the group as defined above, wherein W is

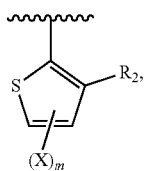

with $R_2$, X and n as defined above, for example compound 134.

In one embodiment, the invention relates to a compound of the general formula (I) of the group as defined above, wherein W is

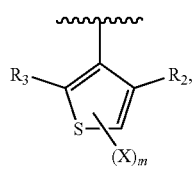

with $R_3$ is H, $R_2$, X and m as defined above.

In one embodiment, the invention relates to a compound of the general formula (I) of the group as defined above, wherein W is

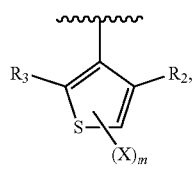

with $R_2$ is H, $R_3$, X and m as defined above, for example compound 133.

In another embodiment, the invention relates to a compound of the general formula (I) as defined above, wherein Y is —$NR_4R_3$, with $R_4$ is —H, or —$C_1$-$C_4$-alkyl, preferably —H or -methyl, and $R_5$ is —H, —$C_1$-$C_4$-alkyl, unsubstituted —$C_3$-$C_4$-cycloalkyl, —$C_4$-cycloalkyl substituted with —COO—$CH_3$, preferably -methyl, -ethyl, -isopropyl, or -cyclopropyl.

A specific subset of the compounds of the invention as defined above are the compounds of the general formula (I), wherein Y is —$NR_4R_3$, with $R_4$ is —H, or —$C_1$-$C_4$-alkyl, preferably —H or -methyl, and $R_5$ is an unsubstituted pyridine residue; or an unsubstituted or substituted phenyl residue, preferably unsubstituted or substituted with one substituent at the para position, wherein the substituents are selected from the group consisting of:

—$C_1$-$C_4$-alkyl, —$C_1$-$C_4$-alkoxy, —$(CH_2)_2$—OH, —COOH, or —CO—O—($C_1$-$C_4$-alkyl).

Another specific subset of the compounds of the invention are the compounds of the general formula (I), wherein Y is —$NR_4R_3$ with N, $R_4$ and $R_5$ forming an unsubstituted or substituted azetidine residue, an unsubstituted or substituted piperidine residue, an unsubstituted or substituted piperazine residue, an unsubstituted or substituted pyrrolidine residue, an unsubstituted or substituted morpholine residue, or an unsubstituted or substituted tetrahydropyridine residue, preferably an unsubstituted or substituted piperidine residue, each optionally and independently substituted with one or more, preferably with one of the following residues:

—$C_1$-$C_4$-alkyl;

—C(OH)-cyclopropyl; —C(COOH)-cyclopropyl;

unsubstituted or substituted —$C_3$-$C_6$-cycloalkyl; preferably hydroxycyclopropyl, or carboxycyclopropyl;

—$(CH_2)_o$—$COOR_7$ with $R_7$ is —H, —$C_1$-$C_8$-alkyl, preferably —H, -methyl, -ethyl, -isopropyl, or -tert-butyl, and o=0, 1 or 2; preferably 0 or 1;

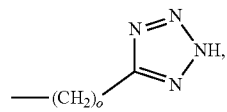

and o is as defined above;

—$(CH_2)_p CONR_8R_9$ with $R_8$ and $R_9$ independently are —H, —OH, —CN or —$C_1$-$C_4$-alkyl, preferably —H or -methyl, and p=0, 1 or 2; preferably 0 or 1;

—$C(CH_3)_2$—COOH;

=O or —OH;

—CO-cyclopropyl;

—CO—($C_1$-$C_4$-alkyl), preferably —CO—$CH_2$—$CH_3$;

—CO—$(CH_2)_q$—$NR_{12}R_{13}$ with $R_{12}$ and $R_{13}$ independently are —H, —$C_1$-$C_4$-alkyl or —CN, preferably —CO—$(CH_2)_q$—$NH_2$, more preferably —CO—$CH_2$—$NH_2$, and q=0, 1 or 2, preferably 0 or 1;

—$NH_2$, —NH—CO-cyclopropyl, —NH—CO—$CH_2$—Cl, —NH—CO—$CH_2$—$CH_3$, —NH—CO—NH—$C(CH_3)_3$, —NH—$SO_2CH_3$, —NH—CO-phenyl, —NOH—CO—$CH_3$;

—F; —CN;

$R_{14}$ and $R_{15}$ forming a pyrrolidinone ring, a cyclopropanecarboxlic acid ring, an oxetane ring, or a —$CH_2$— group; or —$(CH_2)_r SO_2NR_{10}R_{11}$ with $R_{10}$ and $R_{11}$ independently are —H, or —$C_1$-$C_4$-alkyl, preferably —H or -methyl, preferably —$CH_2SO_2NH_2$ and r=0, 1 or 2, preferably 0 or 1.

Another specific subset of the compounds of the invention are the compounds of the general formula (I), wherein N, $R_4$ and $R_5$ together form an unsubstituted or substituted azetidine, piperidine, piperazine or pyrrolidine residue, each optionally and independently substituted with one or more, preferably with one of the following residues:
- —$C_1$-$C_4$-alkyl, unsubstituted or substituted —$C_3$-$C_6$-cycloalkyl;
- —$(CH_2)_o$—$COOR_7$ with
  $R_7$ is —H, —$C_1$-$C_8$-alkyl,
  preferably —H, -methyl, -ethyl, -isopropyl, or -tert-butyl, and
  o=0, 1 or 2; preferably 0 or 1;

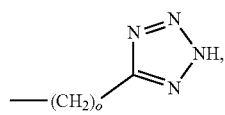

and o is as defined above;
- —$(CH_2)_p CONR_8R_9$ with
  $R_8$ and $R_9$ independently are —H, —OH, —CN, or —$C_1$-$C_4$-alkyl, preferably —H or -methyl, and
  p=0, 1 or 2; preferably 0 or 1;
- =O or —OH;
- —CO-cyclopropyl;
- —CO—($C_1$-$C_4$-alkyl), preferably —CO—$CH_2$—$CH_3$;
- —CO—$(CH_2)_q$—$NR_{12}R_{13}$ with $R_{12}$ and $R_{13}$ independently are —H, —$C_1$-$C_4$-alkyl or —CN, preferably —CO—$(CH_2)_q$—$NH_2$, more preferably —CO—$CH_2$—$NH_2$, and
  q=0, 1 or 2, preferably 0 or 1;
- —$NH_2$, —NH—CO-cyclopropyl, —NH—CO—$CH_2$—Cl, —NH—CO—$CH_2$—$CH_3$, —NH—$SO_2CH_3$, —NH—CO-phenyl, —NOH—CO—$CH_3$;
- —F; —CN;
- $R_{14}$ and $R_{15}$ forming a pyrrolidinone ring or a cyclopropanecarboxlic acid ring; or
- —$(CH_2)_r SO_2NR_{10}R_{11}$ with $R_{10}$ and $R_{11}$ independently are —H, or —$C_1$-$C_4$-alkyl, preferably —H or -methyl, preferably —$CH_2SO_2NH_2$ and
  r=0, 1 or 2, preferably 0 or 1.

Another specific subset of the compounds of the invention are the compounds of the general formula (I), wherein
Y is —$NR_4R_5$ with
  N, $R_4$ and $R_5$ forming an unsubstituted or substituted piperidine reside, an unsubstituted or substituted piperazine residue, an unsubstituted or substituted pyrrolidine residue, or an unsubstituted or substituted morpholine residue, each optionally and independently substituted with one or more, preferably with one of the following residues:
- —$C_1$-$C_4$-alkyl;
- —C(OH)cyclopropyl;
- hydroxycyclopropyl or carboxycyclopropyl;
- —$(CH_2)_o$—$COOR_7$ with
  $R_7$ is —H, —$C_1$-$C_8$-alkyl, preferably —H, -methyl, -ethyl, -isopropyl, or -tert-butyl, and
  o=0, 1 or 2;

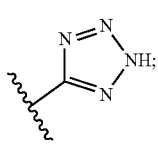 [SMILES: *c1nn[nH]n1]

- —$(CH_2)_p CONR_8R_9$ with
  $R_8$ and $R_9$ independently are —H, —OH, —CN, -methyl, or -tert-butyl and p=0;
- —$C(CH_3)_2$—COOH;
- =O or —OH;
- —CO-cyclopropyl;
- —CO—$CH_2$—$CH_3$;
- —CO-tert-butyl;
- —$NH_2$,
- —CO—$CH_2$—$NH_2$;
- —NH—CO—$CH_2$—$CH_3$, —NH—CO—NH—C$(CH_3)_3$, —NH—$SO_2CH_3$, —NH—CO-phenyl, —NOH—CO—$CH_3$;
- —CN;
- $R_{14}$ and $R_{15}$ forming a pyrrolidinone ring, a cyclopropanecarboxlic acid ring, an oxetane ring; or a —$CH_2$— group;
- —$SO_2NR_{10}R_{11}$ with $R_{10}$ and $R_{11}$ independently are —H or -methyl; or
- —$CH_2SO_2N H_2$.

Another specific subset of the compounds of the invention are the compounds of the general formula (I), wherein N, $R_4$ and $R_5$ together form an unsubstituted or substituted piperidine or pyrrolidine residue, each optionally and independently substituted with one or more, preferably with one, of the following residues:
- —$(CH_2)_o$—$COOR_7$ with
  $R_7$ is —H, —$C_1$-$C_8$-alkyl, preferably —H, -methyl, -ethyl, -isopropyl, or -tert-butyl, and
  o=0, 1 or 2

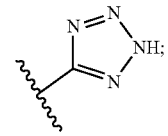 [SMILES: *c1nn[nH]n1]

- —$(CH_2)_p CONR_8R_9$ with
  $R_8$ and $R_9$ independently are —H, —OH, —CN, -methyl or -tert-butyl, and p=0;
- =O or —OH;
- —CO-cyclopropyl;
- —CO—$CH_2$—$CH_3$;
- —CO-tert-butyl;
- —$NH_2$
- —CO—$CH_2$—$NH_2$;
- —CN;
- —$SO_2NR_{10}R_{11}$ with $R_{10}$ and $R_{11}$ independently are —H or -methyl; or
- —$CH_2SO_2NH_2$.

A group of preferred compounds have an unsubstituted piperidine, i.e. N, $R_4$ and $R_5$ together form an unsubstituted piperidine residue.

A more preferred subgroup are compounds having a substituted piperidine residue substituted with —COOH or with —$CH_2COOH$.

Another more preferred subgroup are compounds having a unsubstituted or substituted piperidine residue, optionally and independently substituted with one or more of the following residues:
- —COOH, —$COOCH_3$, —$COOC_2H_5$, —$CH_2COOH$, —$C(CH_3)_2$—COOH, —$CH_2COOCH_3$, —$CH_2COOCH_2CH_3$, —$CONH_2$, —$CONHCH_3$, —$CON(CH_3)_2$, —$SO_2NH_2$ or —$CH_2SO_2NH_2$.

In another embodiment, the invention relates to a compound of the general formula (I) as defined herein, wherein V is —H, —Cl, —F, or -methyl, preferably —H.

In another embodiment, the invention relates to a compound of the general formula (I) as defined herein, wherein
R is -methyl, preferably —(R)-methyl; and
$R_1$ is —H.

In a preferred embodiment, R is —(R)-methyl.

In another embodiment, the invention relates to a compound of the general formula (I) as defined herein, wherein X is at the para-position of the phenyl ring.

Another specific subset of the compounds are the compounds of the general formula (I), wherein
R is -methyl, preferably (R)-methyl;
$R_1$ is —H;
M is CH;
V is —H, —Cl, —F or -methyl;
W is

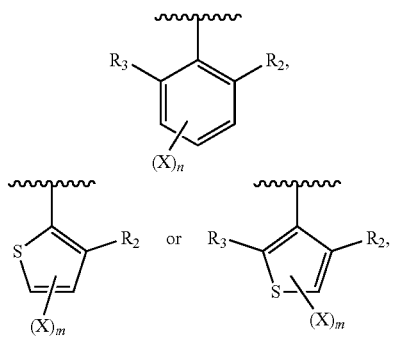

preferably

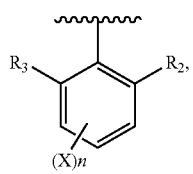

with
$R_2$ and $R_3$ are -methyl, or —Cl with n=1 or 2, preferably di-methyl or di-choro with n=2;
X is —F with m=1;
n=0, 1, or 2
m=0, or 1;
Y is —NR$_4$R$_5$
with
$R_4$ is —H, and
$R_5$ is a pyridine residue,
a phenyl residue substituted at the para position, preferably substituted with —(CH$_2$)$_2$OH, or
a cyclopropyl or isopropyl residue;
or with
N, $R_4$ and $R_5$ are together a piperidine residue, or a pyrrolidine residue, each optionally and independently substituted with one of the following residues: —COOH, —COOCH$_3$, —COOC$_2$H$_5$, —CH$_2$COOH, —C(CH$_3$)$_2$—COOH, —CH$_2$COOCH$_3$, —CH$_2$COOCH$_2$CH$_3$, —CONH$_2$, —CONHCH$_3$, —CON(CH$_3$)$_2$, —SO$_2$NH$_2$ or —CH$_2$SO$_2$NH$_2$.

A more preferred subgroup are compounds, wherein R is (R)-methyl, having a substituted piperidine residue substituted with —COOH or with —CH$_2$COOH.

Another more preferred subgroup of this specific subset are compounds, wherein R is (R)-methyl, having a substituted piperidine residue substituted with —(CH$_2$)$_o$—COOR$_7$ with
$R_7$ is —H, —C$_1$-C$_8$-alkyl,
preferably —H, -methyl, -ethyl, -isopropyl, or -tert-butyl, and
o=0, 1 or 2; preferably 0 or 1;

Another specific subset of compounds are compounds, wherein
R is (R)-methyl;
$R_1$ is —H;
M is CH;
V is —H, —Cl, —F or -methyl;
W is

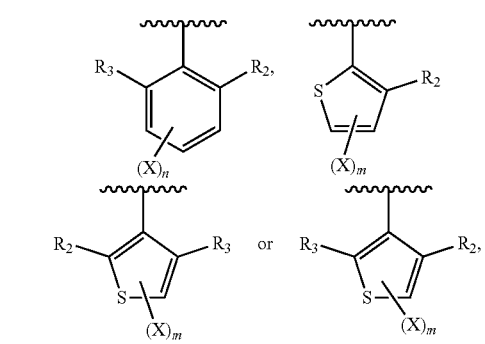

preferably

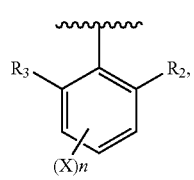

with
$R_2$ and $R_3$ are -methyl, or —Cl, with n=1 or 2, preferably di-methyl or di-choro with n=2;
X is —F with m=1;
n=0, 1, or 2
m=0, or 1;
Y is —NR$_4$R$_5$
with
N, $R_4$ and $R_5$ form a piperidine residue, or a pyrrolidine residue, each optionally and independently substituted with one of the following residues:
—COOH, —COOCH$_3$, —COOC$_2$H$_5$, —CH$_2$COOH, —C(CH$_3$)$_2$—COOH, —CH$_2$COOCH$_3$, —CH$_2$COOCH$_2$CH$_3$, —CONH$_2$, —CONHCH$_3$, —CON(CH$_3$)$_2$, —SO$_2$NH$_2$ or —CH$_2$SO$_2$NH$_2$,
preferably —COOH, —CH$_2$COOH, or —CONHCH$_3$,
more preferably (S)—COOH, (R)—COOH, (S)—CH$_2$COOH or (R)—CH$_2$COOH,
especially a piperidine residue substituted with (S)—COOH, (R)—COOH, (S)—CH$_2$COOH or (R)—CH$_2$COOH.

A more preferred group of compounds are compounds having a substituted piperidine residue where R is (R)-methyl, W is

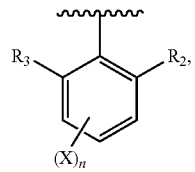

R₁ is —H, V═—H, R₂ and R₃ are independently -methyl or —Cl, preferably —Cl, X is —F, n=1 and wherein the piperidine is substituted with —COOH, —CH₂COOH, —CONHCH₃, —CH₂CONHCH₃, —SO₂NH₂, —SO₂NHCH₃, or —CN.

Another specific subset of compounds are compounds, wherein the piperidine residue or the pyrrolidine residue is substituted at the 3-position.

A more preferred group of compounds of this subset are compounds having any substituted piperidine or pyrrolidine residue as defined above at the 3-position. More preferred within this group are compounds having a substituted piperidine residue substituted with —(CH₂)ₒ—COOR₇ with R₇ is —H, —C₁-C₈-alkyl, preferably —H, -methyl, -ethyl, -isopropyl, or -tert-butyl, and o=0, 1 or 2; preferably 0 or 1; at the 3-position with —COOR₇ or —CH₂COOR₇ at the 3-position, or with R₇ is -isopropyl, -tert-butyl, or with —CONHCH₃ or —CH₂CONHCH₃ at the 3 position.

Another group of preferred compounds of this subset have a substituted piperidine residue substituted with —(CH₂)ᵣSO₂NR₁₀R₁₁ with R₁₀ and R₁₁ independently are —H, or —C₁-C₄-alkyl, preferably —H or -methyl, preferably —CH₂SO₂NH₂ and r=0, 1 or 2, preferably 0 or 1 at the 3 position with R₁₀ is —H and R₁₁ is —H or -methyl.

A more preferred group of compounds are compounds having a substituted piperidine residue, wherein the substitution is at the 3-position, where R is methyl, R₁ is —H, V═—H, R₂ and R₃ is -methyl or —Cl, n, m=0 or 1, X is —F with n=1 or m=1 and wherein the piperidine is substituted with one of the following residues: —COOH, —COOCH₃, —COOC₂H₅, —CH₂COOH, —CH₂COOCH₃, —CH₂COOCH₂CH₃, —CONH₂, —CONHCH₃, —CON(CH₃)₂, —CH₂CONHCH₃, SO₂NH₂, —SO₂NHCH₃, or —CN. An even more preferred subgroup of this group are compounds where R is (R)-methyl A more preferred subgroup are compounds having a substituted piperidine residue substituted with —COOH at the 3-position and wherein R is (R)-methyl, or with —CH₂COOH at the 3-position and wherein R is (R)-methyl.

Another more preferred subgroup are compounds, wherein R is (R)-methyl and having a substituted piperidine residue, wherein the substitution is at the 3-position, substituted with —(CH₂)ₒ—COOR₇ with R₇ is —H, —C₁-C₈-alkyl, preferably —H, -methyl, -ethyl, -isopropyl, or -tert-butyl, and o=0, 1 or 2; preferably 0 or 1, preferably with R₇ is -isopropyl, -tert-butyl, or with —CONHCH₃ or —CH₂CONHCH₃.

An especially preferred group of compounds are compounds having a substituted piperidine residue where R is (R)-methyl, R₁ is —H, V═—H, R₂ and R₃ is -methyl, or —Cl, W is

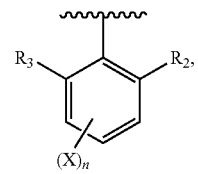

n=0 or 1, X is —F with n=1 and wherein the piperidine is substituted with —COOH, —CH₂COOH, —CONHCH₃, —CH₂CONHCH₃, —SO₂NH₂, —SO₂NHCH₃, or —CN at the 3-position.

A more preferred subgroup are compounds, wherein X is at the para-position, having a substituted piperidine residue substituted with —COOH at the 3-position and wherein R is (R)methyl or with —CH₂COOH at the 3-position and wherein R is (R)-methyl.

Another more preferred subgroup are compounds, wherein X is at the para-position, wherein R is (R)-methyl and having a substituted piperidine residue substituted with —(CH₂)ₒ—COOR₇ with R₇ is —H, —C₁-C₈-alkyl, preferably —H, -methyl, -ethyl, -isopropyl, or -tert-butyl, and o=0, 1 or 2; preferably 0 or 1 at the 3-position, with R₇ is -isopropyl, -tert-butyl, n, or —CONHCH₃ or —CH₂CONHCH₃ at the 3-position.

An especially preferred group of compounds are compounds, wherein X is at the para-position, having a substituted piperidine residue where R is (R)-methyl, R₁ is —H, W is

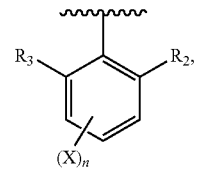

n=0 or 1, R₂ and R₃ are -methyl, or —Cl, preferably —Cl, X is —F with n=1 and wherein the piperidine is substituted with —COOH, —CH₂COOH, —CONHCH₃, —SO₂NH₂, —SO₂NHCH₃, or —CN at the 3-position. An especially preferred subgroup of this group concerns compounds with R₂ is —Cl, X is —F and n=1.

Another specific subset of compounds concerns compounds selected from
(3S)-1-[(2R)-2-[[4-(o-tolyl)-7-quinolyl]oxy]propanoyl]piperidine-3-carboxylic acid,
(3S)-1-[(2R)-2-[[4-(2,6-dimethylphenyl)-7-quinolyl]oxy]propanoyl]piperidine-3-carboxylic acid,
2-[(3R)-1-[(2R)-2-[[4-(2,6-dimethylphenyl)-7-quinolyl]oxy]propanoyl]-3-piperidyl]acetic acid,
ethyl (3S)-1-[(2R)-2-[[4-(2,6-dimethylphenyl)-7-quinolyl]oxy]propanoyl]piperidine-3-carboxylate,
2-[(3S)-1-[(2R)-2-[[4-(2,6-dimethylphenyl)-7-quinolyl]oxy]propanoyl]-3-piperidyl]acetic acid,
ethyl 2-[(3R)-1-[(2R)-2-[[4-(2,6-dimethylphenyl)-7-quinolyl]oxy]propanoyl]-3-piperidyl]acetate,
(3R)-1-[(2R)-2-[[4-(2-chlorophenyl)-7-quinolyl]oxy]propanoyl]piperidine-3-carboxylic acid,
ethyl 2-[(3R)-1-[(2R)-2-[[4-(o-tolyl)-7-quinolyl]oxy]propanoyl]-3-piperidyl]acetate,
(3S)-1-[(2R)-2-[[4-(2-chlorophenyl)-7-quinolyl]oxy]propanoyl]piperidine-3-carboxylic acid, (3S)-1-[(2R)-2-[[4-(2-chloro-4-fluoro-phenyl)-7-quinolyl]oxy]propanoyl]piperidine-3-carboxylic acid,
(2R)-2-[[4-(2-chloro-4-fluoro-phenyl)-7-quinolyl]oxy]-1-[(3S)-3-(2H-tetrazol-5-yl)-1-piperidyl]propan-1-one,
(3S)-1-[(2R)-2-[[4-(2-chlorophenyl)-2-fluoro-7-quinolyl]oxy]propanoyl]piperidine-3-carboxylic acid,
2-[(3R)-1-[(2R)-2-[[4-(o-tolyl)-7-quinolyl]oxy]propanoyl]-3-piperidyl]acetic acid,
ethyl (3S)-1-[(2R)-2-[[4-(o-tolyl)-7-quinolyl]oxy]propanoyl]piperidine-3-carboxylate,
ethyl 2-[(3R)-1-[(2R)-2-[[4-(2-chloro-4-fluoro-phenyl)-7-quinolyl]oxy]propanoyl]-3-piperidyl]acetate,
2-[(3R)-1-[(2R)-2-[[4-(2-chlorophenyl)-7-quinolyl]oxy]propanoyl]-3-piperidyl]acetic acid
(3R)-1-[(2R)-2-[[4-(2-chloro-4-fluoro-phenyl)-7-quinolyl]oxy]propanoyl]piperidine-3-carboxylic acid,
2-[(3R)-1-[(2R)-2-[[4-(2-chloro-4-fluoro-phenyl)-7-quinolyl]oxy]propanoyl]-3-piperidyl]acetic acid,
(3S)-1-[(2R)-2-[[4-(2-chloro-4-fluoro-phenyl)-7-quinolyl]oxy]propanoyl]pyrrolidine-3-carboxylic acid,
(2R)-2-[[4-(2-chloro-4-fluoro-phenyl)-7-quinolyl]oxy]-1-(1-piperidyl)propan-1-one,
2-[(3R)-1-[(2R)-2-[[2-chloro-4-(o-tolyl)-7-quinolyl]oxy]propanoyl]-3-piperidyl]acetic acid,
2-[(3S)-1-[(2R)-2-[[4-(2-chloro-4-fluoro-phenyl)-7-quinolyl]oxy]propanoyl]-3-piperidyl]acetic acid,
rac-(3S)-1-[2-[[4-(2-chlorophenyl)-7-quinolyl]oxy]propanoyl]piperidine-3-carboxylic acid,
1-[(2R)-2-[[4-(2-chloro-4-fluoro-phenyl)-7-quinolyl]oxy]propanoyl]piperidine-4-carboxylic acid,
(3S)-1-[rac-(2R)-2-[[2-chloro-4-(o-tolyl)-7-quinolyl]oxy]propanoyl]piperidine-3-carboxylic acid,
3-[[(2R)-2-[[4-(2-chloro-4-fluoro-phenyl)-7-quinolyl]oxy]propanoyl]amino]benzoic acid
ethyl (3S)-1-[(2R)-2-[[4-(2-chloro-4-fluoro-phenyl)-7-quinolyl]oxy]propanoyl]piperidine-3-carboxylate,
(2R)-2-[[4-(2-chloro-4-fluoro-phenyl)-7-quinolyl]oxy]-1-(4-propanoylpiperazin-1-yl)propan-1-one,
tert-butyl (2R)-2-[[4-(2-chlorophenyl)-7-quinolyl]oxy]propanoate,
(3S)-1-[(2R)-2-[[4-(2-chloro-4-fluoro-phenyl)-7-quinolyl]oxy]propanoyl]piperidine-3-carbonitrile,
(3S)-1-[(2R)-2-[[2-methyl-4-(o-tolyl)-7-quinolyl]oxy]propanoyl]piperidine-3-carboxylic ac id,
(2R)-2-[[4-(2-chloro-4-fluoro-phenyl)-7-quinolyl]oxy]-N-isopropyl-N-methyl-propanamide,
1-[rac-(2R)-2-[[4-(2-chloro-4-fluoro-phenyl)-7-quinolyl]oxy]propanoyl]piperidine-3-sulfonamide,
(3S)-1-[(2R)-2-[[2-chloro-4-(2-chlorophenyl)-7-quinolyl]oxy]propanoyl]piperidine-3-carboxylic acid,
(3S)-1-[(2R)-2-[[2-chloro-4-(4-fluoro-2-methyl-phenyl)-7-quinolyl]oxy]propanoyl]piperidine-3-carboxylic acid,
isopropyl (2R)-2-[[4-(2-chlorophenyl)-7-quinolyl]oxy]propanoate,
methyl 2-[(3R)-1-[(2R)-2-[[4-(2-chloro-4-fluoro-phenyl)-7-quinolyl]oxy]propanoyl]pyrrolidin-3-yl]acetate,
(3S)-1-[(2R)-2-[[4-(2-chloro-4-fluoro-phenyl)-7-quinolyl]oxy]propanoyl]-N-methylpiperidine-3-carboxamide,
2-[(3S)-1-[(2R)-2-[[4-(2-chloro-4-fluoro-phenyl)-7-quinolyl]oxy]propanoyl]pyrrolidin-3-yl]acetic acid,
2-[(3R)-1-[(2R)-2-[[4-(2-chloro-4-fluoro-phenyl)-7-quinolyl]oxy]propanoyl]pyrrolidin-3-yl]acetic acid,
ethyl (3S)-1-[(2R)-2-[[4-(2-chlorophenyl)-2-fluoro-7-quinolyl]oxy]propanoyl]piperidine-3-carboxylate,
(2R)-2-[[4-(2-chloro-4-fluoro-phenyl)-7-quinolyl]oxy]-1-pyrrolidin-1-yl-propan-1-one,
(2R)-2-[[2-chloro-4-(o-tolyl)-7-quinolyl]oxy]propanoic acid,
(2R)-2-[[4-(2-chloro-4-fluoro-phenyl)-7-quinolyl]oxy]propanoic acid,
(2R)-2-[[4-(2-chloro-4-fluoro-phenyl)-7-quinolyl]oxy]-N,N-dimethyl-propanamide,
rac-(3S)-1-[2-[[4-(2-chlorophenyl)-7-quinolyl]oxy]acetyl]piperidine-3-carboxylic acid,
(2R)—N-tert-butyl-2-[[4-(2-chloro-4-fluoro-phenyl)-7-quinolyl]oxy]propanamide,
(2R)-2-[[4-(2-chlorophenyl)-7-quinolyl]oxy]-N-isopropyl-propanamide,
ethyl 2-[(3R)-1-[(2R)-2-[[2-methyl-4-(o-tolyl)-7-quinolyl]oxy]propanoyl]-3-piperidyl]acetate,
ethyl (2R)-2-[[4-(2-chlorophenyl)-7-quinolyl]oxy]propanoate,
ethyl 4-[[(2R)-2-[[4-(2-chloro-4-fluoro-phenyl)-7-quinolyl]oxy]propanoyl]amino]benzoate,
(3S)-1-[(2R)-2-[[2-chloro-4-(o-tolyl)-7-quinolyl]oxy]propanoyl]piperidine-3-carboxamide,
(2R)-2-[[4-(2-chlorophenyl)-7-quinolyl]oxy]-1-(1-piperidyl)propan-1-one,
methyl 3-[[(2R)-2-[[4-(2-chloro-4-fluoro-phenyl)-7-quinolyl]propanoyl]amino]cyclobutanecarboxylate,
(2R)-2-[[4-(2-chloro-4-fluoro-phenyl)-7-quinolyl]oxy]-1-piperazin-1-yl-propan-1-one,
2-[(3R)-1-[(2R)-2-[[2-chloro-4-(2-chloro-4-fluoro-phenyl)-7-quinolyl]oxy]propanoyl]-3-piperidyl]acetic acid,
2-[(3R)-1-[(2R)-2-[[2-chloro-4-(4-fluoro-2-methyl-phenyl)-7-quinolyl]oxy]propanoyl]-3-piperidyl]acetic acid,
ethyl 1-[(2R)-2-[[4-(2-chloro-4-fluoro-phenyl)-7-quinolyl]oxy]propanoyl]piperidine-4-carboxylate,
(3S)-1-[(2R)-2-[[4-(2-chloro-4-fluoro-phenyl)-2-methyl-7-quinolyl]oxy]propanoyl]piperidine-3-carboxylic acid,
4-[[(2R)-2-[[4-(2-chloro-4-fluoro-phenyl)-7-quinolyl]oxy]propanoyl]amino]benzoic acid,
(2R)-2-[[4-(2-chloro-4-fluoro-phenyl)-7-quinolyl]oxy]-N-isopropyl-propanamide,
(3S)-1-[2-[[5-(2-chloro-4-fluoro-phenyl)-1,8-naphthyridin-2-yl]oxy]propanoyl]piperidine-3-carboxylic acid,
4-[(2R)-2-[[4-(2-chloro-4-fluoro-phenyl)-7-quinolyl]oxy]propanoyl]piperazin-2-one,
(3S)-1-[(2R)-2-[[2-chloro-4-(2-chloro-4-fluoro-phenyl)-7-quinolyl]oxy]propanoyl]piperidine-3-carboxylic acid,
2-[(3R)-1-[(2R)-2-[[4-(2-chloro-3-fluoro-phenyl)-7-quinolyl]oxy]propanoyl]-3-piperidyl]acetic acid,
(3S)-1-[(2R)-2-[(4-phenyl-7-quinolyl)oxy]propanoyl]piperidine-3-carboxylic acid,
methyl 2-[(3S)-1-[(2R)-2-[[4-(2-chloro-4-fluoro-phenyl)-7-quinolyl]oxy]propanoyl]pyrrolidin-3-yl]acetate,
2-[(3R)-1-[(2R)-2-[[2-chloro-4-(2-chlorophenyl)-7-quinolyl]oxy]propanoyl]-3-piperidyl]-N-methyl-acetamide,
2-[(3R)-1-[(2R)-2-[[2-methyl-4-(o-tolyl)-7-quinolyl]oxy]propanoyl]-3-piperidyl]acetic acid,
(2R)-2-[[2-chloro-4-(2-chlorophenyl)-7-quinolyl]oxy]-1-[4-(cyclopropanecarbonyl)piperazin-1-yl]propan-1-one,
methyl (3R)-1-[(2R)-2-[[4-(2-chloro-4-fluoro-phenyl)-7-quinolyl]oxy]propanoyl]piperidine-3-carboxylate,
(2R)-2-[[2-chloro-4-(2-chlorophenyl)-7-quinolyl]oxy]-1-(4-propanoylpiperazin-1-yl)propan-1-one,
tert-butyl (2R)-2-[[2-chloro-4-(o-tolyl)-7-quinolyl]oxy]propanoate,
ethyl 2-[(3R)-1-[(2R)-2-[[4-(2-chloro-4-fluoro-phenyl)-2-methyl-7-quinolyl]oxy]propanoyl]-3-piperidyl]acetate,
ethyl (3S)-1-[(2R)-2-[[4-(2-chloro-4-fluoro-phenyl)-7-quinolyl]oxy]propanoyl]pyrrolidine-3-carboxylate, (3S)-1-[(2R)-2-[[2-chloro-4-(2-chlorophenyl)-7-quinolyl]oxy]propanoyl]piperidine-3-carboxamide,
(2R)-2-[[4-(2-chloro-4-fluoro-phenyl)-7-quinolyl]oxy]-N-cyclopropyl-propanamide,
(3S)-1-[(2S)-2-[[4-(2-chlorophenyl)-7-quinolyl]oxy]propanoyl]piperidine-3-carboxylic acid,
2-[(3R)-1-[(2R)-2-[[4-(2-methyl-3-thienyl)-7-quinolyl]oxy]propanoyl]-3-piperidyl]acetic acid,
2-[rac-(3R)-1-[2-[[5-(2-chloro-4-fluoro-phenyl)-1,8-naphthyridin-2-yl]oxy]propanoyl]-3-piperidyl]acetic acid,
(3S)-1-[(2R)-2-[[2-chloro-4-(2-chloro-4-fluoro-phenyl)-7-quinolyl]oxy]propanoyl]piperidine-3-carboxamide,
isopropyl 2-[[4-(2-chlorophenyl)-7-quinolyl]oxy]acetate,
(3S)-1-[(2R)-2-[[4-(4-fluoro-2,6-dimethyl-phenyl)-7-quinolyl]oxy]propanoyl]piperidine-3-carboxylic acid,
(2R)-1-[4-(2-aminoacetyl)piperazin-1-yl]-2-[[2-chloro-4-(2-chlorophenyl)-7-quinolyl]oxy]propan-1-one,
2-[[4-(2-chlorophenyl)-7-quinolyl]oxy]-N, N-dimethyl-propanamide,
ethyl (3S)-1-[2-[[4-(2-chlorophenyl)-7-quinolyl]oxy]acetyl]piperidine-3-carboxylate,
(2R)-2-[[4-(2-chlorophenyl)-7-quinolyl]oxy]-N, N-dimethyl-propanamide,
ethyl 2-[(3S)-1-[(2R)-2-[[4-(2-chloro-4-fluoro-phenyl)-7-quinolyl]oxy]propanoyl]-3-piperidyl]acetate,
(2R)-2-[[4-(2-chlorophenyl)-2-fluoro-7-quinolyl]oxy]propanoic acid,
(2R)-2-[[2-chloro-4-(2-chloro-4-fluoro-phenyl)-7-quinolyl]oxy]propanoic acid,
ethyl 2-[(3R)-1-[(2R)-2-[[2-chloro-4-(2-chlorophenyl)-7-quinolyl]oxy]propanoyl]-3-piperidyl]acetate,
ethyl 2-[(3R)-1-[(2R)-2-[[2-chloro-4-(2-chloro-4-fluoro-phenyl)-7-quinolyl]oxy]propanoyl] 3-piperidyl]acetate,
ethyl (3S)-1-[(2R)-2-[[2-chloro-4-(4-fluoro-2-methyl-phenyl)-7-quinolyl]oxy]propanoyl]piperidine-3-carboxylate,
(2R)-2-[[4-(2-chloro-4-fluoro-phenyl)-7-quinolyl]oxy]-N-(4-pyridyl) propanamide,
(3S)-1-[(2R)-2-[[2-chloro-4-(2-chlorophenyl)-7-quinolyl]oxy]propanoyl]-N-methylpiperidine-3-carboxamide,
methyl 3-[[(2R)-2-[[2-chloro-4-(2-chlorophenyl)-7-quinolyl]oxy]propanoyl]amino]cyclobutanecarboxylate,
2-[(3R)-1-[(2R)-2-[[2-chloro-4-(2-chloro-4-fluoro-phenyl)-7-quinolyl]oxy]propanoyl]-3-piperidyl]-N-methyl-acetamide,
(2R)-2-[[2-chloro-4-(2-chlorophenyl)-7-quinolyl]oxy]-1-(1-piperidyl)propan-1-one,
(3S)-1-[(2R)-2-[[2-chloro-4-(2-chlorophenyl)-7-quinolyl]oxy]propanoyl]-N, N-dimethylpiperidine-3-carboxamide,
2-[(3R)-1-[(2R)-2-[[4-(2-chloro-4-fluoro-phenyl)-2-methyl-7-quinolyl]oxy]propanoyl]-3-piperidyl]acetic acid,
(3R)-1-[(2S)-2-[[4-(2-chlorophenyl)-7-quinolyl]oxy]propanoyl]piperidine-3-carboxylic acid,
(2R)-2-[[4-(2-chlorophenyl)-7-quinolyl]oxy]propanoic acid,
(2R)-2-[[2-chloro-4-(2-chlorophenyl)-7-quinolyl]oxy]-1-piperazin-1-yl-propan-1-one,
(3S)—N-methyl-1-[(2R)-2-[[2-chloro-4-(2-chloro-4-fluoro-phenyl)-7-quinolyl]oxy]propanoyl]piperidine-3-carboxamide,
2-[[4-(o-tolyl)-7-quinolyl]oxy]acetamide,
(2R)-2-[[2-chloro-4-(2-chloro-4-fluoro-phenyl)-7-quinolyl]oxy]-1-(1-piperidyl)propan-1-one,
ethyl 3-[[(2R)-2-[[4-(2-chloro-4-fluoro-phenyl)-7-quinolyl]oxy]propanoyl]amino]benzoate,
2-[[5-(2-chloro-4-fluoro-phenyl)-1,8-naphthyridin-2-yl]oxy]-N-isopropyl-propanamide,
2-[(3R)-1-[(2R)-2-[[4-(2-fluorophenyl)-7-quinolyl]oxy]propanoyl]-3-piperidyl]acetic acid,
tert-butyl (3S)-1-[(2R)-2-[[2-methyl-4-(o-tolyl)-7-quinolyl]oxy]propanoyl]piperidine-3-carboxylate,
2-[1-[(2R)-2-[[4-(2-chlorophenyl)-7-quinolyl]oxy]propanoyl]-4-piperidyl]acetic acid,
(3S)-1-[rac-(2R)-2-[[4-(2,6-dimethylphenyl)-2-methyl-7-quinolyl]oxy]propanoyl]piperidine-3-sulfonamide,
(3R)-1-[rac-(2R)-2-[[4-(2,6-dimethylphenyl)-2-methyl-7-quinolyl]oxy]propanoyl]piperidine-3-sulfonamide,
(3R)-1-[rac-(2R)-2-[[4-(2,6-dimethylphenyl)-2-methyl-7-quinolyl]oxy]propanoyl]piperidine-3-sulfonamide,
(3R)-1-[(2R)-2-[[4-(2-chloro-4-fluoro-phenyl)-2-methyl-7-quinolyl]oxy]propanoyl]piperidine-3-sulfonamide,
(3S)-1-[(2R)-2-[[4-(2-chloro-4-fluoro-phenyl)-7-quinolyl]oxy]propanoyl]piperidine-3-sulfonamide,
(3R)-1-[(2R)-2-[[4-(2-chloro-4-fluoro-phenyl)-7-quinolyl]oxy]propanoyl]piperidine-3-sulfonamide,
3-[1-[(2R)-2-[[4-(2-chlorophenyl)-7-quinolyl]oxy]propanoyl]-4-piperidyl]propanoic acid,
1-[rac-(2R)-2-[[4-(2,6-dimethylphenyl)-7-quinolyl]oxy]propanoyl]piperidine-3-sulfonamide,
2-[(3R)-1-[(2R)-2-[[4-(2,6-dichlorophenyl)-7-quinolyl]oxy]propanoyl]-3-piperidyl]acetic acid,
2-[(3R)-1-[(2R)-2-[[4-(2-ethylphenyl)-7-quinolyl]oxy]propanoyl]-3-piperidyl]acetic acid,
2-[(3R)-1-[(2R)-2-[[4-(2-isopropylphenyl)-7-quinolyl]oxy]propanoyl]-3-piperidyl]acetic acid,
[1-[rac-(2R)-2-[[4-(2-chloro-4-fluoro-phenyl)-7-quinolyl]oxy]propanoyl]-3-piperidyl]methanesulfonamide,
2-[(3R)-1-[(2R)-2-[[4-(2,6-dimethylphenyl)-2-methyl-7-quinolyl]oxy]propanoyl]-3-piperidyl]acetic acid,
(2R)-2-[[4-(2-chloro-4-fluoro-phenyl)-7-quinolyl]oxy]-N-[4-(2-hydroxyethyl)phenyl]propanamide,
(3S)-1-[(2R)-2-[[5-(2-chloro-4-fluoro-phenyl)-1,8-naphthyridin-2-yl]oxy]propanoyl]piperidine-3-carboxylic acid,
(3S)-1-[(2S)-2-[[5-(2-chloro-4-fluoro-phenyl)-1,8-naphthyridin-2-yl]oxy]propanoyl]piperidine-3-carboxylic acid,
(3S)-1-[(2S)-2-[[5-(2-chloro-4-fluoro-phenyl)-1,8-naphthyridin-2-yl]oxy]propanoyl]piperidine-3-carboxylic acid,
2-[(3R)-1-[(2R)-2-[[5-(2-chloro-4-fluoro-phenyl)-1,8-naphthyridin-2-yl]oxy]propanoyl]-3-piperidyl]acetic acid,
2-[(3R)-1-[(2R)-2-[[5-(2-chloro-4-fluoro-phenyl)-1,8-naphthyridin-2-yl]oxy]propanoyl]-3-piperidyl]acetic acid,
(3S)-1-[(2R)-2-[[4-(2,6-dichlorophenyl)-7-quinolyl]oxy]propanoyl]piperidine-3-carboxylic acid,
(2R)-2-[[4-(2-chloro-4-fluoro-phenyl)-7-quinolyl]oxy]-N-(2-pyridyl)propanamide,
(2R)-2-[[4-(2-chloro-4-fluoro-phenyl)-7-quinolyl]oxy]-N-ethyl-propanamide,
(3S)-1-[(2R)-2-[[4-(2,6-dichloro-4-fluoro-phenyl)-7-quinolyl]oxy]propanoyl]piperidine-3-carboxylic acid
2-[(3R)-1-[(2R)-2-[[4-(4-methyl-3-thienyl)-7-quinolyl]oxy]propanoyl]-3-piperidyl]acetic acid
2-[(3R)-1-[(2R)-2-[[4-(3-methyl-2-thienyl)-7-quinolyl]oxy]propanoyl]-3-piperidyl]acetic acid
2-[(3R)-1-[(2R)-2-[[4-(2-(methoxyphenyl)-7-quinolyl]oxy]propanoyl]-3-piperidyl]acetic acid
2-[(3R)-1-[(2R)-2-[[4-[2-(trifluoromethyl)phenyl]-7-quinolyl]oxy]propanoyl]-3-piperidyl]acetic acid,
2-[(3R)-1-[(2R)-2-[[4-[2-(trifluoromethoxy)phenyl]-7-quinolyl]oxy]propanoyl]-3-piperidyl]acetic acid,
(3S)-1-[(2R)-2-[[4-(2,6-dimethylphenyl)-7-quinolyl]oxy]propanoyl]piperidine-3-sulfonamide,
2-[(3R)-1-[2-[[4-(2-chlorophenyl)-7-quinolyl]oxy]-2-methyl-propanoyl]-3-piperidyl]acetic acid, 2-[rac-(3R)-1-[2-[[4-(2-chlorophenyl)-7-quinolyl]oxy]butanoyl]-3-piperidyl]acetic acid,
2-[(3R)-1-[(2R)-2-[[4-(2-chloro-6-methyl-phenyl)-7-quinolyl]oxy]propanoyl]-3-piperidyl]acetic acid,
2-[(3R)-1-[(2R)-2-[[4-(2-bromophenyl)-7-quinolyl]oxy]propanoyl]-3-piperidyl]acetic acid,
2-[(3R)-1-[(2R)-2-[[4-(2-cyanophenyl)-7-quinolyl]oxy]propanoyl]-3-piperidyl]acetic acid,
2-[(3R)-1-[(2R)-2-[[4-(2-ethynylphenyl)-7-quinolyl]oxy]propanoyl]-3-piperidyl]acetic acid,
2-[(3R)-1-[(2R)-2-[[4-[2-(dimethylamino)phenyl]-7-quinolyl]oxy]propanoyl]-3-piperidyl]acetic acid,
2-[(3R)-1-[(2R)-2-[[4-(2-carbamoylphenyl)-7-quinolyl]oxy]propanoyl]-3-piperidyl]acetic acid,
2-[(3R)-1-[(2R)-2-[[4-(2,6-difluorophenyl)-7-quinolyl]oxy]propanoyl]-3-piperidyl]acetic acid,
2-[(3R)-1-[(2R)-2-[[4-(2,4-dimethyl-3-thienyl)-7-quinolyl]oxy]propanoyl]-3-piperidyl]acetic acid,
2-[(3R)-1-[(2R)-2-[[4-[2-chloro-6-(trifluoromethyl)phenyl]-7-quinolyl]oxy]propanoyl]-3-piperidyl]acetic acid,
2-[(3R)-1-[(2R)-2-[[4-(2-bromo-6-chloro-phenyl)-7-quinolyl]oxy]propanoyl]-3-piperidyl]acetic acid,
2-[(3R)-1-[(2R)-2-[[4-[2,6-bis(trifluoromethyl)phenyl]-7-quinolyl]oxy]propanoyl]-3-piperidyl]acetic acid,
2-[(3R)-1-[(2R)-2-[[4-(2-chloro-6-methoxy-phenyl)-7-quinolyl]oxy]propanoyl]-3-piperidyl]acetic acid,
2-[(3R)-1-[(2R)-2-[[4-(2,6-diisopropylphenyl)-7-quinolyl]oxy]propanoyl]-3-piperidyl]acetic acid,
(2R)-1-[(3R)-3-amino-1-piperidyl]-2-[[4-(2,6-dimethylphenyl)-7-quinolyl]oxy]propan-1-one,
(2R)-1-[(3S)-3-amino-1-piperidyl]-2-[[4-(2,6-dimethylphenyl)-7-quinolyl]oxy]propan-1-one,
N-[(3S)-1-[(2R)-2-[[4-(2,6-dimethylphenyl)-7-quinolyl]oxy]propanoyl]-3-piperidyl]propanamide,
N-tert-butyl-4-[(2R)-2-[[4-(2,6-dimethylphenyl)-7-quinolyl]oxy]propanoyl]piperazine-1-carboxamide,
(2R)-2-[[4-(2,6-dimethylphenyl)-7-quinolyl]oxy]-1-[3-(1-hydroxycyclopropyl)-1-piperidyl]propan-1-one,
8-[(2R)-2-[[4-(2,6-dimethylphenyl)-7-quinolyl]oxy]propanoyl]-2,8-diazaspiro[4.5]decan-1-one,
(2R)-2-[[4-(2,6-dimethylphenyl)-7-quinolyl]oxy]-1-(3,5-dimethylpiperazin-1-yl)propan-1-one,
N-[(3S)-1-[(2R)-2-[[4-(2,6-dimethylphenyl)-7-quinolyl]oxy]propanoyl]-3-piperidyl]-N-hydroxy-acetamide,
1-[4-[(2R)-2-[[4-(2,6-dimethylphenyl)-7-quinolyl]oxy]propanoyl]piperazin-1-yl]-2,2-dimethyl-propan-1-one,
N-[(3S)-1-[(2R)-2-[[4-(2,6-dimethylphenyl)-7-quinolyl]oxy]propanoyl]-3-piperidyl]methanesulfonamide,
N-[(3S)-1-[(2R)-2-[[4-(2,6-dimethylphenyl)-7-quinolyl]oxy]propanoyl]-3-piperidyl]benzamide,
(3S)—N-cyano-1-[(2R)-2-[[4-(2,6-dimethylphenyl)-7-quinolyl]oxy]propanoyl]piperidine-3-carboxamide,
(3S)-1-[(2R)-2-[[4-(2,6-dimethylphenyl)-7-quinolyl]oxy]propanoyl]piperidine-3-carbohydroxamic acid,
2-[(3R)-1-[(2R)-2-[[4-(2,6-dimethylphenyl)-7-quinolyl]oxy]propanoyl]-3-piperidyl]ethanehydroxamic acid,
(2R)-1-(3-aminoazetidin-1-yl)-2-[[4-(2,6-dimethylphenyl)-7-quinolyl]oxy]propan-1-one,
(2R)-2-[[4-(2,6-dimethylphenyl)-7-quinolyl]oxy]-1-[3-(1H-tetrazol-5-yl)azetidin-1-yl]propan-1-one,
3-hydroxy-1-[(2R)-2-[[4-(2,6-dimethylphenyl)-7-quinolyl]oxy]propanoyl]piperidine-3-carboxylic acid,
5-[(2R)-2-[[4-(2,6-dimethylphenyl)-7-quinolyl]oxy]propanoyl]-5-azaspiro[2.5]octane-2-carboxylic acid,
(3R)-1-[(2R)-2-[[4-(2,6-dimethylphenyl)-7-quinolyl]oxy]propanoyl]piperidine-3-sulfonamide,
(3S)-1-[(2R)-2-[[4-(2,6-dichloro-4-fluoro-phenyl)-7-quinolyl]oxy]propanoyl]-3-methylpiperidine-3-carboxylic acid,
5-[rac-(2R)-2-[[4-(4-fluoro-2,6-dimethyl-phenyl)-7-quinolyl]oxy]propanoyl]-5-azaspiro[2.5]octane-2-carboxylic acid,
(3R)-1-[(2R)-2-[[4-(4-fluoro-2,6-dimethyl-phenyl)-7-quinolyl]oxy]propanoyl]-3-methylpiperidine-3-carboxylic acid,
(2R)-2-[[4-(4-fluoro-2,6-dimethyl-phenyl)-7-quinolyl]oxy]-1-[(2S)-2-methyl-1-piperidyl]propan-1-one,
5-[rac-(2R)-2-[[4-(2,6-dichloro-4-fluoro-phenyl)-7-quinolyl]oxy]propanoyl]-5-azaspiro[2.5]octane-2-carboxylic acid,
(2R)-2-[[4-(4-fluoro-2,6-dimethyl-phenyl)-7-quinolyl]oxy]-1-morpholino-propan-1-one,
(2R)-2-[[4-(4-fluoro-2,6-dimethyl-phenyl)-7-quinolyl]oxy]-1-(2-oxa-7-azaspiro[3.5]nonan-7-yl)propan-1-one,
rac-(2R)-2-[[4-(4-fluoro-2,6-dimethyl-phenyl)-7-quinolyl]oxy]-1-[3-(1-hydroxycyclopropyl)-1-piperidyl]propan-1-one,
8-[(2R)-2-[[4-(4-fluoro-2,6-dimethyl-phenyl)-7-quinolyl]oxy]propanoyl]-2,8-diazaspiro[4.5]decan-1-one,
1-[1-[rac-(2R)-2-[[4-(4-fluoro-2,6-dimethyl-phenyl)-7-quinolyl]oxy]propanoyl]-3-piperidyl]cyclopropanecarboxylic acid,
2-[(3R)-1-[(2R)-2-[[4-(4-fluoro-2,6-dimethyl-phenyl)-7-quinolyl]oxy]propanoyl]-3-piperidyl]acetic acid,
(3S)-1-[(2R)-2-[[4-(4-fluoro-2,6-dimethyl-phenyl)-7-quinolyl]oxy]propanoyl]-3-methylpiperidine-3-carboxylic acid,
N-[(3S)-1-[(2R)-2-[[4-(4-fluoro-2,6-dimethyl-phenyl)-7-quinolyl]oxy]propanoyl]-3-piperidyl]-N-hydroxy-acetamide,
2-methyl-2-[1-[rac-(2R)-2-[[4-(4-fluoro-2,6-dimethyl-phenyl)-7-quinolyl]oxy]propanoyl]-3-piperidyl]propanoic acid,
(2R)-2-[[4-(4-fluoro-2,6-dimethyl-phenyl)-7-quinolyl]oxy]-1-[(2R)-2-methyl-1-piperidyl]propan-1-one,
(3R)-1-[(2R)-2-[[4-(2,6-dichloro-4-fluoro-phenyl)-7-quinolyl]oxy]propanoyl]-3-methylpiperidine-3-carboxylic acid,
(3S)-1-[(2R)-2-[[4-(2-chloro-4-fluoro-phenyl)-7-quinolyl]oxy]propanoyl]-3-methyl-piperidine-3-carboxylic acid,
[1-[rac-(2R)-2-[[4-(2,6-dimethylphenyl)-7-quinolyl]oxy]propanoyl]-3-piperidyl]methanesulfonamide,
rac-(2R)-1-(2,6-dimethyl-1-piperidyl)-2-[[4-(4-fluoro-2,6-dimethyl-phenyl)-7-quinolyl]oxy]propan-1-one,
2-[(3R)-1-[(2R)-2-[[4-(2,6-dichloro-4-fluoro-phenyl)-7-quinolyl]oxy]propanoyl]-3-piperidyl]acetic acid,
5-[rac-(2R)-2-[[4-(2-chloro-4-fluoro-phenyl)-7-quinolyl]oxy]propanoyl]-5-azaspiro[2.5]octane-2-carboxylic acid,
1-[1-[rac-(2R)-2-[[4-(2-chloro-4-fluoro-phenyl)-7-quinolyl]oxy]propanoyl]-3-piperidyl]cyclopropanecarboxylic acid,
2-methyl-2-[1-[rac-(2R)-2-[[4-(2,6-dichloro-4-fluoro-phenyl)-7-quinolyl]oxy]propanoyl]-3-piperidyl]propanoic acid,
1-[1-[rac-(2R)-2-[[4-(2,6-dichloro-4-fluoro-phenyl)-7-quinolyl]oxy]propanoyl]-3-piperidyl]cyclopropanecarboxylic acid,
2-methyl-2-[1-[rac-(2R)-2-[[4-(2-chloro-4-fluoro-phenyl)-7-quinolyl]oxy]propanoyl]-3-piperidyl]propanoic acid,
(3R)-1-[(2R)-2-[[4-(2-chloro-4-fluoro-phenyl)-7-quinolyl]oxy]propanoyl]-3-methyl-piperidine-3-carboxylic acid,
(2R)-2-[[4-(2,6-dichloro-4-fluoro-phenyl)-7-quinolyl]oxy]-1-[(2S)-2-methyl-1-piperidyl]propan-1-one, rac-(2R)-2-[[4-(2-chloro-4-fluoro-phenyl)-7-quinolyl]oxy]-1-(2-methyl-1-piperidyl)propan-1-one,
(2R)-2-[[4-(2,6-dichloro-4-fluoro-phenyl)-7-quinolyl]oxy]-1-morpholino-propan-1-one,
8-[(2R)-2-[[4-(2,6-dichloro-4-fluoro-phenyl)-7-quinolyl]oxy]propanoyl]-2,8-diazaspiro[4.5]decan-1-one,
rac-(2R)-2-[[4-(2,6-dichloro-4-fluoro-phenyl)-7-quinolyl]oxy]-1-[3-(1-hydroxycyclopropyl)-1-piperidyl]propan-1-one,
(2R)-2-[[4-(2,6-dichloro-4-fluoro-phenyl)-7-quinolyl]oxy]-1-[(2R)-2-methyl-1-piperidyl]propan-1-one,
8-[(2R)-2-[[4-(2-chloro-4-fluoro-phenyl)-7-quinolyl]oxy]propanoyl]-2,8-diazaspiro[4.5]decan-1-one,
(2R)-2-[[4-(2-chloro-4-fluoro-phenyl)-7-quinolyl]oxy]-1-morpholino-propan-1-one,
(2R)-2-[[4-(2-chloro-4-fluoro-phenyl)-7-quinolyl]oxy]-1-[3-(1-hydroxycyclopropyl)-1-piperidyl]propan-1-one,
(2R)-2-[[4-(2,6-dichloro-4-fluoro-phenyl)-7-quinolyl]oxy]-1-(2-oxa-7-azaspiro[3.5]nonan-7-yl)propan-1-one,
N-hydroxy-N-[rac-(3S)-1-[rac-(2R)-2-[[4-(2-chloro-4-fluoro-phenyl)-7-quinolyl]oxy]propanoyl]-3-piperidyl]acetamide,
(2R)-2-[[4-(2-chloro-4-fluoro-phenyl)-7-quinolyl]oxy]-1-(2-oxa-7-azaspiro[3.5]nonan-7-yl)propan-1-one,
(2R)-2-[[4-(2-chloro-4-fluoro-phenyl)-7-quinolyl]oxy]-1-(2,6-dimethyl-1-piperidyl)propan-1-one,
(2R)-2-[[4-(2-chloro-4-fluoro-phenyl)-7-quinolyl]oxy]-1-(2-oxa-8-azaspiro[3.5]nonan-8-yl)propan-1-one,
(2R)-2-[[4-(2-chloro-4-fluoro-phenyl)-7-quinolyl]oxy]-1-(2-oxa-7-azaspiro[3.4]octan-7-yl)propan-1-one,
1-tert-butyl-3-[(3R)-1-[(2R)-2-[[4-(2-chloro-4-fluoro-phenyl)-7-quinolyl]oxy]propanoyl]pyrrolidin-3-yl]urea,
(2R)-2-[[4-(2-chloro-4-fluoro-phenyl)-7-quinolyl]oxy]-1-(3,3,5,5-tetramethylpiperazin-1-yl)propan-1-one,
(2R)-2-[[4-(2-chloro-4-fluoro-phenyl)-7-quinolyl]oxy]-1-(3,5-dimethylpiperazin-1-yl)propan-1-one,
(2R)-2-[[4-(2-chloro-4-fluoro-phenyl)-7-quinolyl]oxy]-1-[(1R)-2,5-diazabicyclo[2.2.1]heptan-2-yl]propan-1-one,
(2R)-2-[[4-(2-chloro-4-fluoro-phenyl)-7-quinolyl]oxy]-1-(2-oxa-6-azaspiro[3.3]heptan-6-yl)propan-1-one,
1-[(2R)-2-[[4-(2-chloro-4-fluoro-phenyl)-7-quinolyl]oxy]propanoyl]-3,6-dihydro-2H-pyridine-5-carboxylic acid,
2-[(3R)-1-[(2R)-2-[[5-(2,6-dichloro-4-fluoro-phenyl)-1,8-naphthyridin-2-yl]oxy]propanoyl]-3-piperidyl]acetic acid, and
2-[(3R)-1-[(2R)-2-[[5-(4-fluoro-2,6-dimethyl-phenyl)-1,8-naphthyridin-2-yl]oxy]propanoyl]-3-piperidyl]acetic acid,
or a pharmaceutically or veterinary acceptable salt, hydrate or solvate thereof.

Processes for the Preparation of Compounds of the General Formula (I)

In another aspect, the present invention provides novel processes for the preparation of compounds of the general formula (I) and novel processes for the preparation of their intermediates.

In one aspect, the invention relates to a process for manufacturing a compound of the general formula (I) as defined herein, wherein V is —H, —OH, —Cl, or —$C_1$-$C_4$-alkyl comprising the step of:

(a) alkylating a compound of formulae ($D_1$ to $D_5$)

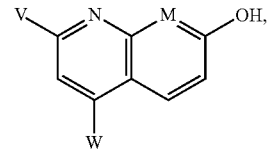

wherein
in $D_1$ V is —H, M is CH, and W is as defined herein,
in $D_2$ V is —OH, M is CH, and W is as defined herein,
in $D_3$ V is —Cl, M is CH, and W is as defined herein,
in $D_4$ V is —H, M is N, and W is as defined herein, and
in $D_5$ V is —$C_1$-$C_4$-alkyl, M is CH, and W is as defined herein,
with an alkylating agent, preferably with an alkylating agent of the formula Z—OH or Z—Br, wherein Z is the group

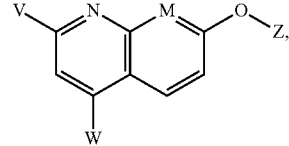

wherein R, $R_1$ and Y are as defined herein,
to obtain a compound of formulae ($E_1$ to $E_5$)

wherein
in $E_1$ V is —H, M is CH, and W and Z are as defined herein,
in $E_2$ V is —OH, M is CH, and W and Z are as defined herein,
in $E_3$ V is —Cl, M is CH, and W and Z are as defined herein,
in $E_4$ V is —H, M is N, and W and Z are as defined herein, and
in $E_4$ V is —$C_1$-$C_4$-alkyl, M is N, and W and Z are as defined herein The compounds of formulae $E_1$ to $E_5$ correspond to the compounds of the general formula (I) as defined herein, wherein V is —H, —Cl or —$C_1$-$C_4$-alkyl.

The compounds of formulae ($D_1$ to $D_5$) used as a starting material in process step (a) are either commercially available, can be prepared in similar manners as described in literature procedures or according to the processes of the invention described below and in the specific Examples.

In process step (a), alkylation of the compounds of formulae ($D_1$ to $D_5$) can be carried out with any suitable alkylating agent under standard alkylation conditions, e.g. with an alkylbromide (Z—Br), or with an alcohol (Z—OH) according to the Mitsunobu reaction (Mitsunobu and Yamada, 1967). Process step (a) can be carried out according to standard procedures known in the art, whereas further guidance can be found in reaction Scheme 2 and in the Examples disclosed below.

In one aspect, the invention relates to a compound of formulae ($D_1$ to $D_5$) as defined above.

In another aspect, the invention relates to a process for manufacturing a compound of the general formula (I) as defined above, wherein V is —F, comprising the step of:

(b) reacting a compound of formula ($E_1$)

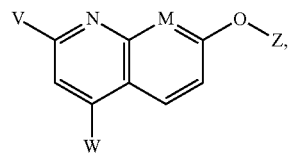

wherein in $E_1$ V is —H, M is CH, and W and Z are as defined herein, with a fluorinating agent, preferably with $AgF_2$, to obtain a compound of formula $E_6$

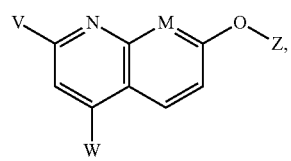

wherein

V is —F, M is CH, and W and Z are as defined herein

In process step (b), fluorination of the compounds of formulae ($E_1$ to $E_3$) can be carried out with any suitable fluorinating agent under standard conditions, e.g. with $AgF_2$. Process step (b) can be carried out according to standard procedures known in the art, whereas further guidance can be found in reaction Scheme 2, in FIG. 3, and in the Examples disclosed below.

The compounds of formulae ($D_1$ and $D_2$) may be prepared according to process steps (c), (d) and (f), or according to process steps (e) and (f), respectively, as described below.

Thus, in another aspect, the present invention relates to a process for the preparation of a compound of the general formulae ($D_1$ and $D_2$)

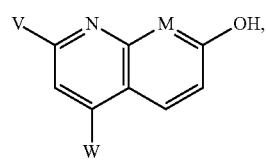

wherein in $D_1$ V is —H, M is CH, and W is as defined herein,
in $D_2$ V is —OH, M is CH, and W is as defined herein, comprising the steps of:

(c) reacting a compound of formula (A)

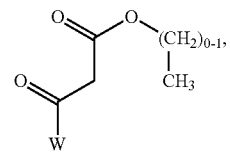

wherein W is as defined above, with 3-methoxy-aniline to obtain a compound of formula (B)

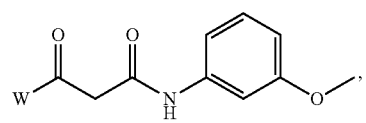

wherein W is as defined above, and (d) cyclisation of a compound of formula (B) as defined above to obtain a compound of formula ($C_2$)

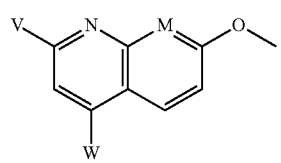

wherein V is —OH, M is —CH, and W is as defined above;

or (e) reacting a compound of formula ($C_{1x}$)

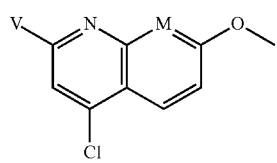

wherein V is H and M is CH with W—$B(OH)_2$, to obtain a compound of formula ($C_1$)

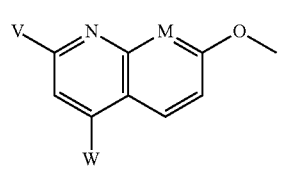

wherein V is —H, M is CH, and W is as defined above; and (f) reacting a compound of formulae (C₁ or C₂) as defined above
with boron tribromide to obtain a compound of formulae

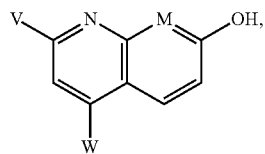
(D₁ to D₂)

wherein
in D₁ V is —H, M is CH, and W is as defined herein,
in D₂ V is —OH, M is CH, and W is as defined herein.

The compounds of formulae (A) (β-ketoesters) and the 3-methoxy-anilines used as a starting material in process step (c) are commercially available or can be obtained by standard procedures known to the skilled person.

The desired quinoline compounds of formula (C₂) may be prepared from the corresponding β-ketoesters of formula (A) and 3-methoxy-aniline in 2 steps through a cyclisation such as the one described by Leonetti et al. (2004).

The compounds of formula (C1₁ₓ) used as a starting material in process step (e) are either commercially available quinoline derivatives or can be prepared in similar manners as de scribed in literature procedures or in the specific examples. Boronic acids or esters used as a starting material in process step (e) are commercially available or can be obtained by standard procedures known to the skilled person. The compounds of formula W—B(OH)₂ may be prepared as described in literature procedures.

The boron tribromide used in process step (f) is commercially available.

Process steps (c), (d), (e) and (f) can be carried out according to standard procedures known in the art, whereas further guidance can be found in the reaction schemes and examples disclosed below. For example the cyclisation of process step (d) can be carried out as described by Leonetti et al. (2004).

In one aspect, the invention relates to a compound of formulae (B, C₁ and C₂) as defined above.

Processes for the preparation of the compounds of formulae D₃ and D₄ are described in Scheme 1 below and in FIG. 2.

In a preferred embodiment, the present invention relates to a process for manufacturing a compound of the invention of formula (IA) as defined above, preferably, wherein V is —Cl, comprising the step of:

(a1) alkylating a compound of formulae (D₁ to D₅) as defined herein, preferably D₃,

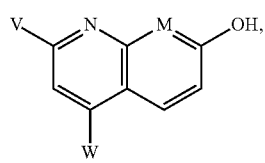
(D₁ to D₅)

wherein V and M are as defined above, and W is

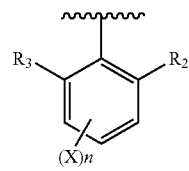

with R₂, R₃, X and n as defined herein,
with an alkylating agent, preferably with an alkylating agent of the formula Z—OH or Z—Br,
wherein Z is the group

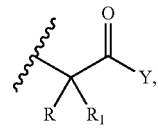

wherein R, R₁ and Y are as defined herein,
to obtain a compound of formula (IA)

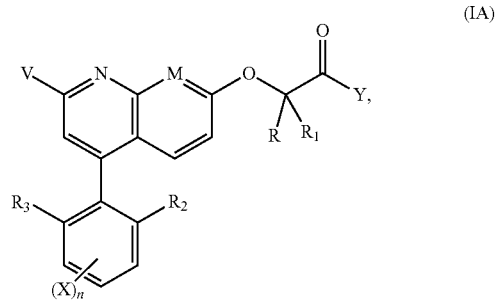
(IA)

wherein R, R₁, R₂, R₃, M, V, X, n and Y are as defined in the preferred group above.

The alkylation of the compounds of formulae (D₁ to D₅) can be carried out with any suitable alkylation agent, e.g. with an alkylbromide (Z—Br), or with an alcohol (Z—OH) according to the Mitsunobu reaction (Mitsunobu and Yamada, 1967). Process step (a) can be carried out according to standard procedures known in the art, whereas further guidance can be found in the reaction schemes and examples disclosed below.

In another aspect, the present invention relates to a process for the preparation of a compound of formula (I) of the invention, wherein Y is —NR₃R₄ as defined above corresponding to a compound of formula (J), comprising the steps of:

(g) hydrolyzing a compound of formula (F)

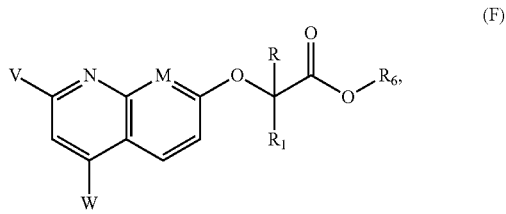
(F)

wherein V, W, M, R, $R_1$, and $R_6$ are as defined above, to obtain a compound of formula (G)

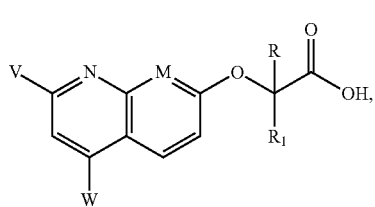
(G)

wherein V, W, M, R, and $R_1$ are as defined above, and
(h) amidating the compound of formula (G) to obtain a compound of formula (J)

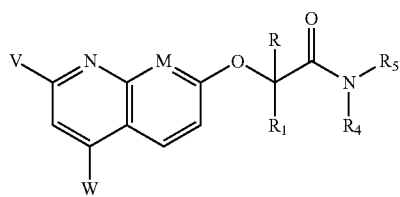
(J)

wherein V, M, W, M, R, $R_1$, $R_4$ and $R_5$, are as defined above.

The compounds of formula (F) used as starting material in process step (g) correspond to compound of formula (I), wherein Y=—$OR_6$, and can be obtained for example by the process for the preparation of compounds of formula (I) as described above.

The optionally substituted amines used as starting materials in process step (h) are commercially available or can be prepared by standard procedures.

In one aspect, the invention relates to an intermediate compound of formula (F) or to an intermediate compound of formula (G) as defined above.

Again, both reaction steps (g) and (h) can be carried out according to standard procedures known in the art, whereas further guidance can be found in the reaction schemes and examples disclosed below. For example, step (h) can be carried out with an optionally substituted amine according to known standard procedures.

In another preferred embodiment, the present invention relates to a process for manufacturing a compound of formula (IA) of the invention, wherein Y is —$NR_3R_4$ as defined above, comprising the steps of:
(g1) hydrolyzing a compound of formula (F1)

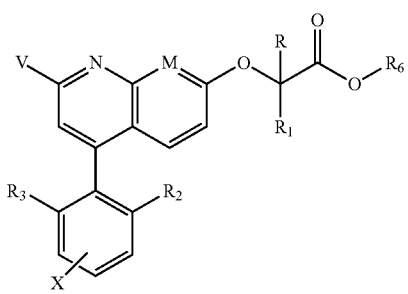
(F1)

wherein V, M, R, $R_1$, $R_2$, $R_3$ and X are as defined above, to obtain a compound of formula (G1)

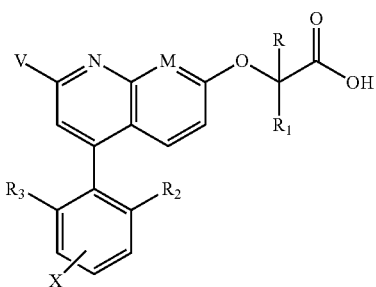
(G1)

wherein V, M, R, $R_1$, $R_2$, $R_3$, Re and X are as defined above,
and
(h1) amidating the compound of formula (G1) to obtain a compound of formula (J1)

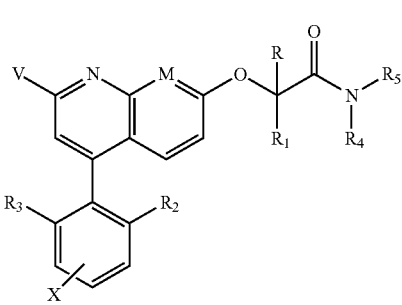
(J1)

wherein V, M, R, $R_1$, $R_2$, $R_3$, $R_4$, $R_5$ and X are as defined above.

Again, both reaction steps (g1) and (h1) can be carried out according to standard procedures known in the art, whereas further guidance can be found in the reaction schemes and examples disclosed below. For example, step (h1) can be carried out with an optionally substituted amine according to known standard procedures.

In one aspect, the invention relates to a compound of formula (F1) or to an intermediate compound of formula (G1) as defined above.

In another aspect, the present invention relates to a process for manufacturing specific embodiments of the compounds of formula (I) of the invention, i.e. compounds of formulae (L) and (M), wherein Y is —$NR_4R_5$ and N, $R_4$ and $R_5$ form a substituted 5- or 6-membered saturated heterocycle as defined herein, comprising the steps of:
(g2) hydrolyzing a compound of formula (K)

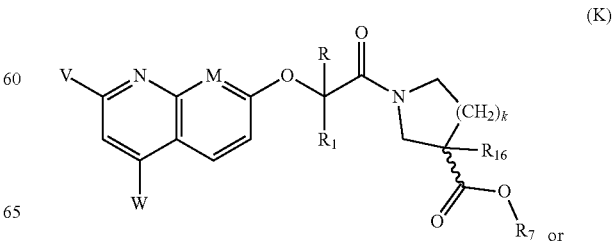
(K)

-continued

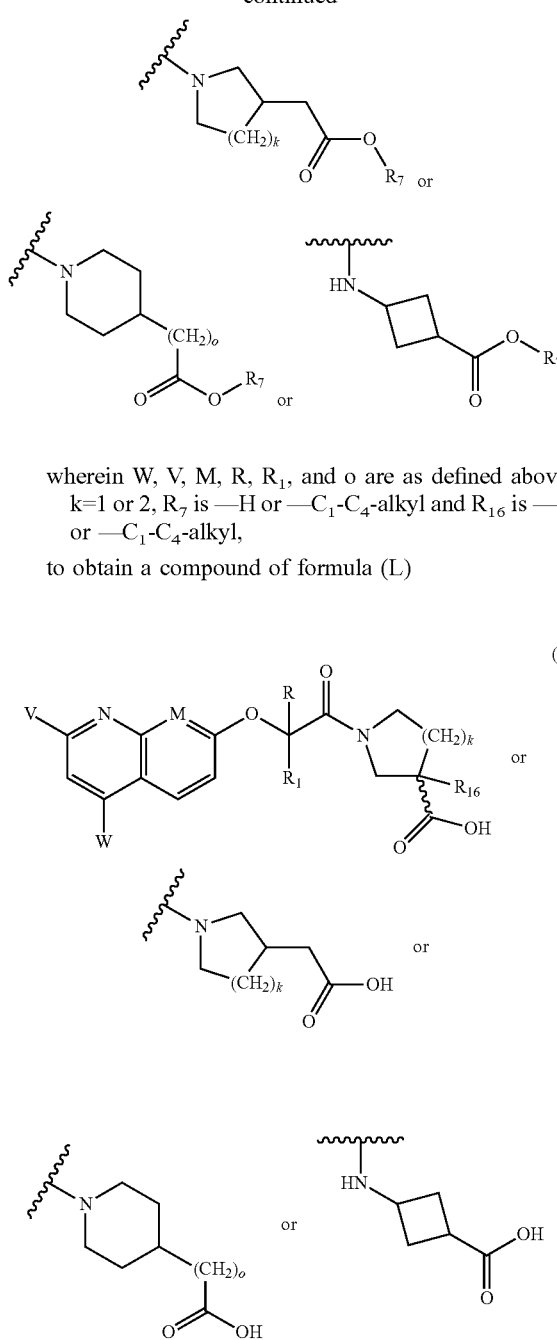

wherein W, V, M, R, $R_1$, and o are as defined above, k=1 or 2, $R_7$ is —H or —$C_1$-$C_4$-alkyl and $R_{16}$ is —H or —$C_1$-$C_4$-alkyl, to obtain a compound of formula (L)

wherein W, V, M, R, $R_1$, and o are as defined above, k=1 or 2, and $R_{16}$ is —H or —$C_1$-$C_4$-alkyl, and
(h2) amidating the compound of formula (L) to obtain a compound of formula (M)

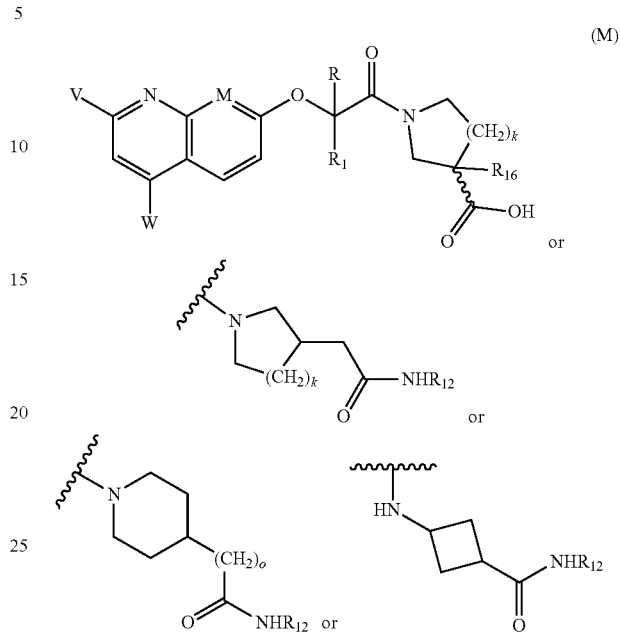

wherein V, W, M, R, $R_1$, and o are as defined above, k=1 or 2, $R_{12}$ is as defined above and $R_{16}$ is —H—$C_1$-$C_4$-alkyl, and Again, both reaction steps (g2) and (h2) can be carried out according to standard procedures known in the art, whereas further guidance can be found in the reaction schemes and examples disclosed below. For example, step (h2) can be carried out with an optionally substituted amine according to known standard procedures.

In one aspect, the invention relates to a compound of formula (K), (L) or (M) as defined above.

Scheme 1 shows the preparation of a compound of formulae ($D_1$ to $D_4$) used as starting materials for the preparation of the compounds of formulae $E_1$ to $E_4$ and $E_6$ corresponding to the compounds of formula (I) as defined above. As mentioned above, the starting materials are either commercially available or are prepared in similar manners as described in literature procedures or in the specific examples. The β-ketoesters of formula (A) and 3-methoxyaniline used as a starting material for the preparation of the compounds of formula (B) are commercially available or can be obtained by standard procedures known to the skilled person.

It is apparent to the skilled person that the sequence of the synthetic steps is dependent on the starting materials' availability and functional group compatibility and could vary from compound to compound.

Scheme 1: Exemplary preparation of a compound of formulae ($D_1$ to $D_4$)
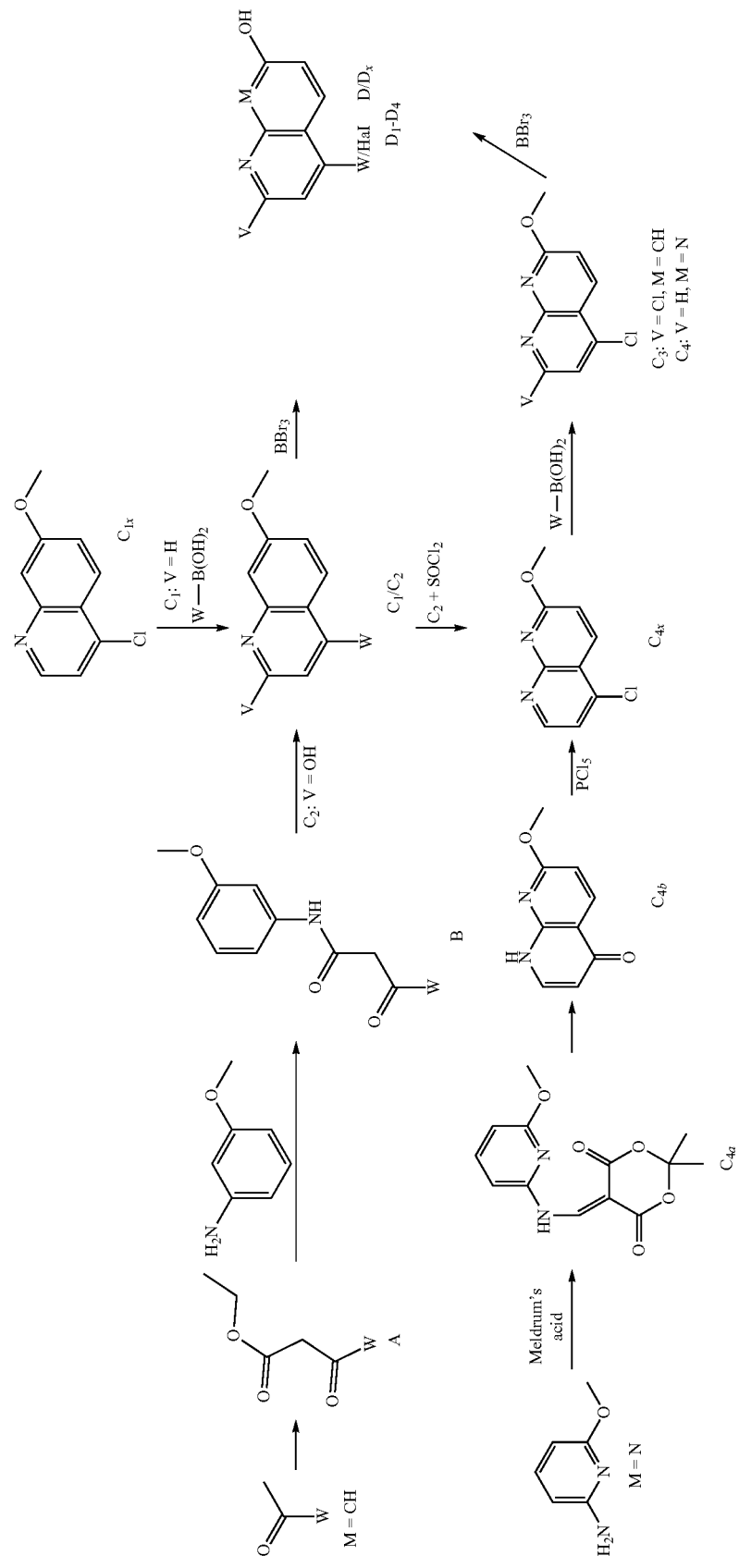

Scheme 2 shows the preparation of a compound of formulae $E_1$ to $E_4$, $E_8$, $E_9$, $E_x$ and $E_6$ corresponding to the compounds of formula (I) as defined above by alkylating a compound of the formulae $D_1$ to $D_4$, $D_8$, $D_9$, or $D_x$ with a commercial alkylbromide (Z—Br) or subjected to a Mitsunobu (Z—OH) reaction.

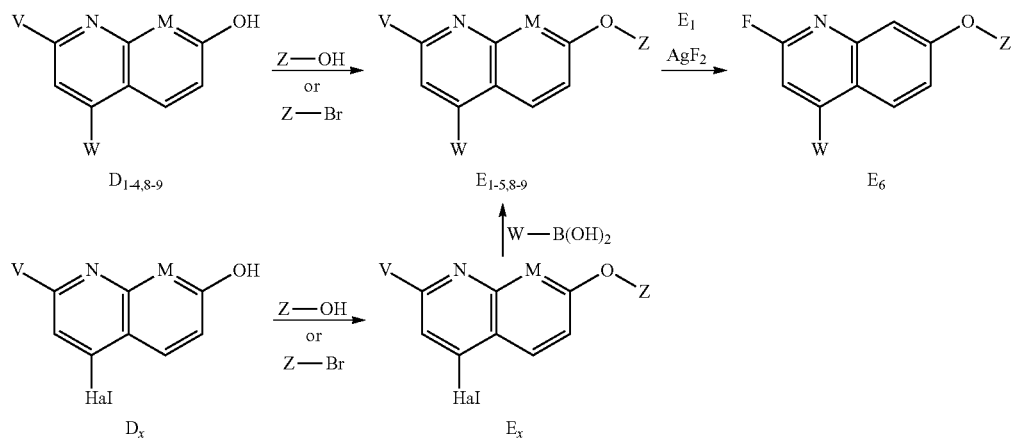

Scheme 2: Exemplary preparation of a compound of formulae ($E_1$ to $E_9$)

Use of the Novel Compounds of Formula (I) as a Medicament

Furthermore, it has been found that the compounds of formula (I) are suitable for use as a medicament. Specifically, it has been found that the compounds of formula (I) can be used in the treatment of cancer, preferably in the treatment of melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

POLRMT inhibitors previously have been described to trigger the death of AML cells allegedly through rather unspecific inhibition of mitochondrial transcription confirms this rational (Bralha et al., 2015). As described in the examples below compounds of the invention were surprisingly and unexpectedly shown to have cytostatic activity on a number of tumor cells and tumor models both in vitro and in vivo.

Accordingly, the compounds of formula (I) of the invention and their pharmaceutically or veterinary acceptable salts, hydrates or solvates, exhibit valuable pharmacological properties and are therefore useful as a medicament or pharmaceutical. The medicament or pharmaceutical can be further formulated with additional pharmaceutically or veterinary acceptable carriers and/or excipients, e.g. for oral administrations in the form of tablets. Tablets may contain suitable binders, lubricants, disintegrating agents, coloring agents, flavoring agents, flow-inducing agents and/or melting agents, generally known in the art.

Thus, in one aspect, the invention relates to a compound of the general formula (I) as defined herein for use as a medicament.

Compounds of the invention exhibit a marked and selective inhibitory effect on the POLRMT. This can be determined for example in the Homogeneous TR-FRET assay (see example 4) or the Quantitative real time-PCR assay (see example 5). The skilled person however may use different assays to determine the direct or indirect inhibition of POLRMT.

As mentioned above, it has been found that the compounds of the invention are useful in the treatment of cancer. There is evidence that in melanoma and especially in metastatic melanoma OXPHOS plays a major role in cancer cells and that inhibition of mitochondria in general may lead to superior treatment success. For example it was shown that H3K4-demethylase (JARID1B) and OXPHOS dependent drug resistance play a role in metastatic melanoma (Roesch et al., 2013). Haq et al. (2013) describe that the standard of care (SoC) treatment with MEK inhibitors in melanoma leads to PGC1-a-dependent increase in OXPHOS as a drug-resistance escape route. It was also shown that the inhibition of mutated BRAF by vemurafenib increases OXPHOS dependency of BRAF mutated melanoma cells (Schöckel et al., 2015). And further, enhanced OXPHOS, glutaminolysis and 6-oxidation constitute the metastatic phenotype of melanoma cells (Rodrigues et al., 2016).

For pancreatic cancer selective killing of OXPHOS-dependent Panc-1 cells has been de scribed for treatment with arctigenin (Brecht et al., 2017). In hepatocellular carcinoma, standard of care (SoC) treatment with MEK inhibitor is leading to PGC1-a-dependent in crease in OXPHOS as a drug-resistance escape route (Bhat et al., 2013, Ling et al., 2017). For lymphoma it has been demonstrated that OXPHOS is dependent on mt-complex III inhibitor antimycin A (Dörr et al., 2013). As described above acute myeloid leukemia, POLRMT inhibitors previously have been described to trigger the death of AML cells allegedly through rather unspecific inhibition of mitochondrial transcription (Bralha et al., 2015).

Also breast cancer should be a suitable cancer indication as overexpression of progesterone receptor is present in more than 50% of all breast cancer patients, whereas progesterone is stimulating mitochondrial activity with subsequent inhibition of apoptosis (Nadji et al., 2005, Behera et al., 2009). Further, the inhibition of mTOR leads to a shift towards OXPHOS-dependence and there is a glucose-dependent effect of mTOR inhibitors in combination with metformin (Pelican et al., 2014, Ariaans et al., 2017). Additionally, it is described that mitochondrial dysfunction caused by metformin prevents tumor growth in breast cancer (Sanchez-Alvarez et al., 2013).

For glioblastoma it is known that malignant repopulation is dependent on OXPHOS (Yeung et al., 2014). With respect to cervical cancer, POLRTM inhibitors inhibit free fatty acid oxidation (data not shown), which otherwise promote cervical cancer cell proliferation (Rodriguez-Enriquez et al., 2015). In renal cancer there is evidence that Birt-Hogg-Dubé renal tumors are associated with up-regulation of mitochondrial gene expression (Klomp et al., 2010). In colon carcinoma the rational is based on the finding that 5-fluorouracil resistant colorectal/colon cancer cells are addicted to OXPHOS to survive and enhance stem-like traits (Denise et al., 2015).

Accordingly, in another aspect, the invention relates to compounds of formula (I) of the invention as defined herein for use in the treatment of cancer, preferably melanoma, metastatic melanoma, pancreatic cancer, hepatocellular carcinoma, lymphoma, acute myeloid leukemia, breast cancer, glioblastoma, cervical cancer, renal cancer, colorectal cancer or ovarian cancer.

The compounds of the invention are preferably useful in a method for treating cancer in simultaneous, alternating or subsequent combination with another cancer therapy, preferably selected from chemotherapy, immunotherapy, hormone therapy, stem cell transplantation therapy, radiation therapy or surgery. It is likely that the cytostatic activity of the POLRMT inhibitors on tumor cells can be further enhanced by combining the treatment with the respective standard of care in order to get improved/additive treatment results. In this context simultaneous, alternating or subsequent application of the various treatments is envisaged. Any of the standard classes of cancer therapy, chemotherapy, immunotherapy, hormone therapy, stem cell transplantation therapy, radiation therapy or surgery, appears to be feasible for combination with the POLRMT inhibitors of this invention.

Thus, in another aspect, the invention relates to a compound of the general formula (I) as defined herein for use in a method for treating cancer in simultaneous, alternating or subsequent combination with another cancer therapy, preferably selected from chemotherapy, immunotherapy, hormone therapy, stem cell transplantation therapy, radiation therapy or surgery.

EXAMPLES

Abbreviations and Acronyms

Figure 1:
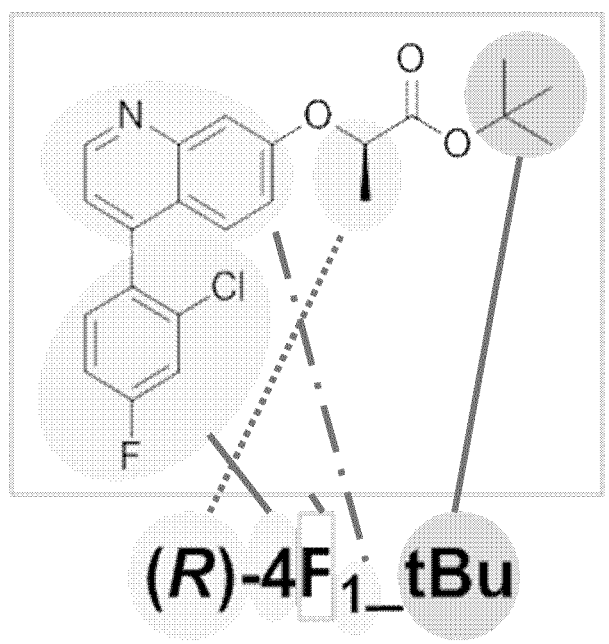
FIG. 1 shows an Example of numbering of a compound of formula F.

Abbreviations and Acronyms used in the description of the chemistry and in the Examples that follow are:

Abs Absolute configuration (at least one stereocenter)
aq. aqueous
BB building block
$BBr_3$ boron tribromide
BPO benzoyl peroxide
br. broad
$Bu_3SnN_3$ tributyltin azide
$CDCl_3$ deuterated chloroform
$CD_3OD$ deuterated methanol
$CHCl_3$ chloroform
cHex cyclohexane
$Cs_2CO_3$ caesium carbonate
d doublet
DCM dichloromethane
DIAD diisopropylazodicarboxylate
DIPEA Diisopropylethylamine
DMF dimethylformamide
DMSO dimethylsulfoxide
DMSO-$d_6$ deuterated dimethylsulfoxide
EDC 1-Ethyl-3-(3-dimethylaminopropyl)carbodiimide
ES electrospray
$Et_3N$ triethylamine
$Et_2O$ diethylether
EtOAc ethyl acetate
EtOH ethanol
FA formic acid
h hour
HATU O-(7-Azabenzotriazol-1-yl)-N,N, W, W-tetramethyluronium-hexafluorphosphate
HCl hydrochloric acid
$H_2O$ water
HOBt 1H-benzo[d][1,2,3]triazol-1-ol
$H_3PO_4$ polyphosphoric acid
$K_2CO_3$ potassium carbonate
m multiplet
MeCN acetonitrile
MeOH methanol
min minutes
MS mass spectrometry
$N_2$ nitrogen
$NaHCO_3$ sodium hydrogencarbonate
NaCl sodium chloride
NaH sodium hydride
$NH_4Cl$ ammonium chloride
NMR nuclear magnetic resonance
$PCl_5$ phosphorus (V) chloride
Pd(amphos)$Cl_2$ Bis(di-tert-butyl(4-dimethylaminophenyl)phosphine) dichloropalladium(II)
Pd(PPh$_3$)$_4$ Tetrakis(triphenylphosphine)palladium(0)
PPh$_3$ triphenylphosphine
q quartet
quint quintet
rt room temperature
s singlet
sat. saturated
SOCl$_2$ thionyl chloride
t triplet
TFA trifluoroacetic acid
THF tetrahydrofuran

1. METHODS OF MAKING THE COMPOUNDS OF FORMULA (I) OF THE PRESENT INVENTION

In general, the compounds of formula (I) used of the invention might be prepared by standard techniques known in the art, by known processes analogous thereto, and/or by the processes described herein, using starting materials which are either commercially available or producible according to conventional chemical methods. The particular processes to be utilised in the preparation of the compounds of formula (I) of this invention depends upon the specific compound desired. Such factors as the type of substitution at various locations of the molecule and the commercial availability of the starting materials play a role in the path to be followed and in the chosen reaction conditions for the preparation of the specific compounds of formula (I) of this invention. Those factors are readily recognised by one of ordinary skill in the art.

The following preparative methods are presented to aid the reader in the synthesis of the compounds of the present invention.

2. EXPERIMENTAL PROCEDURES

LC-MS Method

HPLC—electrospray mass spectra (HPLC ES-MS) were obtained using a Waters Acquity Ultra Performance Liquid Chromatography (UPLC) equipped with a SQ 3100 Mass detector spectrometer.

Column: Acquity UPLC BEH C18 1.7 μm, 2.1×50 mm

Flow: 0.500 mL/min

Eluents: A: $H_2O$ with 0.05% formic acid and B: MeCN with 0.05% formic acid.

Gradient: elution from 5% to 100% B over 3.5 min with an initial hold of 0.5 min and a final hold at 100% B of 0.5 min. Total run time: 5 min.

The gradient described could be altered in function of the physico-chemical properties of the compound analyzed and is in no way restrictive.

Preparative HPLC Method

Preparative HPLC was performed using a Waters System consisting of a Waters 2767 Sample Manager, a Waters 2545 Binary Gradient Module, a Waters SFO (System Fluidics Organizer), a Waters 3100 Mass Detector, and a Waters 2498 UV/Visible Detector.

Column: XBridge® Prep C18 5 μm OBD™, 19×150 mm

Flow: 20 mL/min

Eluents: A: $H_2O$ with 0.1% TFA and B: MeCN with 0.1% TFA.

Alternatively, preparative HPLC was performed using an Agilent System consisting of a Agilent Infinity 1260 Autosampler, an Agilent Infinity 1260 Binary Gradient Module, an Agilent 6120 Quadrupole Mass Detector and an Agilent Infinity 1260 DAD VL UV/Visible Detector.

Column: XBridge® BEH Prep C18 5 μm, 19 mm×150 mm

Flow: 32 mL/min

Eluents: A: $H_2O$ with 0.1% TFA and B: MeCN with 0.1% TFA.

General Gradient: elution from X % to Y % B over 20 min with an initial hold of 2 min and a final increase to 100% B over 2 min and hold at 100% B of 2 min followed by a 1 min gradient back to the initial composition. Total run time: 26 min. X=Y−30% where Y=concentration of elution on the above described LC-MS method.

The gradient described could be altered in function of the physico-chemical properties of the compound analyzed and is in no way restrictive.

Chiral LC-MS Method

Chiral HPLC—electrospray mass spectra (HPLC ES-MS) were obtained using a Waters Acquity Ultra Performance Liquid Chromatography (UPLC) equipped with a SQ 3100 Mass detector spectrometer.

Column: Lux 5 u Cellulose-2; 150×4.6 mm

Flow: 0.500 mL/min-1.000 mL/min

Eluents: A: $H_2O$ with 0.05% formic acid and B: MeCN with 0.05% formic acid.

Gradient elution from X % to Y % B over 15 min with an initial hold of 0.5 min and a return to 100% B and final hold at of 2.5 min. Total run time: 18 min.

The gradient could be altered in function of the physico-chemical properties of the compound analyzed and is in no way restrictive.

Alternatively, Chiral HPLC—electrospray mass spectra (HPLC ES-MS) were obtained using an Agilent 1100 Series with DAD detector spectrometer.

Column: Lux 5 μm Cellulose-2; 150×4.6 mm

Flow: 1.500 mL/min

Eluents for reverse phase analysis (1) and normal phase analysis (2) are described below:

Eluents (1): A: $H_2O$ with 20 mM $NH_4HCO_3$, 0.1% DEA and B: MeCN with 0.1% DEA.

Gradient: elution from 25-50% B over 20 min.

Eluents (2): A: n-Hexane with 0.1% DEA and B: Isopropanol with 0.1% DEA.

Gradient: elution from 60-90% B over 20 min.

The gradient could be altered in function of the physico-chemical properties of the compound analysed and is in no way restrictive.

Chiral Preparative HPLC Method

Preparative HPLC was performed using a Waters System consisting of a Waters 2767 Sample Manager, a Waters 2545 Binary Gradient Module, a Waters SFO (System Fluidics Organizer), a Waters 3100 Mass Detector, and a Waters 2498 UV/Visible Detector.

Column: Lux 5 u Cellulose-2, 150×21.2 mm (Phenomenex)

Flow: 20 mL/min-30 mL/min

Eluents: A: $H_2O$ with 0.1% TFA and B: MeCN with 0.1% TFA.

The gradient could be altered in function of the physico-chemical properties of the compound analyzed and is in no way restrictive.

GC-MS Method

Gas Chromatography—Mass spectra were obtained using Agilent 7820A GC with 5977E MSD Column: HP-5MS 30 m, 0.25 mm ID, 0.25 μm Flow: 2 mL/min. He Injection: 100 μl/s, 250° C.; Split Flow: 20 mL/min. Split Ratio: 10

Detection: Agilent 5977E

Gradient: 0 min 50° C.; 0.5 min 50° C.; 7.6 min 300° C.; 9.6 min 300° C.

The gradient described could be altered in function of the physico-chemical properties of the compound analyzed and is in no way restrictive.

NMR Methods

Proton ($^1H$) nuclear magnetic resonance (NMR) spectra were measured with an Oxford Varian 400/54 (400 MHz) spectrometer or a Bruker Avance II (300 MHz) spectrometer with residual protonated solvent ($CHCl_3$ δ 7.26; MeOH δ 3.30; DMSO δ 2.49) as standard. The NMR data of the synthesized examples are in agreement with their corresponding structural assignments.

Numbering

The specific and unequivocal numbering of the intermediates comprising a subscript, defining the substituents of the quinoline scaffold, and a prefix, defining the substituents of the phenyl group, is explained in Table 1 and Table 2. In particular, in Table 2, Examples of intermediates at different stages are given for a specific aryl substituent. The numbering of intermediates F and G is self-explanatory and highlighted in Table 4 of the synthetic methods: an indication of the stereochemistry ((R), (S) or (rac)) and a suffix defining the type of ester (_Et or _tBu) are given. (gem) describes the gem-dimethyl-compound and (rac)-Et refers to the ethyl substituted linker. FIG. 1 shows a general example of numbering structures F. Numbering of the most advanced intermediates and final compounds is unique and assigned in the procedures for preparing the compounds of the invention or in Table 6.

TABLE 1

Numbering of the scaffolds of intermediates of formulas C-E: Subscripts

| Structure | Subscript | Examples |
|---|---|---|
| V, M, O-Z, W, Hal scaffold | W/Hal | $C_{1\text{-}6}\text{-}E_{1\text{-}6}/C_{1x\text{-}6x}\text{-}E_{1x\text{-}6x}$ |
| V = H, M = CH | 1/1x | $E_1$ structure |
| V = OH, M = CH | 2/2x | $C_2\text{-}E_2$ |
| V = Cl, M = CH | 3/3x | $C_3\text{-}E_3$ |
| V = H, M = N | 4/4x | $C_4\text{-}E_4$ |
| V = Me, M = CH | 5/5x | $C_5\text{-}E_5$ |
| V = F, M = CH | 6/6x | $C_6\text{-}E_6$ |

TABLE 2

Numbering of intermediates of formulas A-E: Prefix

| Structure | Prefix | Examples |
|---|---|---|
| W | W | 1-7A-E |
| phenyl | 1 | 1E |
| 2-chlorophenyl | 2 | 2C |
| 2-methylphenyl | 3 | 3D |
| 2-chloro-4-fluorophenyl | 4 | 4A |
| 2-methyl-4-fluorophenyl | 5 | 5A-E |
| 2,6-dimethylphenyl | 6 | 6B |
| 2,6-dichlorophenyl | 7 | 7A-E |
| 2,6-dimethyl-4-fluorophenyl | 8 | 8A-E |

TABLE 2-continued

Numbering of intermediates of formulas A-E: Prefix

| Structure | Prefix | Examples |
|---|---|---|
| 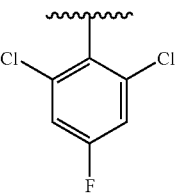 [SMILES: *c1c(Cl)cc(F)cc1Cl] | 9 | 9A-E |

Synthetic Methods

Figure 2:
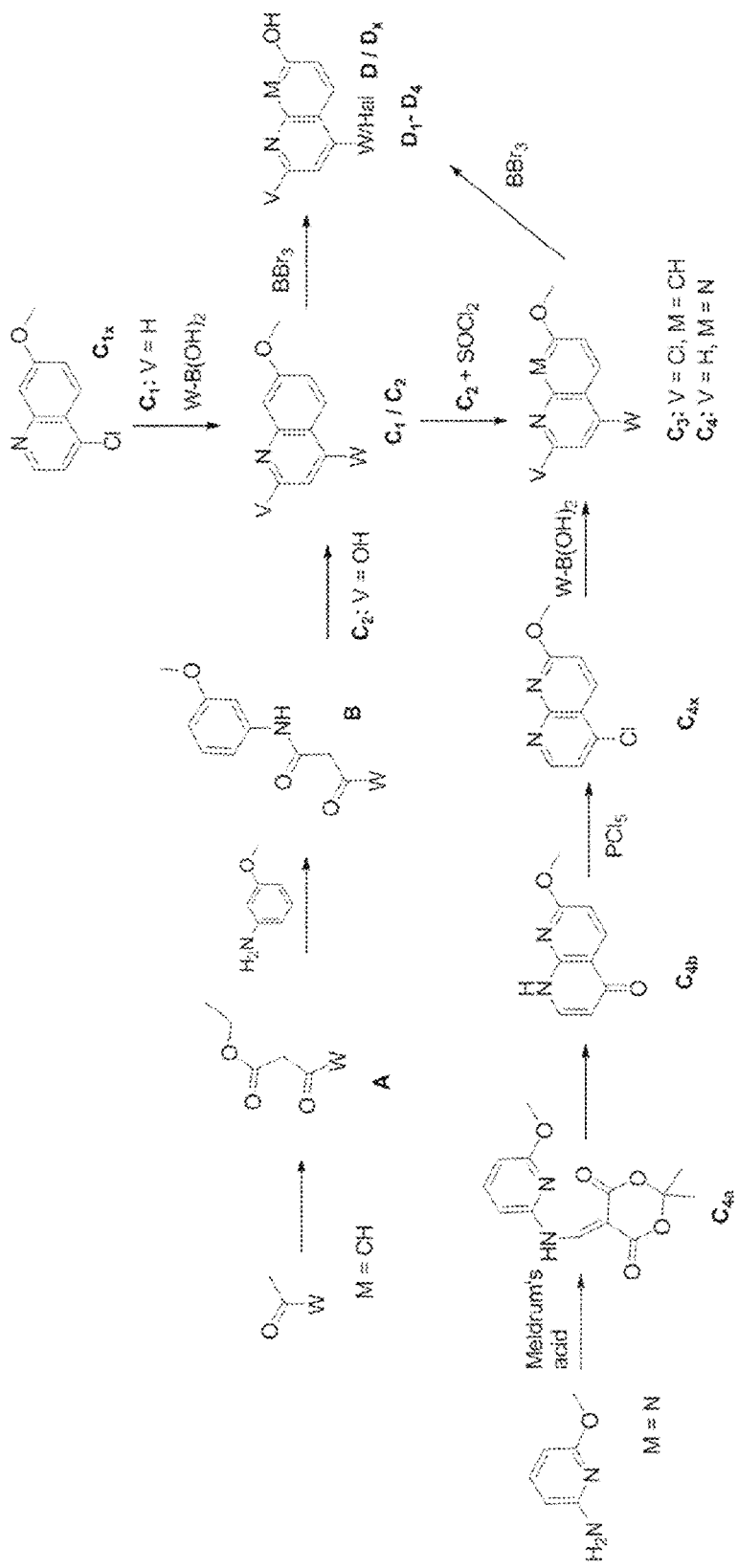
FIG. 2 corresponds to Scheme 1. Scheme 1 shows an exemplary preparation of a compound of formula (D), specifically $D_1$-$D_4$. All residues of the formulae shown in Scheme 1 are as defined herein.

The general synthesis of a compound of this invention is described below in Schemes 1-4. The starting materials are either commercially available or are prepared in similar manners as described in literature procedures or in the specific examples. The desired quinolines D, were either commercially available (such as 4-chloro-2-methylquinolin-7-ol, CAS 148018-30-8) or were synthesized from the possibly substituted 4-chloro-7-methoxyquinolines through a Suzuki Coupling to obtain compounds C, followed by demethylation with $BBr_3$. Alternatively, the intermediate quinolines C where substituent V is OH or Cl were prepared from the corresponding β-ketoesters and 3-methoxy-aniline followed by cyclisation and potential further halogenation as described by Chen et al. (2015) and Upton et al. (1986) and highlighted in Scheme 1 (see FIG. 2).

When the β-ketoesters could not be purchased, they were synthesized from the required acetophenones and ethyl potassium malonate under basic conditions in a similar manner as indicated in Scheme 1. Alternative syntheses, for example starting from benzoylchlorides and diethylcarbonate, are dearly also possible.

In the case of 1,8-naphthyridines, where M is N, the specific synthesis, analogue to what suggested by Nicoleti et al. (2012) was employed, which is also outlined in Scheme 1 and is described for intermediates $C_{4x}$ and $C_4$.

Scheme 1: Exemplary preparation of a compound of formulae (D)
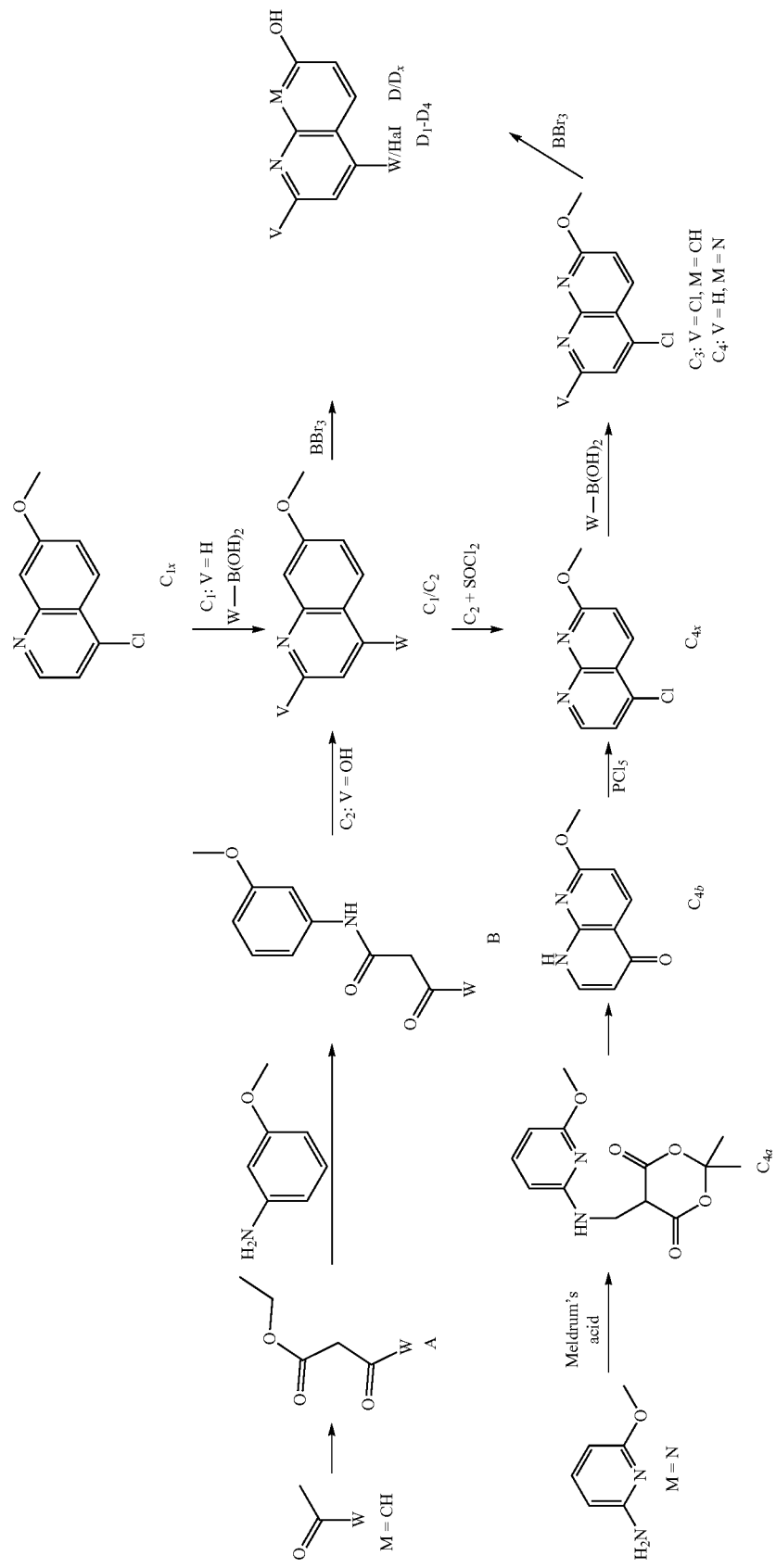

It should be apparent to those skilled in the art that the sequence of the synthetic steps is dependent on starting materials availability and functional group compatibility and could vary from compound to compound.

Figure 3:
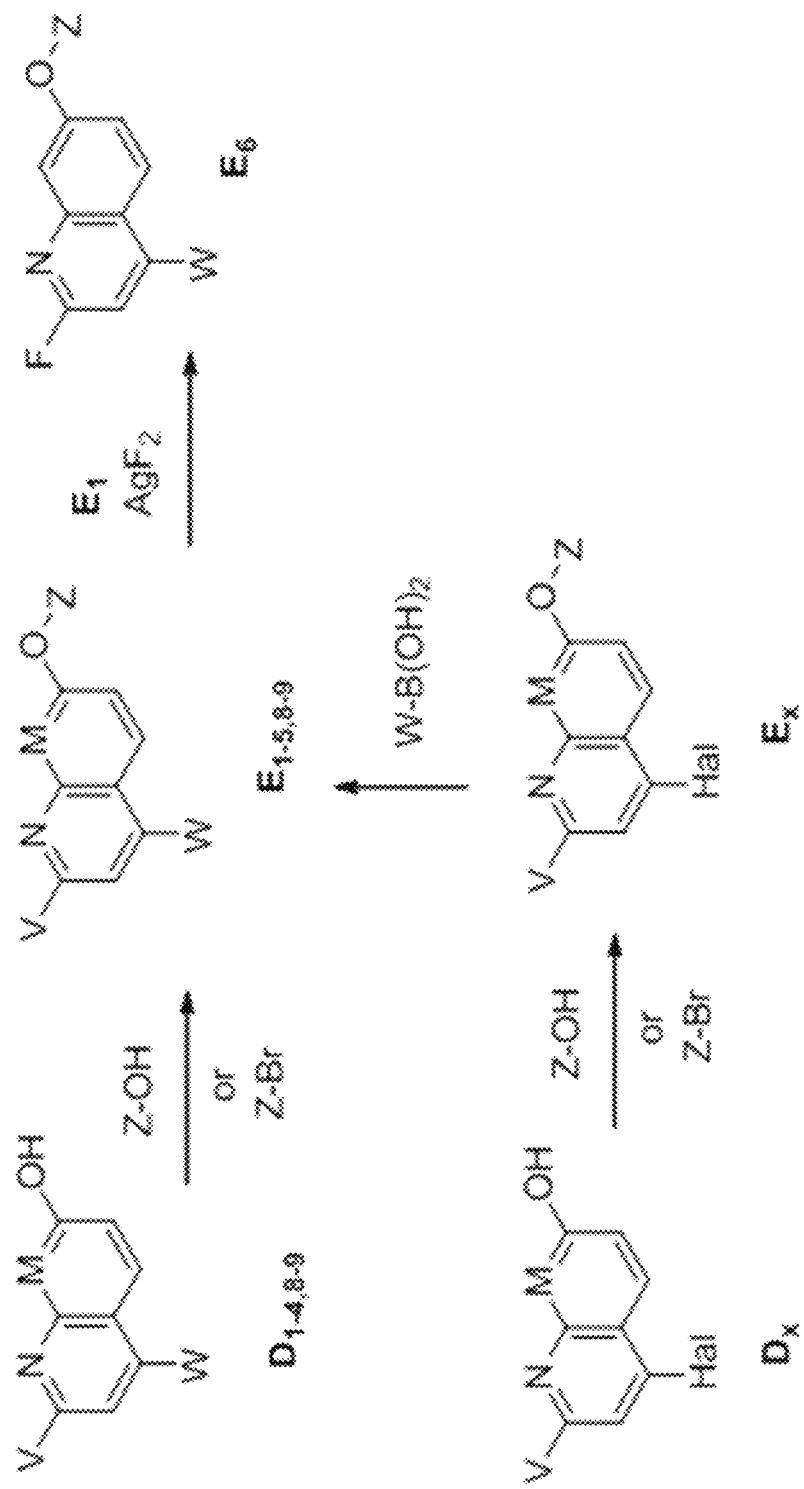
FIG. 3 corresponds to Scheme 2. Scheme 2 shows an exemplary preparation of a compound of formula (E), specifically $E_1$-$E_6$. All residues of the formulae shown in Scheme 2 are as defined herein.

The quinoline can be further alkylated with a commercial alkylbromide (Z—Br) or subjected to a Mitsunobu (Z—OH) reaction with a commercial alcohol to produce compounds of formula E as outlined in Scheme 2 (see FIG. 3).

Scheme 2: Exemplary preparation of a compound of formulae (E)

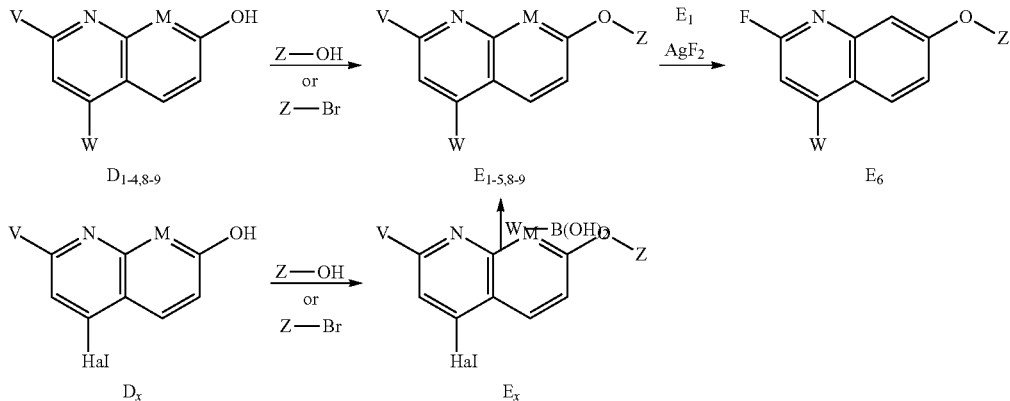

In particular, and for the purpose of rapid diversification, the Mitsunobu/alkylation reaction step (D to E and $D_1$ to $E_1$) and the Suzuki Coupling step ($C_x$ to C and $E_x$ to E), described in Schemes 1 and 2, could be reversed. This was applied, for example, to the synthesis of different mono- and bis-ortho-substituted phenyl intermediates ((R)-$2F_1$_Et, (R)-$3F_1$_tBu, (R)-$4F_1$_tBu, (R)-$6F_1$_tBu, (R)-$3F_5$_tBu, (R)-$4F_5$_tBu, (R)-$6F_5$_tBu), (R)-$4F_4$_Et, (R)-$8F_4$_Et, and (R)-$9F_4$_Et. Building block $D_{5x}$ (Table 3) is commercially available, and was used in the Mitsunobu reaction directly to obtain intermediate (R)—$F_{5x}$_Bu. Conditions for the Suzuki Coupling of intermediates $E_x$ are described in method M3a and M3b.

Scheme 2 also illustrates how intermediate $E_1$ (V=H) could be transformed into intermediate $E_6$ (V=F) through reaction with $AgF_2$ as described by Fier and Hartwig (2013) or other fluorination agents known in the art. The specific procedures are listed below.

Figure 4:
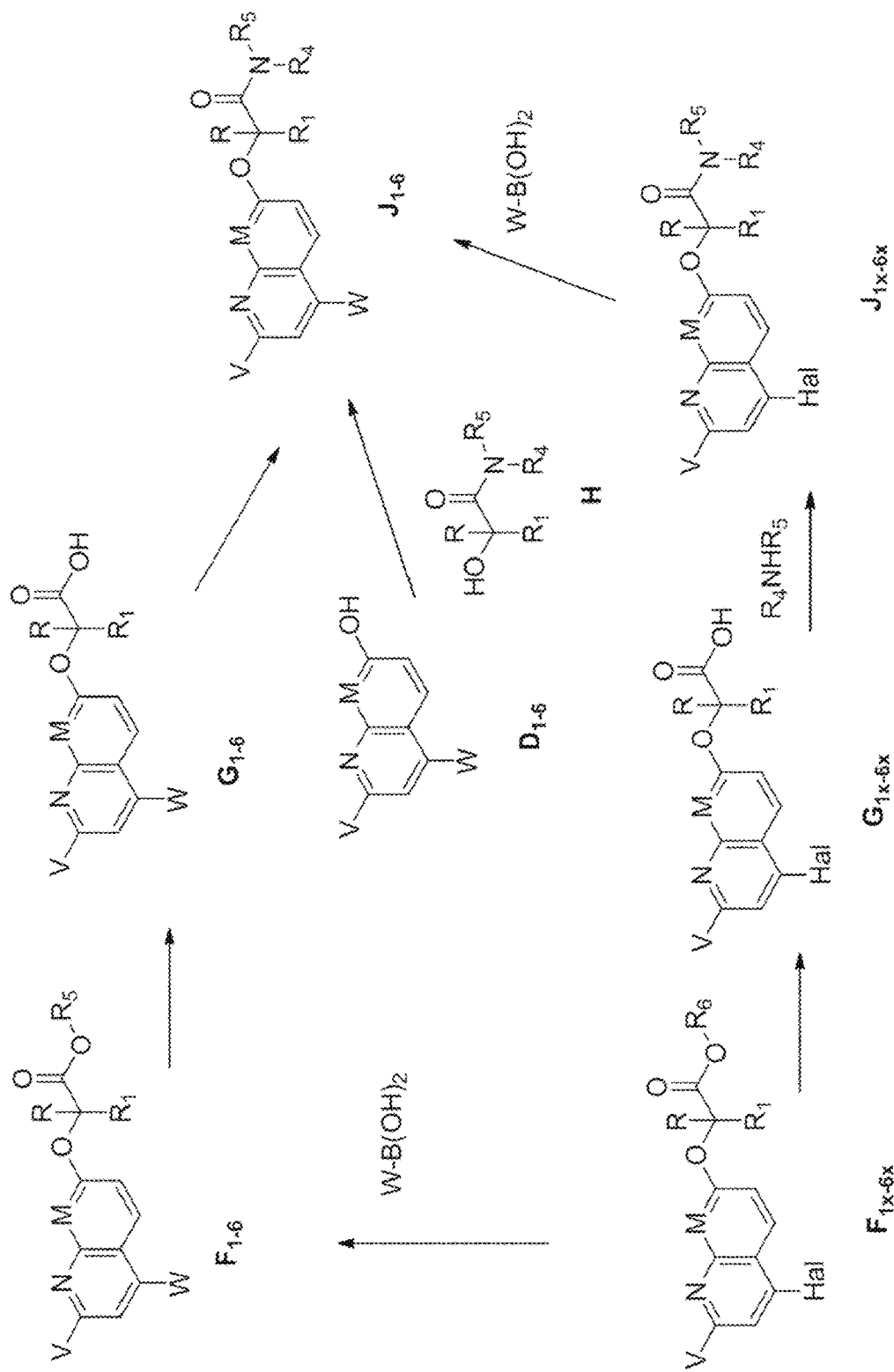
FIG. 4 corresponds to Scheme 3. Scheme 3 shows an exemplary preparation of a compound of formula (J), specifically $J_1$-$J_6$. All residues of the formulae shown in Scheme 3 are as defined herein.

For the Examples of this invention, Z was generally a potentially substituted alkyl acetate group (compound F); which was usually further modified by hydrolysis to the corresponding carboxylic acid G, followed by coupling with a commercially available, optionally substituted amine, according to standard procedures known in the art, and as described in Scheme 3 (see FIG. 4), to produce structure J. Alternatively, the Mitsunobu reaction could be carried out with a suitable, synthesized or commercially available 2-hydroxyacetamide H to obtain a compound of structure J directly. Again, for the purpose of parallel synthesis and rapid diversification of group W, intermediate $F_{1x-6x}$ could be modified using a similar reaction sequence to obtain compounds of formula J through intermediates $G_{1x-6x}$ and $J_{1x-6x}$, carrying a halogen substituent, which is subjected to a Suzuki coupling in the final stages of the synthesis. Alternatively, intermediates $F_{1x-6x}$ can be transformed into intermediate $F_{1-6}$ via Suzuki coupling.

Scheme 3: Exemplary preparation of a compound of formula (J)

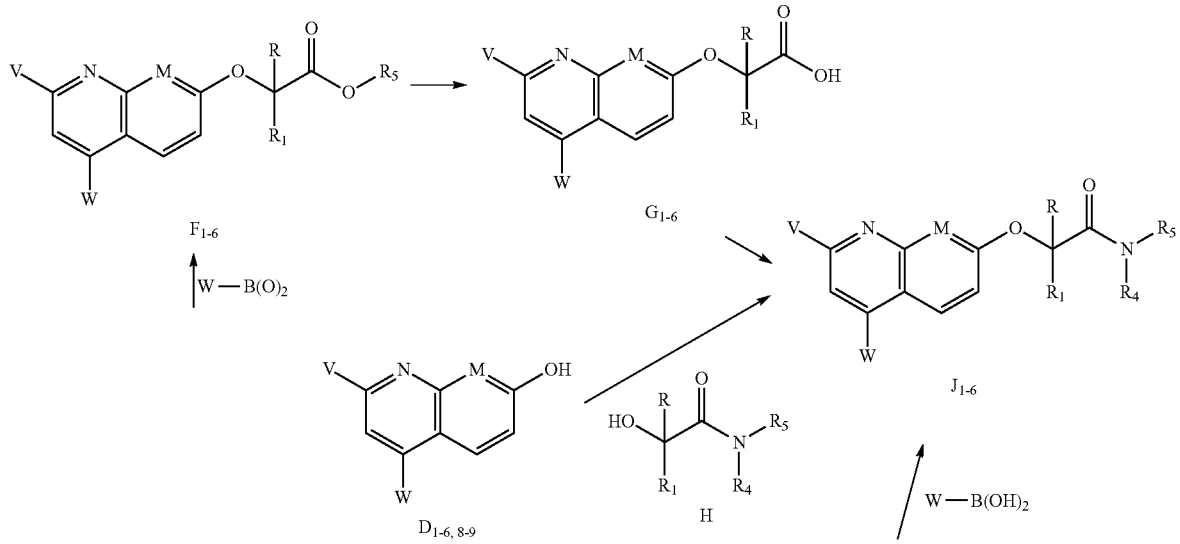

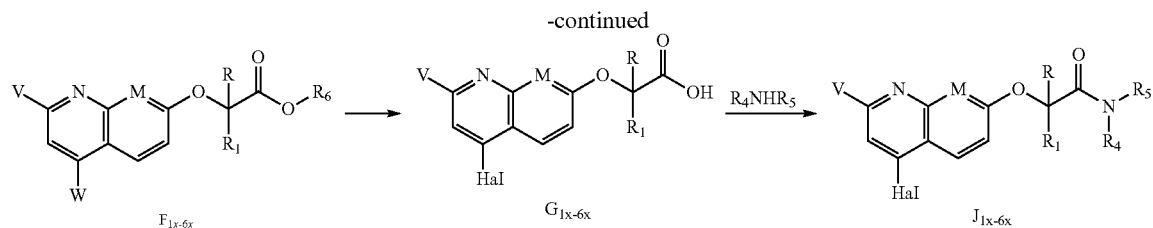

Figure 5:
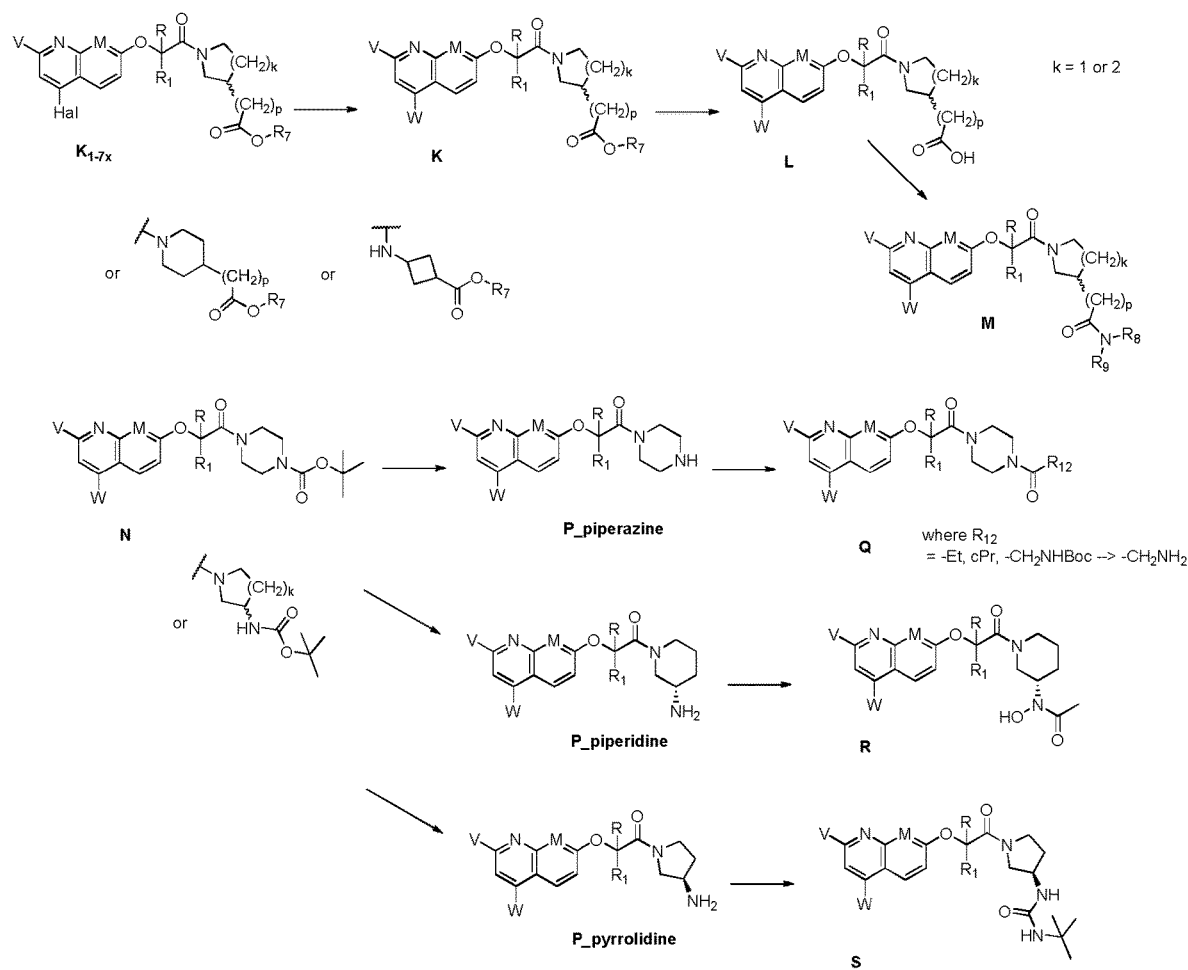
FIG. 5 corresponds to Scheme 4. Scheme 4 shows an exemplary preparation of a compound of formulae (K), (L), (M), (P), (Q), (R) and (S). All residues of the formulae shown in Scheme 3 are as defined herein.

When $R_4$ and $R_5$ form an optionally substituted cyclic amide, this amide can carry an ester moiety or a carbamate moiety, as highlighted in formulas $K_x$, K or N of Scheme 4, which can be further hydrolyzed or deprotected to obtain compounds of substructure L or P. As it will be obvious to a person skilled in the art, compounds K could be obtained by linear synthesis through a coupling reaction as for compounds of formula J as described in Scheme 3, or in a parallel manner using compounds K. Examples are outlined in Scheme 4 (see FIG. 5). The amide could also carry a nitrile moiety (compound 11), which could be transformed into a tetrazole to produce a carboxylic acid bioisostere, as in exemplified with M12 for compound 30. When the commercially available ester building blocks were racemic, or intermediate F was prepared according to method M7, the coupling reaction was sometimes followed by chiral preparative HPLC to allow separation of the diastereomers.

In case of non-commercially available amide building blocks, the synthesis of compounds M required further derivatization of compound L, in a way that is described in method M11a. Amines P could also be further modified using methods known in the art, to obtain amides of formula Q. An example of such modification is described in method M11d for compound 28. Further hydrolysis of Q, when Q carries a Boc-protected amine, is also possible, as in the case of compound 85. When P was a primary amine, this could also be further modified using methods known in the art, to obtain, over three subsequent reactions and without isolation of the intermediates, N-hydroxyacetamides of formula R; or it could be reacted with an isocyanate to obtain ureas of formula S. Examples of such modifications are described herein exemplarily for compounds 209 and 214. Additionally, the tetrazole derivative 11 described in Table 6 was synthesized from the corresponding nitrile, compound 30, according to method 12.

The compounds of formulae E, F, G, J, K, L, M, P, Q, R, and S are compounds of the general formula I of the invention.

Scheme 4: Exemplary preparation of a compound of formulae (K), (L), (M), (P), (Q), (R), and (S).

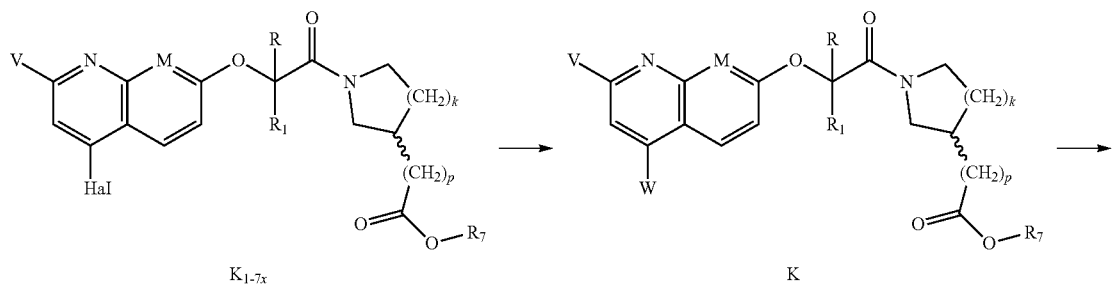

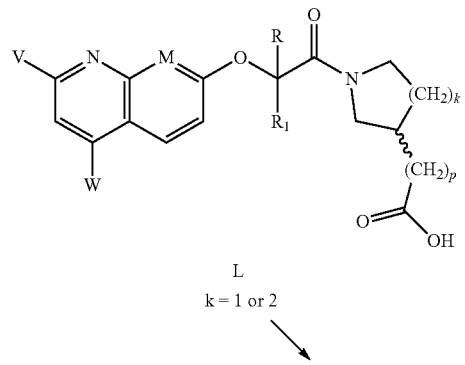

L
k = 1 or 2

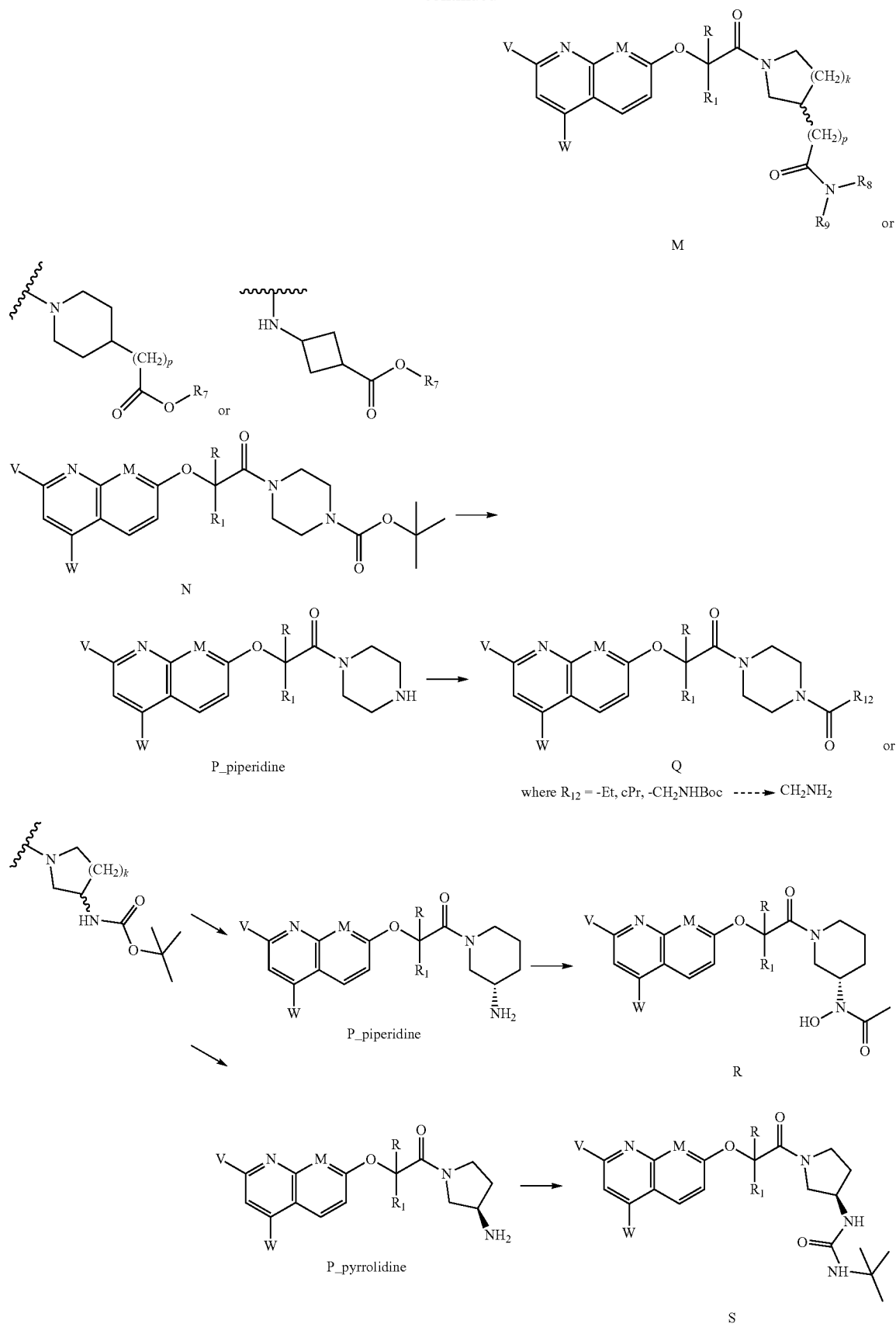

3. EXPERIMENTAL EXAMPLES OF THE INVENTION

The following specific examples are presented to illustrate the invention, but they should not be construed as limiting the scope of the invention in any way. In the tables listing the intermediates, the compounds might have characterization such as (M+H)+ mass spectrometry data, HPLC purity and/or NMR. Those that have no characterization are commercially avail able, and a CAS number is given.

3.1 Preparation of Intermediates for the Preparation of Compounds of Formula (I)

At least one intermediate example per method is described below:

3.1.1 Synthesis of Substituted β-Ketoesters of Formula (A)

Intermediate 4A—Synthesis According to Method 1 (M1)

Ethyl 3-(2-chloro-4-fluorophenyl)-3-oxopropanoate

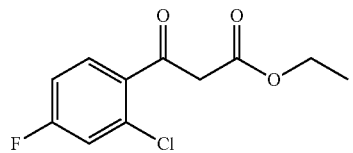 [SMILES: CCOC(=O)CC(=O)c1ccc(F)cc1Cl]

60% NaH in mineral oil (34.2 g, 852 mmol) was washed with pentane and dried under a flow of $N_2$. Dry toluene (2.4 L) was added and the suspension was cooled to 0° C. Diethyl carbonate (192 g, 1.62 mol) was added dropwise over a period of 35 min, the mixture was stirred 30 min, upon which 2-Chloro-4-fluoroacetophenone (70 g, 406 mmol) was added over a period of 35 min. The cooling bath was removed, and the reaction heated to 50° C. and stirred for 20 h. The reaction mixture was allowed to cool to rt and was poured onto ice-water (2.5 L). The aqueous layer was extracted with $Et_2O$, then acidified to pH 2 with 10% aq. HCl and extracted with $Et_2O$. The combined organic phases were washed with $H_2O$ and brine, dried over $MgSO_4$, filtered and evaporated in vacuo to yield the desired product 4A (37.9 g, 38%) as a mixture of tautomers, which was used in the following step without further purification.

$^1$H NMR (300 MHz, Chloroform-d) δ 7.63 (dd, J=8.7, 6.0 Hz, 1H), 7.14-6.93 (m, 2H), 4.12 (q, J=7.2 Hz, 2H), 3.96 (s, 2H), 1.18 (t, J=7.1 Hz, 3H)-tautomer 1, ethyl 3-(2-chloro-4-fluorophenyl)-3-oxopropanoate $^1$H NMR (300 MHz, Chloroform-d) δ 12.43 (s, 1H), 7.52 (dd, J=8.7, 6.1 Hz, 1H), 7.14-6.93 (m, 2H), 5.48 (s, 1H), 4.21 (q, J=7.1 Hz, 2H), 1.27 (t, J=7.1 Hz, 3H)-tautomer 2, (Z)-ethyl 3-(2-chloro-4-fluorophenyl)-3-hydroxyacrylate MS (ES) $C_{11}H_{10}ClFO_3$ requires: 244/246, found: 245/247 (M+H)+, ~93%

3.1.2 Preparation of Intermediate Compounds of Formula (B)

Intermediate 4B—Synthesis According to Method 2 (M2)

3-(2-chloro-4-fluorophenyl)-N-(3-methoxyphenyl)-3-oxopropanamide

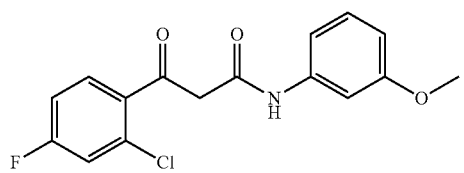 [SMILES: COc1cccc(NC(=O)CC(=O)c2ccc(F)cc2Cl)c1]

A mixture of compound 4A (20.8 g, 85 mmol) and 3-methoxyaniline (10.47 g, 9.5 mL, 85 mmol) was heated to 140° C. and stirred for 3.5 h. The mixture was allowed to cool to rt and diluted with 1,4-dioxane (90 mL) before addition of 10% aq. HCl solution (45 mL). The reaction was stirred for 2 h, upon which the mixture was diluted with $H_2O$ and extracted with EtOAc. The combined organic layers were washed with $H_2O$ and brine, dried over $MgSO_4$, filtered and evaporated in vacuo. The crude was purified by flash chromatography on silica gel using a gradient of EtOAc in cHex to yield the desired product 4B (12.2 g, 45%) as a mixture of tautomers, which was used in the following step without further purification.

$^1$H NMR (300 MHz, Chloroform-d) δ 8.83 (s, 1H), 7.63 (dd, J=8.7, 5.9 Hz, 1H), 7.28-6.86 (m, 5H), 6.66-6.56 (m, 1H), 4.02 (s, 2H), 3.74 (s, 3H).-tautomer 1,3-(2-chloro-4-fluorophenyl)-N-(3-methoxyphenyl)-3-oxopropanamide $^1$H NMR (300 MHz, Chloroform-d) δ 13.96 (s, 1H), 7.55 (dd, J=8.8, 6.2 Hz, 1H), 7.28-6.86 (m, 6H), 6.66-6.56 (m, 1H), 5.48 (s, 1H), 3.72 (s, 3H).-tautomer 2, (Z)-3-(2-chloro-4-fluorophenyl)-3-hydroxy-N-(3-methoxyphenyl)acrylamide MS (ES) $C_{16}H_{13}ClFO_3$ requires: 321/323, found: 322/324 (M+H)+, ~94%

3.1.3 Preparation of Intermediate Compounds of Formula (C)

Intermediate 2C$_1$— Synthesis According to Method 3a (M3a)

4-(2-chlorophenyl)-7-methoxyquinoline (2C$_1$)

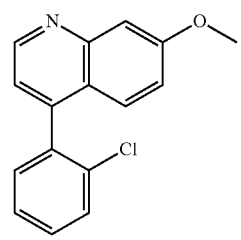 [SMILES: COc1ccc2c(-c3ccccc3Cl)ccnc2c1]

A mixture of 4-chloro-7-methoxyquinoline $C_{1x}$ (1.5 g, 7.75 mmol), Pd(amphos)Cl$_2$ (274 mg, 0.387 mmol), 2-chlorophenylboronic acid (1.82 g, 11.6 mmol) and $K_2CO_3$ (3.2 g, 22.8 mmol) was purged with N$_2$ before addition of toluene (35 mL) and H$_2$O (5 mL). The reaction was then stirred at 85° C. for 3.5 h, upon which the mixture was diluted with DCM and washed with H$_2$O. The aqueous phase was extracted with DCM, and the combined organic layers were washed with a sat. NaHCO$_3$ solution and brine, dried over MgSO$_4$, filtered and evaporated in vacuo. The crude was purified by flash chromatography on silica gel using a gradient of EtOAc in cHex to yield the desired product 2C$_1$ (1.0 g, 48%) as a yellow solid.

$^1$H NMR (300 MHz, Chloroform-d) δ 8.82 (d, J=4.5 Hz, 1H), 7.55-7.39 (m, 2H), 7.42-7.25 (m, 3H), 7.30-7.19 (m, 1H), 7.20-7.01 (m, 2H), 3.90 (s, 3H).

MS (ES) C$_{16}$H$_{12}$ClNO requires: 269/271, found: 270/272 (M+H)$^+$, 91%

Intermediate 4C$_2$— Synthesis According to Method 4 (M4)

4-(2-chloro-4-fluorophenyl)-7-methoxyquinolin-2 (1H)-one (4C$_2$)

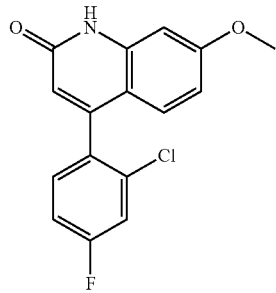 [SMILES: COc1ccc2c(-c3ccc(F)cc3Cl)cc(=O)[nH]c2c1]

A mixture of compound 4B (12.2 g, 37.9 mmol) and H$_3$PO$_4$ (100 g) was heated to 150° C. for 1 h, upon which the reaction was carefully quenched by slow addition of a 2N NaOH aq. solution (400 mL). The precipitate was filtered, washed with H$_2$O and dried in vacuo to yield the desired product 4C$_2$ (9.75 g, 85%) as a yellow solid.

$^1$H NMR (300 MHz, Chloroform-d) δ 12.21 (s, 1H), 7.28-7.17 (m, 2H), 7.06 (td, J=8.2, 2.6 Hz, 1H), 6.95 (d, J=9.0 Hz, 1H), 6.83 (d, J=2.4 Hz, 1H), 6.68 (dd, J=8.9, 2.4 Hz, 1H), 6.41 (s, 1H), 3.84 (s, 3H).

MS (ES) C$_{16}$H$_{11}$ClFO$_2$ requires: 303/305, found: 304/306 (M+H)$^+$, 89%

Intermediate 4C$_3$ —Synthesis According to Method 5 (M5)

2-chloro-4-(2-chloro-4-fluorophenyl)-7-methoxyquinoline (4C$_3$)

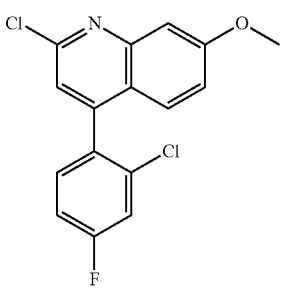 [SMILES: COc1ccc2c(-c3ccc(F)cc3Cl)cc(Cl)nc2c1]

To compound 4C$_2$ (9.75 g, 32.1 mmol) was added dry DMF (2.5 mL) and SOCl$_2$ (110 mL). The resulting mixture was heated at 50° C. for 22 h, upon which the mixture was allowed to cool to rt and slowly poured over water-ice (~800 mL). The mixture was then extracted with Et$_2$O and the combined organic layers were washed with H$_2$O and brine, dried over MgSO$_4$, filtered and evaporated in vacuo. The crude was purified by flash chromatography on silica gel using a gradient of EtOAc in cHex to yield the desired product 4C$_3$ (5.18 g, 50%) as an off-white solid.

$^1$H NMR (300 MHz, Chloroform-d) δ 7.35 (d, J=2.6 Hz, 1H), 7.30-7.10 (m, 3H), 7.15-6.97 (m, 3H), 3.87 (s, 3H).

MS (ES) C$_{16}$H$_{10}$Cl$_2$FO requires: 321/323, found: 322/324 (M+H)$^+$, 92%

All 7-methoxyquinoline intermediates C were synthesized in a similar manner as for intermediates 2C$_1$, 4C$_2$ or 4C$_3$.

Intermediate C$_{4a}$—Synthesis According to Nicoleti et al. (2012)

5-(((6-methoxypyridin-2 yl)amino)methylene)-2,2-dimethyl-1,3-dioxane-4,6-dione (C$_{4a}$)

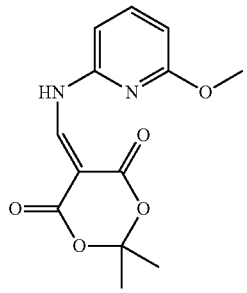 [SMILES: COc1cccc(NC=C2C(=O)OC(C)(C)OC2=O)n1]

A mixture of Meldrum acid (26 g, 179 mmol) and 110 mL of trimethyl orthoformate was refluxed for 2 h. The solution was allowed to cool to rt, 2-amino-6-methoxypyridine (10 g, 80.6 mmol) was added and the solution refluxed for 30 min. The mixture was cooled to rt, and the resulting precipitate was filtered, washed with EtOH (60 mL) and dried in vacuo to yield the desired product C$_{4a}$ (20.89 g, 93%) as an orange solid.

$^1$H NMR (300 MHz, DMSO-d$_6$) δ 11.34 (d, J=13.8 Hz, 1H), 9.19 (d, J=13.9 Hz, 1H), 7.79 (t, J=7.9 Hz, 1H), 7.22 (d, J=7.6 Hz, 1H), 6.71 (d, J=8.1 Hz, 1H), 3.91 (s, 3H), 1.69 (s, 6H).

MS (ES) C$_{13}$H$_{14}$N$_2$O$_5$ requires: 278, found: 279 (M+H)$^+$, 100%

7-methoxy-1,8-naphthyridin-4(1H)-one (C$_{4b}$)

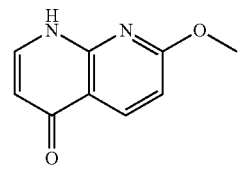

Diphenyl ether (860 mL) was heated to 150° C. and intermediate C$_{4a}$ (20.8 g, 74.82 mmol) was added slowly.

The resulting mixture was heated to 225° C. for 90 min, upon which it was allowed to cool to rt. The mixture was diluted with Et$_2$O. The resulting precipitate was filtered, washed with Et$_2$O and dried in vacuo, to yield the desired product C$_{4b}$ (11.06 g, 84%) as an as an orange solid.

$^1$H NMR (300 MHz, DMSO-d$_6$) δ 11.98 (s, 1H), 8.29 (d, J=8.7 Hz, 1H), 7.76 (d, J=7.5 Hz, 1H), 6.79 (d, J=8.7 Hz, 1H), 6.03 (d, J=7.6 Hz, 1H), 3.96 (s, 3H).

MS (ES) C$_9$H$_8$N$_2$O$_2$ requires: 176, found: 177 (M+H)$^+$, 99%

5-chloro-2-methoxy-1,8-naphthyridine (C$_{4x}$)

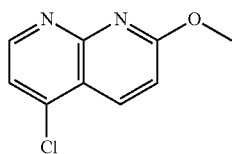

A solution of compound C$_{4b}$ (11 g, 62.4 mmol) in PCl$_5$ (225 mL) was heated to 95° C. for 2 h, after which the mixture was allowed to cool to rt and ice was added slowly under vigorous stirring. The pH of the mixture was adjusted to ~8 by careful addition of 25% aq. NH$_3$OH solution. The resulting solid was filtered, washed with H$_2$O and dried in vacuo, to yield the desired product C$_{4x}$ (11.36 g, 86%) as a yellow solid.

$^1$H NMR (300 MHz, Chloroform-d) δ 8.75 (d, J=4.9 Hz, 1H), 8.33 (d, J=9.0 Hz, 1H), 7.34 (d, J=4.9 Hz, 1H), 7.01 (d, J=9.0 Hz, 1H), 4.10 (s, 3H).

MS (ES) C$_9$H$_7$ClN$_2$O requires: 194/196, found: 195/197 (M+H)$^+$, 95%

5-(2-chloro-4-fluorophenyl)-2-methoxy-1,8-naphthyridine (4C$_4$)—Synthesis According to Method 3b (M3b)

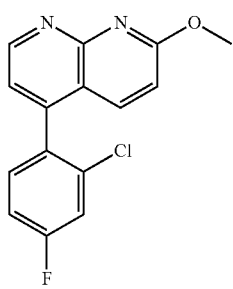 [SMILES: COc1ccc2c(-c3ccc(F)cc3Cl)ccnc2n1]

To a mixture of compound C$_{4x}$ (10.45 g, 53.7 mmol), 2-chloro-4-fluorophenylboronic acid (11.2 g, 64.4 mmol) and Pd(PPh$_3$)$_4$ (3.1 g, 2.68 mmol) was added toluene (135 mL), EtOH (18 mL) and 2M aq. Na$_2$CO$_3$ solution (48 mL, 96 mmol). The mixture was stirred under N$_2$ atmosphere at 80° C. for 15 h. The reaction was then diluted with H$_2$O and extracted with DCM. The combined organic layers were washed with brine, dried over MgSO$_4$, filtered and evaporated in vacuo. The crude was purified by flash chromatography on silica gel using a gradient of MeOH in DCM to yield compound 4C$_4$ (12.86 g, 83%) as a yellow solid.

$^1$H NMR (300 MHz, Chloroform-d) δ 8.93 (d, J=4.6 Hz, 1H), 7.62 (d, J=9.0 Hz, 1H), 7.33-7.11 (m, 3H), 7.08 (ddd, J=8.6, 7.9, 2.6 Hz, 1H), 6.88 (d, J=9.0 Hz, 1H), 4.11 (s, 3H).

MS (ES) C$_{15}$H$_{10}$ClFN$_2$O requires: 288/290, found: 289/291 (M+H)$^+$, 86%.

All 2-methoxy-1,8-naphthyridine intermediates C were synthesized in a similar manner as intermediates 4C$_4$.

3.1.4 Preparation of Intermediate Compounds of Formula (D)

5-(2-chloro-4-fluorophenyl)-1,8-naphthyridin-2-ol (4D$_4$)—Synthesis According to Method 6 (M6)

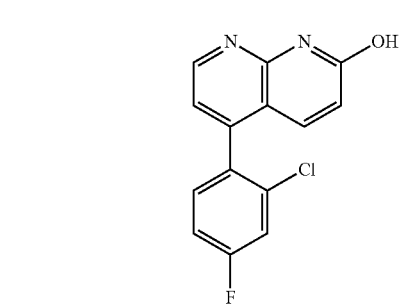 [SMILES: Oc1ccc2c(-c3ccc(F)cc3Cl)ccnc2n1]

Compound 4C$_4$ (12.85 g, 44.5 mmol) was dissolved in DCM (95 mL) and BBr$_3$ (25 g, 99.8 mmol) in DCM (40 mL) was added at −50° C. The mixture was allowed to warm up to rt and was stirred for 18 h, upon which it was cooled to 0° C. Additional BBr$_3$ (25 g, 99.8 mmol) in DCM (40 mL) was added. The reaction mixture was then stirred at rt for 6 days before being carefully poured over a mixture of ice-water (~500 mL) and aq. 25% NH$_4$OH solution (150 mL) under vigorous stirring. The resulting precipitate was twice filtered, washed with H$_2$O and dried in vacuo to yield the desired product 4D$_4$ (9.88 g, 81%) as a yellow solid.

$^1$H NMR (300 MHz, DMSO-d6) δ 12.34 (s, 1H), 8.60 (d, J=4.9 Hz, 1H), 7.71 (dd, J=8.9, 2.6 Hz, 1H), 7.53 (dd, J=8.6, 6.2 Hz, 1H), 7.49-7.31 (m, 2H), 7.17 (d, J=4.9 Hz, 1H), 6.55 (dd, J=9.8, 1.9 Hz, 1H).

MS (ES) C$_{14}$H$_8$ClFN$_2$O requires: 274/276, found: 275/277 (M+H)$^+$, 89%.

The following quinoline and naphthyridine intermediates D in Table 3, unless commercially available, were synthesized from intermediates C according to M6 in a similar manner as for intermediate 4D$_4$.

TABLE 3

| | 7-Hydroxy-Quinolines of formula (D and D$_x$) | |
|---|---|---|
| Intermediate | Structure | (M + H)$^+$, purity |
| D$_{1x}$ | (structure shown) | CAS: 181950-57-2 |

TABLE 3-continued

7-Hydroxy-Quinolines of formula (D and $D_x$)

| Intermediate | Structure | $(M + H)^+$, purity |
|---|---|---|
| 1$D_1$ | 4-phenylquinolin-7-ol | MS (ES) $C_{15}H_{11}NO$ requires: 221, found 222 $(M + H)^+$, >95% |
| 2$D_1$ | 4-(2-chlorophenyl)quinolin-7-ol | MS (ES) $C_{15}H_{11}ClNO$ requires: 255/257, found: 256/258 $(M + H)^+$, 92% |
| 3$D_1$ | 4-(o-tolyl)quinolin-7-ol | MS (ES) $C_{16}H_{13}NO$ requires: 235, found: 236 $(M + H)^+$, 90% |
| 4$D_1$ | 4-(2-chloro-4-fluorophenyl)quinolin-7-ol | MS (ES) $C_{15}H_9ClFNO$ requires: 273/275, found: 274/276 $(M + H)^+$, 91% |
| 6$D_1$ | 4-(2,6-dimethylphenyl)quinolin-7-ol | MS (ES) $C_{17}H_{15}NO$ requires: 249, found: 250 $(M + H)^+$, 91% |
| 7$D_1$ | 4-(2,6-dichlorophenyl)quinolin-7-ol | MS (ES) $C_{15}H_9Cl_2NO$ requires: 289/291, found: 290/292 $(M + H)^+$, 92% |
| 8$D_1$ | 4-(4-fluoro-2,6-dimethylphenyl)quinolin-7-ol | MS (ES) $C_{17}H_{14}FNO$ requires: 267/268, found: 268/269 $(M + H)^+$, 89% |
| 9$D_1$ | 4-(2,6-dichloro-4-fluorophenyl)quinolin-7-ol | MS (ES) $C_{15}H_8Cl_2FNO$ requires: 307/309, found: 308/310 $(M + H)^+$, 99% |
| 1$D_2$ | 7-hydroxy-4-phenylquinolin-2(1H)-one | MS (ES) $C_{15}H_{11}NO_2$ requires: 237, found: 238 $(M + H)^+$, 85% |
| 3$D_2$ | 7-hydroxy-4-(o-tolyl)quinolin-2(1H)-one | MS (ES) $C_{16}H_{13}NO_2$ requires: 251, found: 252 $(M + H)^+$, 93% |
| 2$D_3$ | 2-chloro-4-(2-chlorophenyl)quinolin-7-ol | MS (ES) $C_{15}H_9Cl_2NO$ requires: 289/291, found: 290/292 $(M + H)^+$, >95% |

TABLE 3-continued

7-Hydroxy-Quinolines of formula (D and $D_x$)

| Intermediate | Structure | $(M + H)^+$, purity |
|---|---|---|
| $3D_3$ | 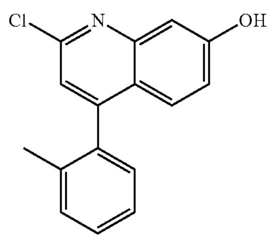 [SMILES: Cc1ccccc1-c1cc(Cl)nc2cc(O)ccc12] | MS (ES) $C_{16}H_{12}ClNO$ requires: 269/271, found: 270/272 $(M + H)^+$, >95% |
| $4D_3$ | 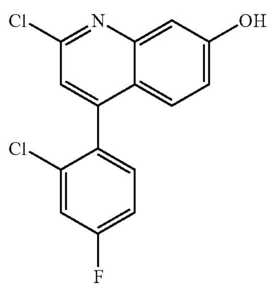 [SMILES: Oc1ccc2c(-c3ccc(F)cc3Cl)cc(Cl)nc2c1] | MS (ES) $C_{15}H_8Cl_2FNO$ requires: 307/309, found: 308/310 $(M + H)^+$, 92% |
| $5D_3$ | 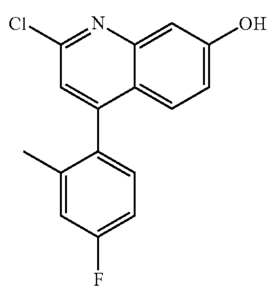 [SMILES: Cc1cc(F)ccc1-c1cc(Cl)nc2cc(O)ccc12] | MS (ES) $C_{16}H_{11}ClFNO$ requires: 287/289, found: 288/290 $(M + H)^+$, 93% |
| $6D_3$ | 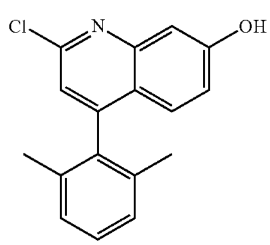 [SMILES: Cc1cccc(C)c1-c1cc(Cl)nc2cc(O)ccc12] | MS (ES) $C_{17}H_{14}ClNO$ requires: 283/285, found: 284/286 $(M + H)^+$, 31%- used without purification |
| $4D_4$ | 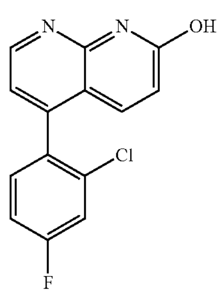 [SMILES: Oc1ccc2c(-c3ccc(F)cc3Cl)ccnc2n1] | MS (ES) $C_{14}H_8ClFN_2O$ requires: 274/276, found: 275/277 $(M + H)^+$, 89% |
| $8D_4$ | | MS (ES) $C_{16}H_{13}FN_2O$ requires: 268/269, found: 269/270 $(M + H)^+$, 78% |
| $9D_4$ | | MS (ES) $C_{14}H_7Cl_2FN_2O$ requires: 308/310, found: 309/311 $(M + H)^+$, 58% |
| $D_{5x}$ | | CAS: 148018-30-8 |

3.1.5 Preparation of Compounds of Formula (E and F)

Compound of Formula E (106)—Synthesis According to Method 7 (M7)

2-((4-(o-tolyl)quinolin-7-yl)oxy)acetamide (106)

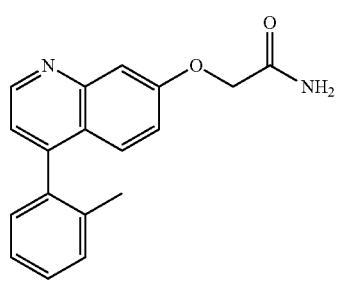 [SMILES: Cc1ccccc1-c1ccnc2cc(OCC(N)=O)ccc12]

Intermediate $3D_1$ (80 mg, 0.34 mmol) was suspended in dry DMF (1.5 mL) and $Cs_2CO_3$ (286 mg, 0.879 mmol) was added, followed by 2-bromoacetamide (47 mg, 0.34 mmol) in dry DMF (1 mL). The reaction was stirred at rt for 24 h. The mixture was diluted with EtOAc (50 mL) and the organic phase was washed with $H_2O$ and brine. The organic layer was dried over $MgSO_4$, filtered and evaporated in vacuo. The crude was purified by preparative TLC on silica gel using an eluent mixture of DCM: MeOH 19:1 containing 0.05% of 25% NH$_4$OH solution to yield the desired product (106) (12 mg, 12%) as a white solid.

$^1$H NMR (300 MHz, Chloroform-d) δ 8.84 (d, J=4.5 Hz, 1H), 7.45 (d, J=2.6 Hz, 1H), 7.37 (d, J=9.2 Hz, 1H), 7.34-7.21 (m, 3H), 7.16-7.05 (m, 3H), 6.52 (s, 1H), 5.69 (s, 1H), 4.61 (s, 2H), 1.96 (s, 3H).

MS (ES) C$_{18}$H$_{16}$N$_2$O$_2$ requires: 292, found: 293 (M+H)$^+$, 96%

(rac)-4F$_4$_Et—Synthesis According to Method 7 (M7)

ethyl 2-((5-(2-chloro-4-fluorophenyl)-1,8-naphthyridin-2 yl)oxy)propanoate (rac)-4F$_4$_Et)

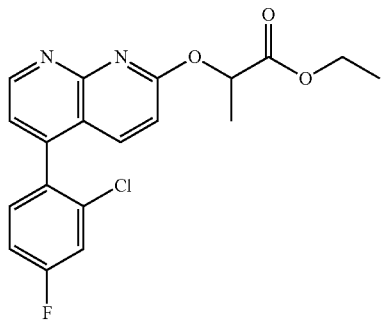 [SMILES: CCOC(=O)C(C)Oc1ccc2c(-c3ccc(F)cc3Cl)ccnc2n1]

Intermediate 4D$_4$ (1 g, 3.64 mmol) was reacted with ethyl-2-bromopropionate (0.71 mL, 5.46 mmol) according to M7 to yield the desired product (rac)-4F$_4$_Et (1.03 g, 75%).

$^1$H NMR (300 MHz, Chloroform-d) δ 8.93 (d, J=4.6 Hz, 1H), 7.68 (d, J=9.0 Hz, 1H), 7.34-7.14 (m, 3H), 7.18-6.96 (m, 2H), 5.84 (qd, J=7.0, 4.5 Hz, 1H), 4.29-4.06 (m, 2H), 1.62 (d, J=7.0 Hz, 3H), 1.23 (t, J=7.1 Hz, 3H).

MS (ES) C$_{19}$H$_{16}$ClFN$_2$O$_3$ requires: 374/376, found: 375/377 (M+H)$^+$, 97%

(R)-4F$_1$_Et—Synthesis According to Method 8 (M8)

(R)-ethyl 2-((4-(2-chloro-4-fluorophenyl)quinolin-7-yl)oxy)propanoate ((R)-4F$_1$_Et)

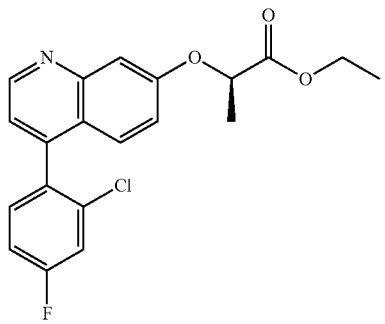 [SMILES: CCOC(=O)[C@@H](C)Oc1ccc2c(-c3ccc(F)cc3Cl)ccnc2c1]

Intermediate 4D$_1$ (100 mg, 0.365 mmol) and PPh$_3$ (105 mg, 0.402 mmol) were dissolved in THF (5.5 mL), and (−)-Ethyl (S)-2-hydroxypropionate (50 μl, 0.438 mmol) was added. The reaction was cooled to 0° C. and DIAD (79 μl, 0.402 mmol) was added dropwise. The reaction was then stirred at rt for 1 h, upon which further reagents were added in the same amounts, and the reaction stirred for a further 6 h. The mixture was diluted with EtOAc and washed with a sat. NaHCO$_3$ solution, a sat. NH$_4$Cl solution, and H$_2$O. The organic layer was dried over MgSO$_4$, filtered and evaporated in vacuo. The crude product was purified by flash chromatography on silica gel using a gradient of EtOAc in cHex to yield the desired product (R)-4F$_1$_Et (163 mg, ~20% excess weight), which was carried through to the following step without further purification.

MS (ES) C$_{20}$H$_{17}$ClFNO$_3$ requires: 373/375, found: 374/376 (M+H)$^+$, 94%

3.1.6 Preparation of Intermediate Compounds of Formula (F$_x$) Through Intermediates (D$_x$)

Intermediate (R)—F$_{1x}$_tBu—Synthesis According to Method 8 (M8)

(R)-tert butyl 2-((4-chloroquinolin-7-yl)oxy)propanoate (R)—F$_{1x}$_tBu

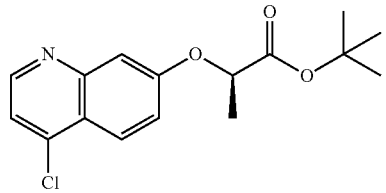 [SMILES: C[C@@H](Oc1ccc2c(Cl)ccnc2c1)C(=O)OC(C)(C)C]

4-chloroquinolin-7-ol (D$_{1x}$) (200 mg, 1.11 mmol) was reacted with tert-butyl (2S)-2-hydroxypropanoate (244 mg, 1.67 mmol) according to M8 to yield the desired product (R)-F$_{1x}$tBu (222 mg, 65%) as a colorless glue.

$^1$H NMR (400 MHz, DMSO-d$_6$) δ 8.76 (d, J=4.7 Hz, 1H), 8.13 (d, J=9.2 Hz, 1H), 7.60 (dd, J=4.8, 0.5 Hz, 1H), 7.47-7.40 (m, 1H), 7.31 (d, J=2.6 Hz, 1H), 5.06 (q, J=6.7 Hz, 1H), 1.57 (dd, J=6.8, 0.6 Hz, 3H), 1.39 (d, J=0.5 Hz, 9H).

MS (ES) C$_{16}$H$_{18}$ClNO$_3$ requires: 307/309, found: 308/310 (M+H)$^+$, 100%

(R)-4F$_1$_tBu—Synthesis According to Method 3b (M3b)

(R)-tert butyl 2-((4-(2-chloro-4-fluorophenyl)quinolin-7-yl)oxy)propanoate ((R)-4F$_1$_tBu)

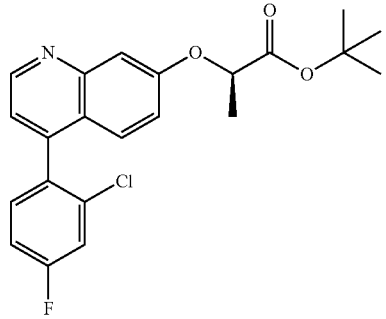 [SMILES: C[C@@H](Oc1ccc2c(-c3ccc(F)cc3Cl)ccnc2c1)C(=O)OC(C)(C)C]

Intermediate (R)-F$_{1x}$_tBu (110 mg, 0.356 mmol) was reacted with (2-chloro-4-fluorophenyl)boronic acid (75 mg, 0.427 mmol) according to M3b to yield the desired product (R)-4F$_1$_tBu (95 mg, 66%) as a white solid.

$^1$H NMR (400 MHz, DMSO-d$_6$) δ 8.87 (d, J=4.4 Hz, 1H), 7.67 (dt, J=8.9, 2.7 Hz, 1H), 7.51 (ddd, J=8.5, 7.3, 6.2 Hz, 1H), 7.45-7.36 (m, 1H), 7.35-7.18 (m, 4H), 5.05-4.93 (m, 1H), 1.55 (d, J=6.7 Hz, 3H), 1.40 (s, 9H).

MS (ES) C$_{22}$H$_{21}$ClFNO$_3$ requires: 401/403, found: 402/404 (M+H)$^+$, 92%

(R)-2F$_6$_tBu—Synthesis According to Fier and Hartwig (2013)

(R)-tert butyl 2-((4-(2-chlorophenyl)-2-fluoroquinolin-7-yl)oxy)propanoate ((R)-2F$_6$_tBu)

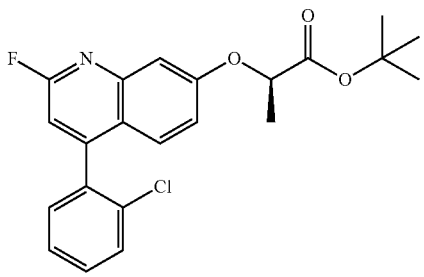 [SMILES: C[C@@H](Oc1ccc2c(-c3ccccc3Cl)cc(F)nc2c1)C(=O)OC(C)(C)C]

Compound (R)-2F$_1$_tBu (34.5 mg, 0.090 mmol) was dissolved in dry ACN (1 mL) and AgF$_2$ (39.4 mg, 0.270 mmol) was added at rt. The resulting suspension was stirred under N$_2$ atmosphere for 2 h. A second aliquot of AgF$_2$ (39.4 mg, 0.270 mmol) was added and stirring was continued for 90 min. The mixture was diluted with EtOAc and washed with sat. NaHCO$_3$ solution and brine. The organic layer was dried over MgSO$_4$, filtered through a plug of celite and evaporated in vacuo. The crude was purified by flash chromatography on silica gel using a gradient of EtOAc in cHex to yield the desired product (R)-2F$_6$_tBu (14.3 mg, 40%) as a colorless oil.

$^1$H NMR (400 MHz, Chloroform-d) δ 7.59-7.53 (m, 1H), 7.48-7.35 (m, 3H), 7.34-7.29 (m, 1H), 7.22 (dd, J=5.5, 2.6 Hz, 1H), 7.18-7.12 (m, 1H), 6.87 (dd, J=2.2, 1.0 Hz, 1H), 4.81 (qd, J=6.8, 4.4 Hz, 1H), 1.66 (d, J=6.8 Hz, 3H), 1.48 (s, 9H).

MS (ES) C$_{22}$H$_{21}$ClFNO$_3$ requires: 401/403, found: 402/404 (M+H)$^+$, 100%

3.1.7 Preparation of Compounds of Formula (G)

(R)-4G$_1$—Synthesis According to Method 9 (M9)

(R)-2-((4-(2-chloro-4-fluorophenyl)quinolin-7-yl)oxy)propanoic acid ((R)-4G$_1$)-44

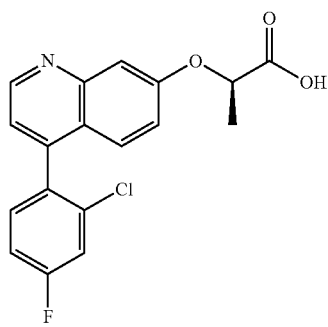 [SMILES: C[C@@H](Oc1ccc2c(-c3ccc(F)cc3Cl)ccnc2c1)C(=O)O]

Compound (R)-4F$_1$_Et (156 g, ~0.365 mmol) was dissolved in THF (6.3 mL) and 2M NaOH aq. solution (1.3 mL) was added. MeOH was added dropwise until the mixture became homogeneous. The reaction was stirred at rt for 30 min. The mixture was acidified with 2M HCl to pH5 and extracted with EtOAc. The combined organic layers were washed with H$_2$O, dried over MgSO$_4$, filtered, and evaporated in vacuo. The crude was purified by column chromatography using a gradient of MeOH in DCM to yield the desired product (R)-4G$_1$ (44) (66 mg, 52% over 2 steps) as a white solid.

$^1$H NMR (400 MHz, DMSO-d$_6$) δ 8.85 (dd, J=4.4, 0.6 Hz, 1H), 7.67 (dt, J=8.9, 2.3 Hz, 1H), 7.49 (ddd, J=8.1, 6.2, 1.8 Hz, 1H), 7.39 (tt, J=8.5, 2.4 Hz, 1H), 7.32-7.27 (m, 2H), 7.26 (dd, J=4.4, 0.6 Hz, 1H), 7.22 (dd, J=9.2, 2.6 Hz, 1H), 5.00 (q, J=6.5 Hz, 1H), 1.55 (d, J=6.8 Hz, 3H).

MS (ES) C$_{18}$H$_{13}$ClFNO$_3$ requires: 345/347, found: 346/348 (M+H)$^+$, 96%

(R)-4G$_1$—Synthesis According to Method 10a (M10a)

(R)-2-((4-(2-chloro-4-fluorophenyl)quinolin-7-yl)oxy)propanoic acid trifluoroacetic acid salt ((R)-4G$_1$)-44

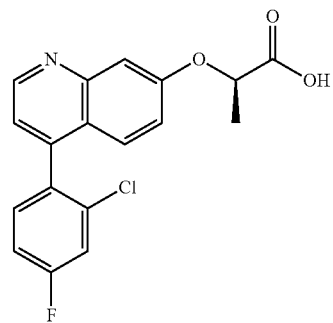 [SMILES: C[C@@H](Oc1ccc2c(-c3ccc(F)cc3Cl)ccnc2c1)C(=O)O]

Compound (R)-4F$_1$_tBu (93 mg, 0.232 mmol) was dissolved in a 4:1 DCM:TFA solution (2.3 ml) and the reaction was stirred at rt for 1.5 h, upon which the solvents were removed in vacuo and a fresh 4:1 DCM:TFA solution (2.3 ml) was added and the mixture stirred for further 4 h. The solvents were evaporated in vacuo to yield the desired product (R)-4G$_1$ (44) (132 mg, ~23% excess weight) as a brown glue (TFA salt), which was used in the following step without further purification.

$^1$H NMR (400 MHz, DMSO-d$_6$) δ 8.99 (d, J=4.7 Hz, 1H), 7.70 (ddd, J=8.9, 2.5, 1.8 Hz, 1H), 7.53 (ddd, J=8.9, 6.2, 3.0 Hz, 1H), 7.49-7.39 (m, 3H), 7.39-7.30 (m, 2H), 5.09 (q, J=6.8 Hz, 1H), 1.59 (d, J=6.8 Hz, 3H).

MS (ES) C$_{18}$H$_{13}$ClFNO$_3$ requires: 345/347, found: 346/348 (M+H)$^+$, 92%

The ethyl esters and carboxylic acids shown in Table 4 were synthesized in a similar manner as described for intermediates (rac)-4F$_4$_Et, (R)-4F$_1$_Et, (R)—F$_{1x}$, (R)-4F$_1$_tBu, (R)-2F$_6$_tBu and (R)-4G$_1$.

TABLE 4

| Compounds | Structure | $(M + H)^+$, purity |
|---|---|---|
| (R)-F$_{1x}$_Et<br>(R)-F$_{1x}$_tBu<br>(R)-G$_{1x}$ | quinoline with 4-Cl, 7-O-CH(CH$_3$)-C(O)OR$_5$ | Et: MS (ES) C$_{14}$H$_{14}$ClNO$_3$ requires: 279/281, found: 280/282 (M + H)$^+$, >95%<br>tBu: MS (ES) C$_{16}$H$_{18}$ClNO$_3$ requires: 307/309, found: 308/310 (M + H)$^+$, 100%<br>H: MS (ES) C$_{12}$H$_{10}$ClNO$_3$ requires: 251/253, found: 252/253 (M + H)$^+$, >95% |
| (R)-1F$_1$_Et<br>(R)-1F$_1$_tBu<br>(R)-1G$_1$ | quinoline with 4-phenyl, 7-O-CH(CH$_3$)-C(O)OR$_5$ | Et: MS (ES) C$_{20}$H$_{17}$ClFNO$_3$ requires: 373/375, found: 374/376 (M + H)$^+$, 94%<br>tBu: MS (ES) C$_{22}$H$_{21}$ClFNO$_3$ requires: 401/403, found: 402/404 (M + H)$^+$, 92%<br>H: MS (ES) C$_{18}$H$_{13}$ClFNO$_3$ requires: 345/347, found: 346/348 (M + H)$^+$, 92% |
| 2F$_1$_Et<br>2G$_1$ | quinoline with 4-(2-chlorophenyl), 7-O-CH$_2$-C(O)OR$_5$ | Et: MS (ES) C$_{19}$H$_{16}$ClNO$_3$ requires: 341/343, found: 342/344 (M + H)$^+$, 92%<br>H: MS (ES) C$_{17}$H$_{12}$ClNO$_3$ requires: 313/315, found: 314/316 (M + H)$^+$, 93% |
| (R)-2F$_1$_Et<br>(R)-2F$_1$_tBu<br>(R)-2G$_1$ | quinoline with 4-(2-chlorophenyl), 7-O-CH(CH$_3$)-C(O)OR$_5$ | Et: MS (ES) C$_{20}$H$_{18}$ClNO$_3$ requires: 355/357, found: 356/358 (M + H)$^+$, >95%<br>tBu: MS (ES) C$_{22}$H$_{22}$ClNO$_3$ requires: 383/385, found: 384/386 (M + H)$^+$, 92%<br>H: MS (ES) C$_{18}$H$_{14}$ClNO$_3$ requires: 327/329, found: 328/330 (M + H)$^+$, >95% |
| (R)-3F$_1$_tBu<br>(R)-3G$_1$ | quinoline with 4-(2-methylphenyl), 7-O-CH(CH$_3$)-C(O)OR$_5$ | tBu: MS (ES) C$_{23}$H$_{25}$NO$_3$ requires: 363, found: 364 (M + H)$^+$, 96%<br>H: MS (ES) C$_{19}$H$_{17}$NO$_3$ requires: 307, found: 308 (M + H)$^+$, 96% |

TABLE 4-continued

| Esters and carboxylic acids compounds (F) and (G) | | |
|---|---|---|
| Compounds | Structure | (M + H)+, purity |
| (R)-4F$_1$_Et<br>(R)-4F$_1$_tBu<br>(R)-4G$_1$ | | Et: MS (ES) C$_{20}$H$_{17}$ClFNO$_3$ requires: 373/375, found: 374/376 (M + H)+, 94%<br>tBu: MS (ES) C$_{22}$H$_{21}$ClFNO$_3$ requires: 401/403, found: 402/404 (M + H)+, 92%<br>H: MS (ES) C$_{18}$H$_{13}$ClFNO$_3$ requires: 345/347, found: 346/348 (M + H)+, 92% |
| (R)-6F$_1$_Et<br>(R)-6G$_1$ | | Et: MS (ES) C$_{22}$H$_{23}$NO$_3$ requires: 349, found: 350 (M + H)+, >95%<br>H: MS (ES) C$_{20}$H$_{19}$NO$_3$ requires: 321, found: 322 (M + H)+, >95% |
| (gem)-2F$_1$_Et<br>(gem)-2G$_1$ | | Et: MS (ES) C$_{21}$H$_{20}$ClNO$_3$ requires: 369/371, found: 370/372 (M + H)+, 98%<br>H: MS (ES) C$_{19}$H$_{16}$ClNO$_3$ requires: 341/343, found: 342/344 (M + H)+, 92% |
| (rac)-Et-2F$_1$_Et<br>(rac)-Et-2G$_1$ | | Et: MS (ES) C$_{21}$H$_{20}$ClNO$_3$ requires: 369/371, found: 370/372 (M + H)+, 98%<br>H: MS (ES) C$_{19}$H$_{16}$ClNO$_3$ requires: 341/343, found: 342/344 (M + H)+, 97% |
| (R)-7F$_1$_Et<br>(R)-7G$_1$ | | Et: MS (ES) C$_{20}$H$_{17}$Cl$_2$NO$_3$ requires: 389/391, found: 390/392 (M + H)+, >95%<br>H: MS (ES) C$_{18}$H$_{13}$Cl$_2$NO$_3$ requires: 361/363, found: 362/364 (M + H)+, >95% |

TABLE 4-continued

Esters and carboxylic acids compounds (F) and (G)

| Compounds | Structure | (M + H)+, purity |
|---|---|---|
| (R)-8F$_1$_Et<br>(R)-8G$_1$ | 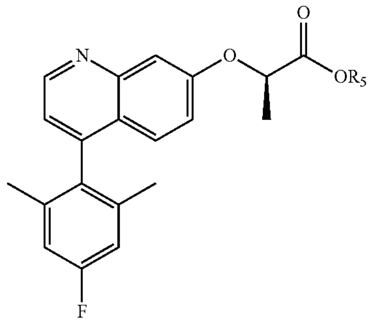 | Et: MS (ES) C$_{22}$H$_{22}$FNO$_3$ requires: 367/368, found: 368/369 (M + H)+, 95%<br>H: MS (ES) C$_{20}$H$_{18}$FNO$_3$ requires: 339/340, found: 340/341 (M + H)+, >99% |
| (R)-9F$_1$_Et<br>(R)-9G$_1$ | 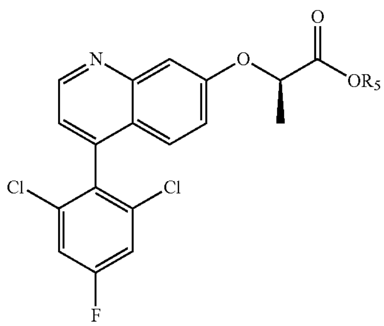 | Et: MS (ES) C$_{20}$H$_{16}$Cl$_2$FNO$_3$ requires: 408/409, found: 408/410 (M + H)+, 95%<br>H: MS (ES) C$_{18}$H$_{12}$Cl$_2$FNO$_3$ requires: 380/382, found: 381/383 (M + H)+, used as crude |
| (R)-1F$_3$_tBu<br>(R)-1G$_3$ | 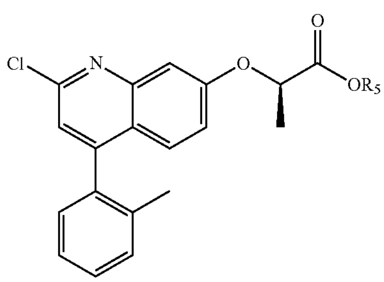 | tBu: MS (ES) C$_{23}$H$_{24}$ClNO$_3$ requires: 397/399, found: 398/400 (M + H)+, >95%<br>H: MS (ES) C$_{19}$H$_{16}$ClNO$_3$ requires: 341/343, found: 342/344 (M + H)+, >95% |
| (R)-2F$_3$_Et<br>(R)-2G$_3$ | 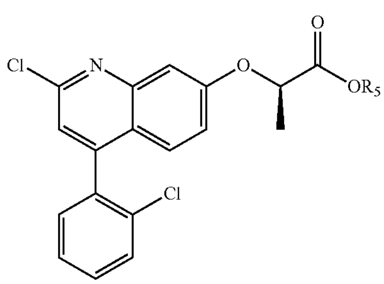 | Et: MS (ES) C$_{20}$H$_{17}$Cl$_2$NO$_3$ requires: 389/391, found: 390/392 (M + H)+, >95%<br>H: MS (ES) C$_{18}$H$_{13}$Cl$_2$NO$_3$ requires: 361/363, found: 362/364 (M + H)+, >95% |
| (R)-4F$_3$_Et<br>(R)-4G$_3$ | 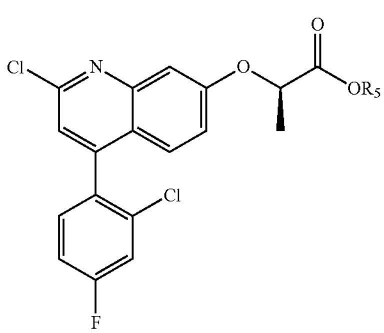 | Et: MS (ES) C$_{20}$H$_{16}$Cl$_2$FNO$_3$ requires: 407/409, found: 408/410 (M + H)+, >95%<br>H: MS (ES) C$_{18}$H$_{12}$Cl$_2$FNO$_3$ requires: 379/381, found: 380/382 (M + H)+, >95% |

TABLE 4-continued

Esters and carboxylic acids compounds (F) and (G)

| Compounds | Structure | $(M + H)^+$, purity |
|---|---|---|
| (R)-6F$_3$_Et<br>(R)-6G$_3$ | 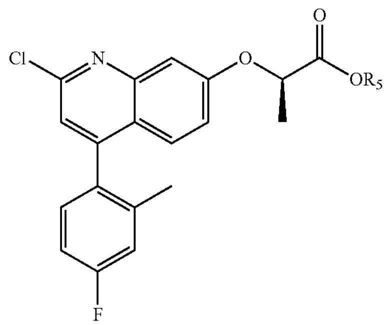 | Et: MS (ES) $C_{21}H_{19}ClFNO_3$ requires: 387/389, found: 388/390 $(M + H)^+$, >95%<br>H: MS (ES) $C_{19}H_{15}ClFNO_3$ requires: 359/361, found: 360/362 $(M + H)^+$, >95% |
| (rac)-4F$_4$_Et<br>(rac)-4G$_4$ | 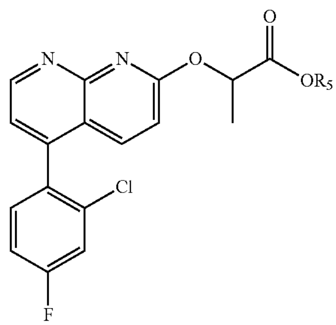 | Et: MS (ES) $C_{19}H_{16}ClFN_2O_3$ requires: 374/376, found: 375/377 $(M + H)^+$, 97%<br>H: MS (ES) $C_{19}H_{16}ClFN_2O_3$ requires: 374/376, found: 375/377 $(M + H)^+$, 97% |
| (R)-8F$_4$_Et<br>(R)-8G$_4$ | 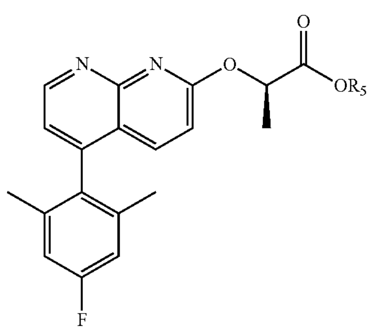 | Et: MS (ES) $C_{21}H_{21}FN_2O_3$ requires: 368/369, found: 369/370 $(M + H)^+$, 86%<br>H: MS (ES) $C_{19}H_{17}FN_2O_3$ requires: 340/341, found: 341/342 $(M + H)^+$, 94% |
| (R)-9F$_4$_Et<br>(R)-9G$_4$ | 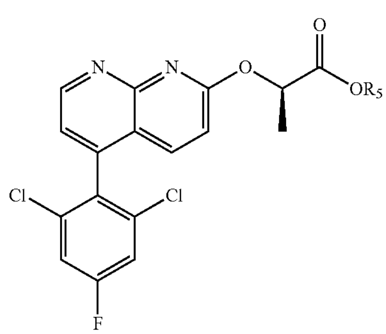 | Et: MS (ES) $C_{19}H_{15}Cl_2FN_2O_3$ requires: 408/410, found: 409/411 $(M + H)^+$, 89%<br>H: MS (ES) $C_{17}H_{11}Cl_2FN_2O_3$ requires: 380/382, found: 381/383 $(M + H)^+$, used as crude |
| (R)-F$_{5x}$_tBu | 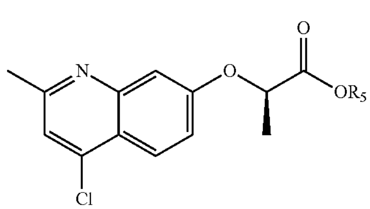 | tBu: MS (ES) $C_{17}H_{20}ClNO_3$ requires: 321/323, found: 322/324 $(M + H)^+$, 100% |

TABLE 4-continued

Esters and carboxylic acids compounds (F) and (G)

| Compounds | Structure | (M + H)⁺, purity |
|---|---|---|
| (R)-3F$_5$_tBu (R)-3G$_5$ | | tBu: MS (ES) C$_{24}$H$_{27}$NO$_3$ requires: 377, found: 378 (M + H)⁺, 96%<br>H: MS (ES) C$_{20}$H$_{19}$NO$_3$ requires: 321, found: 322 (M + H)⁺, 96% |
| (R)-4F$_5$_tBu (R)-4G$_5$ | | tBu: MS (ES) C$_{23}$H$_{23}$ClFNO$_3$ requires: 415/417, found: 416/418 (M + H)⁺, 100%<br>H: MS (ES) C$_{19}$H$_{15}$ClFNO$_3$ requires: 359/361, found: 360/362 (M + H)⁺, 98% |
| (R)-6F$_5$_tBu (R)-6G$_5$ | | tBu: MS (ES) C$_{25}$H$_{29}$NO$_3$ requires: 391, found: 392 (M + H)⁺, 97%<br>H: MS (ES) C$_{21}$H$_{21}$NO$_3$ requires: 335, found: 336 (M + H)⁺, 97% |
| (R)-2F$_6$_tBu (R)-2G$_6$ | | tBu: MS (ES) C$_{22}$H$_{21}$ClFNO$_3$ requires: 401/403, found: 402/404 (M + H)⁺, 100%<br>H: MS (ES) C$_{18}$H$_{13}$ClFNO$_3$ requires: 345/347, found: 346/348 (M + H)⁺, 96% |

3.1.8 Preparation of Compounds of Formula (J)

Compound 63—Synthesis According to Method 11a (M11a)

(R)-4-(2-((4-(2-chloro-4-fluorophenyl)quinolin-7-yl)oxy)propanoyl)piperazin-2-one (63)

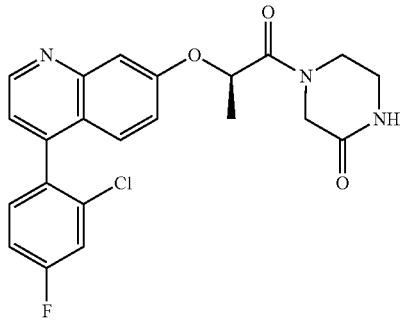 [SMILES: C[C@@H](Oc1ccc2c(-c3ccc(F)cc3Cl)ccnc2c1)C(=O)N1CCNC(=O)C1]

Compound (R)-4G, (35.0 mg, 0.101 mmol) and 2-oxopiperazine (16.2 mg, 0.162 mmol) were dissolved in dry DMF (0.8 mL). DIPEA (51.6 µL, 39.3 mg, 0.304 mmol) and HATU (57.7 mg, 0.152 mmol) were added, and the mixture was stirred at rt overnight. The reaction was diluted with EtOAc and washed with H$_2$O, sat. NaHCO$_3$ solution and brine. The organic phase was dried over MgSO$_4$, filtered and evaporated in vacuo. The crude product was purified by flash chromatography on silica gel using a gradient of MeOH in DCM to yield the de sired product 63 (31.5 mg, 73%) as a white solid.

$^1$H NMR (400 MHz, DMSO-d$_6$) δ 8.89 (d, J=4.4 Hz, 1H), 8.14 (d, J=10.8 Hz, 1H), 7.69 (ddd, J=8.9, 2.6, 1.3 Hz, 1H), 7.52 (dd, J=8.6, 6.2 Hz, 1H), 7.45-7.21 (m, 5H), 5.57 (q, J=6.6 Hz, 1H), 4.40-4.07 (m, 1H), 4.06-3.52 (m, 3H), 3.30-3.13 (m, 2H), 1.51 (ddd, J=13.4, 6.5, 2.5 Hz, 3H).

MS (ES) C$_{22}$H$_{19}$ClFN$_3$O$_3$ requires: 427/429, found: 428/430 (M+H)$^+$, 97%

3.1.9 Preparation of Intermediate Compounds of Formula (K)

Compound 15—Synthesis According to Method 11b (M11 b)

ethyl 2-((R)-1-((R)-2-((4-(2-chloro-4-fluorophenyl)quinolin-7-yl)oxy)propanoyl)piperidin-3-yl)acetate (15)

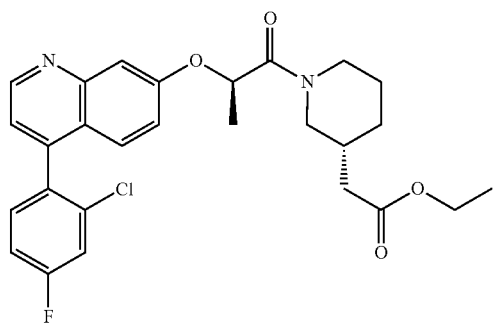 [SMILES: CCOC(=O)C[C@H]1CCCN(C(=O)[C@@H](C)Oc2ccc3c(-c4ccc(F)cc4Cl)ccnc3c2)C1]

Compound (R)-4G$_1$ (129 mg, 0.282 mmol), EDC·HCl (135 mg, 0.704 mmol), and HOBt·xH$_2$O (108 mg, 0.704 mmol) were dissolved in DMF (4 mL) and (S)-piperidine-3-carboxylic acid ethyl ester hydrochloride (146 mg, 0.704 mmol) was added slowly. Et$_3$N (98 µL, 0.704 mmol) was added, and the mixture was stirred at rt overnight. The reaction was diluted with EtOAc and washed with H$_2$O, a sat. NaHCO$_3$ solution, and again with H$_2$O. The organic phase was dried over MgSO$_4$, filtered and evaporated in vacuo. The crude product was purified by flash chromatography on silica gel using a gradient of EtOAc in cHex to yield the de sired product 15 (50 mg, 36%) as a colorless glue.

$^1$H NMR (400 MHz, DMSO-d$_6$) δ 8.88 (dd, J=7.3, 4.4 Hz, 1H), 7.73-7.63 (m, 1H), 7.52 (dd, J=8.6, 6.2 Hz, 1H), 7.42 (dddd, J=8.7, 7.8, 3.0, 2.2 Hz, 1H), 7.34-7.20 (m, 4H), 5.65-5.35 (m, 1H), 4.20 (d, J=13.1 Hz, 2H), 4.11-3.92 (m, 3H), 3.19-2.60 (m, 1H), 2.36-2.12 (m, 2H), 1.91-1.45 (m, 8H), 1.19-1.09 (m, 3H).

MS (ES) C$_{27}$H$_{28}$ClFN$_2$O$_4$ requires: 498/500, found: 499/501 (M+H)$^+$, 97%.

Intermediate (R,R)-2K$_{1x\_Cl}$—Synthesis According to Method 11c (M11c)

ethyl 2-((R)-1-((R)-2-((4-chloroquinolin-7-yl)oxy)propanoyl)piperidin-3 yl)acetate ((R,R)-2K$_{1x}$)

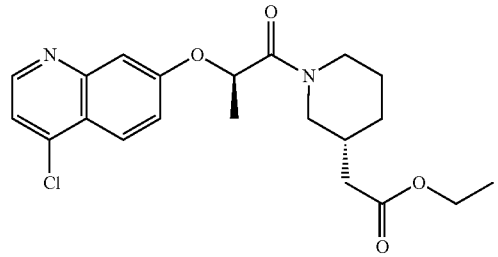 [SMILES: CCOC(=O)C[C@H]1CCCN(C(=O)[C@@H](C)Oc2ccc3c(Cl)ccnc3c2)C1]

A mixture of intermediate (R)-G$_{1x}$ (1.2 g, 4.77 mmol) and 1,1'-carbonyldiimidazole (775 mg, 4.77 mmol) in dry THF (24 mL) was stirred at room temperature for 1.5 hours. The reaction mixture was poured over a solution of ethyl-(R)-2-(3-piperidyl)acetate hydrochloride (990 mg, 4.47 mmol) and triethylamine (506 mg, 5.00 mmol) in dry THF (24 mL). After stirring for 12 hours, the mixture was diluted with EtOAc and washed with H$_2$O. The aqueous phase was further extracted with EtOAc. The combined organic layers were dried over MgSO$_4$, filtered and evaporated in vacuo. The crude was purified by flash chromatography using a gradient of EtOAc in cHex to yield the desired product (R,R)-2K$_{1x}$ (1.36 g, 70%) as white solid.

$^1$H NMR (300 MHz, Chloroform-d) δ 8.61 (t, J=5.3 Hz, 1H), 8.07 (dd, J=9.1, 4.1 Hz, 1H), 7.36-7.16 (m, 3H), 5.24-5.08 (m, 1H), 4.50-4.14 (m, 1H), 4.13-3.74 (m, 4H), 3.16-2.72 (m, 1H), 2.57 (ddd, J=13.2, 7.8, 3.2 Hz, 1H), 2.29-1.98 (m, 2H), 1.92-1.70 (m, 1H), 1.68-1.26 (m, 4H), 1.28-1.06 (m, 5H).

MS (ES) C$_{21}$H$_{25}$ClN$_2$O$_4$ requires: 404/406, found: 405/407 (M+H)$^+$, 100%.

Intermediate (R,S)-1K$_{1\_I}$—Synthesis According to Bissember and Banwell (2009)

(S)-ethyl 1-((R)-2-((4-iodoquinolin-7-yl)oxy)propanoyl)piperidine-3-carboxylate ((R,S)-1K$_{1\_I}$)

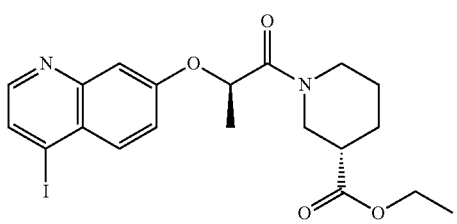 [SMILES: CCOC(=O)[C@H]1CCCN(C(=O)[C@@H](C)Oc2ccc3c(I)ccnc3c2)C1]

Intermediate (R,S)-1K$_{1\_Cl}$ (379 mg, 0.97 mmol) was dissolved in MeCN (1.5 mL) and NaI (1.45 g, 9.7 mmol) and AcCl were added (112 mg, 1.43 mmol). The suspension was heated to 80° C. for 5 min in a microwave. The mixture was diluted with DCM and washed with H$_2$O, a sat. Na$_2$S$_2$O$_3$ solution, H$_2$O, and brine. The organic layer was dried over MgSO$_4$, filtered and evaporated in vacuo to yield the desired product (R,S)-1K$_{1\_I}$ (481 mg, ~100%) as yellow solid.

$^1$H NMR (300 MHz, Chloroform-d) δ 8.28 (d, J=3.9 Hz, 1H), 7.92-7.75 (m, 2H), 7.32-7.21 (m, 2H), 5.27-5.12 (m, 1H), 4.51-4.09 (m, 3H), 4.08-3.75 (m, 2H), 3.44-2.76 (m, 2H), 2.57-2.36 (m, 1H), 2.31-1.85 (m, 1H), 1.80-1.54 (m, 3H), 1.26-1.09 (m, 5H).

MS (ES) C$_{20}$H$_{23}$IN$_2$O$_4$ requires: 482, found: 483 (M+H)$^+$, 86%.

The library building blocks shown in Table 5 were synthesized in a similar manner.

TABLE 5

| Intermediates | Structure | (M +H)$^+$, purity |
|---|---|---|
| (R,S)-1K$_{1\_Cl}$ | | MS (ES) C$_{20}$H$_{23}$ClN$_2$O$_4$ quires: 390/392, found: 391/393 (M + H)$^+$, 89% |
| (R,S)-1K$_{1\_I}$ | | MS (ES) C$_{20}$H$_{23}$IN$_2$O$_4$ requires: 482, found: 483 (M + H)$^+$, 89% |
| (R,R)-2K$_{1x}$ | | MS (ES) C$_{21}$H$_{25}$ClN$_2$O$_4$ quires: 404/406, found: 405/407 (M + H)$^+$, 100% |

3.1.10 Preparation of Intermediate Compound (S,S)-1H for the Direct Synthesis of Intermediates of formula (K)

Intermediate (S,S)-1H—Synthesis According to Method 11a (M11a)

(S)-ethyl 1-((S)-2-hydroxypropanoyl)piperidine 3-carboxylate ((S,S)-1H)

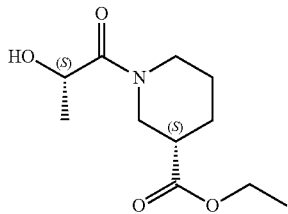

L-(+)-Lactic acid (10 g, 111 mmol) and (S)-(+)-Nipecotic acid ethyl ester (17.5 g, 111 mmol) were reacted according to M11a to yield the desired product (S,S)-1H (12.7 g, 50%) as an off-white solid.

$^1$H-NMR (300 MHz, CDCl$_3$) δ 4.59-4.40 (m, 2H), 4.20-4.09 (m, 2H), 3.84-3.62 (m, 2H), 3.15-2.70 (m, 2H), 2.50-2.40 (m, 1H), 2.21-2.08 (m, 1H), 1.80-1.51 (m, 3H), 1.32-1.25 (m, 6H).

GC-MS C$_{11}$H$_{19}$NO$_4$ requires: 229, found: 229 (M'), 93%.

3.1.11 Preparation of Intermediate Compounds of Formula (N)

Compound 4N$_1$_piperazine—Synthesis According to Method 11a (M11a)

(R)-tert butyl 4-(2-((4-(2-chloro-4-fluorophenyl) quinolin-7-yl)oxy)propanoyl)piperazine-1-carboxylate (4N$_1$_piperazine)

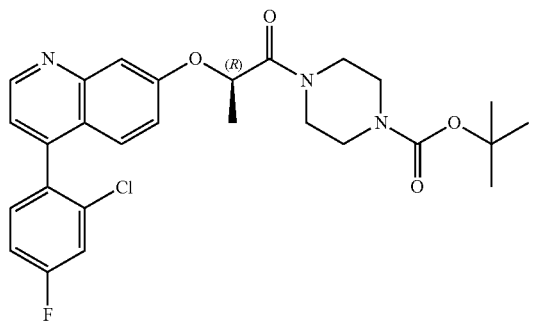

Compound (R)-4G$_1$ (100.0 mg, 0.289 mmol) and tert-butyl piperazine-1-carboxylate (80.8 mg, 0.434 mmol) were reacted according to M11a to yield the desired product 4N$_1$ piperazine after lyophilization (114 mg, 77%) as a white solid.

$^1$H NMR (400 MHz, DMSO-d$_6$) δ 8.89 (d, J=4.4 Hz, 1H), 7.69 (ddd, J=8.9, 2.6, 0.9 Hz, 1H), 7.54-7.49 (m, 1H), 7.45-7.39 (m, 1H), 7.37-7.28 (m, 3H), 7.23 (ddd, J=9.3, 2.7, 1.0 Hz, 1H), 5.59-5.49 (m, 1H), 3.78-3.66 (m, 1H), 3.62-3.50 (m, 2H), 3.45-3.20 (m, 5H), 1.51 (dd, J=6.5, 2.1 Hz, 3H), 1.46-1.39 (m, 9H).

MS (ES) C$_2$H$_{29}$ClFN$_3$O$_4$ requires: 513/515, found: 514/516 (M+H)$^+$, 96%.

Intermediate (4N$_1$_piperidine-NH$_2$)—Synthesis According to Method (M11a)

Tert butyl N-[(3S)-1-[(2R)-2-[[4-(2-chloro-4-fluorophenyl)-7-quinolyl]oxy]propanoyl]-3-piperidyl]carbamate (4N$_1$_piperidine-NH$_2$)

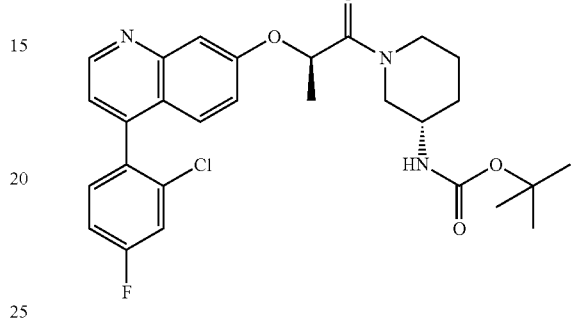

Intermediate (R)-4G$_1$ (200.0 mg, 0.578 mmol) and (S)-3-Boc-aminopiperidine (174.0 mg, 0.868 mmol) were reacted according to M11a to yield the desired product 4N$_1$_piperidine-NH$_2$ (277 mg, 91%), which was used in the following step without further purification.

$^1$H NMR (300 MHz, DMSO-d$_6$) δ 8.89 (dd, J=8.5, 4.5 Hz, 1H), 7.70 (dd, J=8.9, 2.8 Hz, 1H), 7.55-7.39 (m, 2H), 7.33-7.21 (m, 4H), 5.57-5.42 (m, 1H), 3.99-3.90 (m, 1H), 3.21-2.82 (m, 3H), 1.92-1.67 (m, 3H), 1.52 (d, J=6.4 Hz, 3H), 1.43-1.32 (m, 12H).

MS (ES) C$_{28}$H$_{31}$ClFN$_3$O$_4$ requires: 527/529, found: 528/530 (M+H)$^+$, 95%.

Compound (4N$_1$_pirrolidine-NH$_2$)—Synthesis According to Method (M11a)

Tert-butyl N-[(3R)-1-[(2R)-2-[[4-(2-chloro-4-fluorophenyl)-7-quinolyl]oxy]propanoyl]pyrrolidin-3-yl] carbamate (4N$_1$_pirrolidine-NH$_2$)

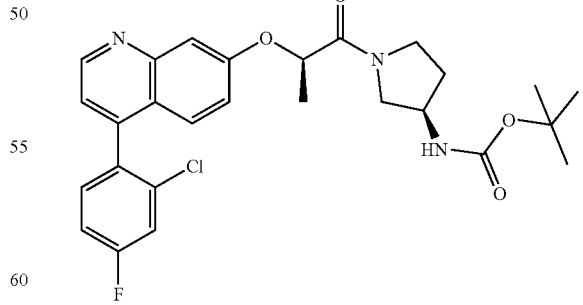

Intermediate (R)-4G$_1$ (100.0 mg, 0.289 mmol) and (R)-3-(Boc-amino)pyrrolidine hydrochloride (97.0 mg, 0.434 mmol) were reacted according to M11a to yield the desired product 4N$_1$ pyrrolidine-NH$_2$ (139 mg, 94%) as an off-white solid.

$^1$H NMR (300 MHz, DMSO-d$_6$) δ 8.89 (d, J=4.4 Hz, 1H), 7.70 (dd, J=8.9, 2.4 Hz, 1H), 7.54-7.39 (m, 2H), 7.33-7.20 (m, 4H), 5.28-5.23 (m, 1H), 4.12-3.84 (m, 2H), 3.55-3.16 (m, 2H), 2.69 (s, 1H), 2.27-1.70 (m, 3H), 1.51-1.47 (m, 3H), 1.38 (s, 9H).

3.1.12 Preparation of Compounds of Formula (P)

Compound 4P$_1$_piperazine—Synthesis According to Method 10a (M10a)

(R)-2-((4-(2-chloro-4-fluorophenyl)quinolin-7 yl)oxy)-1-(piperazin-1 yl)propan-1-one 2×TFA salt (4P$_1$_piperazine)_55

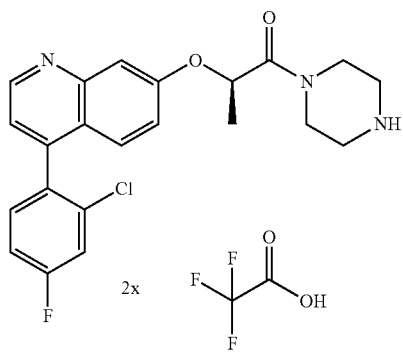 [SMILES: C[C@@H](Oc1ccc2c(-c3ccc(F)cc3Cl)ccnc2c1)C(=O)N1CCNCC1 ; O=C(O)C(F)(F)F]

Intermediate 4N$_1$_piperazine (111 mg, 0.215 mmol) was reacted according to M10a to yield the desired product 4P$_1$_piperazine (55) (135 mg, 97%) as a white solid after coevaporation with toluene.

$^1$H NMR (400 MHz, DMSO-d$_6$) δ 8.94 (d, J=4.6 Hz, 1H), 7.70 (dd, J=8.9, 2.6 Hz, 1H), 7.52 (dd, J=8.6, 6.2 Hz, 1H), 7.51-7.39 (m, 1H), 7.43-7.33 (m, 3H), 7.27 (dt, J=9.2, 2.0 Hz, 1H), 5.58 (p, J=6.7 Hz, 1H), 3.94-3.59 (m, 4H), 3.25-3.02 (m, 4H), 1.51 (dd, J=6.5, 2.3 Hz, 3H).

MS (ES) C$_{22}$H$_{21}$ClFN$_3$O$_2$ requires: 413/415, found: 414/416 (M+H)$^+$, 97%.

Compound 4P$_1$_piperidine-NH$_2$—Synthesis According to Method 10b (M10b)

(2R)-1-[(3S)-3-amino-1-piperidyl]-2-[[4-(2-chloro-4-fluoro-phenyl)-7-quinolyl]oxy]propan-1-one hydrochloride (4P$_1$_piperidine-NH$_2$)

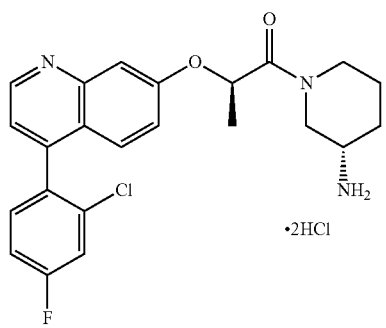 [SMILES: C[C@@H](Oc1ccc2c(-c3ccc(F)cc3Cl)ccnc2c1)C(=O)N1CCC[C@H](N)C1]

Intermediate 4N$_1$_piperidine-NH$_2$ (270 mg, 0.511 mmol) was dissolved in 0.5 mL of 1,4-dioxane with 1.3 mL of 4N HCl in 1,4-dioxane and stirred at rt over 2.5 days. The solvents were evaporated in vacuo to yield the desired product 4P$_1$_piperidine-NH$_2$ (240 mg, 99%) as a white solid (HCl salt) after freeze drying.

$^1$H NMR (300 MHz, DMSO-d$_6$) δ 9.22 (m, 1H), 8.58 (bs, 1H), 8.30 (bs, 2H), 7.81-7.46 (m, 7H), 5.64 (m, 1H), 4.46-4.41 (m, 1H), 4.14-3.67 (m, 2H), 3.28-3.08 (m, 2H), 2.87-2.79 (m, 1H), 2.08-1.83 (m, 2H), 1.63-1.53 (m, 4H).

MS (ES) C$_{23}$H$_{23}$ClFN$_3$O$_2$ requires: 427/429, found: 428/430 (M+H)$^+$, 95%.

Compound 4P$_1$ piperidine-NH$_2$—Synthesis According to Method 10b (M10b)

(2R)-1-[(3R)-3-aminopyrrolidin-1-yl]-2-[[4-(2-chloro-4-fluoro-phenyl)-7-quinolyl]oxy]propan-1-one hydrochloride (4P$_1$_piperidine-NH$_2$)

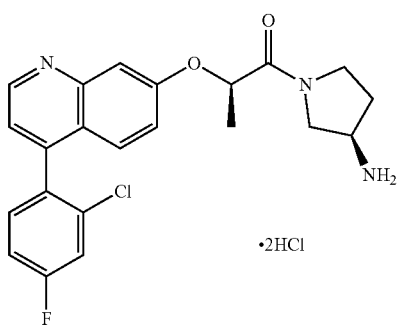 [SMILES: C[C@@H](Oc1ccc2c(-c3ccc(F)cc3Cl)ccnc2c1)C(=O)N1CC[C@@H](N)C1]

Intermediate 4N$_1$_pyrrolidine-NH$_2$ (137 mg, 0.267 mmol) was reacted with HCl in dioxane according to Method 10b to yield the desired product 4P$_1$_pyrrolidine-NH$_2$ (106 mg, 91%) as a white solid (HCl salt) after freeze drying.

$^1$H NMR (300 MHz, DMSO-d$_6$) δ 9.28-9.19 (m, 1H), 8.54-8.44 (m, 3H), 7.84-7.49 (m, 7H), 5.33-5.23 (m, 1H), 4.37-3.51 (m, 5H), 2.50-2.26 (m, 2H), 1.58 (d, J=1.6 Hz, 3H).

MS (ES) C$_{22}$H$_{21}$ClFN$_3$O$_2$ requires: 413/415, found: 414/416 (M+H)$^+$, 95%.

3.2. Preparation of Compounds of Formula (I) of the Invention

Compound 18—Synthesis According to Method 9 (M9)

2-((R)-1-((R)-2-((4-(2-chloro-4-fluorophenyl)quinolin-7-yl)oxy)propanoyl)piperidin-3-yl)acetic acid (18)

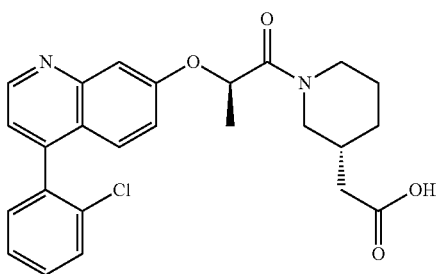

Compound 4K (48 mg, 0.096 mmol) was reacted with 2 M NaOH aq. solution according to M9 to yield the desired product 18 (33 mg, 73%) as a white solid.

$^1$H NMR (400 MHz, DMSO-$d_6$) δ 8.86 (dd, J=9.3, 4.4 Hz, 1H), 7.67 (dd, J=8.9, 2.5 Hz, 1H), 7.49 (t, J=7.4 Hz, 1H), 7.40 (ddt, J=10.7, 8.6, 2.2 Hz, 1H), 7.32-7.18 (m, 4H), 5.47 (dt, J=33.1, 7.4 Hz, 1H), 4.34-3.88 (m, 2H), 3.13-2.87 (m, 1H), 2.64-2.04 (m, 3H), 2.01-1.44 (m, 6H), 1.35-1.16 (m, 2H).

MS (ES) $C_{25}H_{24}ClFN_2O_4$ requires: 470/472, found: 471/473 (M+H)$^+$, 98%

Compound 8K—Synthesis According to Method 3a (M3a)

ethyl 2-((R)-1-((R)-2-((4-(2-ethylphenyl)quinolin-7-yl)oxy)propanoyl)piperidin-3-yl)acetate (8K)

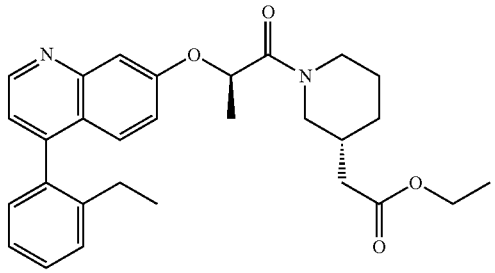 [SMILES: CCOC(=O)C[C@H]1CCCN(C(=O)[C@@H](C)Oc2ccc3c(-c4ccccc4CC)ccnc3c2)C1]

Intermediate (R,R)-2K$_{1x}$ (50 mg, 0.123 mmol) was reacted with (2-ethylphenyl)boronic acid according to M3a. The reaction was evaporated in vacuo to yield the crude desired product 8K which was used in the following step without further purification.

MS (ES) $C_{29}H_{34}N_2O_4$ requires: 474, found: 475 (M+H)$^+$, 70%.

Compound 121—Synthesis According to Method 9 (M9)

2-((R)-1-((R)-2-((4-(2-ethylphenyl)quinolin-7-yl)oxy)propanoyl)piperidin-3-yl)acetic acid (I21)

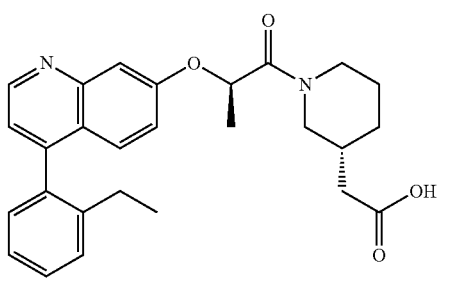 [SMILES: CCc1ccccc1-c1ccnc2cc(O[C@H](C)C(=O)N3CCC[C@H](CC(=O)O)C3)ccc12]

Crude 8K (160 mg) was reacted with 2 M NaOH aq. solution according to M9 to yield the desired product 121 (31 mg, 56% over 2 steps) as a white solid.

$^1$H NMR (300 MHz, DMSO-$d_6$) δ 8.85 (dd, J=7.8, 4.5 Hz, 1H), 7.51-7.41 (m, 2H), 7.40-7.30 (m, 1H), 7.30-7.13 (m, 5H), 5.49 (dd, J=27.5, 6.2 Hz, 1H), 4.24 (d, J=12.9 Hz, 1H), 4.17-3.94 (m, 1H), 3.22-2.54 (m, 1H), 2.44-2.07 (m, 3H), 1.92-1.58 (m, 4H), 1.51 (dd, J=16.4, 6.4 Hz, 3H), 1.33-1.19 (m, 3H), 0.99-0.82 (m, 3H).

MS (ES) $C_{27}H_{90}N_2O_4$ requires: 466, found: 467 (M+H)$^+$, 99%.

The tetrazole derivative 11 described in Table 6 was synthesized from the corresponding nitrile according to Method 12:

Compound 11—Synthesis According to Method 12 (M12)

(R)-1-((S)-3-(2H-tetrazol-5-yl)piperidin-1 yl)-2-((4-(2-chloro-4-fluorophenyl)quinolin-7-yl)oxy)propan-1-one (30)

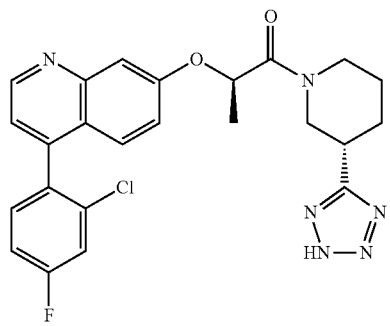 [SMILES: C[C@@H](Oc1ccc2c(-c3ccc(F)cc3Cl)ccnc2c1)C(=O)N1CCC[C@H](c2nn[nH]n2)C1]

Compound 30 (16 mg, 0.036 mmol) was dissolved in o-dichlorobenzene (360 μl) and Bu$_3$SnN$_3$ (61 mg, 0.182 mmol) was added in a sealed tube. The reaction was stirred at 125° C. for 1 h, then at rt overnight. The crude product was absorbed onto Hydromatrix and purified by flash chromatography on silica gel using a gradient of MeOH in DCM to yield the desired product 11 (12.6 mg, 73%) as an off-white solid.

$^1$H NMR (400 MHz, DMSO-$d_6$) δ 8.90 (t, J=4.2 Hz, 1H), 7.70 (ddd, J=8.9, 2.5, 1.2 Hz, 1H), 7.53 (dd, J=8.6, 6.2 Hz, 1H), 7.47-7.28 (m, 4H), 7.24 (dd, J=9.2, 2.6 Hz, 1H), 5.60 (dt, J=37.7, 6.8 Hz, 1H), 4.49 (dd, J=102.7, 12.9 Hz, 1H), 4.22 (dd, J=52.2, 13.2 Hz, 1H), 3.56-2.75 (m, 2H), 2.30-2.11 (m, 1H), 1.84 (dd, J=35.4, 18.1 Hz, 2H), 1.53 (ddd, J=18.3, 6.6, 2.3 Hz, 4H), 1.39-1.08 (m, 1H).

MS (ES) $C_{24}H_{22}ClFN_6O_2$ requires: 480/482, found: 481/483 (M+H)$^+$, 99%.

The isopropylic ester 36 was synthesized from precursor (R)-2G$_1$ as described below:

Compound 36—Synthesis According to Method 13 (M13)

(R)-isopropyl 2-((4-(2-chlorophenyl)quinolin-7 yl)oxy)propanoate FA salt (36)

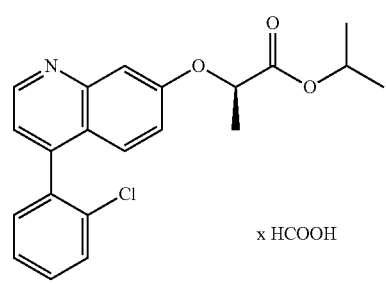 [SMILES: CC(C)OC(=O)[C@@H](C)Oc1ccc2c(-c3ccccc3Cl)ccnc2c1]

x HCOOH

Compound (R)-2G₁ (20 mg, 0.061 mmol) was dissolved in isopropanol (1 mL) and 1 drop conc. $H_2SO_4$ was added. The mixture was stirred at rt overnight, then heated to 60° C. for 4 h, and stirred at it overnight. The reaction mixture was evaporated in vacuo and the crude product was purified by flash chromatography on reverse phase silica gel using a gradient of MeCN in $H_2O$ (both solvents containing 0.05% FA) to yield the desired product 36 as a FA salt (16 mg, 73%) as a beige glue.

¹H NMR (400 MHz, DMSO-d₆) δ 8.87 (d, J=4.4 Hz, 1H), 7.66 (dt, J=7.7, 2.0 Hz, 1H), 7.58-7.48 (m, 2H), 7.43 (ddd, J=7.2, 5.0, 2.0 Hz, 1H), 7.33-7.26 (m, 3H), 7.24 (dd, J=9.2, 2.5 Hz, 1H), 5.21-5.08 (m, 1H), 4.96 (pd, J=6.2, 1.1 Hz, 1H), 1.56 (d, J=6.7 Hz, 3H), 1.23 (dd, J=6.2, 3.2 Hz, 3H), 1.14 (dd, J=6.3, 1.4 Hz, 3H).

MS (ES) $C_{21}H_{20}ClNO_3$ requires: 369/371, found: 370/372 (M+H)⁺, 98%.

Compound 98—Method 11a (M11a)

2-((R)-1-((R)-2-((2-chlor-4-(2-chloro-4-fluorophenyl)quinolin-7-yl)oxy)propanoyl)piperidin-3-yl)-N-methylacetamide (98)

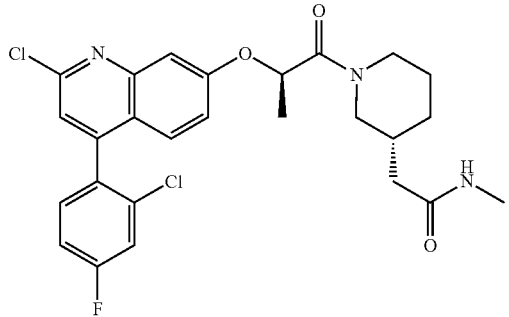 [SMILES: CNC(=O)C[C@H]1CCCN(C(=O)[C@@H](C)Oc2ccc3c(-c4ccc(F)cc4Cl)cc(Cl)nc3c2)C1]

Compound 56 (27 mg, 0.053 mmol) and 2M methylamine in THF (0.13 mL, 0.26 mmol) were reacted according to M11a to yield the desired product 98 after lyophilization (5.6 mg, 20%) as a white solid.

¹H NMR (300 MHz, Chloroform-d) δ 8.82 (t, J=4.1 Hz, 1H), 7.55-6.98 (m, 7H), 5.97 (m, 1H), 5.39-5.06 (m, 1H), 4.43-3.56 (m, 2H), 3.48-3.29 (m, 2H), 3.06-2.45 (m, 3H), 2.27 (s, 1H), 2.10-1.68 (m, 3H), 1.71-1.54 (m, 3H), 1.33-0.72 (m, 1H).

MS (ES) $C_{25}H_{25}ClFN_3O_3$ requires: 469/471, found: 470/472 (M+H)⁺, 99%.

Compound 28—Method 11d (M11d)

(R)-2-((4-(2-chloro-4-fluorophenyl)quinolin-7-yl)oxy)-1-(4-propionylpiperazin-1-yl)propan-1-one (28)

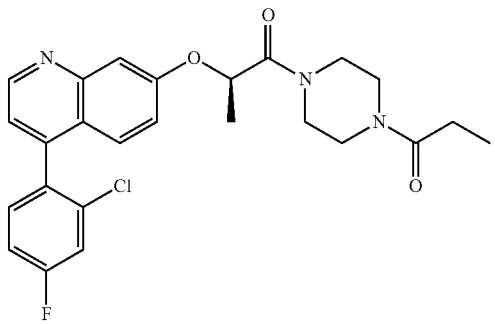 [SMILES: CCC(=O)N1CCN(C(=O)[C@@H](C)Oc2ccc3c(-c4ccc(F)cc4Cl)ccnc3c2)CC1]

To an ice-cold solution of compound 4N₁_piperazine (20.3 mg, 0.043 mmol) and DIPEA (29 μL, 0.172 mmol) in dry DCM (1 mL), propionyl chloride (4.5 μL, 0.052 mmol) in dry DCM (0.5 mL) was added dropwise. The resulting mixture was stirred at 0° C. for 30 min followed by 3 h at rt. The reaction was then diluted with DCM and washed with $H_2O$, a sat. $NaHCO_3$ solution and brine. The organic phase was dried over $MgSO_4$, filtered and evaporated in vacuo. The crude product was purified by flash chromatography on silica gel using a gradient of MeOH in DCM to yield the desired product 28 (25.5 mg, 68%) as a white solid.

¹H NMR (400 MHz, DMSO-d₆) δ 8.89 (dd, J=4.4, 0.8 Hz, 1H), 7.69 (ddd, J=8.9, 2.5, 1.1 Hz, 1H), 7.55-7.48 (m, 1H), 7.45-7.21 (m, 5H), 5.57 (s, 1H), 3.81-3.34 (m, 8H), 2.34 (d, J=8.0 Hz, 2H), 1.52 (dd, J=6.5, 2.5 Hz, 3H), 0.99 (tdd, J=7.4, 2.1, 0.8 Hz, 3H).

MS (ES) $C_{25}H_{25}ClFN_3O_3$ requires: 469/471, found: 470/472 (M+H)⁺, 96%.

Compound 209

N-hydroxy-N-[(3S)-1-[(2R)-2-[[4-(2-chloro-4-fluoro-phenyl)-7-quinolyl]oxy]propanoyl]-3-piperidyl]acetamide (209)

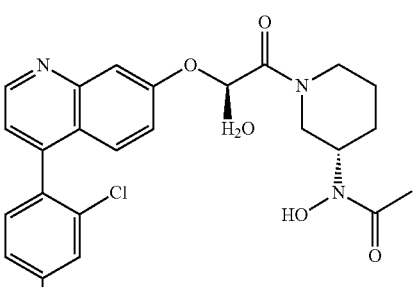

The desired compound was synthesized in three steps starting from intermediate 4P₁_piperidine-NH₂:

A solution of BPO (355 mg, 1.10 mmol) in DCM (5.5 mL) was added quickly to a mixture of intermediate 4P₁_piperidine-NH₂ (240 mg, 0.517 mmol) in buffer solution at pH 10 (NaOH/NaHCO₃, 5.5 mL) at rt. The reaction mixture was stirred for 2 h at rt, and the pH adjusted to ~10 by the addition of 10 M NaOH. Further BPO (355 mg, 1.10 mmol) was added, and the mixture stirred at rt for 18 h, upon which the reaction was deemed complete. Acetyl chloride (328 mg, 4.14 mmol) was added, and the reaction was further stirred at rt for 18 h. The mixture was extracted DCM, and the combined organic phases were washed with $Na_2CO_3$ and brine, dried over $MgSO_4$, and the solvents removed in vacuo, to yield (39 mg, 13%) of the desired intermediate N-(benzoyloxy)-acetamide, which was taken to the next step without further analysis or purification.

MS (ES) $C_{32}H_{29}ClFN_3O_5$ requires: 589/591, found: 590/592 (M+H)⁺, 91%

The crude N-(benzoyloxy)-N-(piperidin-3-yl)acetamide was treated with 3.5N $NH_3$ in MeOH (0.4 mL) at rt for 1 h. The solvents were removed in vacuo and the residue purified by preparative HPLC using $NH_4HCO_3$ as an additive to yield the desired product 209 (18 mg, 56% over 3 steps) as a white solid.

¹H NMR (300 MHz, DMSO-d₆) δ 9.83-9.58 (m, 1H), 8.88 (dd, J=8.9, 4.4 Hz, 1H), 7.68 (dd, J=8.8, 2.1 Hz, 1H), 7.57-7.38 (m, 2H), 7.36-7.19 (m, 4H), 5.61-5.46 (m, 1H), 4.36-3.96 (m, 3H), 3.02-2.63 (m, 1H), 2.02-1.97 (m, 3H), 1.87-1.77 (m, 4H), 1.58-1.22 (m, 4H).

MS (ES) $C_{23}H_{26}ClFN_3O_4$ requires: 485/487, found: 486/488 (M+H)⁺, 98%.

Compound 214—Synthesis According to Method 14 (M14)

1-tertbutyl-3-[(3R)-1-[(2R)-2-[[4-(2-chloro-4-fluorophenyl)-7-quinolyl]oxy]propanoyl]pyrrolidin-3-yl]urea_214

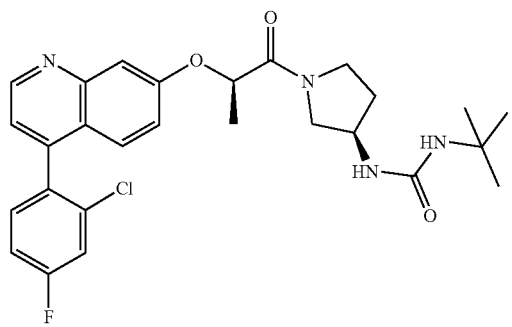 [SMILES: C[C@@H](Oc1ccc2c(-c3ccc(F)cc3Cl)ccnc2c1)C(=O)N1CC[C@@H](NC(=O)NC(C)(C)C)C1]

4P₁_pyrrolidine-NH₂·HCl (109 mg, 0.242 mmol) was dissolved in DCM (1.0 mL) at 0° C. under the atmosphere of nitrogen. DIPEA (66 mg, 0.508 mmol) was added to the suspension, followed by tert-butyl isocyanate (29 mg, 0.290 mmol), and the reaction was stirred and allowed to slowly warm up to rt over 4 h. The reaction mixture was concentrated, and the residue was purified by preparative HPLC using NH₄HCO₃ as an additive to yield the desired product 214 (65 mg, 52%) as a white solid.

¹H NMR (300 MHz, DMSO-d₆) δ 8.90-8.80 (m, 1H), 7.69 (dd, J=8.7, 1.9 Hz, 1H), 7.54-7.39 (m, 2H), 7.35-7.20 (m, 4H), 5.97-5.94 (m, 1H), 5.59-5.54 (m, 1H), 5.32-5.21 (m, 1H), 4.21-3.98 (m, 1H), 3.93-3.75 (m, 1H), 3.60-3.39 (m, 2H), 3.29-3.06 (m, 1H), 2.16-1.93 (m, 1H), 1.84-1.59 (m, 1H), 1.50-1.48 (m, 3H), 1.21-1.20 (m, 9H).

MS (ES) $C_{27}H_{30}ClFN_4O_3$ requires: 512/514, found: 513/515 (M+H)⁺, 95%.

The compounds exemplifying the invention are described in Table 6.

When not otherwise specified, it should be assumed that M7, M11a, M11b, M11c, M12 or M13, optionally followed by M9, M10a, M10b, M11d, or M14 were used to yield the target compound. Tetrazoles can be obtained from the corresponding nitriles as exemplified in M8. Piperazines carbamates N could also be further modified according to M10a to obtain amines P followed by M11a, M11b, M11c or M11d to yield amides of formula Q. Primary amines such as compounds of formula P_piperidine-NH₂ could be further modified to obtain N-hydroxyacetamides of formula R, using the multi-step method described for compound 209. Primary amines such as compounds of formula P_pyrrolidine could be further modified to obtain ureas of formula S, by reacting with tert-butyl-isocyanate as described for compound 214. It should be apparent to a person skilled in the art that reaction conditions such as temperature, dilution, reaction time or work-up procedures, including pH adjustment, are dependent on reaction partners and functional group compatibility and could vary from compound to compound.

Generally, enantiomeric excess (ee) of the compounds (esters F and K, carboxylic acids G) was not measured, and was assumed equal to the value determined by chiral HPLC for the final compounds (usually carboxylic acids L). Chiral separation of the diastereomeric mixture was occasionally required to improve ee, particularly when any of the hydroxy-quinolines of formula D were alkylated via M7. Use of HATU as a coupling reagent (M11a) usually resulted in lower ee as compared to the coupling mixture EDC·HCl/HOBt·xH₂O (M11b).

TABLE 6

Compounds of formula (I) of the invention

| Ex | Structure | BB | ¹H-NMR | LC purity % ee |
|---|---|---|---|---|
| 1 | 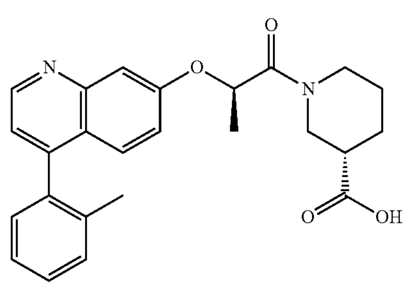 [SMILES: Cc1ccccc1-c1ccnc2cc(O[C@H](C)C(=O)N3CCC[C@H](C(=O)O)C3)ccc12] | 3D₁ + (S,S)-1H + M9 | (300 MHz, DMSO-d₆) δ 12.50 (s, 1H), 8.90 (t, J = 4.2 Hz, 1H), 7.54-7.19 (m, 8H), 5.56-5.54 (m, 1H), 4.49-3.87 (m, 2H), 3.59-3.10 (m, 2H), 3.08-2.74 (m, 1H), 2.48-2.25 (m, 1H), 2.14-1.77 (m, 4H), 1.76-1.60 (m, 2H), 1.54 (dd, J = 10.2, 6.4 Hz, 3H). | 99% |

TABLE 6-continued

Compounds of formula (I) of the invention

| Ex | Structure | BB | ¹H-NMR | LC purity % ee |
|----|-----------|----|--------|----------------|
| 2 | 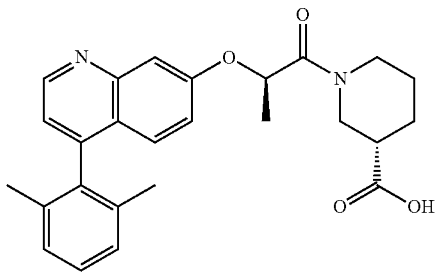 [SMILES: Cc1cccc(C)c1-c1ccnc2cc(O[C@H](C)C(=O)N3CCC[C@H](C(=O)O)C3)ccc12] | 4 | (300 MHz, DMSO-d₆) δ 12.41 (s, 1H), 8.88 (t, J = 4.5 Hz, 1H), 7.35-7.08 (m, 7H), 5.60-5.47 (m, 1H), 4.44-3.84 (m, 2H), 3.65-2.74 (m, 2H), 2.46-2.21 (m, 1H), 2.19-1.74 (m, 1H), 1.88-1.77 (m, 6H), 1.71-1.55 (m, 2H), 1.50 (dd, J = 10.5, 6.3 Hz, 3H), 1.40-1.09 (m, 1H). | 95% |
| 3 | 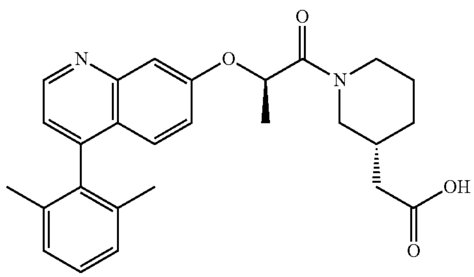 [SMILES: Cc1cccc(C)c1-c1ccnc2cc(O[C@H](C)C(=O)N3CCC[C@H](CC(=O)O)C3)ccc12] | 6 | (300 MHz, Chloroform-d) δ 8.88-8.74 (m, 1H), 7.45 (s, 1H), 7.31-7.20 (m, 3H), 7.17-7.07 (m, 3H), 5.43-5.07 (m, 1H), 4.12-3.67 (m, 3H), 3.38-2.93 (m, 2H), 2.58-2.25 (m, 2H), 2.23-2.05 (m, 1H), 1.81 (d, J = 5.6 Hz, 6H), 1.90-1.29 (m, 6H). | 98% |
| 4 | 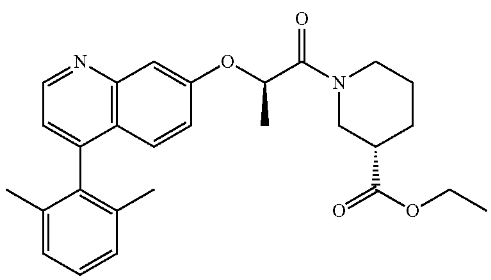 [SMILES: CCOC(=O)[C@H]1CCCN(C(=O)[C@@H](C)Oc2ccc3c(-c4c(C)cccc4C)ccnc3c2)C1] | 6D₁ + (S,S)-1H | (300 MHz, Chloroform-d) δ 8.82 (t, J = 4.1 Hz, 1H), 7.33 (d, J = 2.5 Hz, 1H), 7.27-7.15 (m, 2H), 7.15-6.98 (m, 4H), 5.19 (dq, J = 16.1, 6.6 Hz, 1H), 4.54-4.21 (m, 1H), 4.08 (dq, J = 23.5, 7.0, 6.5 Hz, 2H), 3.93-3.24 (m, 1H), 3.03 (ddd, J = 38.7, 13.6, 10.2 Hz, 1H), 2.87-2.56 (m, 2H), 2.37 (dtd, J = 82.7, 10.4, 4.5 Hz, 1H), 2.10 (s, 1H), 1.82 (d, J = 3.0 Hz, 6H), 1.80-1.55 (m, 4H), 1.44-1.08 (m, 1H), 1.16 (t, J = 7.1 Hz, 3H). | 95% |
| 5 | 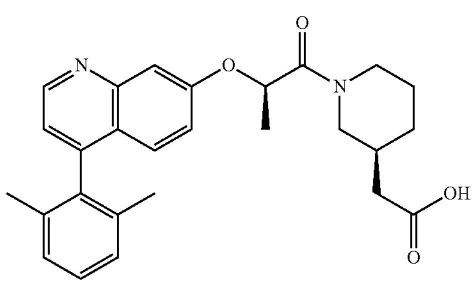 [SMILES: Cc1cccc(C)c1-c1ccnc2cc(O[C@H](C)C(=O)N3CCC[C@@H](CC(=O)O)C3)ccc12] | (R)-6G₁ + M11a + M9 | (300 MHz, Chloroform-d) δ 9.30 (s, 1H), 8.83 (dd, J = 28.5, 4.8 Hz, 1H), 7.38-7.04 (m, 7H), 5.41-5.05 (m, 1H), 4.39 (d, J = 13.7 Hz, 1H), 4.34-3.79 (m, 1H), 3.26-3.12 (m, 1H), 2.90-2.64 (m, 1H), 2.55 (dd, J = 16.1, 4.0 Hz, 1H), 2.33 (dd, J = 16.3, 10.2 Hz, 1H), 2.22-2.02 (m, 1H), 2.03-1.85 (m, 1H), 1.83-1.74 (m, 7H), 1.72-1.41 (m, 4H), 1.34 (d, J = 12.3 Hz, 1H). | 94% |
| 6 | 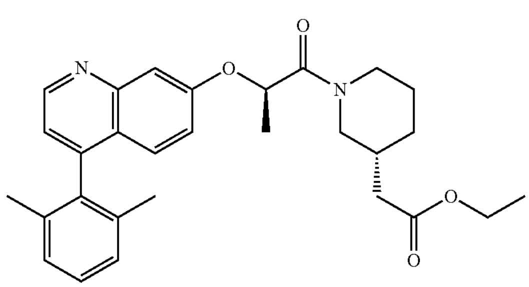 [SMILES: CCOC(=O)C[C@H]1CCCN(C(=O)[C@@H](C)Oc2ccc3c(-c4c(C)cccc4C)ccnc3c2)C1] | (R)-6G₁ | (300 MHz, Chloroform-d) δ 8.82 (dd, J = 9.8, 4.5 Hz, 1H), 7.40-7.02 (m, 7H), 5.30-5.11 (m, 1H), 4.56-3.45 (m, 5H), 3.12-2.52 (m, 2H), 2.32-1.98 (m, 2H), 1.93-1.74 (m, 7H), 1.71-1.54 (m, 4H), 1.50-1.06 (m, 5H). | 91% |

TABLE 6-continued

Compounds of formula (I) of the invention

| Ex | Structure | BB | ¹H-NMR | LC purity % ee |
|---|---|---|---|---|
| 7 | 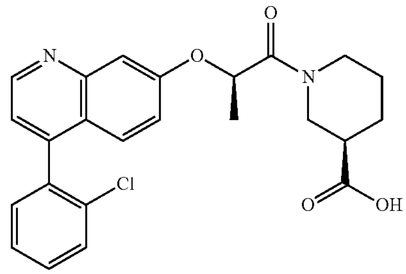 [SMILES: C[C@@H](Oc1ccc2c(-c3ccccc3Cl)ccnc2c1)C(=O)N1CCC[C@@H](C(=O)O)C1] | 71 | (400 MHz, DMSO-$d_6$) δ 8.89 (t, J = 4.6 Hz, 1H), 7.73-7.65 (m, 1H), 7.60-7.50 (m, 2H), 7.44 (dd, J = 7.3, 1.9 Hz, 1H), 7.37-7.26 (m, 3H), 7.22 (dd, J = 9.2, 2.6 Hz, 1H), 5.67-5.40 (m, 1H), 4.47-3.94 (m, 2H), 3.20 (s, 2H), 2.82 (t, J = 12.0 Hz, 1H), 2.63-2.16 (m, 1H), 2.08-1.90 (m, 1H), 1.82-1.56 (m, 2H), 1.54-1.30 (m, 3H). | 98% ee86% |
| 8 | 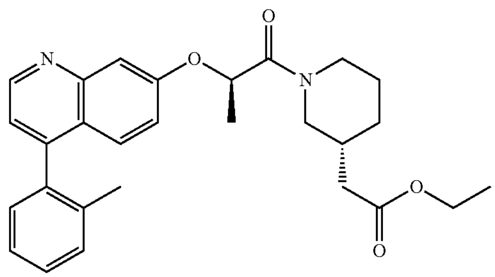 [SMILES: CCOC(=O)C[C@H]1CCCN(C(=O)[C@@H](C)Oc2ccc3c(-c4ccccc4C)ccnc3c2)C1] | (R)-3G₁ | (400 MHz, DMSO-$d_6$) δ 8.85 (dd, J = 7.1, 4.4 Hz, 1H), 7.47-7.16 (m, 8H), 5.61-5.35 (m, 1H), 4.19 (d, J = 11.6 Hz, 1H), 4.11-3.91 (m, 2H), 3.19-2.90 (m, 1H), 2.71-2.10 (m, 3H), 2.01-1.95 (m, 3H), 1.87-1.46 (m, 6H), 1.32-1.20 (m, 3H), 1.14 (qd, J = 7.0, 2.0 Hz, 3H). | 100% |
| 9 | 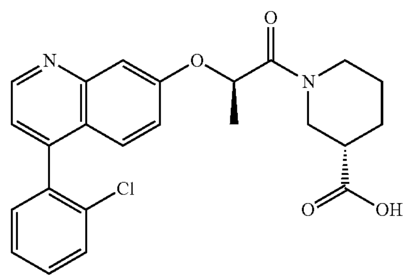 | 2D₁ + (S,S)-1H + M9 | (400 MHz, DMSO-$d_6$) δ 8.88 (t, J = 4.9 Hz, 1H), 7.68 (dt, J = 7.6, 1.3 Hz, 1H), 7.61-7.50 (m, 2H), 7.44 (dd, J = 7.2, 2.0 Hz, 1H), 7.38-7.25 (m, 3H), 7.22 (dd, J = 9.1, 2.4 Hz, 1H), 5.56 (q, J = 6.5 Hz, 1H), 4.45-3.83 (m, 2H), 3.53-3.08 (m, 2H), 3.01-2.73 (m, 1H), 2.43-2.23 (m, 1H), 2.10-1.86 (m, 1H), 1.86-1.29 (m, 2H), 1.55-1.45 (m, 3H). | 97% ee85% |
| 10 | 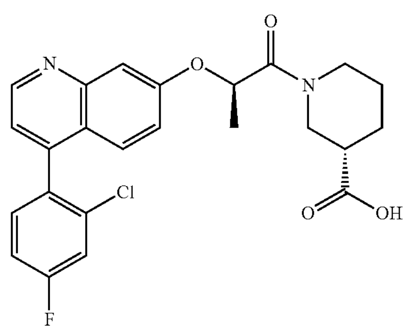 [SMILES: C[C@@H](Oc1ccc2c(-c3ccc(F)cc3Cl)ccnc2c1)C(=O)N1CCC[C@H](C(=O)O)C1] | 27 | (400 MHz, DMSO-$d_6$) δ 8.88 (t, J = 4.9 Hz, 1H), 7.69 (ddd, J = 9.0, 2.7, 1.4 Hz, 1H), 7.52 (dd, J = 8.6, 6.2 Hz, 1H), 7.42 (tt, J = 6.7, 5.9, 2.4 Hz, 1H), 7.37-7.26 (m, 3H), 7.22 (dd, J = 9.3, 2.5 Hz, 1H), 5.61-5.50 (m, 1H), 4.47-3.83 (m, 2H), 3.22-2.73 (m, 2H), 2.44-2.21 (m, 2H), 2.10-1.88 (m, 1H), 1.84-1.27 (m, 2H), 1.50 (dd, J = 13.5, 6.6 Hz, 3H). | 98% |
| 11 | 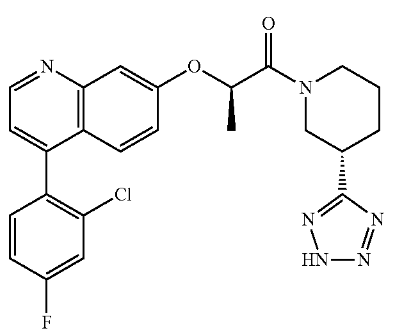 [SMILES: C[C@@H](Oc1ccc2c(-c3ccc(F)cc3Cl)ccnc2c1)C(=O)N1CCC[C@H](c2nn[nH]n2)C1] | 30 | (400 MHz, DMSO-$d_6$) δ 8.90 (t, J = 4.2 Hz, 1H), 7.70 (ddd, J = 8.9, 2.5, 1.2 Hz, 1H), 7.53 (dd, J = 8.6, 6.2 Hz, 1H), 7.47-7.28 (m, 4H), 7.24 (dd, J = 9.2, 2.6 Hz, 1H), 5.60 (dt, J = 37.7, 6.8 Hz, 1H), 4.49 (dd, J = 102.7, 12.9 Hz, 1H), 4.22 (dd, J = 52.2, 13.2 Hz, 1H), 3.56-2.75 (m, 2H), 2.30-2.11 (m, 1H), 1.84 (dd, J = 35.4, 18.1 Hz, 2H), 1.53 (ddd, J = 18.3, 6.6, 2.3 Hz, 4H), 1.39-1.08 (m, 1H). | 99% |

TABLE 6-continued

Compounds of formula (I) of the invention

| Ex | Structure | BB | ¹H-NMR | LC purity % ee |
|---|---|---|---|---|
| 12 | 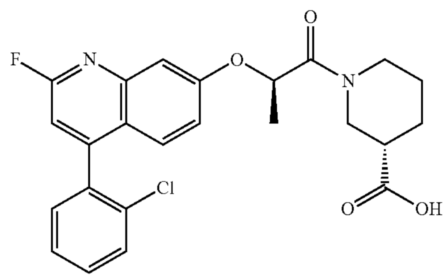 [SMILES: C[C@@H](Oc1ccc2c(-c3ccccc3Cl)cc(F)nc2c1)C(=O)N1CCC[C@H](C(=O)O)C1] | (R)-2G₆ + M11a + M10a | (400 MHz, DMSO-d₆) δ 12.47 (br. s, 1H), 7.70 (dt, J = 7.9, 1.3 Hz, 1H), 7.63-7.47 (m, 3H), 7.31-7.15 (m, 4H), 5.57 (q, J = 6.3 Hz, 1H), 4.44-3.75 (m, 2H), 3.22-2.62 (m, 2H), 2.46-2.22 (m, J = 1.9 Hz, 1H), 2.35-2.23 (m, 1H), 2.07-1.89 (m, 1H), 1.82-1.28 (m, 5H). | 94% |
| 13 | 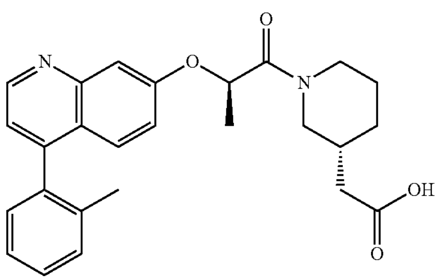 [SMILES: Cc1ccccc1-c1ccnc2cc(O[C@H](C)C(=O)N3CCC[C@H](CC(=O)O)C3)ccc12] | 8 | (400 MHz, DMSO-d₆) δ 12.15 (br. s, 1H), 8.83 (s, 1H), 7.52-7.09 (m, 8H), 5.58-5.34 (m, J = 33.9 Hz, 1H), 4.32-3.91 (m, 2H), 3.14-2.61 (m, 1H), 2.65 (s, 2H), 2.28-2.03 (m, 2H), 1.95 (s, 3H), 1.90-1.40 (m, 5H), 1.23 (s, 2H). | 99% |
| 14 | 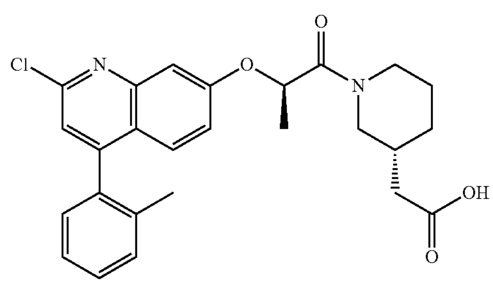 [SMILES: Cc1ccccc1-c1cc(Cl)nc2cc(O[C@H](C)C(=O)N3CCC[C@H](CC(=O)O)C3)ccc12] | (R)-3G₁ | (300 MHz, Chloroform-d) δ 8.79 (d, J = 4.4 Hz, 1H), 7.40-7.03 (m, 8H), 5.20 (dq, J = 13.0, 6.8 Hz, 1H), 4.37 (dd, J = 55.5, 13.3 Hz, 1H), 4.20-3.96 (m, 2H), 3.92-3.20 (m, 1H), 3.17-2.13 (m, 3H), 2.08-1.89 (m, 4H), 1.81-1.27 (m, 8H), 1.16 (td, J = 7.1, 1.2 Hz, 3H). | 97% |
| 15 | 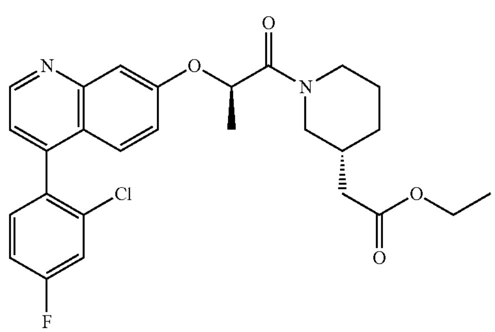 [SMILES: CCOC(=O)C[C@H]1CCCN(C(=O)[C@@H](C)Oc2ccc3c(-c4ccc(F)cc4Cl)ccnc3c2)C1] | (R)-4G₁ | 400 MHz, DMSO-d₆) δ 8.88 (dd, J = 7.3, 4.4 Hz, 1H), 7.73-7.63 (m, 1H), 7.52 (dd, J = 8.6, 6.2 Hz, 1H), 7.46-7.38 (m, 1H), 7.34-7.20 (m, 4H), 5.65-5.35 (m, 1H), 4.20 (d, J = 13.1 Hz, 2H), 4.11-3.92 (m, 3H), 3.19-2.60 (m, 1H), 2.36-2.12 (m, 2H), 1.91-1.45 (m, 8H), 1.19-1.09 (m, 3H). | 95% |
| 16 | 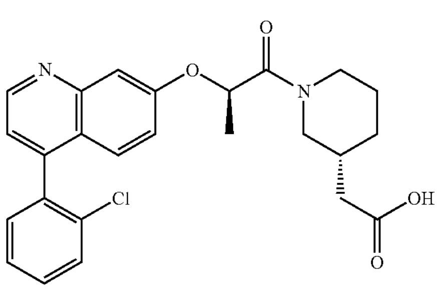 [SMILES: C[C@@H](Oc1ccc2c(-c3ccccc3Cl)ccnc2c1)C(=O)N1CCC[C@H](CC(=O)O)C1] | (R)-2G₁ + M11b + M9 | (400 MHz, DMSO-d₆) δ 8.86 (dd, J = 8.8, 4.4 Hz, 1H), 7.66 (d, J = 7.7 Hz, 1H), 7.58-7.48 (m, 2H), 7.42 (d, J = 7.3 Hz, 1H), 7.33-7.16 (m, 4H), 5.61-5.36 (m, 1H), 4.35-3.88 (m, 2H), 3.00 (d, J = 58.4 Hz, 2H), 2.14 (d, J = 36.0 Hz, 2H), 1.93-1.42 (m, 6H), 1.23 (s, 2H). | 97% |

TABLE 6-continued

Compounds of formula (I) of the invention

| Ex | Structure | BB | ¹H-NMR | LC purity % ee |
|---|---|---|---|---|
| 17 | 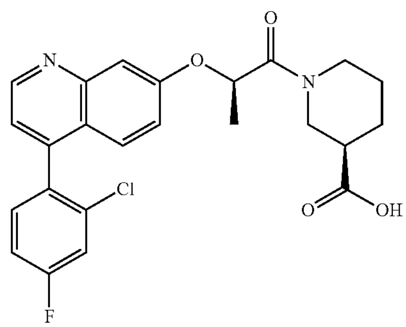 [SMILES: C[C@@H](Oc1ccc2c(-c3ccc(F)cc3Cl)ccnc2c1)C(=O)N1CCC[C@@H](C(=O)O)C1] | 71 | (300 MHz, DMSO-d₆) δ 12.57 (s, 1H), 8.95 (t, J = 4.1 Hz, 1H), 7.76 (dd, J = 9.0, 2.5 Hz, 1H), 7.65-7.24 (m, 6H), 5.73-5.50 (m, 1H), 4.50-3.99 (m, 2H), 3.34-3.14 (m, 2H), 2.99-2.76 (m, 1H), 2.69-2.21 (m, 2H), 2.16-1.61 (m, 1H), 1.57 (dd, J = 6.5, 2.8 Hz, 3H), 1.49-1.27 (m, 1H). | 100% |
| 18 | 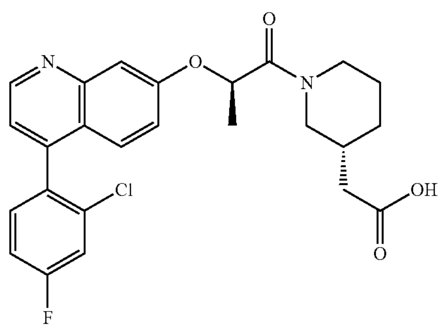 [SMILES: C[C@@H](Oc1ccc2c(-c3ccc(F)cc3Cl)ccnc2c1)C(=O)N1CCC[C@H](CC(=O)O)C1] | 15 | (400 MHz, DMSO-d₆) δ 8.86 (dd, J = 9.3, 4.4 Hz, 1H), 7.67 (dd, J = 8.9, 2.5 Hz, 1H), 7.49 (t, J = 7.4 Hz, 1H), 7.40 (ddt, J = 10.7, 8.6, 2.2 Hz, 1H), 7.32-7.18 (m, 4H), 5.47 (dt, J = 33.1, 7.4 Hz, 1H), 4.34-3.88 (m, 2H), 3.13-2.87 (m, 1H), 2.64-2.04 (m, 3H), 2.01-1.44 (m, 6H), 1.35-1.16 (m, 2H). | 99% |
| 19 | 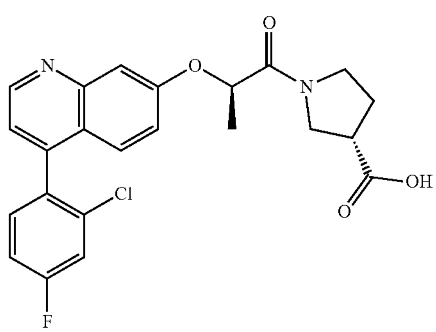 [SMILES: C[C@@H](Oc1ccc2c(-c3ccc(F)cc3Cl)ccnc2c1)C(=O)N1CC[C@H](C(=O)O)C1] | 75 | (300 MHz, Chloroform-d) δ 8.88 (d, J = 4.5 Hz, 1H), 7.69 (dd, J = 8.9, 2.5 Hz, 1H), 7.52 (dd. J = 8.7, 6.2 Hz, 1H), 7.41 (td, J = 8.5, 2.5 Hz, 1H), 7.34-7.19 (m, 4H), 5.33-5.23 (m, 1H), 3.92-3.21 (m, 5H), 3.17-2.99 (m, 1H), 2.23-1.88 (m, 1H), 1.55-1.44 (m, 3H). | 98% |
| 20 | 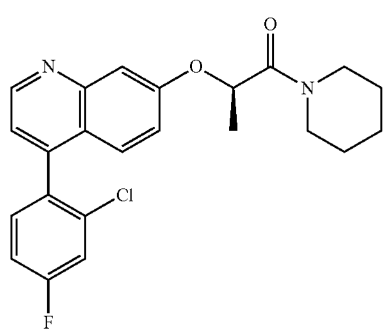 [SMILES: C[C@@H](Oc1ccc2c(-c3ccc(F)cc3Cl)ccnc2c1)C(=O)N1CCCCC1] | 4G₁ | (400 MHz, DMSO-d₆) δ 8.88 (dd, J = 4.4, 0.7 Hz, 1H), 7.81-7.63 (m, 1H), 7.52 (ddt, J = 8.2, 6.2, 0.9 Hz, 1H), 7.46-7.38 (m, 1H), 7.34-7.26 (m, 3H), 7.22 (dd, J = 9.1, 2.6 Hz, 1H), 5.51 (p, J = 6.6 Hz, 1H), 3.72-3.39 (m, 4H), 1.72-1.37 (m, 9H). | 100% |

TABLE 6-continued

Compounds of formula (I) of the invention

| Ex | Structure | BB | $^1$H-NMR | LC purity % ee |
|---|---|---|---|---|
| 21 | 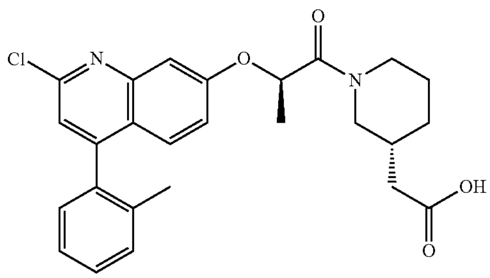 [SMILES: Cc1ccccc1-c1cc(Cl)nc2cc(O[C@H](C)C(=O)N3CCC[C@H](CC(=O)O)C3)ccc12] | 3G$_3$ + M11a + M9 | (300 MHz, DMSO-d$_6$) δ 12.19 (s, 1H), 7.53-7.16 (m, 8H), 5.64-5.44 (m, 1H), 4.37-3.84 (m, 2H), 3.18-2.89 (m, 1H), 2.64 (s, 1H), 2.23 (t, J = 4.7 Hz, 1H), 2.14 (dd, J = 6.9, 4.1 Hz, 1H), 2.01 (s, 3H), 1.80 (s, 2H), 1.67 (s, 1H), 1.53 (dd, J = 16.3, 6.4 Hz, 3H), 1.26 (s, 1H). | 99% |
| 22 | 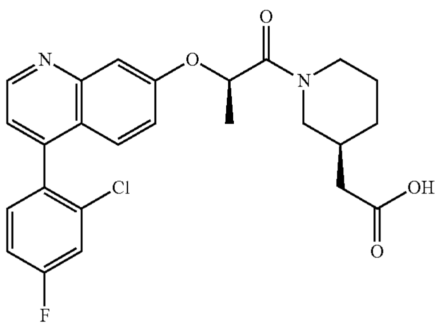 [SMILES: C[C@@H](Oc1ccc2c(-c3ccc(F)cc3Cl)ccnc2c1)C(=O)N1CCC[C@@H](CC(=O)O)C1] | 89 | (300 MHz, DMSO-d$_6$) δ 12.25 (s, 1H), 8.95 (dd, J = 5.9, 4.4 Hz, 1H), 7.76 (dd, J = 8.9, 2.5 Hz, 1H), 7.63-7.44 (m, 2H), 7.41-7.33 (m, 3H), 7.29 (dd, J = 9.1, 2.6 Hz, 1H), 5.54 (dt, J = 10.7, 7.0 Hz, 1H), 4.20 (ddd, J = 52.0, 31.3, 13.1 Hz, 2H), 3.30-2.81 (m, 1H), 2.68-2.56 (m, 1H), 2.39-1.66 (m, 5H), 1.63-1.51 (m, 3H), 1.48-1.20 (m, 2H). | 90% |
| 23 | 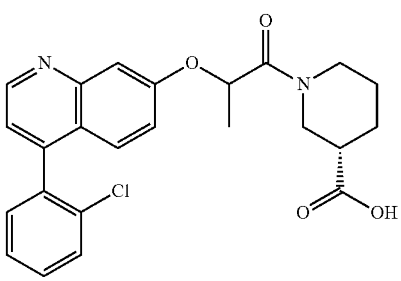 [SMILES: CC(Oc1ccc2c(-c3ccccc3Cl)ccnc2c1)C(=O)N1CCC[C@H](C(=O)O)C1] | 2D$_1$ + (S,S)-1H + M9 | (300 MHz, Methanol-d4) δ 8.77-8.66 (m, 1H), 7.57-7.47 (m, 1H), 7.52-7.11 (m, 7H), 5.55-5.26 (m, 1H), 4.53-3.67 (m, 2H), 3.58-2.58 (m, 1H), 2.54-2.21 (m, 1H), 2.15-1.29 (m, 7H) | 91%-racemisation occurred |
| 24 | 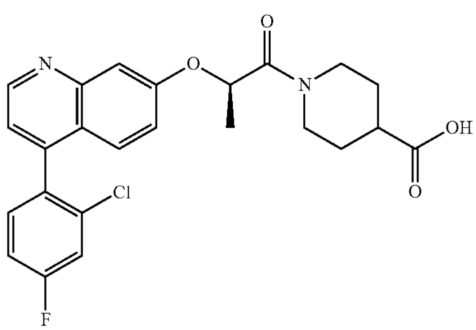 [SMILES: C[C@@H](Oc1ccc2c(-c3ccc(F)cc3Cl)ccnc2c1)C(=O)N1CCC(C(=O)O)CC1] | 58 | (300 MHz, DMSO-d$_6$) δ 12.32 (s, 1H), 8.86-8.76 (m, 1H), 7.63 (dd, J = 8.9, 2.6 Hz, 1H), 7.51-7.29 (m, 2H), 7.30-7.11 (m, 4H), 5.56-4.75 (m, 1H), 4.24-3.88 (m, 1H), 3.24-2.35 (m, 3H), 2.50 (s, 1H), 1.97-0.74 (m, 7H). | 100% |
| 25 | 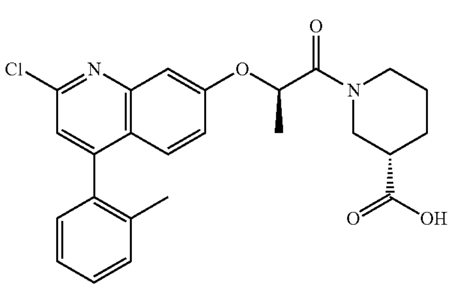 [SMILES: Cc1ccccc1-c1cc(Cl)nc2cc(O[C@H](C)C(=O)N3CCC[C@H](C(=O)O)C3)ccc12] | 3D$_3$ + (S,S)-1H + M9 | (300 MHz, DMSO-d$_6$) δ 12.50 (s, 1H), 7.47-7.17 (m, 8H), 5.56 (dd, J = 6.6, 4.0 Hz, 1H), 4.36-3.84 (m, 2H), 3.32 (s, 1H), 3.00-2.78 (m, 1H), 2.43-2.20 (m, 1H), 1.98 (d, J = 1.8 Hz, 4H), 1.80-1.42 (m, 5H), 1.27 (d, J = 25.9 Hz, 1H). | 98% |

TABLE 6-continued

Compounds of formula (I) of the invention

| Ex | Structure | BB | $^1$H-NMR | LC purity % ee |
|---|---|---|---|---|
| 26 | 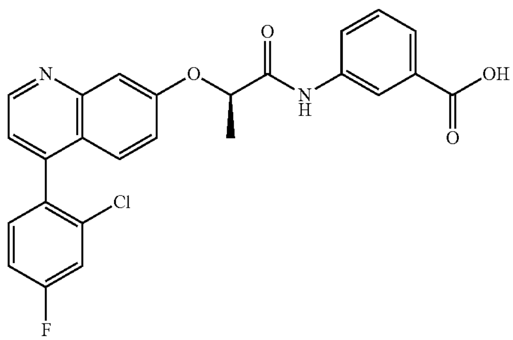 [SMILES: C[C@@H](Oc1ccc2c(-c3ccc(F)cc3Cl)ccnc2c1)C(=O)Nc1cccc(C(=O)O)c1] | (R)-4G$_1$ + M11a + M9 | (300 MHz, DMSO-d$_6$) δ 13.06 (s, 1H), 10.59 (d, J = 4.0 Hz, 1H), 8.91 (dd, J = 4.4, 1.7 Hz, 1H), 8.32 (q, J = 2.2 Hz, 1H), 7.98-7.86 (m, 1H), 7.79-7.64 (m, 2H), 7.60-7.41 (m, 4H), 7.39 (d, J = 2.1 Hz, 2H), 7.33 (dd, J = 4.4, 1.0 Hz, 1H), 5.19 (q, J = 6.5 Hz, 1H), 1.74-1.65 (m, 3H). | 100% |
| 27 | 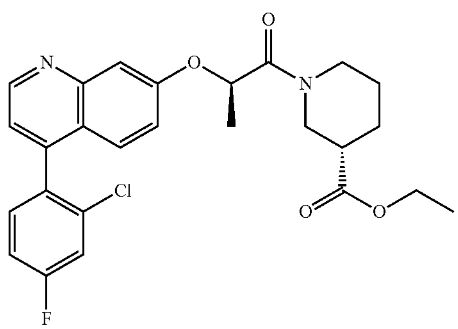 [SMILES: CCOC(=O)[C@H]1CCCN(C(=O)[C@@H](C)Oc2ccc3c(-c4ccc(F)cc4Cl)ccnc3c2)C1] | 4D$_1$ + (S,S)-1H or (R)-4G$_1$ | (400 MHz, DMSO-d$_6$) δ 8.88 (t, J = 5.2 Hz, 1H), 7.74-7.64 (m, 1H), 7.51 (ddd, J = 9.4, 6.1, 3.5 Hz, 1H), 7.42 (tt, J = 8.5, 2.5 Hz, 1H), 7.36-7.26 (m, 3H), 7.22 (dt, J = 9.3, 2.0 Hz, 1H), 5.69-5.42 (m, 1H), 4.32-3.42 (m, 5H), 3.27-2.92 (m, 2H), 2.65-2.28 (m, 1H), 2.09-1.85 (m, 1H), 1.82-1.55 (m, 2H), 1.51 (dd, J = 14.1, 6.4 Hz, 3H), 1.15 (t, J = 7.1 Hz, 3H). | 95% |
| 28 | 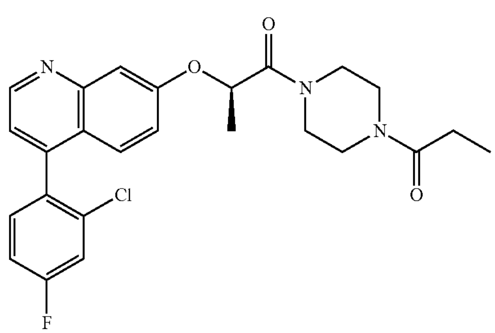 [SMILES: CCC(=O)N1CCN(C(=O)[C@@H](C)Oc2ccc3c(-c4ccc(F)cc4Cl)ccnc3c2)CC1] | 1P | (400 MHz, DMSO-d$_6$) δ 8.89 (dd, J = 4.4, 0.8 Hz, 1H), 7.69 (ddd, J = 8.9, 2.5, 1.1 Hz, 1H), 7.55-7.48 (m, 1H), 7.45-7.21 (m, 5H), 5.57 (s, 1H), 3.81-3.34 (m, 8H), 2.34 (d, J = 8.0 Hz, 2H), 1.52 (dd, J = 6.5, 2.5 Hz, 3H), 0.99 (tdd, J = 7.4, 2.1, 0.8 Hz, 3H). | 96% |
| 29 | 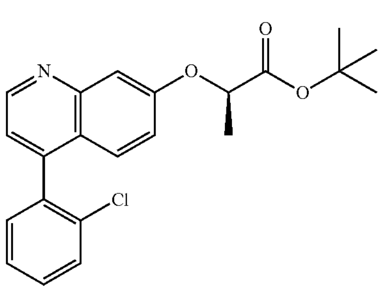 [SMILES: C[C@@H](Oc1ccc2c(-c3ccccc3Cl)ccnc2c1)C(=O)OC(C)(C)C] | (R)-F$_{1x}$ | (400 MHz, Chloroform-d) δ 8.88 (d, J = 4.5 Hz, 1H), 7.58-7.53 (m, 1H), 7.47-7.37 (m, 4H), 7.35-7.29 (m, 1H), 7.24-7.15 (m, 2H), 4.86 (qd, J = 6.8, 4.3 Hz, 1H), 1.67 (d, J = 6.8 Hz, 3H), 1.48 (s, 9H). | 95% |

TABLE 6-continued

Compounds of formula (I) of the invention

| Ex | Structure | BB | ¹H-NMR | LC purity % ee |
|---|---|---|---|---|
| 30 | 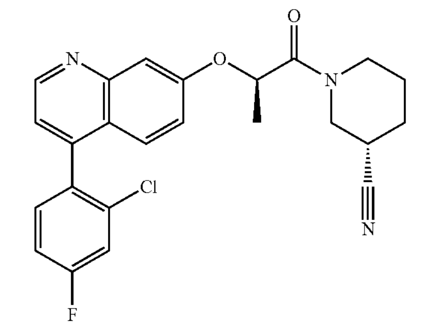 [SMILES: C[C@@H](Oc1ccc2c(-c3ccc(F)cc3Cl)ccnc2c1)C(=O)N1CCC[C@H](C#N)C1] | (R)-4G$_1$ | (300 MHz, Chloroform-d) δ 8.81 (d, J = 4.5 Hz, 1H), 7.38 (td, J = 11.5, 9.3, 5.5 Hz, 2H), 7.30-7.00 (m, 5H), 5.26-5.10 (m, 1H), 4.26-3.82 (m, 1H), 3.77-3.68 (m, 1H), 3.42 (tdd, J = 29.1, 13.9, 7.8 Hz, 2H), 2.98-2.48 (m, 1H), 1.99 (s, 1H), 1.80 (d, J = 12.7 Hz, 2H), 1.67-1.25 (m, 4H). | 98% |
| 31 | 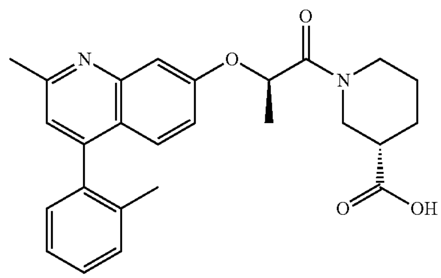 [SMILES: Cc1cc(-c2ccccc2C)c2ccc(O[C@H](C)C(=O)N3CCC[C@H](C(=O)O)C3)cc2n1] | (R)-3G$_5$ + M11a + M10a | (400 MHz, DMSO-d$_6$) δ 7.63-7.19 (m, 8H), 5.56 (q, J = 6.7 Hz, 1H), 4.32-3.79 (m, 2H), 3.51-3.12 (m, 1H), 2.83 (s, 4H), 2.44-2.26 (m, 2H), 2.02 (s, 4H), 1.79-1.47 (m, 5H). | 97% |
| 32 | 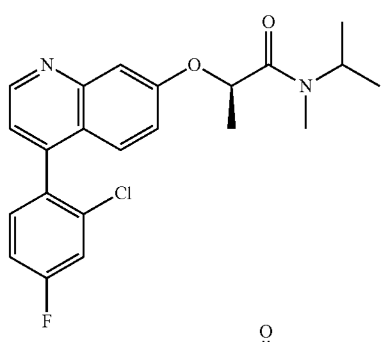 | (R)-4G$_1$ | (300 MHz, Chloroform-d) δ 8.89-8.75 (m, 1H), 7.43-7.00 (m, 7H), 5.26-5.06 (m, 1H), 4.90-4.16 (m, 1H), 2.84 (dd, J = 48.2, 1.4 Hz, 3H), 1.60 (ddd, J = 6.6, 5.4, 1.1 Hz, 3H), 1.26-0.98 (m, 6H). | 99% |
| 33 | 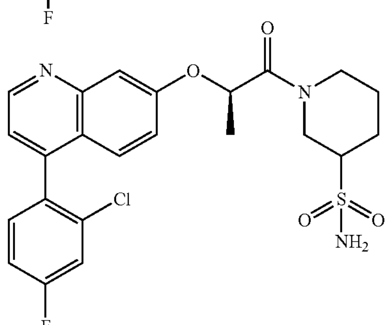 | (R)-4G$_1$ | (300 MHz, Chloroform-d) δ 8.80 (d, J = 4.8 Hz, 1H), 7.48-7.21 (m, 4H), 7.17-7.01 (m, 3H), 5.80-5.05 (m, 2H), 4.67-4.21 (m, 2H), 3.98-3.23 (m, 2H), 3.17-2.69 (m, 1H), 2.61-1.71 (m, 2H), 1.69-1.12 (m, 4H). | 100% |
| 34 | 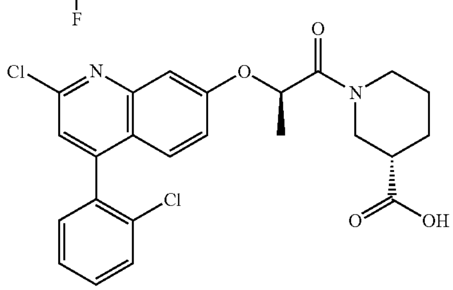 | 2G$_3$ + M11a + M9 | (400 MHz, DMSO-d$_6$) δ 12.45 (s, 1H), 7.73-7.67 (m, 1H), 7.63-7.47 (m, 3H), 7.39 (d, J = 2.6 Hz, 1H), 7.36-7.23 (m, 3H), 5.57 (q, J = 6.6 Hz, 1H), 4.16 (dd, J = 113.6, 13.5 Hz, 1H), 3.93 (s, 1H), 3.52-3.05 (m, 1H), 3.04-2.79 (m, 1H), 2.47-2.22 (m, 1H), 2.06-1.87 (m, 1H), 1.82-1.55 (m, 2H), 1.54-1.44 (m, 3H), 1.28 (d, J = 35.1 Hz, 1H). | 99% |

TABLE 6-continued

Compounds of formula (I) of the invention

| Ex | Structure | BB | ¹H-NMR | LC purity % ee |
|---|---|---|---|---|
| 35 | 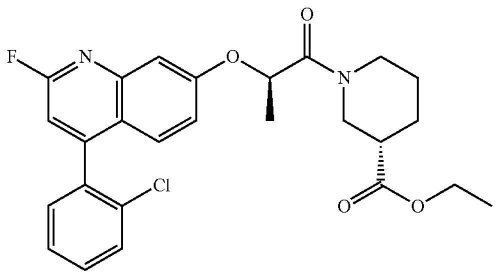 [SMILES: CCOC(=O)[C@H]1CCCN(C(=O)[C@@H](C)Oc2ccc3c(-c4ccccc4Cl)cc(F)nc3c2)C1] | 6G$_3$ + M11a + M9 | (300 MHz, Chloroform-d) δ 7.44-7.21 (m, 1H), 7.18-6.87 (m, 6H), 5.47-5.00 (m, 1H), 4.35-3.60 (m, 3H), 3.38-3.08 (m, 1H), 2.66-2.46 (m, 1H), 2.18-2.00 (m, 1H), 1.99-1.91 (m, 4H), 1.91-1.76 (m, 2H), 1.73-1.42 (m, 3H). | 99% |
| 36 | 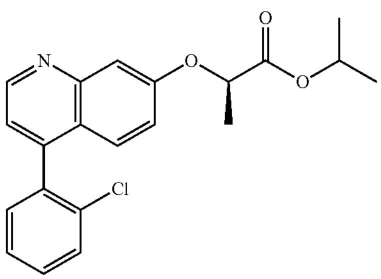 [SMILES: CC(C)OC(=O)[C@@H](C)Oc1ccc2c(-c3ccccc3Cl)ccnc2c1] | (R)-2G$_1$ | (400 MHz, DMSO-d$_6$) δ 8.87 (d, J = 4.4 Hz, 1H), 7.66 (dt, J = 7.7, 2.0 Hz, 1H), 7.58-7.48 (m, 2H), 7.43 (ddd, J = 7.2, 5.0, 2.0 Hz, 1H), 7.33-7.26 (m, 3H), 7.24 (dd, J = 9.2, 2.5 Hz, 1H), 5.21-5.08 (m, 1H), 4.96 (pd, J = 6.2, 1.1 Hz, 1H), 1.56 (d, J = 6.7 Hz, 3H), 1.23 (66, J = 6.2, 3.2 Hz, 3H), 1.14 (dd, J = 6.3, 1.4 Hz, 3H). | 98% |
| 37 | 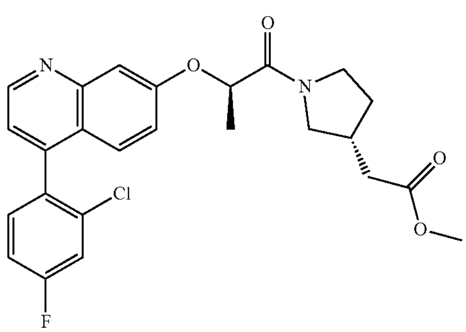 [SMILES: COC(=O)C[C@H]1CCN(C(=O)[C@@H](C)Oc2ccc3c(-c4ccc(F)cc4Cl)ccnc3c2)C1] | (R)-4G$_1$ | (300 MHz, Chloroform-d) δ 8.81 (d, J = 4.6 Hz, 1H), 7.37-7.20 (m, 4H), 7.19-7.03 (m, 3H), 4.99 (p, J = 6.5 Hz, 1H), 3.87-3.49 (m, 5H), 3.43-3.30 (m, 1H), 3.10-1.95 (m, 5H), 1.72-1.46 (m, 4H). | 97% |
| 38 | 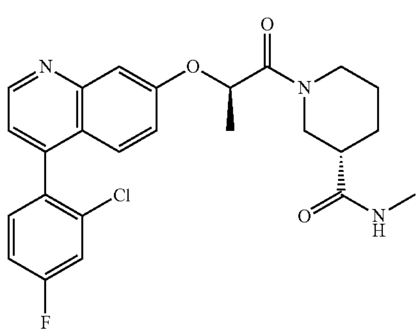 [SMILES: CNC(=O)[C@H]1CCCN(C(=O)[C@@H](C)Oc2ccc3c(-c4ccc(F)cc4Cl)ccnc3c2)C1] | 66 | (300 MHz, Chloroform-d) δ 8.82 (t, J = 4.1 Hz, 1H), 7.55-6.98 (m, 7H), 5.97 (m, 1H), 5.39-5.06 (m, 1H), 4.43-3.56 (m, 2H), 3.48-3.29 (m, 2H), 3.06-2.45 (m, 3H), 2.27 (s, 1H), 2.10-1.68 (m, 3H), 1.71-1.54 (m, 3H), 1.33-0.72 (m, 1H). | 99% |

TABLE 6-continued

Compounds of formula (I) of the invention

| Ex | Structure | BB | ¹H-NMR | LC purity % ee |
|---|---|---|---|---|
| 39 | 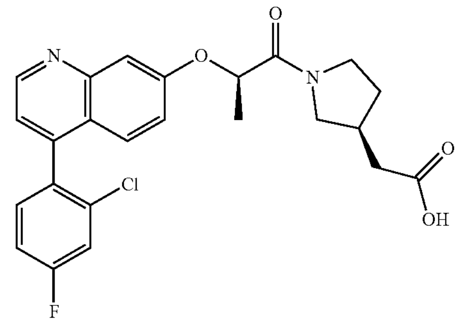 [SMILES: C[C@@H](Oc1ccc2c(-c3ccc(F)cc3Cl)ccnc2c1)C(=O)N1CC[C@@H](CC(=O)O)C1] | 67 | (300 MHz, DMSO-d₆) δ 12.10 (s, 1H), 8.75 (d, J = 4.3 Hz, 1H), 7.56 (dd, J = 8.9, 2.6 Hz, 1H), 7.38 (dd, J = 8.6, 6.2 Hz, 1H), 7.29 (tdd, J = 8.5, 2.6, 1.4 Hz, 1H), 7.21-7.06 (m, 4H), 5.20-5.06 (m, 1H), 3.92-3.68 (m, 1H), 3.52-3.08 (m, 2H), 3.08-2.76 (m, 1H), 2.51-2.32 (m, 1H), 2.23 (dd, J = 7.4, 3.6 Hz, 2H), 2.06-1.81 (m, 1H), 1.63-1.28 (m, 4H). | 100% |
| 40 | 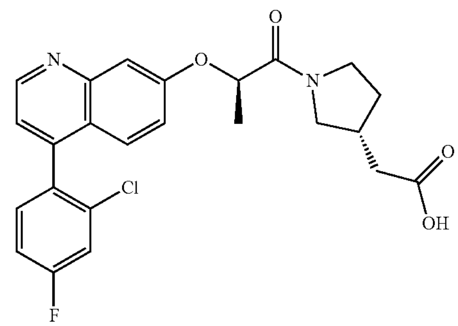 [SMILES: C[C@@H](Oc1ccc2c(-c3ccc(F)cc3Cl)ccnc2c1)C(=O)N1CC[C@H](CC(=O)O)C1] | 37 | (300 MHz, DMSO-d₆) δ 12.25 (s, 1H), 8.89 (d, J = 4.4 Hz, 1H), 7.70 (dd, J = 8.9, 2.5 Hz, 1H), 7.58-7.39 (m, 2H), 7.35-7.19 (m, 4H), 5.24 (p, J = 6.3 Hz, 1H), 3.82-3.56 (m, 2H), 3.33 (s, 3H), 2.47-2.30 (m, 2H), 2.21-1.92 (m, 1H), 1.73-1.46 (m, 4H). | 100% |
| 41 | 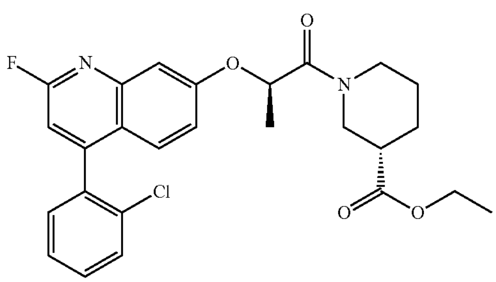 [SMILES: CCOC(=O)[C@H]1CCCN(C(=O)[C@@H](C)Oc2ccc3c(-c4ccccc4Cl)cc(F)nc3c2)C1] | (R)-2G₆ | (400 MHz, Chloroform-d) δ 7.56 (dd, J = 7.7, 1.4 Hz, 1H), 7.49-7.34 (m, 3H), 7.33-7.22 (m, 2H), 7.15 (q, J = 8.0, 7.4 Hz, 1H), 6.87 (d, J = 5.7 Hz, 1H), 5.34-5.12 (m, 1H), 4.57-3.74 (m, 4H), 3.55-2.89 (m, 2H), 2.43 (dt, J = 86.3, 9.7 Hz, 1H), 2.15-1.96 (m, 1H), 1.85-1.60 (m, 5H), 1.25 (p, J = 7.1 Hz, 4H). | 98% |
| 42 | 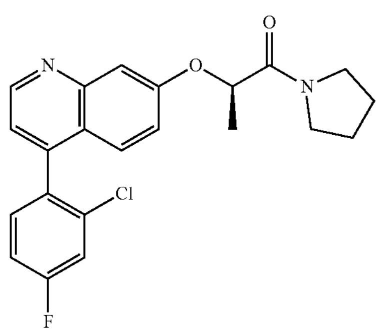 [SMILES: C[C@@H](Oc1ccc2c(-c3ccc(F)cc3Cl)ccnc2c1)C(=O)N1CCCC1] | (R)-4G₁ | (300 MHz, Chloroform-d) δ 8.80 (d, J = 4.6 Hz, 1H), 7.38-7.00 (m, 7H), 5.01 (q, J = 6.6 Hz, 1H), 3.70 (ddd, J = 9.7, 7.8, 4.1 Hz, 1H), 3.56-3.33 (m, 3H), 2.09-1.65 (m, 4H), 1.60 (d, J = 6.5 Hz, 3H). | 99% |
| 43 | 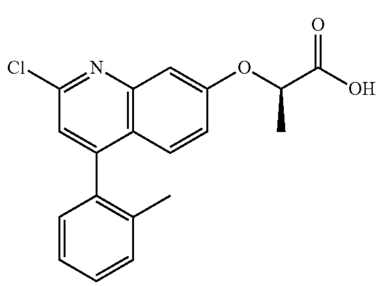 [SMILES: Cc1ccccc1-c1cc(Cl)nc2cc(O[C@H](C)C(=O)O)ccc12] | 73 | (300 MHz, Chloroform-d) δ 7.62 (t, J = 2.8 Hz, 1H), 7.47-7.07 (m, 7H), 5.15-5.01 (m, 1H), 2.08-1.97 (m, 3H), 1.87 (d, J = 6.9 Hz, 3H). | 93% |

TABLE 6-continued

Compounds of formula (I) of the invention

| Ex | Structure | BB | ¹H-NMR | LC purity % ee |
|---|---|---|---|---|
| 44 | 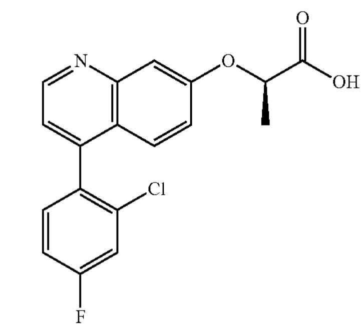 [SMILES: C[C@@H](Oc1ccc2c(-c3ccc(F)cc3Cl)ccnc2c1)C(=O)O] | (R)-4F₁_Et | (400 MHz, DMSO-d₆) δ 8.85 (dd, J = 4.4, 0.6 Hz, 1H), 7.67 (dt, J = 8.9, 2.3 Hz, 1H), 7.49 (ddd, J = 8.1, 6.2, 1.8 Hz, 1H), 7.39 (tt, J = 8.5, 2.4 Hz, 1H), 7.32-7.27 (m, 2H), 7.26 (dd, J = 4.4, 0.6 Hz, 1H), 7.22 (dd, J = 9.2, 2.6 Hz, 1H), 5.00 (q, J = 6.5 Hz, 1H), 1.55 (d, J = 6.8 Hz, 3H). | 96% |
| 45 | 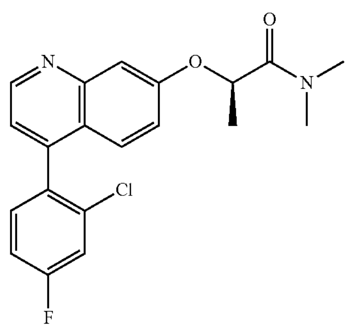 [SMILES: C[C@@H](Oc1ccc2c(-c3ccc(F)cc3Cl)ccnc2c1)C(=O)N(C)C] | 4G₁ | (400 MHz, DMSO-d₆) δ 8.88 (d, J = 4.4 Hz, 1H), 7.69 (ddd, J = 8.9, 2.6, 1.4 Hz, 1H), 7.51 (ddd, J = 7.9, 6.2, 1.5 Hz, 1H), 7.42 (tt, J = 8.5, 2.3 Hz, 1H), 7.35-7.19 (m, 4H), 5.58-5.41 (m, 1H), 3.16 (d, J = 7.5 Hz, 3H), 2.87 (d, J = 3.0 Hz, 3H), 1.50 (dd, J = 6.5, 1.5 Hz, 3H). | 97% |
| 46 | 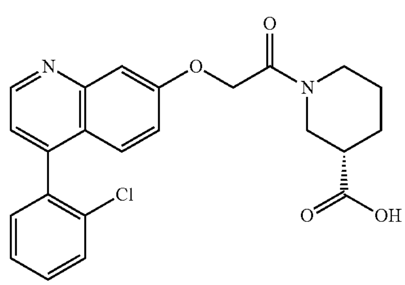 [SMILES: O=C(O)[C@H]1CCCN(C(=O)COc2ccc3c(-c4ccccc4Cl)ccnc3c2)C1] | 2G + M11b + M9 | (400 MHz, DMSO-d₆) δ 12.47 (br. s, 1H), 8.89 (d, J = 4.4 Hz, 1H), 7.68 (dd, J = 7.8, 1.4 Hz, 1H), 7.55 (dtd, J = 15.9, 7.4, 1.6 Hz, 2H), 7.45 (dt, J = 4.7, 2.0 Hz, 2H), 7.33-7.22 (m, 3H), 5.17-4.96 (m, 2H), 4.42-3.67 (m, 2H), 3.51-3.02 (m, 2H), 2.92-2.53 (m, 1H), 2.45-1.34 (m, 4H). | 100% |
| 47 | 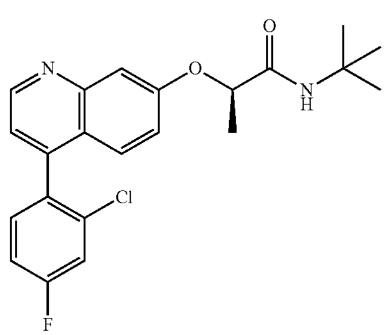 [SMILES: C[C@@H](Oc1ccc2c(-c3ccc(F)cc3Cl)ccnc2c1)C(=O)NC(C)(C)C] | (R)-4G₁ | (300 MHz, Chloroform-d) δ 8.89-8.77 (m, 1H), 7.47 (d, J = 2.6 Hz, 1H), 7.45-7.18 (m, 3H), 7.20-7.00 (m, 3H), 6.21 (d, J = 11.0 Hz, 1H), 4.71 (qd, J = 6.7, 3.3 Hz, 1H), 1.56 (dd, J = 6.7, 0.9 Hz, 3H), 1.28 (d, J = 2.8 Hz, 9H). | 97% |

TABLE 6-continued

Compounds of formula (I) of the invention

| Ex | Structure | BB | $^1$H-NMR | LC purity % ee |
|---|---|---|---|---|
| 48 | 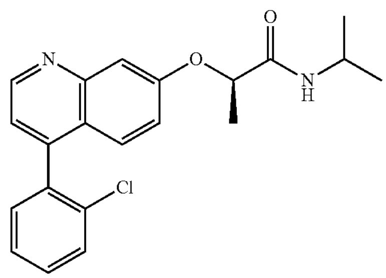 [SMILES: CC(C)NC(=O)[C@@H](C)Oc1ccc2c(-c3ccccc3Cl)ccnc2c1] | (R)-2G$_1$ | (400 MHz, DMSO-d$_6$) δ 8.88 (dd, J = 4.5, 0.8 Hz, 1H), 8.13 (t, J = 7.7 Hz, 1H), 7.68 (dq, J = 7.6, 1.3 Hz, 1H), 7.61-7.49 (m, 2H), 7.44 (ddd, J = 7.0, 3.4, 1.5 Hz, 1H), 7.35-7.20 (m, 3H), 4.86 (q, J = 6.6 Hz, 1H), 4.07-3.69 (m, 1H), 1.49 (dt, J = 6.5, 1.2 Hz, 3H), 1.10 (ddd, J = 6.4, 5.3, 0.9 Hz, 3H), 1.04 (ddd, J = 6.2, 5.0, 0.9 Hz, 3H). | 100% |
| 49 | 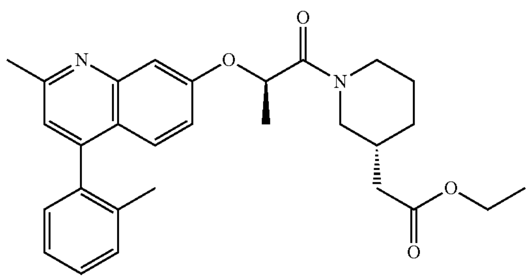 [SMILES: CCOC(=O)C[C@H]1CCCN(C(=O)[C@@H](C)Oc2ccc3c(-c4ccccc4C)cc(C)nc3c2)C1] | (R)-3G$_5$ | (400 MHz, DMSO-d$_6$) δ 7.49-7.05 (m, 8H), 5.53-5.34 (m, 1H), 4.32-3.82 (m, 4H), 3.04 (dq, J = 69.0, 11.4, 10.4 Hz, 1H), 2.66 (s, 4H), 2.37-2.08 (m, 2H), 1.98 (d, J = 3.6 Hz, 3H), 1.79 (s, 2H), 1.70-1.45 (m, 4H), 1.32-1.20 (m, 2H), 1.15 (qd, J = 7.0, 2.3 Hz, 3H). | 100% |
| 50 | 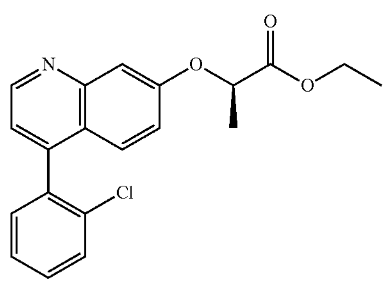 [SMILES: CCOC(=O)[C@@H](C)Oc1ccc2c(-c3ccccc3Cl)ccnc2c1] | 2D$_1$ | (300 MHz, Chloroform-d) δ 8.82 (d, J = 4.4 Hz, 1H), 7.52-7.45 (m, 1H), 7.43-7.26 (m, 4H), 7.27-7.21 (m, 1H), 7.17-7.09 (m, 2H), 4.90 (qd, J = 6.8, 2.4 Hz, 1H), 4.27-4.10 (m, 2H), 1.63 (d, J = 6.8 Hz, 3H), 1.22 (t, J = 7.1 Hz, 3H). | 94% |
| 51 | 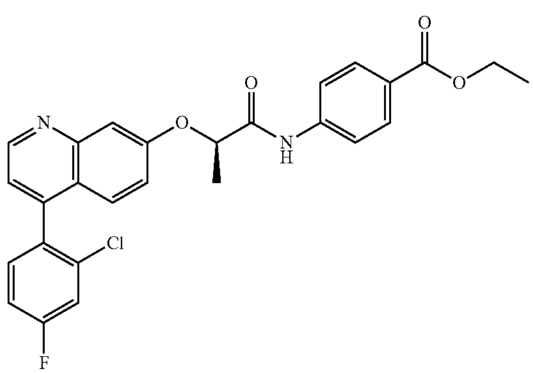 [SMILES: CCOC(=O)c1ccc(NC(=O)[C@@H](C)Oc2ccc3c(-c4ccc(F)cc4Cl)ccnc3c2)cc1] | (R)-4G$_1$ | (300 MHz, Chloroform-d) δ 8.84 (d, J = 4.4 Hz, 1H), 8.48-8.34 (m, 1H), 7.99-7.87 (m, 2H), 7.59 (dq, J = 8.6, 2.3 Hz, 3H), 7.41 (dd, J = 9.1, 1.0 Hz, 1H), 7.31-7.02 (m, 5H), 5.01 (qd, J = 6.8, 1.8 Hz, 1H), 4.28 (q, J = 7.1 Hz, 2H), 1.70 (d, J = 6.7 Hz, 3H), 1.31 (t, J = 7.1 Hz, 3H). | 100% |
| 52 | 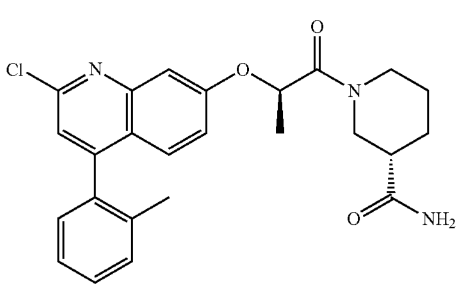 [SMILES: Cc1ccccc1-c1cc(Cl)nc2cc(O[C@H](C)C(=O)N3CCC[C@H](C(N)=O)C3)ccc12] | 25 | (300 MHz, Chloroform-d) δ 7.38-7.02 (m, 7H), 6.93-6.76 (m, 1H), 6.31 (d, J = 90.5 Hz, 1H), 5.87-5.36 (m, 1H), 5.28-5.06 (m, 1H), 4.06-2.96 (m, 3H), 2.49-2.11 (m, 1H), 2.13-1.90 (m, 5H), 1.89-1.62 (m, 2H), 1.58 (d, J = 6.5 Hz, 3H), 1.61-1.25 (m, 1H). | 100% |

TABLE 6-continued

Compounds of formula (I) of the invention

| Ex | Structure | BB | ¹H-NMR | LC purity % ee |
|---|---|---|---|---|
| 53 | 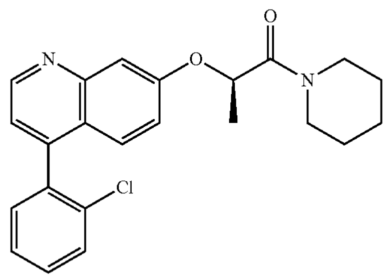 [SMILES: C[C@@H](Oc1ccc2c(-c3ccccc3Cl)ccnc2c1)C(=O)N1CCCCC1] | (R)-2G₁ | (300 MHz, Chloroform-d) δ 8.81 (d, J = 4.5 Hz, 1H), 7.54-7.42 (m, 1H), 7.43-7.27 (m, 4H), 7.26-7.21 (m, 1H), 7.20-7.03 (m, 2H), 5.17 (td, J = 7.0, 5.8 Hz, 1H), 3.63-3.39 (m, 4H), 1.69-1.31 (m, 10H). | 92% |
| 54 | 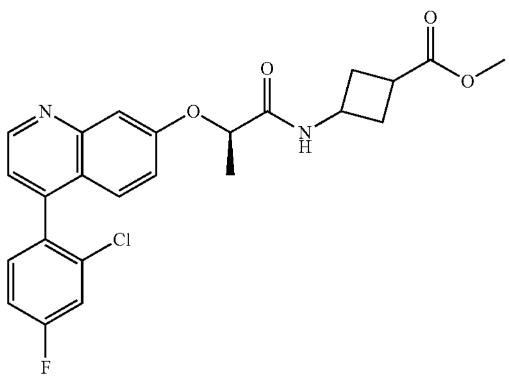 [SMILES: COC(=O)C1CC(NC(=O)[C@@H](C)Oc2ccc3c(-c4ccc(F)cc4Cl)ccnc3c2)C1] | (R)-4G₁ | (400 MHz, DMSO-d₆) δ 8.89 (d, J = 4.4 Hz, 1H), 8.66-8.56 (m, 1H), 7.69 (ddd, J = 8.9, 2.6, 17 Hz, 1H), 7.52 (ddd, J = 8.8, 6.2, 2.8 Hz, 1H), 7.45-7.24 (m, 5H), 4.88 (dtd, J = 8.6, 4.3, 2.5 Hz, 1H), 4.45-4.08 (m, 1H), 3.60 (dd, J = 9.3, 1.1 Hz, 3H), 3.10-2.76 (m, 1H), 2.46-2.04 (m, 4H), 1.50 (ddd, J = 6.9, 5.8, 1.5 Hz, 3H). | 96% |
| 55 | 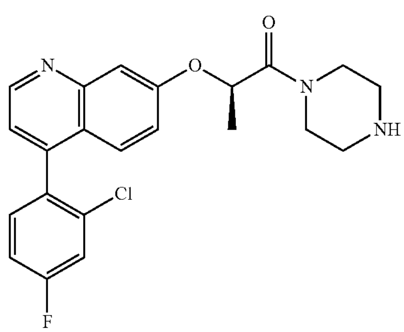 [SMILES: C[C@@H](Oc1ccc2c(-c3ccc(F)cc3Cl)ccnc2c1)C(=O)N1CCNCC1] | 4N₁_piperazine | (400 MHz, DMSO-d₆) δ 8.94 (d, J = 4.6 Hz, 1H), 7.70 (dd, J = 8.9, 2.6 Hz, 1H), 7.52 (dd, J = 8.6, 6.2 Hz, 1H), 7.51-7.39 (m, 1H), 7.43-7.33 (m, 3H), 7.27 (dt, J = 9.2, 2.0 Hz, 1H), 5.58 (p, J = 6.7 Hz, 1H), 3.94-3.59 (m, 4H), 3.25-3.02 (m, 4H), 1.51 (dd, J = 6.5, 2.3 Hz, 3H). | 97% |
| 56 | 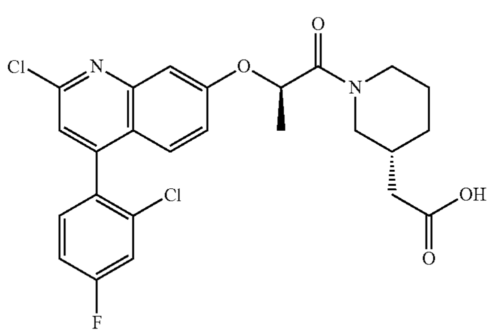 [SMILES: C[C@@H](Oc1ccc2c(-c3ccc(F)cc3Cl)cc(Cl)nc2c1)C(=O)N1CCC[C@H](CC(=O)O)C1] | 93 | (300 MHz, Chloroform-d) δ 7.33-7.21 (m, 4H), 7.17-7.00 (m, 3H), 5.26-5.09 (m, 1H), 4.43-4.30 (m, 1H), 4.16-4.00 (m, 1H), 3.84-3.06 (m, 1H), 2.96-2.62 (m, 2H), 2.38-1.75 (m, 4H), 1.71-1.52 (m, 4H), 1.46-1.11 (m, 2H). | 98% |

TABLE 6-continued

Compounds of formula (I) of the invention

| Ex | Structure | BB | ¹H-NMR | LC purity % ee |
|----|-----------|----|--------|----------------|
| 57 | 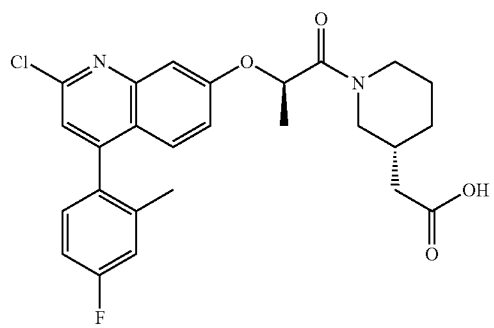 [SMILES: Cc1cc(F)ccc1-c1cc(Cl)nc2cc(O[C@H](C)C(=O)N3CCC[C@H](CC(=O)O)C3)ccc12] | (R)-6G₃ + M11a + M9 | (300 MHz, Chloroform-d) δ 7.33-7.21 (m, 2H), 7.14-6.86 (m, 5H), 6.69 (s, 1H), 5.27-5.07 (m, 1H), 4.64-2.45 (m, 4H), 2.38-2.09 (m, 2H), 2.15-1.73 (m, 5H), 1.70-1.12 (m, 6H). | 100% |
| 58 | 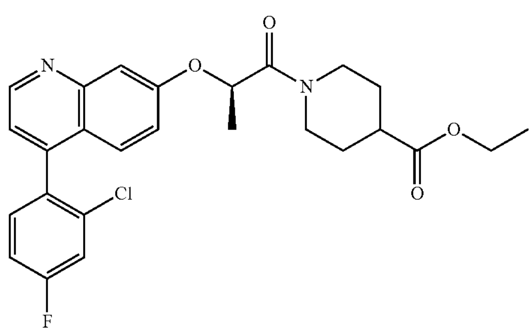 [SMILES: CCOC(=O)C1CCN(C(=O)[C@@H](C)Oc2ccc3c(-c4ccc(F)cc4Cl)ccnc3c2)CC1] | (R)-4G₁ | (300 MHz, Chloroform-d) δ 8.81 (t, J = 5.5 Hz, 1H), 7.48-7.31 (m, 2H), 7.28-7.20 (m, 2H), 7.18-7.01 (m, 3H), 5.23-5.12 (m, 1H), 4.34 (d, J = 14.6 Hz, 1H), 4.16-3.90 (m, 3H), 3.44-3.01 (m, 1H), 2.95-2.78 (m, 1H), 2.58-2.39 (m, 1H), 2.02-1.46 (m, 7H), 1.18 (q, J = 7.1 Hz, 3H). | 96% |
| 59 | 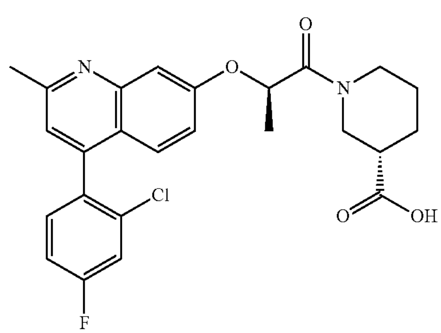 [SMILES: Cc1cc(-c2ccc(F)cc2Cl)c2ccc(O[C@H](C)C(=O)N3CCC[C@H](C(=O)O)C3)cc2n1] | (R)-4G₅ + M11a + M9 | (400 MHz, DMSO-d₆) δ 7.73 (dd, J = 8.9, 2.5 Hz, 1H), 7.58-7.19 (m, 6H), 5.67-5.44 (m, 1H), 4.31-3.79 (m, 2H), 3.50-3.08 (m, 1H), 2.98-2.72 (m, 4H), 2.43-2.25 (m, 1H), 1.96 (d, J = 15.8 Hz, 1H), 1.77-1.44 (m, 6H). | 98% |
| 60 | 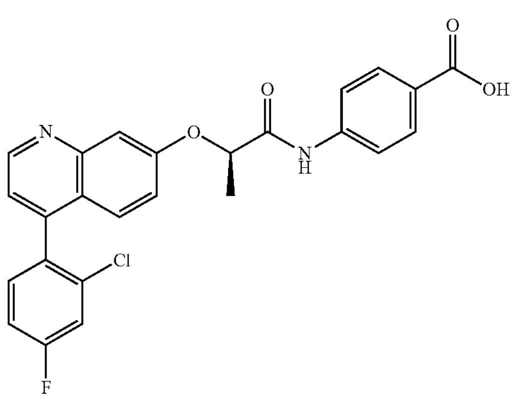 [SMILES: C[C@@H](Oc1ccc2c(-c3ccc(F)cc3Cl)ccnc2c1)C(=O)Nc1ccc(C(=O)O)cc1] | 51 | (300 MHz, DMSO-d₆) δ 10.66 (d, J = 4.3 Hz, 1H), 8.87 (dd, J = 4.4, 1.5 Hz, 1H), 7.91 (dd, J = 8.6, 1.7 Hz, 2H), 7.82-7.66 (m, 3H), 7.61-7.26 (m, 6H), 5.18 (q, J = 6.5 Hz, 1H), 1.67 (d, J = 6.5 Hz, 3H). | 94% |

TABLE 6-continued

Compounds of formula (I) of the invention

| Ex | Structure | BB | ¹H-NMR | LC purity % ee |
|---|---|---|---|---|
| 61 | 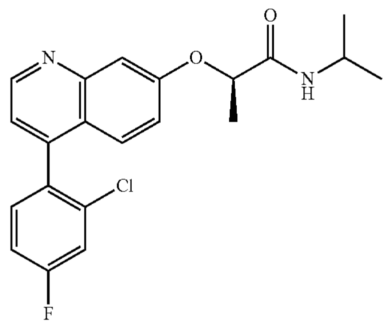 [SMILES: CC(C)NC(=O)[C@@H](C)Oc1ccc2c(-c3ccc(F)cc3Cl)ccnc2c1] | (R)-4G₁ | (300 MHz, Chloroform-d) δ 12.78 (s, 1H), 8.85 (d, J = 4.5 Hz, 1H), 7.48 (d, J = 2.6 Hz, 1H), 7.37 (d, J = 9.2 Hz, 1H), 7.25 (ddd, J = 8.7, 6.5, 2.4 Hz, 2H), 7.24-7.02 (m, 3H), 6.28-6.15 (m, 1H), 4.81 (qd, J = 6.7, 2.7 Hz, 1H), 4.17-3.94 (m, 1H), 1.58 (d, J = 6.9 Hz, 3H), 1.13 (dd, J = 6.6, 2.3 Hz, 3H), 1.03 (dd, J = 6.5, 3.8 Hz, 3H). | 97% |
| 62 | 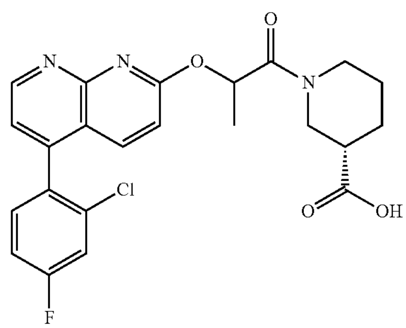 [SMILES: CC(Oc1ccc2c(-c3ccc(F)cc3Cl)ccnc2n1)C(=O)N1CCC[C@H](C(=O)O)C1] | (rac)-4G₄ + M11a + M9 | (300 MHz, Chloroform-d) δ 8.92-8.76 (m, 1H), 7.77-7.59 (m, 1H), 7.35-7.00 (m, 5H), 6.23-5.63 (m, 1H), 4.88-4.43 (m, 2H), 3.49-2.67 (m, 2H), 2.55 (tt, J = 12.6, 3.7 Hz, 1H), 2.31-2.16 (m, 1H), 2.08-1.80 (m, 1H), 1.56 (dd, J = 13.1, 6.8 Hz, 3H), 1.77-1.12 (m, 2H). | 99% |
| 63 | 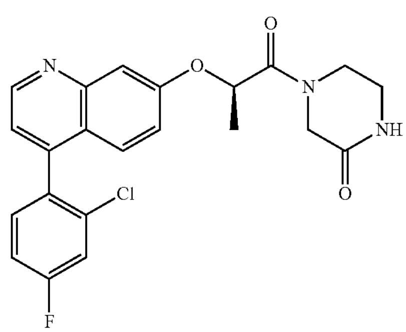 [SMILES: C[C@@H](Oc1ccc2c(-c3ccc(F)cc3Cl)ccnc2c1)C(=O)N1CCNC(=O)C1] | (R)-4G₁ | (400 MHz, DMSO-d₆) δ 8.89 (d, J = 4.4 Hz, 1H), 8.14 (d, J = 10.8 Hz, 1H), 7.69 (ddd, J = 8.9, 2.6, 1.3 Hz, 1H), 7.52 (dd, J = 8.6, 6.2 Hz, 1H), 7.45-7.21 (m, 5H), 5.57 (q, J = 6.6 Hz, 1H), 4.40-4.07 (m, 1H), 4.06-3.52 (m, 3H), 3.30-3.13 (m, 2H), 1.51 (ddd, J = 13.4, 6.5, 2.5 Hz, 3H). | 97% |
| 64 | 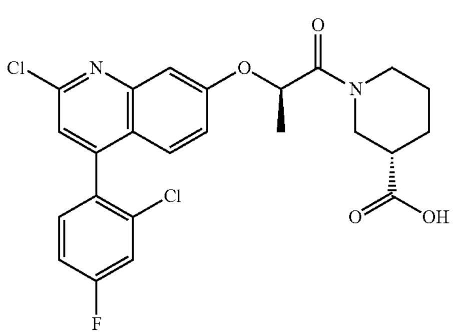 [SMILES: C[C@@H](Oc1ccc2c(-c3ccc(F)cc3Cl)cc(Cl)nc2c1)C(=O)N1CCC[C@H](C(=O)O)C1] | (R)-4G₃ + M11a + M9 | (300 MHz, DMSO-d₆) δ 12.41 (s, 1H), 7.59 (ddd, J = 8.9, 2.6, 1.0 Hz, 1H), 7.44 (ddd, J = 7.9, 6.2, 1.7 Hz, 1H), 7.38-7.25 (m, 2H), 7.24-7.07 (m, 3H), 5.51-5.40 (m, 1H), 4.25-3.68 (m, 2H), 3.39-2.94 (m, 1H), 2.87-2.65 (m, 1H), 2.45-1.73 (m, 2H), 1.66-1.42 (m, 3H), 1.36 (dd, J = 10.2, 6.4 Hz, 3H). | 99% |

TABLE 6-continued

Compounds of formula (I) of the invention

| Ex | Structure | BB | ¹H-NMR | LC purity % ee |
|---|---|---|---|---|
| 65 | 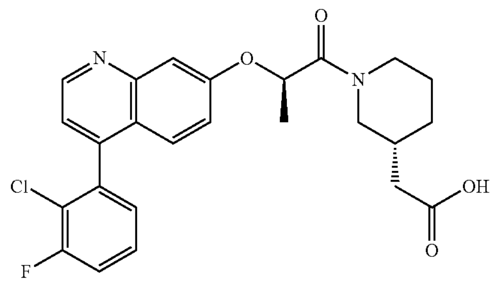 [SMILES: C[C@@H](Oc1ccc2c(-c3cccc(F)c3Cl)ccnc2c1)C(=O)N1CCC[C@H](CC(=O)O)C1] | (R,R)-2K$_{1x}$ | (300 MHz, DMSO-d$_6$) δ 12.32 (s, 1H), 8.98 (dd, J = 7.4, 4.4 Hz, 1H), 7.66 (qd, J = 8.6, 6.1 Hz, 2H), 7.53-7.19 (m, 5H), 5.70-5.49 (m, 1H), 4.38-4.03 (m, 2H), 3.25-2.96 (m, 1H), 2.84-2.46 (m, 1H), 2.36-2.13 (m, 2H), 2.00-1.66 (m, 3H), 1.59 (dd, J = 16.0, 6.4 Hz, 3H), 1.33 (s, 2H). | 90% |
| 66 | 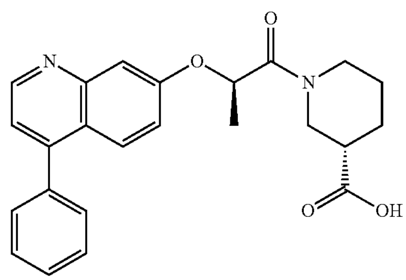 [SMILES: C[C@@H](Oc1ccc2c(-c3ccccc3)ccnc2c1)C(=O)N1CCC[C@H](C(=O)O)C1] | 1D$_1$ + (S,S)-1H + M9 | (300 MHz, DMSO-d$_6$) δ 12.49 (s, 1H), 8.85 (t, J = 4.1 Hz, 1H), 7.76 (dd, J = 9.3, 2.4 Hz, 1H), 7.65-7.48 (m, 5H), 7.40-7.20 (m, 3H), 5.57 (q, J = 6.5 Hz, 1H), 4.42-3.88 (m, 2H), 3.50-3.08 (m, 2H), 3.01-2.68 (m, 1H), 2.43-1.72 (m, 2H), 1.73-1.45 (m, 4H), 1.26 (d, J = 15.3 Hz, 1H). | 97% |
| 67 | 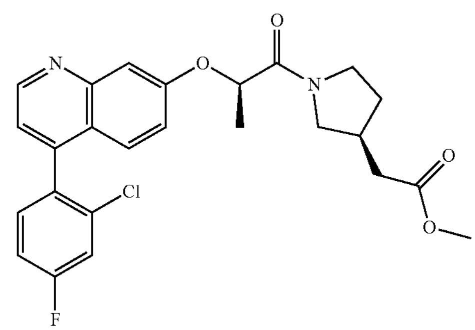 [SMILES: COC(=O)C[C@@H]1CCN(C(=O)[C@@H](C)Oc2ccc3c(-c4ccc(F)cc4Cl)ccnc3c2)C1] | (R)-4G$_1$ | (300 MHz, Chloroform-d) δ 8.81 (d, J = 4.5 Hz, 1H), 7.39-7.01 (m, 7H), 5.01 (dq, J = 6.8, 5.5 Hz, 1H), 4.04-3.60 (m, 5H), 3.59-3.29 (m, 1H), 3.15-3.00 (m, 1H), 2.76-2.24 (m, 3H), 2.20-1.98 (m, 1H), 1.85-1.36 (m, 4H). | 100% |
| 68 | 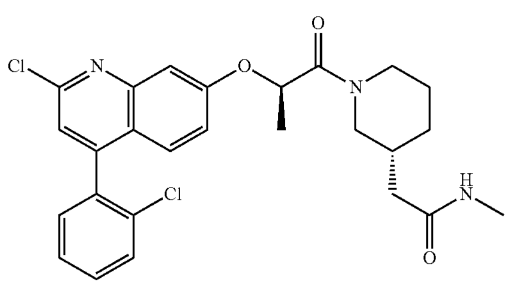 [SMILES: CNC(=O)C[C@H]1CCCN(C(=O)[C@@H](C)Oc2ccc3c(-c4ccccc4Cl)cc(Cl)nc3c2)C1] | 83 | (300 MHz, Chloroform-d) δ 7.49 (dt, J = 7.6, 2.1 Hz, 1H), 7.43-7.17 (m, 5H), 7.16-7.07 (m, 2H), 6.62-6.37 (m, 1H), 5.23-5.00 (m, 1H), 3.92-3.78 (m, 1H), 3.71-3.06 (m, 2H), 2.82-2.67 (m, 3H), 2.49-2.26 (m, 1H), 2.24-1.84 (m, 1H), 1.72 (td, J = 8.8, 4.2 Hz, 1H), 1.61 (dd, J = 17.1, 6.6 Hz, 4H), 1.52-0.65 (m, 4H). | 100% |
| 69 | 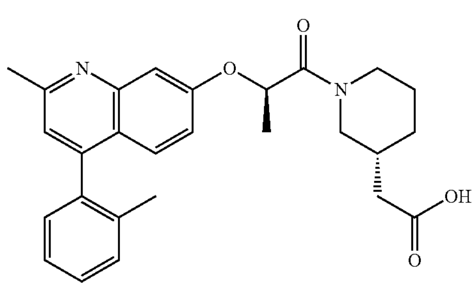 [SMILES: Cc1cc(-c2ccccc2C)c2ccc(O[C@H](C)C(=O)N3CCC[C@H](CC(=O)O)C3)cc2n1] | 49 | (400 MHz, DMSO-d$_6$) δ 7.65-7.18 (m, 8H), 5.50 (dt, J = 24.4, 6.9 Hz, 1H), 4.41-3.68 (m, 2H), 2.84 (s, 4H), 2.70-2.54 (m, 1H), 2.37-2.07 (m, 2H), 2.03 (s, 3H), 1.80 (s, 3H), 1.70-1.50 (m, 4H), 1.25 (s, 1H) | 100% |

TABLE 6-continued

Compounds of formula (I) of the invention

| Ex | Structure | BB | ¹H-NMR | LC purity % ee |
|---|---|---|---|---|
| 70 | 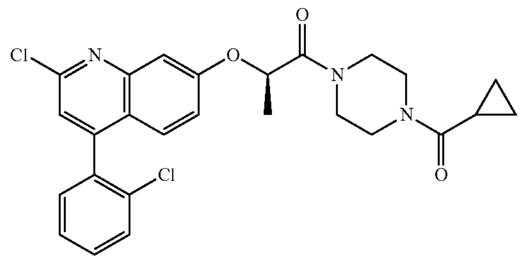 [SMILES: C[C@@H](Oc1ccc2c(-c3ccccc3Cl)cc(Cl)nc2c1)C(=O)N1CCN(C(=O)C2CC2)CC1] | 104 | (400 MHz, DMSO-d₆) δ 7.71-7.67 (m, 1H), 7.62-7.52 (m, 2H), 7.49 (dt, J = 7.3, 2.1 Hz, 1H), 7.40 (s, 1H), 7.37-7.24 (m, 3H), 5.59 (s, 1H), 3.68 (s, 8H), 1.99 (s, 1H), 1.52 (dd, J = 6.5, 2.6 Hz, 3H), 0.82-0.62 (m, 4H). | 100% |
| 71 | 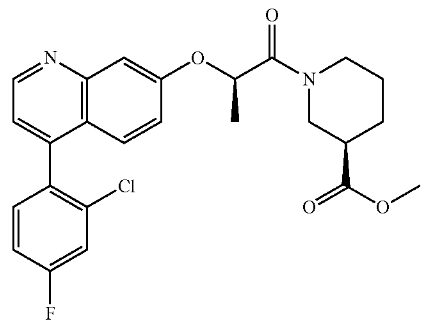 [SMILES: COC(=O)[C@@H]1CCCN(C(=O)[C@@H](C)Oc2ccc3c(-c4ccc(F)cc4Cl)ccnc3c2)C1] | (R)-4G₁ | (300 MHz, Chloroform-d) δ 8.82 (t, J = 4.0 Hz, 1H), 7.46-7.01 (m, 7H), 5.21 (dt, J = 32.8, 6.5 Hz, 1H), 4.66-3.81 (m, 3H), 3.73-3.10 (m, 4H), 3.06-2.44 (m, 2H), 2.42-1.86 (m, 2H), 1.82-1.13 (m, 4H). | 100% |
| 72 | 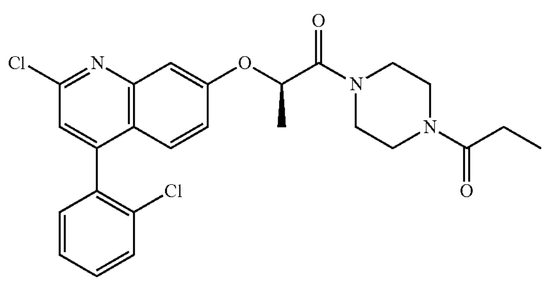 [SMILES: CCC(=O)N1CCN(C(=O)[C@@H](C)Oc2ccc3c(-c4ccccc4Cl)cc(Cl)nc3c2)CC1] | 104 | (400 MHz, DMSO-d₆) δ 7.71-7.67 (m, 1H), 7.63-7.46 (m, 3H), 7.40 (s, 1H), 7.36-7.24 (m, 3H), 5.58 (d, J = 6.3 Hz, 1H), 3.77-3.37 (m, 8H), 2.34 (d, J = 7.6 Hz, 2H), 1.51 (dd, J = 6.5, 2.6 Hz, 3H), 1.05-0.94 (m, 3H). | 100% |
| 73 | 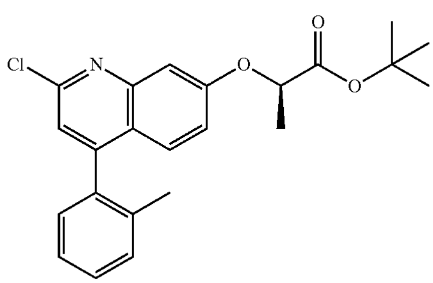 [SMILES: Cc1ccccc1-c1cc(Cl)nc2cc(O[C@H](C)C(=O)OC(C)(C)C)ccc12] | 3D₃ | (300 MHz, Chloroform-d) δ 7.37-7.20 (m, 5H), 7.15-7.04 (m, 3H), 4.75 (qd, J = 6.8, 2.5 Hz, 1H), 1.97 (d, J = 1.6 Hz, 3H), 1.59 (d, J = 6.8 Hz, 3H), 1.41 (d, J = 2.9 Hz, 9H). | 95% |
| 74 | 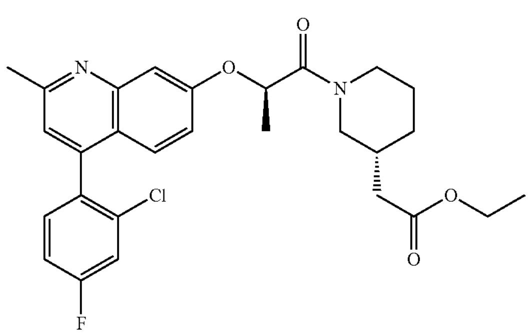 [SMILES: CCOC(=O)C[C@H]1CCCN(C(=O)[C@@H](C)Oc2ccc3c(-c4ccc(F)cc4Cl)cc(C)nc3c2)C1] | (R)-4G₅ | (400 MHz, DMSO-d₆) δ 7.67 (dd, J = 8.9, 2.5 Hz, 1H), 7.50 (t, J = 7.5 Hz, 1H), 7.41 (tt, J = 8.6, 2.3 Hz, 1H), 7.33-7.10 (m, 4H), 5.61-5.30 (m, 1H), 4.28-3.85 (m, 4H), 3.04 (dq, J = 63.3, 11.6 Hz, 1H), 2.73-2.51 (m, 4H), 2.37-2.11 (m, 3H), 1.89-1.45 (m, 7H), 1.15 (dt, J = 7.1, 4.9 Hz, 3H). | 99% |

TABLE 6-continued

Compounds of formula (I) of the invention

| Ex | Structure | BB | ¹H-NMR | LC purity % ee |
|---|---|---|---|---|
| 75 | 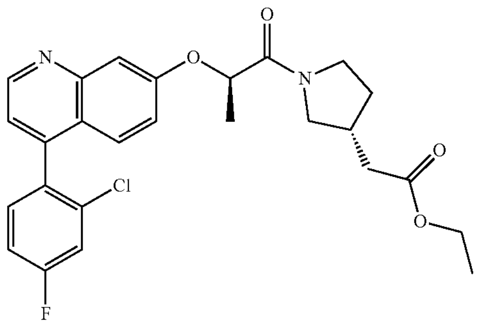 [SMILES: CCOC(=O)C[C@H]1CCN(C(=O)[C@@H](C)Oc2ccc3c(-c4ccc(F)cc4Cl)ccnc3c2)C1] | (R)-4G₁ | (300 MHz, DMSO-d₆) δ 8.89 (d, J = 4.5 Hz, 1H), 7.70 (dd, J = 8.9, 2.6 Hz, 1H), 7.61-7.39 (m, 2H), 7.44-7.17 (m, 4H), 5.28 (tt, J = 6.5, 4.5 Hz, 1H), 4.16 (qd, J = 7.1, 2.4 Hz, 1H), 4.05 (q, J = 7.1 Hz, 1H), 3.97-3.36 (m, 4H), 3.31-3.07 (m, 1H), 2.28-1.97 (m, 2H), 1.57-1.46 (m, 3H), 1.26-1.08 (m, 3H). | 100% |
| 76 | 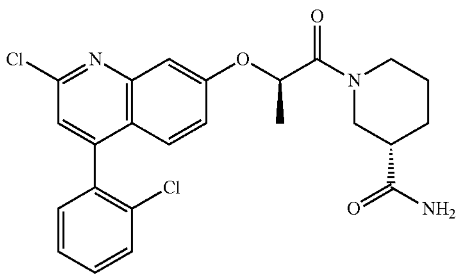 [SMILES: C[C@@H](Oc1ccc2c(-c3ccccc3Cl)cc(Cl)nc2c1)C(=O)N1CCC[C@H](C(N)=O)C1] | 34 | (300 MHz, Chloroform-d) δ 7.48 (dd, J = 7.6, 1.7 Hz, 1H), 7.42-7.28 (m, 4H), 7.26-7.06 (m, 4H), 6.51-5.96 (m, 1H), 5.77-5.40 (m, 1H), 5.28-5.06 (m, 1H), 4.14-3.96 (m, 1H), 3.96-3.72 (m, 1H), 3.71-2.88 (m, 2H), 2.51-2.36 (m, 1H), 2.17-125 (m, 7H). | 100% |
| 77 | 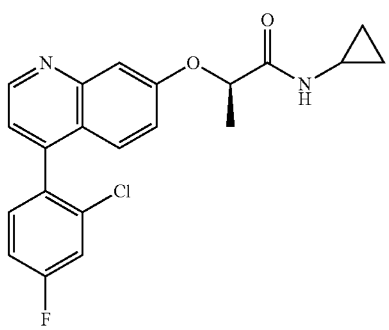 [SMILES: C[C@@H](Oc1ccc2c(-c3ccc(F)cc3Cl)ccnc2c1)C(=O)NC1CC1] | (R)-4G₁ | (300 MHz, DMSO-d₆) δ 8.73 (d, J = 4.5 Hz, 1H), 8.24-8.12 (m, 1H), 7.54 (dt, J = 8.8, 2.0 Hz, 1H), 7.36 (ddd, J = 8.4, 6.2, 2.1 Hz, 1H), 7.26 (tt, J = 8.5, 2.2 Hz, 1H), 7.20-7.06 (m, 4H), 4.68 (q, J = 6.5 Hz, 1H), 2.55-2.43 (m, 1H), 1.33 (d, J = 6.4 Hz, 3H), 0.51-0.41 (m, 2H), 0.32-0.22 (m, 2H). | 100% |
| 78 | 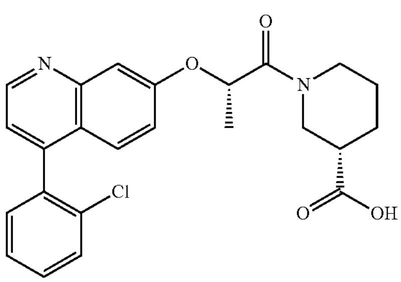 | | (400 MHz, DMSO-d₆) δ 8.89 (t, J = 4.6 Hz, 1H), 7.68 (dt, J = 7.7, 1.2 Hz, 1H), 7.61-7.49 (m, 2H), 7.47-7.42 (m, 1H), 7.38-7.26 (m, 3H), 7.22 (dd, J = 9.2, 2.6 Hz, 1H), 5.83-5.40 (m, 1H), 4.44-3.95 (m, 2H), 3.27-3.10 (m, 1H), 2.82 (t, J = 12.0 Hz, 1H), 2.63-1.89 (m, 2H), 1.83-1.28 (m, 6H). | 98%, ee90% |
| 79 | 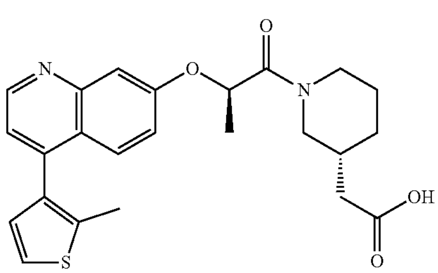 [SMILES: Cc1sccc1-c1ccnc2cc(O[C@H](C)C(=O)N3CCC[C@H](CC(=O)O)C3)ccc12] | (R,R)-2K₁ₓ | (300 MHz, DMSO-d₆) δ 8.83 (dd, J = 7.9, 4.4 Hz, 1H), 7.61-7.48 (m, 2H), 7.32-7.18 (m, 3H), 7.09 (d, J = 5.2 Hz, 1H), 5.61-5.40 (m, 1H), 4.30-3.94 (m, 2H), 3.15-2.87 (m, 2H), 2.50 (p, J = 1.9 Hz, 2H), 2.27 (s, 3H), 2.24-1.95 (m, 2H), 1.92-1.59 (m, 1H), 1.52 (dd, J = 17.0, 6.4 Hz, 3H), 1.30-1.06 (m, 3H). | 99% |

TABLE 6-continued

Compounds of formula (I) of the invention

| Ex | Structure | BB | ¹H-NMR | LC purity % ee |
|----|-----------|-----|--------|----------------|
| 80 | 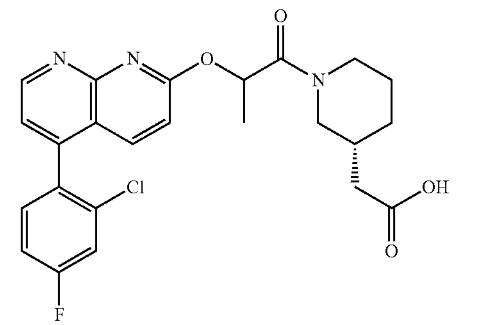 [SMILES: CC(Oc1ccc2c(-c3ccc(F)cc3Cl)ccnc2n1)C(=O)N1CCC[C@H](CC(=O)O)C1] | (rac)-4G₄ + M11a + M9 | (300 MHz, Chloroform-d) δ 9.02-8.74 (m, 1H), 7.75-7.60 (m, 1H), 7.32-7.00 (m, 5H), 6.46-5.63 (m, 1H), 4.52-4.22 (m, 1H), 4.09-3.68 (m, 1H), 3.60-3.30 (m, 1H), 3.29-2.03 (m, 3H), 1.88-1.67 (m, 1H), 1.65-1.49 (m, 3H), 1.50-1.13 (m, 2H). | 98% |
| 81 | 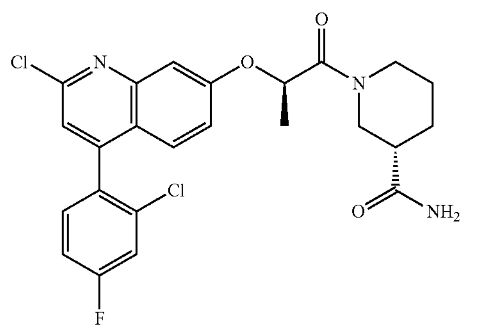 [SMILES: C[C@@H](Oc1ccc2c(-c3ccc(F)cc3Cl)cc(Cl)nc2c1)C(=O)N1CCC[C@H](C(N)=O)C1] | 64 | (300 MHz, Chloroform-d) δ 7.36-7.20 (m, 4H), 7.18-7.03 (m, 3H), 6.43-5.73 (m, 1H), 5.56-5.03 (m, 2H), 4.11-3.00 (m, 4H), 2.47 (d, J = 10.8 Hz, 1H), 2.08 (dd, J = 15.4, 8.9 Hz, 1H), 1.91-1.13 (m, 6H). | 100% |
| 82 | 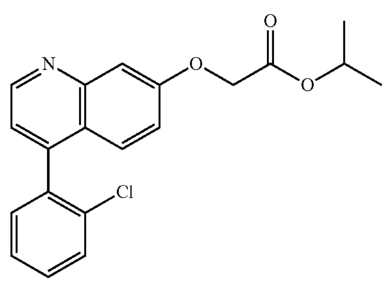 [SMILES: CC(C)OC(=O)COc1ccc2c(-c3ccccc3Cl)ccnc2c1] | 2G₁ | (400 MHz, DMSO-d₆) δ 8.90 (dd, J = 4.4, 0.7 Hz, 1H), 7.71-7.66 (m, 1H), 7.61-7.51 (m, 2H), 7.48-7.43 (m, 1H), 7.40 (d, J = 2.5 Hz, 1H), 7.35-7.25 (m, 3H), 5.03 (pd, J = 6.3, 0.8 Hz, 1H), 4.95 (d, J = 0.7 Hz, 2H), 1.24 (d, J = 6.2 Hz, 6H). | 97% |
| 83 | 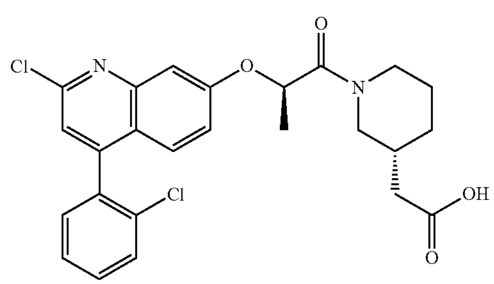 | 92 | (300 MHz, Chloroform-d) δ 7.49 (dd, J = 7.6, 1.6 Hz, 1H), 7.42-7.03 (m, 7H), 5.30-5.07 (m, 1H), 4.33-3.61 (m, 2H), 3.28-2.71 (m, 2H), 2.54-1.72 (m, 5H), 1.72-1.36 (m, 4H), 1.32-1.15 (m, 1H). | 90% |
| 84 | 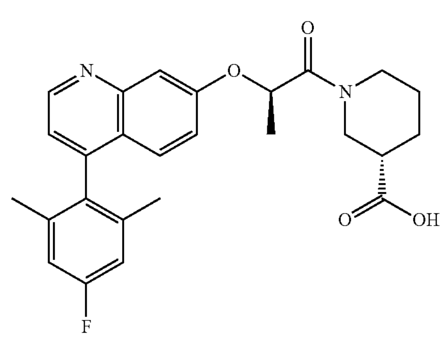 [SMILES: Cc1cc(F)cc(C)c1-c1ccnc2cc(O[C@H](C)C(=O)N3CCC[C@H](C(=O)O)C3)ccc12] | (R,S)-1K₁_Cl | (300 MHz, DMSO-d₆) δ 12.60 (s, 1H), 8.95 (t, J = 4.6 Hz, 1H), 7.43-7.12 (m, 6H), 5.60 (q, J = 6.5 Hz, 1H), 4.52-3.88 (m, 2H), 3.59-3.14 (m, 1H), 3.12-2.92 (m, 1H), 2.96-2.72 (m, 1H), 2.40 (d, J = 35.6 Hz, 1H), 2.18-1.51 (m, 10H), 1.24-1.16 (m, 2H). | 91% |

TABLE 6-continued

Compounds of formula (I) of the invention

| Ex | Structure | BB | ¹H-NMR | LC purity % ee |
|---|---|---|---|---|
| 85 | 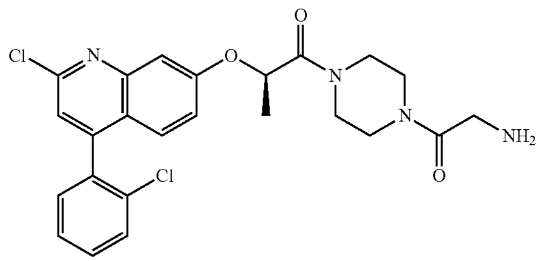 [SMILES: C[C@@H](Oc1ccc2c(-c3ccccc3Cl)cc(Cl)nc2c1)C(=O)N1CCN(C(=O)CN)CC1] | 104 + M10a | (400 MHz, DMSO-d₆) δ 8.03 (s, 3H), 7.70 (dd, J = 8.0, 1.3 Hz, 1H), 7.63-7.46 (m, 3H), 7.41 (s, 1H), 7.37-7.25 (m, 3H), 5.61 (dt, J = 14.6, 7.1 Hz, 1H), 3.91 (s, 2H), 3.80-3.36 (m, 8H), 1.53 (d, J = 5.7 Hz, 3H). - TFA Salt | 99% |
| 86 | 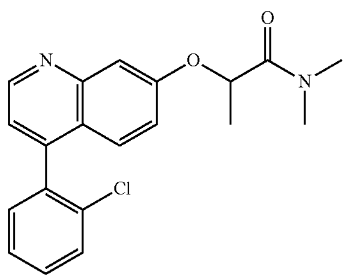 [SMILES: CC(Oc1ccc2c(-c3ccccc3Cl)ccnc2c1)C(=O)N(C)C] | 2D₁ | (300 MHz, Chloroform-d) δ 8.81 (dd, J = 4.5, 0.9 Hz, 1H), 7.53-7.42 (m, 1H), 7.42-7.02 (m, 6H), 5.16 (qd, J = 6.6, 2.5 Hz, 1H), 3.09 (d, J = 1.0 Hz, 3H), 2.94 (d, J = 2.2 Hz, 3H), 1.60 (d, J = 6.6 Hz, 3H). | 93% |
| 87 | 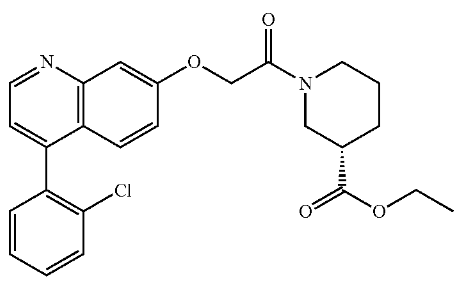 [SMILES: CCOC(=O)[C@H]1CCCN(C(=O)COc2ccc3c(-c4ccccc4Cl)ccnc3c2)C1] | 2G₁ | (400 MHz, DMSO-d₆) δ 8.89 (d, J = 4.4 Hz, 1H), 7.68 (dd, J = 7.8, 1.5 Hz, 1H), 7.55 (dtd, J = 15.9, 7.4, 1.7 Hz, 2H), 7.49-7.43 (m, 2H), 7.34-7.23 (m, 3H), 5.21-4.97 (m, 2H), 4.34-3.41 (m, 4H), 3.21-2.92 (m, 2H), 2.48-2.37 (m, 1H), 2.05-1.38 (m, 4H), 1.28-1.12 (m, 3H). | 93% |
| 88 | 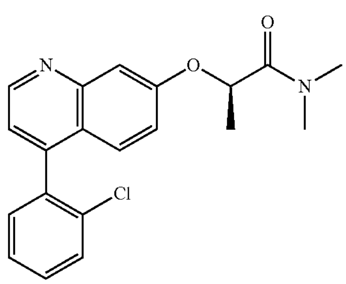 [SMILES: C[C@@H](Oc1ccc2c(-c3ccccc3Cl)ccnc2c1)C(=O)N(C)C] | 2D₁ | (400 MHz, DMSO-d₆) δ 8.88 (d, J = 4.4 Hz, 1H), 7.68 (d, J = 7.8 Hz, 1H), 7.61-7.49 (m, 2H), 7.48-7.40 (m, 1H), 7.36-7.18 (m, 4H), 5.57-5.45 (m, 1H), 3.16 (d, J = 7.3 Hz, 3H), 2.87 (d, J = 3.0 Hz, 3H), 1.50 (dd, J = 6.5, 1.5 Hz, 3H). | 100% |
| 89 | 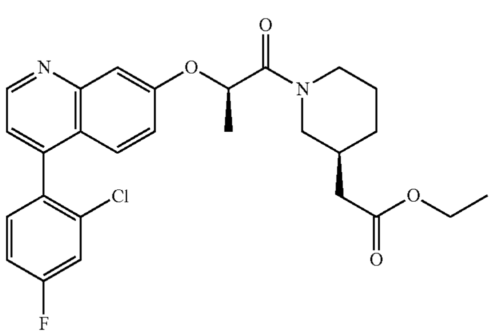 [SMILES: CCOC(=O)C[C@@H]1CCCN(C(=O)[C@@H](C)Oc2ccc3c(-c4ccc(F)cc4Cl)ccnc3c2)C1] | (R)-4G₁ | (300 MHz, Chloroform-d) δ 8.81 (t, J = 4.0 Hz, 1H), 7.45-7.28 (m, 2H), 7.28-7.20 (m, 2H), 7.18-7.00 (m, 3H), 5.28-5.10 (m, 1H), 4.37 (t, J = 13.1 Hz, 1H), 4.17-3.82 (m, 3H), 3.27-2.65 (m, 1H), 2.65-2.41 (m, 1H), 2.28-1.28 (m, 9H), 1.28-1.09 (m, 4H). | 98% |

TABLE 6-continued

Compounds of formula (I) of the invention

| Ex | Structure | BB | ¹H-NMR | LC purity % ee |
|---|---|---|---|---|
| 90 | 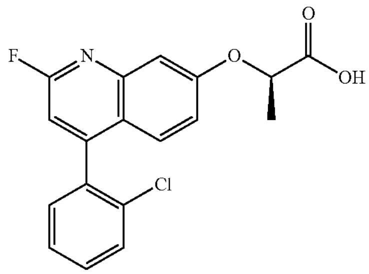 [SMILES: C[C@@H](Oc1ccc2c(-c3ccccc3Cl)cc(F)nc2c1)C(=O)O] | (R)-2F₆_tBu | (400 MHz, Chloroform-d) δ 7.59-7.50 (m, 2H), 7.49-7.35 (m, 3H), 7.34-7.13 (m, 2H), 6.87 (t, J = 1.4 Hz, 1H), 5.06 (p, J = 6.7 Hz, 1H), 1.84 (dd, J = 6.8, 1.2 Hz, 3H). | 96% |
| 91 | 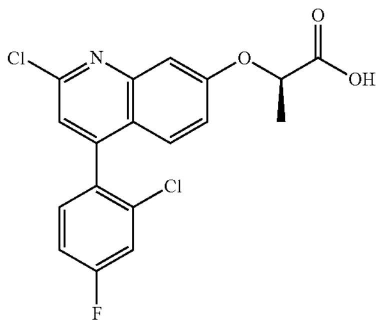 [SMILES: C[C@@H](Oc1ccc2c(-c3ccc(F)cc3Cl)cc(Cl)nc2c1)C(=O)O] | (R)-4F₃_Et | (300 MHz, DMSO-d₆) δ 7.72 (dt, J = 8.9, 2.3 Hz, 1H), 7.58 (ddd, J = 8.2, 6.2, 1.8 Hz, 1H), 7.51-7.37 (m, 2H), 7.37-7.22 (m, 3H), 5.03 (d, J = 7.0 Hz, 1H), 1.56 (d, J = 6.7 Hz, 3H). | 99% |
| 92 | 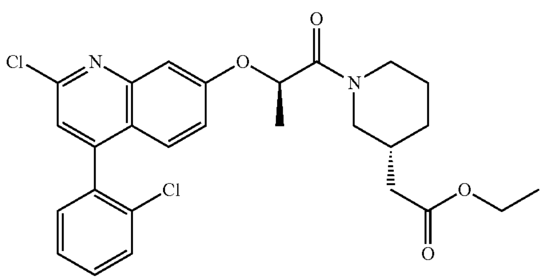 [SMILES: CCOC(=O)C[C@H]1CCCN(C(=O)[C@@H](C)Oc2ccc3c(-c4ccccc4Cl)cc(Cl)nc3c2)C1] | (R)-2G₃ | (300 MHz, Chloroform-d) δ 7.48 (dd, J = 7.6, 1.7 Hz, 1H), 7.44-7.21 (m, 4H), 7.27-7.13 (m, 1H), 7.19-7.06 (m, 2H), 5.16 (p, J = 6.1, 5.5 Hz, 1H), 4.51-4.13 (m, 1H), 4.06 (qd, J = 7.2, 3.1 Hz, 3H), 3.13-2.74 (m, 1H), 2.57 (dd, J = 17.3, 9.5 Hz, 1H), 2.31-2.15 (m, 1H), 2.12-1.74 (m, 2H), 1.68-1.55 (m, 6H), 1.25-1.10 (m, 4H). | 95% |
| 93 | 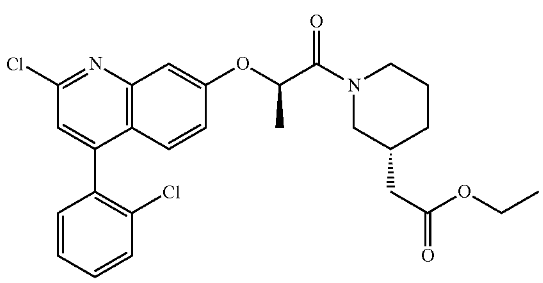 [SMILES: CCOC(=O)C[C@H]1CCCN(C(=O)[C@@H](C)Oc2ccc3c(-c4ccccc4Cl)cc(Cl)nc3c2)C1] | (R)-4G₃ | (300 MHz, DMSO-d₆) δ 7.73 (dd, J = 8.9, 2.5 Hz, 1H), 7.63-7.51 (m, 1H), 7.51-7.38 (m, 2H), 7.38-7.19 (m, 3H), 5.61-5.44 (m, 1H), 4.18 (dd, J = 21.8, 12.7 Hz, 1H), 4.10-3.83 (m, 3H), 3.01 (dd, J = 38.7, 24.1 Hz, 1H), 2.69-2.53 (m, 1H), 2.36-2.10 (m, 2H), 1.89-1.59 (m, 3H), 1.51 (dd, J = 12.2, 6.4 Hz, 3H), 1.26 (s, 2H), 1.16 (t, J = 7.1 Hz, 3H). | 98% |
| 94 | 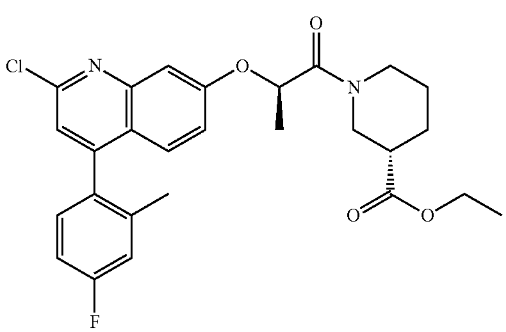 [SMILES: CCOC(=O)[C@H]1CCCN(C(=O)[C@@H](C)Oc2ccc3c(-c4ccc(F)cc4C)cc(Cl)nc3c2)C1] | (R)-6G₃ | (300 MHz, Chloroform-d) δ 7.34-6.88 (m, 7H), 5.14 (dq, J = 12.8, 6.6 Hz, 1H), 4.52-4.14 (m, 1H), 4.12-2.41 (m, 4H), 2.32-2.13 (m, 1H), 2.11-1.72 (m, 5H), 1.71-1.48 (m, 5H), 1.45-1.08 (m, 4H). | 100% |

TABLE 6-continued

Compounds of formula (I) of the invention

| Ex | Structure | BB | ¹H-NMR | LC purity % ee |
|---|---|---|---|---|
| 95 | 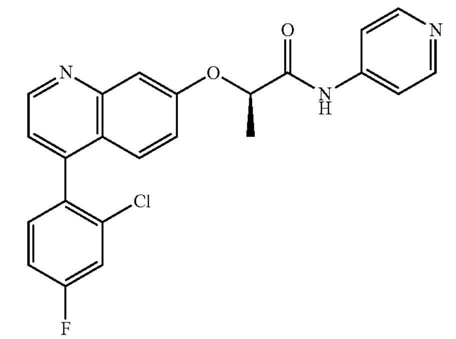 [SMILES: C[C@@H](Oc1ccc2c(-c3ccc(F)cc3Cl)ccnc2c1)C(=O)Nc1ccncc1] | (R)-4G₁ | (400 MHz, DMSO-d₆) δ 11.68 (s, 1H), 8.93 (dd, J = 4.6, 1.4 Hz, 1H), 8.78-8.69 (m, 2H), 8.18-8.10 (m, 2H), 7.71 (dd, J = 8.9, 2.5 Hz, 1H), 7.56-7.33 (m, 6H), 5.31 (qd, J = 6.6, 2.8 Hz, 1H), 1.70 (dd, J = 6.6, 1.5 Hz, 3H). | 100% |
| 96 | 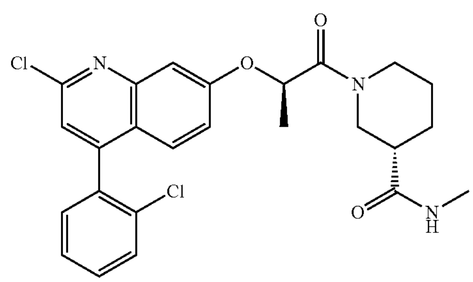 [SMILES: CNC(=O)[C@H]1CCCN(C(=O)[C@@H](C)Oc2ccc3c(-c4ccccc4Cl)cc(Cl)nc3c2)C1] | 34 | (300 MHz, Chloroform-d) δ 8.06-7.64 (m, 1H), 7.49 (dt, J = 7.6, 1.4 Hz, 1H), 7.45-7.27 (m, 3H), 7.23 (dt, J = 6.5, 2.9 Hz, 2H), 7.17-7.06 (m, 2H), 6.37-5.32 (m, 1H), 5.13 (q, J = 6.3 Hz, 1H), 4.43-3.22 (m, 3H), 2.89 (s, 1H), 2.82 (s, 1H), 2.80-2.73 (m, 1H), 2.70 (d, J = 4.4 Hz, 2H), 2.42-2.31 (m, 1H), 2.18-1.98 (m, 1H), 1.87-1.75 (m, 1H), 1.69-1.53 (m, 3H). | 96% |
| 97 | 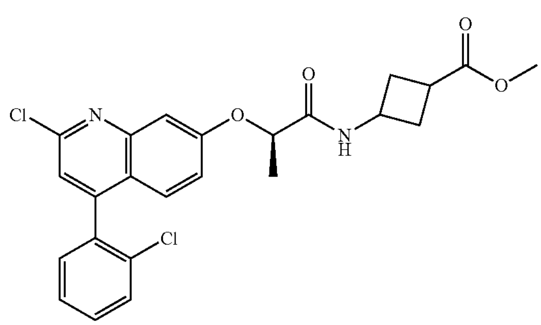 [SMILES: COC(=O)C1CC(NC(=O)[C@@H](C)Oc2ccc3c(-c4ccccc4Cl)cc(Cl)nc3c2)C1] | 2G₃ | (400 MHz, DMSO-d₆) δ 8.60 (td, J = 8.4, 7.9, 4.0 Hz, 1H), 7.69 (dt, J = 8.0, 1.5 Hz, 1H), 7.63-7.51 (m, 2H), 7.49 (dt, J = 7.5, 2.3 Hz, 1H), 7.41-7.39 (m, 1H), 7.35-7.28 (m, 3H), 4.98-4.82 (m, 1H), 4.41-4.11 (m, 1H), 3.66-3.55 (m, 3H), 3.08-2.77 (m, 1H), 2.47-2.04 (m, 4H), 1.53-1.45 (m, 3H). | 100% |
| 98 | 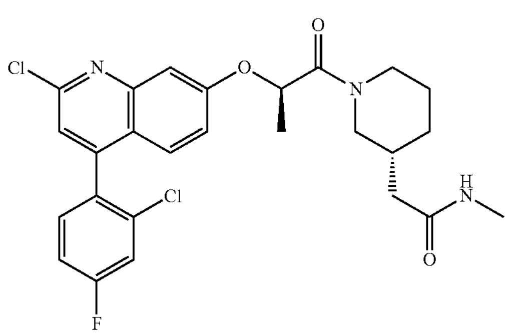 [SMILES: CNC(=O)C[C@H]1CCCN(C(=O)[C@@H](C)Oc2ccc3c(-c4ccc(F)cc4Cl)cc(Cl)nc3c2)C1] | 56 | (300 MHz, Chloroform-d) δ 7.34-7.03 (m, 7H), 6.54-6.35 (m, 1H), 5.21-5.01 (m, 1H), 3.91-3.76 (m, 1H), 3.69-3.07 (m, 3H), 2.82-2.67 (m, 3H), 2.47-2.12 (m, 2H), 2.01-1.30 (m, 6H), 1.20 (d, J = 8.2 Hz, 2H). | 100% |

TABLE 6-continued

Compounds of formula (I) of the invention

| Ex | Structure | BB | ¹H-NMR | LC purity % ee |
|---|---|---|---|---|
| 99 | 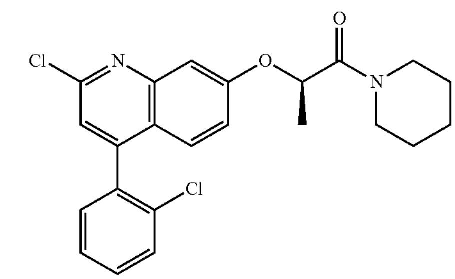 [SMILES: C[C@@H](Oc1ccc2c(-c3ccccc3Cl)cc(Cl)nc2c1)C(=O)N1CCCCC1] | 2D₃ | (300 MHz, Chloroform-d) δ 7.53-7.41 (m, 1H), 7.44-7.06 (m, 7H), 5.12 (qd, J = 6.6, 1.7 Hz, 1H), 3.70-3.54 (m, 1H), 3.52-3.32 (m, 3H), 1.59 (dd, J = 6.6, 1.3 Hz, 9H). | 100% |
| 100 | 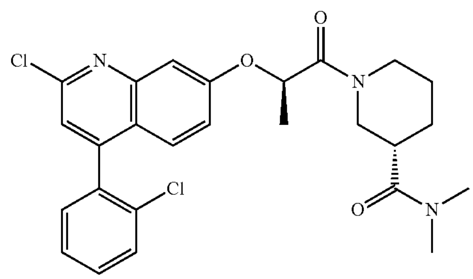 [SMILES: C[C@@H](Oc1ccc2c(-c3ccccc3Cl)cc(Cl)nc2c1)C(=O)N1CCC[C@H](C(=O)N(C)C)C1] | 34 | (300 MHz, Chloroform-d) δ 7.49 (dd, J = 7.7, 1.7 Hz, 1H), 7.45-7.18 (m, 5H), 7.17-7.01 (m, 2H), 5.21-4.99 (m, 1H), 4.55 (d, J = 9.9 Hz, 1H), 4.29-3.83 (m, 1H), 3.35-2.92 (m, 3H), 2.85 (d, J = 7.6 Hz, 3H), 2.79-2.66 (m, 2H), 2.60-2.16 (m, 1H), 1.97-1.17 (m, 7H). | 100% |
| 101 | 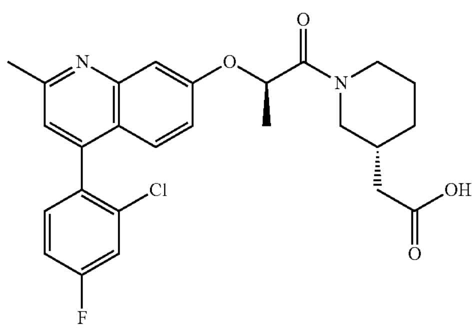 [SMILES: Cc1cc(-c2ccc(F)cc2Cl)c2ccc(O[C@H](C)C(=O)N3CCC[C@H](CC(=O)O)C3)cc2n1] | 74 | (400 MHz, DMSO-d₆) δ 7.75 (dd, J = 8.9, 2.5 Hz, 1H), 7.63-7.43 (m, 4H), 7.40-7.26 (m, 2H), 5.66-5.35 (m, 1H), 4.35-3.80 (m, 2H), 2.84 (s, 4H), 2.60 (d, J = 10.1 Hz, 1H), 2.28-2.19 (m, 1H), 2.12 (dt, J = 15.2, 7.8 Hz, 1H), 1.89-1.48 (m, 6H), 1.26 (s, 2H). | 98% |
| 102 | 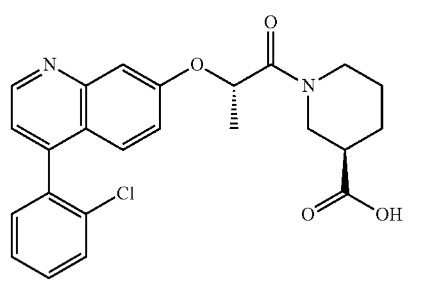 [SMILES: C[C@H](Oc1ccc2c(-c3ccccc3Cl)ccnc2c1)C(=O)N1CCC[C@@H](C(=O)O)C1] | | (400 MHz, DMSO-d₆) δ 8.89 (t, J = 4.9Hz, 1H), 7.68 (dt, J = 7.7, 1.3 Hz, 1H), 7.60-7.49 (m, 2H), 7.45 (dd, J = 7.3, 1.9 Hz, 1H), 7.38-7.26 (m, 3H), 7.22 (dd, J = 9.2, 2.5 Hz, 1H), 5.80-5.46 (m, 1H), 4.42-3.85 (m, 2H), 3.58-3.09 (m, 1H), 3.04-2.76 (m, 1H), 2.47-2.21 (m, 1H), 2.10-1.89 (m, 1H), 1.85-1.56 (m, 2H), 1.55-1.45 (m, 3H), 1.33 (s, 1H). | 94% ee 85% |
| 103 | 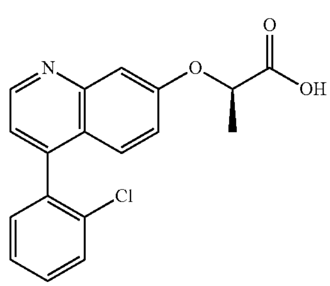 [SMILES: C[C@@H](Oc1ccc2c(-c3ccccc3Cl)ccnc2c1)C(=O)O] | (R)-2F₁_Et | (400 MHz, DMSO-d₆) δ 13.19 (s, 1H), 8.88 (d, J = 4.4 Hz, 1H), 7.72-7.65 (m, 1H), 7.61-7.49 (m, 2H), 7.48-7.41 (m, 1H), 7.35-7.21 (m, 4H), 5.05 (q, J = 6.7 Hz, 1H), 1.58 (dd, J = 6.7, 0.9 Hz, 3H). | 94% |

TABLE 6-continued

Compounds of formula (I) of the invention

| Ex | Structure | BB | ¹H-NMR | LC purity % ee |
|---|---|---|---|---|
| 104 | 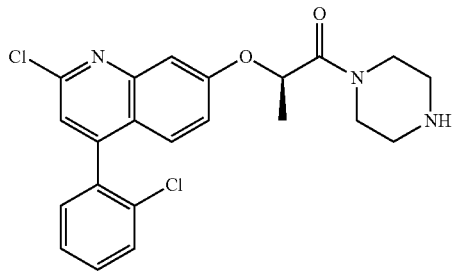 [SMILES: C[C@@H](Oc1ccc2c(-c3ccccc3Cl)cc(Cl)nc2c1)C(=O)N1CCNCC1] | 2G₃ + M11a + M101 | (400 MHz, DMSO-d₆) δ 8.88 (s, 2H), 7.70 (dd, J = 7.9, 1.4 Hz, 1H), 7.58 (dtd, J = 20.0, 7.4, 1.6 Hz, 2H), 7.49 (ddd, J = 7.5, 5.6, 1.9 Hz, 1H), 7.42 (d, J = 1.1 Hz, 1H), 7.38 (d, J = 2.4 Hz, 1H), 7.33-7.25 (m, 2H), 5.59 (p, J = 6.6 Hz, 1H), 3.95-3.60 (m, 4H), 3.27-3.05 (m, 4H), 1.52 (dd, J = 6.5, 2.6 Hz, 3H). - TFA Salt | 100% |
| 105 | 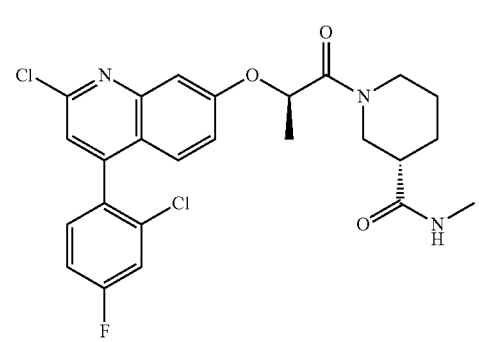 [SMILES: CNC(=O)[C@H]1CCCN(C(=O)[C@@H](C)Oc2ccc3c(-c4ccc(F)cc4Cl)cc(Cl)nc3c2)C1] | 64 | (300 MHz, Chloroform-d) δ 7.34-7.24 (m, 1H), 7.31-7.10 (m, 4H), 7.16-7.01 (m, 3H), 6.42-5.31 (m, 1H), 5.23-5.06 (m, 1H), 4.35-3.25 (m, 3H), 2.83-2.73 (m, 1H), 2.72-2.63 (m, 2H), 2.42-2.27 (m, 1H), 2.16-1.99 (m, 1H), 1.87-1.73 (m, 1H), 1.73-1.49 (m, 5H). | 100% |
| 106 | 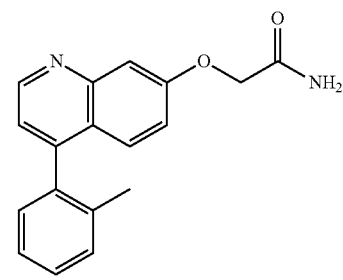 [SMILES: Cc1ccccc1-c1ccnc2cc(OCC(N)=O)ccc12] | 3D₁ | (300 MHz, Chloroform-d) δ 8.84 (d, J = 4.5 Hz, 1H), 7.45 (d, J = 2.6 Hz, 1H), 7.37 (d, J = 9.2 Hz, 1H), 7.34-7.21 (m, 3H), 7.16-7.05 (m, 3H), 6.52 (s, 1H), 5.69 (s, 1H), 4.61 (s, 2H), 1.96 (s, 3H). | 96% |
| 107 | 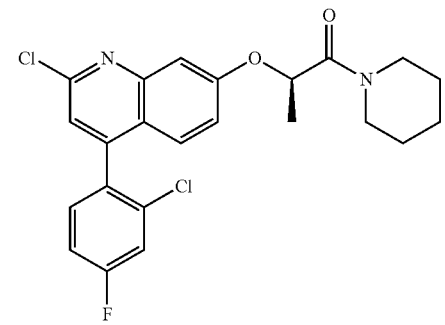 [SMILES: C[C@@H](Oc1ccc2c(-c3ccc(F)cc3Cl)cc(Cl)nc2c1)C(=O)N1CCCCC1] | 4G₃ | (300 MHz, DMSO-d₆) δ 7.80 (dd, J = 8.9, 2.5 Hz, 1H), 7.65 (dd, J = 8.6, 6.1 Hz, 1H), 7.59-7.46 (m, 1H), 7.49 (s, 1H), 7.44-7.28 (m, 3H), 5.61 (p, J = 6.3 Hz, 1H), 3.79-3.59 (m, 2H), 3.57-3.49 (d, J = 5.3 Hz, 2H), 1.74-1.62 (m, 4H), 1.61-1.44 (m, 5H). | 99% |
| 108 | 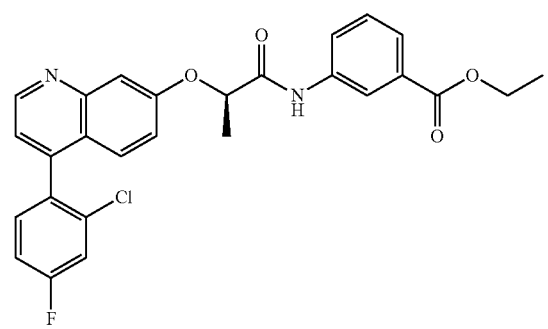 [SMILES: CCOC(=O)c1cccc(NC(=O)[C@@H](C)Oc2ccc3c(-c4ccc(F)cc4Cl)ccnc3c2)c1] | 4G₁ | (300 MHz, Chloroform-d) δ 8.84 (d, J = 4.5 Hz, 1H), 8.35 (d, J = 7.2 Hz, 1H), 8.01-7.89 (m, 2H), 7.73 (dq, J = 7.7, 1.5 Hz, 1H), 7.59 (t, J = 2.5 Hz, 1H), 7.47-7.02 (m, 7H), 5.08-4.95 (m, 1H), 4.30 (q, J = 7.2 Hz, 2H), 1.70 (d, J = 6.6 Hz, 3H), 1.31 (t, J = 7.1 Hz, 3H). | 100% |

TABLE 6-continued

Compounds of formula (I) of the invention

| Ex | Structure | BB | ¹H-NMR | LC purity % ee |
|---|---|---|---|---|
| 109 | 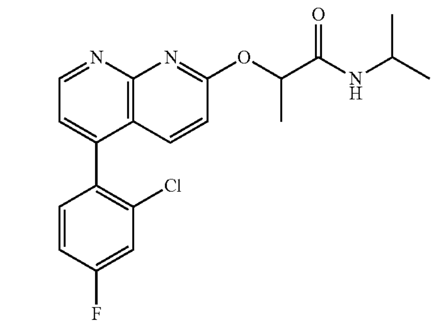 [SMILES: CC(C)NC(=O)C(C)Oc1ccc2c(-c3ccc(F)cc3Cl)ccnc2n1] | (rac)-4G₄ | (300 MHz, Chloroform-d) δ 8.95 (dd, J = 4.6, 1.7 Hz, 1H), 7.76-7.66 (m, 1H), 7.33-7.19 (m, 3H), 7.10 (td, J = 8.2, 2.5 Hz, 1H), 6.99 (d, J = 8.9 Hz, 1H), 6.36 (s, 1H), 5.88 (p, J = 6.8 Hz, 1H), 4.14-3.99 (m, 1H), 1.60 (dd, J = 6.7, 2.0 Hz, 3H), 1.22-1.06 (m, 6H). | 100% |
| 110 | 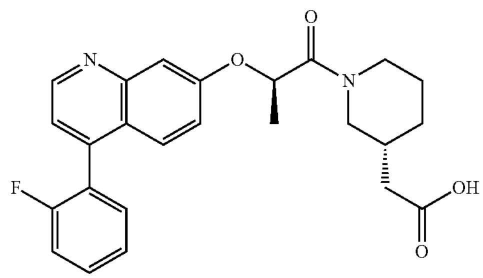 [SMILES: C[C@@H](Oc1ccc2c(-c3ccccc3F)ccnc2c1)C(=O)N1CCC[C@H](CC(=O)O)C1] | (R,R)-2K₁ₓ | (300 MHz, DMSO-d₆) δ 12.28 (s, 1H), 8.95 (dd, J = 7.2, 4.5 Hz, 1H), 7.68 (tdd, J = 7.4, 5.3, 2.0 Hz, 1H), 7.63-7.35 (m, 5H), 7.41-7.27 (m, 2H), 5.69-5.49 (m, 1H), 4.35-4.02 (m, 2H), 3.09 (dt, J = 40.8, 12.0 Hz, 1H), 2.81-2.46 (m, 1H), 2.36-2.09 (m, 2H), 2.00-1.65 (m, 3H), 1.58 (dd, J = 15.9, 6.4 Hz, 3H), 1.31 (s, 2H). | 100% |
| 111 | 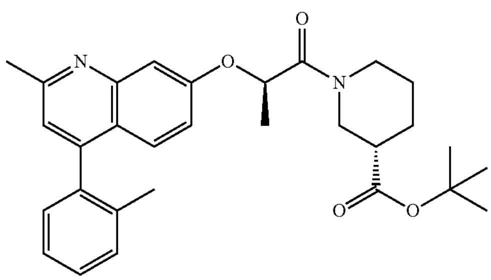 [SMILES: Cc1cc(-c2ccccc2C)c2ccc(O[C@H](C)C(=O)N3CCC[C@H](C(=O)OC(C)(C)C)C3)cc2n1] | (R)-3G₅ | (400 MHz, DMSO-d₆) δ 7.45-7.30 (m, 4H), 7.28-7.16 (m, 2H), 7.10 (d, J = 10.9 Hz, 2H), 5.48 (d, J = 8.3 Hz, 1H), 4.23-3.20 (m, 3H), 3.18-2.88 (m, 1H), 2.64 (s, 4H), 2.40-2.25 (m, 2H), 1.98 (d, J = 3.3 Hz, 4H), 1.76-1.43 (m, 4H), 1.37 (d, J = 2.8 Hz, 9H). | 97% |
| 112 | 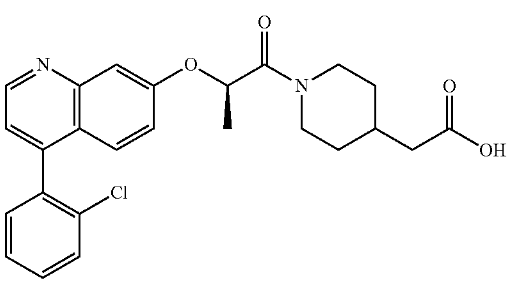 [SMILES: C[C@@H](Oc1ccc2c(-c3ccccc3Cl)ccnc2c1)C(=O)N1CCC(CC(=O)O)CC1] | (R)-2G₁ + M11a + M9 | (300 MHz, Chloroform-d) δ 9.05-8.71 (m, 1H), 8.15 (br. s, 1H), 7.49 (dd, J = 7.6, 1.7 Hz, 1H), 7.48-7.28 (m, 3H), 7.34-7.12 (m,4H), 5.29-5.09 (m, 1H), 4.59 (t, J = 15.8 Hz, 1H), 3.99 (t, J = 16.0 Hz, 1H), 3.65-3.07 (m, 1H), 2.83-2.60 (m, 1H), 2.38 (dd, J = 41.1, 6.6 Hz, 2H), 2.23-1.75 (m, 3H), 1.62 (dd, J = 6.7, 3.8 Hz, 3H), 1.49 (m, 1H), 1.31-1.11 (m, 1H). | 96% |
| 113 | 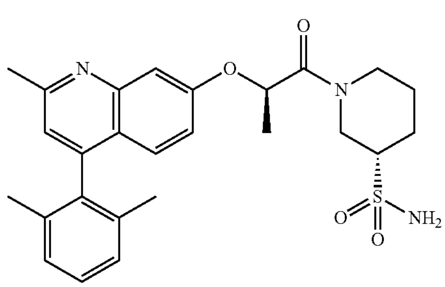 [SMILES: Cc1cc(-c2c(C)cccc2C)c2ccc(O[C@H](C)C(=O)N3CCC[C@H](S(N)(=O)=O)C3)cc2n1] | (R)-6G₅ | (400 MHz, DMSO-d₆) δ 7.54-7.42 (m, 1H), 7.39-7.23 (m, 6H), 6.98 (d, J = 32.2 Hz, 2H), 5.63-5.42 (m, 1H), 4.81-3.95 (m, 2H), 3.39-2.99 (m, 1H), 2.95-2.57 (m, 5H), 2.30-2.09 (m, 1H), 1.93-1.63 (m, 9H), 1.62-1.46 (m, 3H). | 95% |

TABLE 6-continued

Compounds of formula (I) of the invention

| Ex | Structure | BB | ¹H-NMR | LC purity % ee |
|---|---|---|---|---|
| 114 | 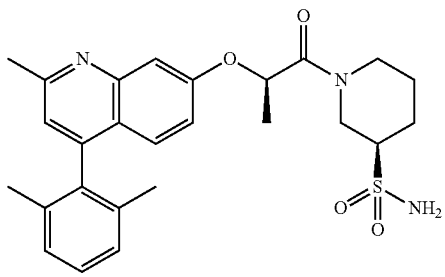 [SMILES: Cc1cc(-c2c(C)cccc2C)c2ccc(O[C@H](C)C(=O)N3CCC[C@@H](S(N)(=O)=O)C3)cc2n1] | (R)-6G$_5$ | (400 MHz, DMSO-d$_6$) δ 7.61-7.48 (s, 1H), 7.46-7.22 (m, 6H), 7.01-6.89 (m, 2H), 5.58-5.37 (m, 1H), 4.86-4.04 (m, 2H), 3.26-3.04 (m, 1H), 2.95-2.78 (m, 4H), 2.74-2.58 (m, 1H), 2.18 (d, J = 12.7 Hz, 1H), 1.96-1.77 (m, 7H), 1.75-1.37 (m, 5H). | 100% |
| 115 | 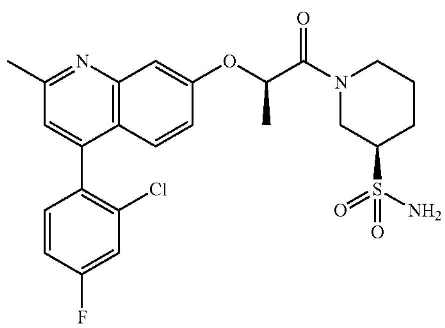 [SMILES: Cc1cc(-c2ccc(F)cc2Cl)c2ccc(O[C@H](C)C(=O)N3CCC[C@@H](S(N)(=O)=O)C3)cc2n1] | (R)-4G$_5$ | (400 MHz, DMSO-d$_6$) δ 7.82-7.68 (m, 1H), 7.61-7.21 (m, 6H), 7.07-6.89 (m, 2H), 5.61-5.36 (m, 1H), 4.84-4.07 (m, 2H), 3.30-3.07 (m, 1H), 2.91-2.58 (m, 5H), 2.23-2.08 (m, 1H), 1.93-1.76 (m, 1H), 1.76-1.62 (m, 1H), 1.62-1.49 (m, 3H), 1.50-1.33 (m, 1H). | 100% |
| 116 | 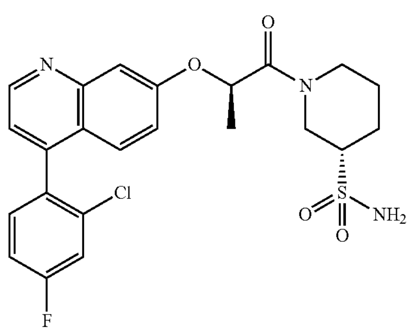 [SMILES: C[C@@H](Oc1ccc2c(-c3ccc(F)cc3Cl)ccnc2c1)C(=O)N1CCC[C@H](S(N)(=O)=O)C1] | (R)-4G$_1$ | (400 MHz, DMSO-d$_6$) δ 8.99 (d, J = 4.5 Hz, 1H), 7.72 (dd, J = 8.9, 2.6 Hz, 1H), 7.54 (ddd, J = 8.4, 6.1, 3.8 Hz, 1H), 7.48-7.37 (m, 3H), 7.35-7.26 (m, 2H), 7.04-6.86 (m, 2H), 5.69-5.38 (m, 1H), 4.83-3.97 (m, 2H), 3.38-2.57 (m, 3H), 2.29-2.06 (m, 1H), 1.96-1.45 (m, 6H). | 100% |
| 117 | 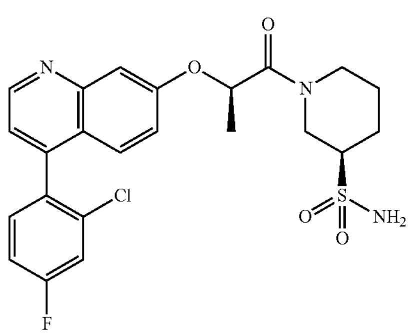 [SMILES: C[C@@H](Oc1ccc2c(-c3ccc(F)cc3Cl)ccnc2c1)C(=O)N1CCC[C@@H](S(N)(=O)=O)C1] | (R)-4G$_1$ | (400 MHz, DMSO-d$_6$) δ 9.01 (d, J = 4.8 Hz, 1H), 7.73 (ddd, J = 8.9, 2.6, 1.3 Hz, 1H), 7.60-7.27 (m, 6H), 7.07-6.87 (m, 2H), 5.64-5.36 (m, 1H), 4.89-4.04 (m, 2H), 3.32-3.07 (m, 1H), 2.92-2.55 (m, 2H), 2.31-2.07 (m, 1H), 1.97-1.32 (m, 6H). | 100% |

TABLE 6-continued

Compounds of formula (I) of the invention

| Ex | Structure | BB | ¹H-NMR | LC purity % ee |
|---|---|---|---|---|
| 118 | 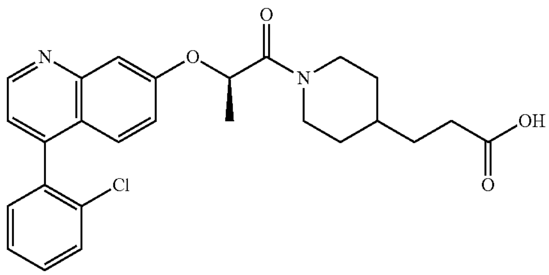 [SMILES: C[C@@H](Oc1ccc2c(-c3ccccc3Cl)ccnc2c1)C(=O)N1CCC(CCC(=O)O)CC1] | (R)-2G₁ + M11a + M9 | (300 MHz, DMSO-d₆) δ 12.06 (s, 1H), 8.89 (dd, J = 4.5, 2.6 Hz, 1H), 7.69 (dd, J = 7.5, 1.8 Hz, 1H), 7.64-7.47 (m, 2H), 7.45 (dd, J = 7.1, 2.3 Hz, 1H), 7.38-7.18 (m, 4H), 5.60-5.46 (m, 1H), 4.34 (d, J = 12.7 Hz, 1H), 4.12 (s, 1H), 3.13 (dd, J = 30.7, 16.5 Hz, 1H), 2.61 (t, J = 13.0 Hz, 1H), 2.34-2.15 (m, 2H), 1.80-1.61 (m, 2H), 1.57-0.74 (m, 6H). | 98% |
| 119 | 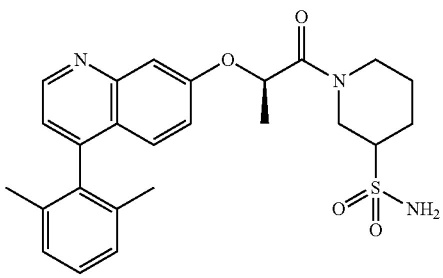 [SMILES: Cc1cccc(C)c1-c1ccnc2cc(O[C@H](C)C(=O)N3CCCC(S(N)(=O)=O)C3)ccc12] | (R)-6G₁ | (300 MHz, DMSO-d₆) δ 9.03 (t, J = 4.8Hz, 1H), 7.51-7.23 (m, 7H), 7.21-7.06 (m, 2H), 5.76-5.39 (m, 1H), 4.75 (dd, J = 118.6, 12.4 Hz, 1H), 4.48-4.19 (m, 1H), 3.42-3.14 (m, 1H), 3.03-2.89 (m, 1H), 2.81 (t, J = 11.8 Hz, 1H), 2.41-2.18 (m, 1H), 2.09-1.77 (m, 9H), 1.73-1.52 (m, 3H). | 95% |
| 120 | 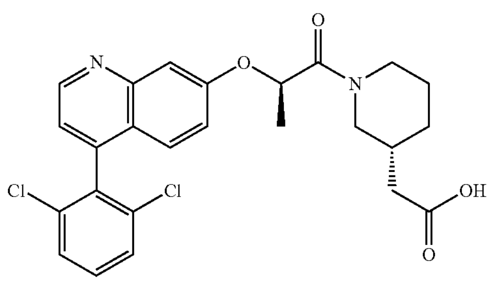 [SMILES: C[C@@H](Oc1ccc2c(-c3c(Cl)cccc3Cl)ccnc2c1)C(=O)N1CCC[C@H](CC(=O)O)C1] | (R)-7G₁ + M11a + M9 | (300 MHz, DMSO-d₆) δ 8.93 (dd, J = 8.4, 4.5 Hz, 1H), 7.71 (d, J = 8.0 Hz, 2H), 7.66-7.54 (m, 1H), 7.36-7.13 (m, 4H), 5.62-5.43 (m, 1H), 4.31-4.18 (m, 1H), 4.17-3.94 (m, 1H), 3.14-2.90 (m, 1H), 2.74-2.40 (m, 1H), 2.29-2.07 (m, 2H), 1.92-1.44 (m, 6H), 1.33-1.20 (m, 2H). | 97% |
| 121 | 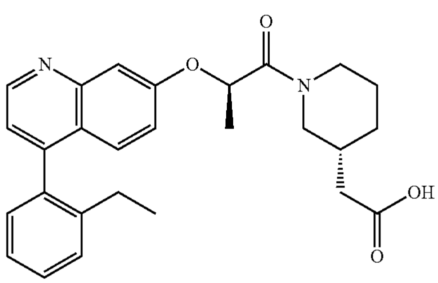 [SMILES: CCc1ccccc1-c1ccnc2cc(O[C@H](C)C(=O)N3CCC[C@H](CC(=O)O)C3)ccc12] | (R,R)-2K₁ₓ | (300 MHz, DMSO-d₆) δ 8.85 (dd, J = 7.8, 4.5 Hz, 1H), 7.51-7.41 (m, 2H), 7.40-7.30 (m, 1H), 7.30-7.13 (m, 5H), 5.49 (dd, J = 27.5, 6.2 Hz, 1H), 4.24 (d, J = 12.9 Hz, 1H), 4.17-3.94 (m, 1H), 3.22-2.54 (m, 1H), 2.44-2.07 (m, 3H), 1.92-1.58 (m, 4H), 1.58-1.43 (m, 3H), 1.33-1.19 (m, 3H), 0.99-0.82 (m, 3H). | 99% |
| 122 | 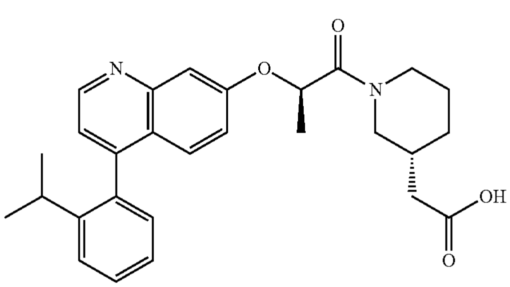 | (R,R)-2K₁ₓ | (300 MHz, DMSO-d₆) δ 12.21 (br. s, 1H), 8.81 (dd, J = 7.8, 4.4 Hz, 1H), 7.56-7.40 (m, 2H), 7.35-7.06 (m, 6H), 5.56-5.37 (m, 1H), 4.20 (d, J = 12.9 Hz, 1H), 4.14-3.91 (m, 1H), 3.16-2.51 (m, 1H), 2.47-2.36 (m, 1H), 2.24-2.02 (m, 2H), 1.89-1.56 (m, 4H), 1.53-1.40 (m, 3H), 1.28-1.17 (m, 2H), 1.06-0.94 (m, 6H). | 99% |

TABLE 6-continued

Compounds of formula (I) of the invention

| Ex | Structure | BB | ¹H-NMR | LC purity % ee |
|---|---|---|---|---|
| 123 | 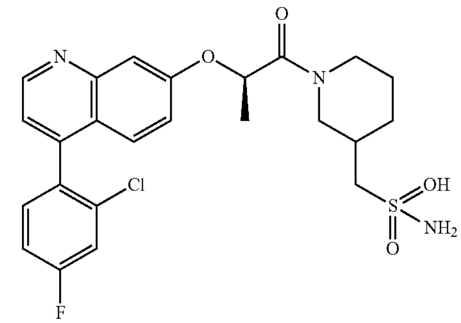 [SMILES: C[C@@H](Oc1ccc2c(-c3ccc(F)cc3Cl)ccnc2c1)C(=O)N1CCCC(CS(N)(=O)=O)C1] | (R)-4G₁ | (300 MHz, DMSO-d₆) δ 8.99 (dd, J = 9.0, 4.5 Hz, 1H), 7.74 (dd, J = 8.9, 2.5 Hz, 1H), 7.63-7.23 (m, 6H), 7.11-6.98 (m, 1H), 6.94-6.75 (m, 1H), 5.68-5.38 (m, 1H), 4.42-3.87 (m, 2H), 3.37-2.58 (m, 4H), 2.32-1.87 (m, 2H), 1.87-1.29 (m, 6H). | 99% |
| 124 | 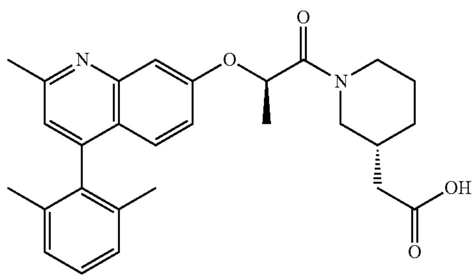 [SMILES: Cc1cc(-c2c(C)cccc2C)c2ccc(O[C@H](C)C(=O)N3CCC[C@H](CC(=O)O)C3)cc2n1] | (R)-6G₅ + M11a + M9 | (300 MHz, DMSO-d₆) δ 12.17 (s, 1H), 7.35-7.01 (m, 7H), 5.54-5.35 (m, 1H), 4.37-3.80 (m, 2H), 3.19-2.87 (m, 1H), 2.78-2.41 (m, 4H), 2.31-2.07 (m, 2H), 1.90-1.73 (m, 8H), 1.69-1.62 (m, 1H), 1.58-1.43 (m, 4H), 1.33-1.20 (m, 2H). | 92% |
| 125 | 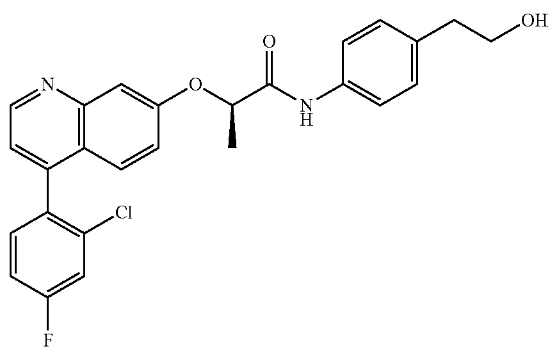 [SMILES: C[C@@H](Oc1ccc2c(-c3ccc(F)cc3Cl)ccnc2c1)C(=O)Nc1ccc(CCO)cc1] | (R)-4G₁ | (400 MHz, DMSO-d₆) δ 10.27 (d, J = 5.3 Hz, 1H), 8.96 (d, J = 4.7 Hz, 1H), 7.72 (dd, J = 9.0, 2.5 Hz, 1H), 7.57-7.36 (m, 8H), 7.15 (dd, J = 8.5, 2.3 Hz, 2H), 5.12 (q, J = 6.4 Hz, 1H), 3.55 (td, J = 7.1, 1.1 Hz, 2H), 2.66 (t, J = 6.9 Hz, 2H), 1.64 (dd, J = 6.6, 1.5 Hz, 3H). | 100% |
| 126 | 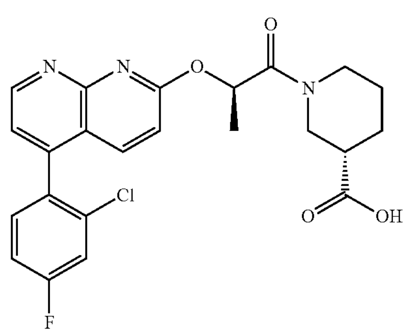 [SMILES: C[C@@H](Oc1ccc2c(-c3ccc(F)cc3Cl)ccnc2n1)C(=O)N1CCC[C@H](C(=O)O)C1] | 62 + chiral HPLC separation | (300 MHz, DMSO-d₆) δ 12.37 (s, 1H), 9.20-8.85 (m, 1H), 7.81-7.67 (m, 2H), 7.61-7.49 (m, 1H), 7.50-7.35 (m, 2H), 7.16 (d, J = 9.0 Hz, 1H), 6.08-5.82 (m, 1H), 4.45-3.94 (m, 2H), 3.49-3.06 (m, 1H), 2.82-2.63 (m, 1H), 2.40 (s, 1H), 2.21-1.94 (m, 1H), 1.67 (d, J = 17.1 Hz, 2H), 1.55-1.19 (m, 4H). | 95% |

TABLE 6-continued

Compounds of formula (I) of the invention

| Ex | Structure | BB | ¹H-NMR | LC purity % ee |
|---|---|---|---|---|
| 127 | 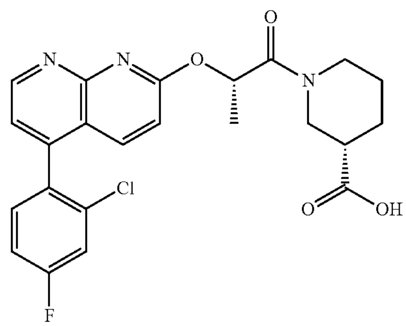 [SMILES: C[C@H](Oc1ccc2c(-c3ccc(F)cc3Cl)ccnc2n1)C(=O)N1CCC[C@H](C(=O)O)C1] | 62 + chiral HPLC separation | (400 MHz, DMSO-$d_6$) δ 12.38 (br. s, 1H), 8.97 (d, J = 4.5 Hz, 1H), 7.77-7.66 (m, 2H), 7.52 (dt, J = 8.9, 5.8 Hz, 1H), 7.46-7.34 (m, 2H), 7.13 (d, J = 9.1 Hz, 1H), 6.07-5.88 (m, 1H), 4.52-3.90 (m, 2H), 3.24-2.54 (m, 1H), 2.35-1.63 (m, 4H), 1.48 (d, J = 6.6 Hz, 5H). | 93% |
| 128 | 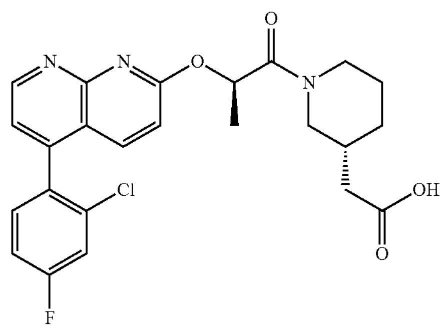 [SMILES: C[C@@H](Oc1ccc2c(-c3ccc(F)cc3Cl)ccnc2n1)C(=O)N1CCC[C@H](CC(=O)O)C1] | 80 + chiral HPLC separation | (400 MHz, DMSO-$d_6$) δ 8.98 (t, J = 5.1 Hz, 1H), 7.79-7.68 (m, 2H), 7.60-7.51 (m, 1H), 7.48-7.36 (m, 2H), 7.16 (dd, J = 9.0, 3.4 Hz, 1H), 6.07-5.83 (m, 1H), 4.28-3.93 (m, 2H), 3.18-3.05 (m, 1H), 2.86-2.31 (m, 2H), 2.23-2.04 (m, 2H), 1.99-1.59 (m, 2H), 1.57-1.43 (m, 3H), 1.39-1.20 (m, 2H). | 98% |
| 129 | 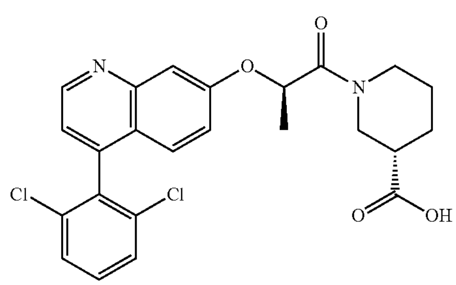 [SMILES: C[C@@H](Oc1ccc2c(-c3c(Cl)cccc3Cl)ccnc2c1)C(=O)N1CCC[C@H](C(=O)O)C1] | (R)-7G$_1$ + M11a + M9 | (300 MHz, DMSO-$d_6$) δ 12.55 (br. s, 1H), 8.94 (t, J = 4.9 Hz, 1H), 7.76-7.66 (m, 2H), 7.66-7.54 (m, 1H), 7.39-7.13 (m, 4H), 5.63-5.53 (m, 1H), 4.46-3.81 (m, 2H), 3.54-3.12 (m, 1H), 3.08-2.70 (m, 1H), 2.61-1.73 (m, 3H), 1.73-1.17 (m, 5H). | 98% |
| 130 | 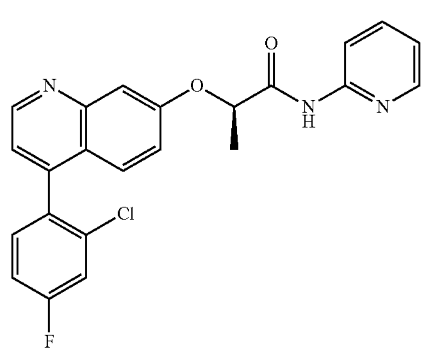 [SMILES: C[C@@H](Oc1ccc2c(-c3ccc(F)cc3Cl)ccnc2c1)C(=O)Nc1ccccn1] | (R)-4G$_1$ | (400 MHz, DMSO-$d_6$) δ 10.98 (d, J = 10.2 Hz, 1H), 8.96 (d, J = 4.7 Hz, 1H), 8.38 (dd, J = 4.8, 2.2 Hz, 1H), 8.03 (dd, J = 8.4, 3.9 Hz, 1H), 7.85-7.66 (m, 2H), 7.59-7.33 (m, 6H), 7.16 (ddt, J = 7.3, 4.9, 1.2 Hz, 1H), 5.32 (q, J = 6.6 Hz, 1H), 1.65 (d, J = 6.5 Hz, 3H). | 100% |

TABLE 6-continued

Compounds of formula (I) of the invention

| Ex | Structure | BB | ¹H-NMR | LC purity % ee |
|---|---|---|---|---|
| 131 | 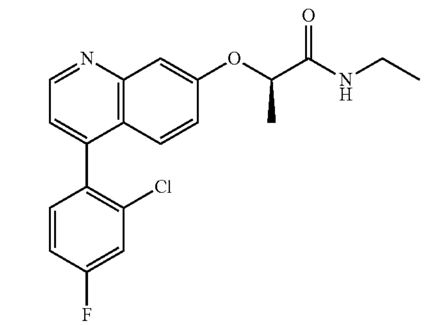 [SMILES: CCNC(=O)[C@@H](C)Oc1ccc2c(-c3ccc(F)cc3Cl)ccnc2c1] | (R)-4G₁ | (400 MHz, DMSO-d₆) δ 8.99 (dd, J = 4.7, 0.9 Hz, 1H), 8.28 (q, J = 5.8 Hz, 1H), 7.72 (ddd, J = 8.9, 2.6, 1.1 Hz, 1H), 7.54 (ddd, J = 9.0, 6.2, 3.0 Hz, 1H), 7.44 (ddt, J = 13.6, 9.2, 3.3 Hz, 4H), 7.35 (ddd, J = 9.2, 2.5, 1.4 Hz, 1H), 4.91 (q, J = 6.6 Hz, 1H), 3.18-3.05 (m, 2H), 1.52 (dd, J = 6.6, 1.4 Hz, 3H), 1.01 (td, J = 7.2, 4.4 Hz, 3H). | 100% |
| 132 | 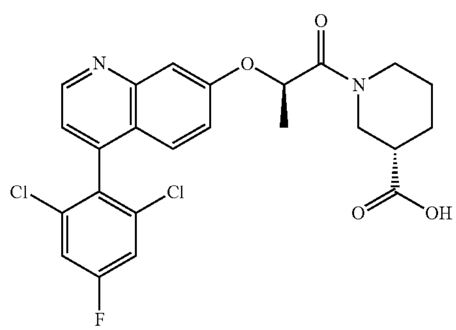 [SMILES: C[C@@H](Oc1ccc2c(-c3c(Cl)cc(F)cc3Cl)ccnc2c1)C(=O)N1CCC[C@H](C(=O)O)C1] | (R,S)-1L₁_₁ | (300 MHz, DMSO-d₆) δ 8.94 (t, J = 5.1 Hz, 1H), 7.80 (d, J = 8.7 Hz, 2H), 7.39-7.14 (m, 4H), 5.65-5.53 (m, 1H), 4.44-3.80 (m, 2H), 3.56-3.08 (m, 1H), 3.06-2.70 (m, 1H), 2.32 (dd, J = 34.5, 7.6 Hz, 1H), 1.98 (d, J = 42.0 Hz, 1H), 1.83-1.12 (m, 6H). | 92% |
| 133 | 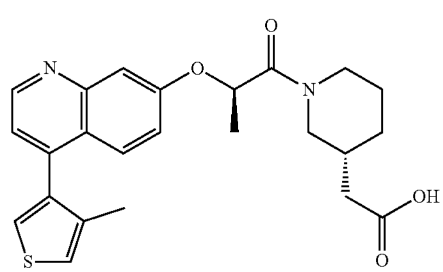 [SMILES: Cc1cscc1-c1ccnc2cc(O[C@H](C)C(=O)N3CCC[C@H](CC(=O)O)C3)ccc12] | (R,R)-2K₁ₓ | (300 MHz, DMSO-d₆) δ 12.30 (s, 1H), 8.89 (dd, J = 7.4, 4.4 Hz, 1H), 7.66 (d, J = 3.2 Hz, 1H), 7.63-7.45 (m, 2H), 7.38-7.25 (m, 3H), 5.56 (dq, J = 28.9, 6.5 Hz, 1H), 4.30 (d, J = 12.6 Hz, 1H), 4.14 (dd, J = 36.9, 13.3 Hz, 1H), 3.09 (dt, J = 42.5, 12.1 Hz, 1H), 2.82-2.45 (m, 1H), 2.36-2.09 (m, 2H), 2.04 (s, 3H), 1.97-1.64 (m, 3H), 1.58 (dd, J = 16.0, 6.4 Hz, 3H), 1.41-1.21 (m, 2H). | 100% |
| 134 | 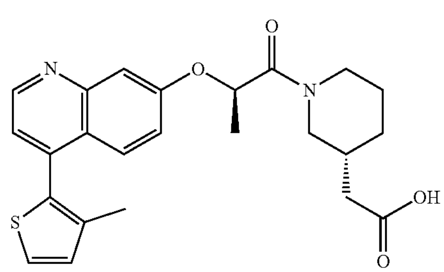 [SMILES: Cc1ccsc1-c1ccnc2cc(O[C@H](C)C(=O)N3CCC[C@H](CC(=O)O)C3)ccc12] | (R,R)-2K₁ₓ | (300 MHz, DMSO-d₆) δ 12.32 (s, 1H), 8.90 (dd, J = 7.5, 4.5 Hz, 1H), 7.77 (d, J = 5.1 Hz, 1H), 7.74-7.67 (m, 1H), 7.43-7.26 (m, 3H), 7.20 (d, J = 5.1 Hz, 1H), 5.57 (dq, J = 28.1, 6.6 Hz, 1H), 4.30 (d, J = 12.6 Hz, 1H), 4.13 (dd, J = 36.0, 13.4 Hz, 1H), 3.23-2.92 (m, 1H), 2.76-2.47 (m, 1H), 2.36-2.11 (m, 2H), 2.10 (d, J = 1.4 Hz, 3H), 1.86 (q, J = 17.3, 15.2 Hz, 3H), 1.58 (dd, J = 16.1, 6.4 Hz, 3H), 1.33 (d, J = 13.0 Hz, 2H). | 100% |

TABLE 6-continued

Compounds of formula (I) of the invention

| Ex | Structure | BB | $^1$H-NMR | LC purity % ee |
|---|---|---|---|---|
| 135 | 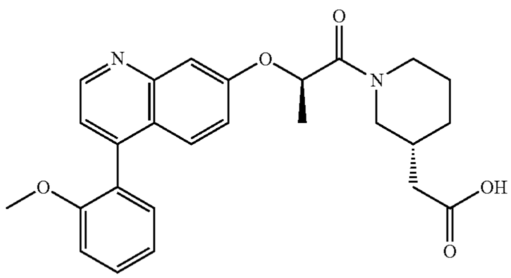 [SMILES: COc1ccccc1-c1ccnc2cc(O[C@H](C)C(=O)N3CCC[C@H](CC(=O)O)C3)ccc12] | (R,R)-2K$_{1x}$ | (300 MHz, DMSO-d$_6$) δ 12.32 (s, 1H), 8.88 (dd, J = 7.2, 4.5 Hz, 1H), 7.58 (td, J = 7.9, 1.8 Hz, 1H), 7.44 (dt, J = 10.7, 2.9 Hz, 1H), 7.37-7.12 (m, 6H), 5.64-5.45 (m, 1H), 4.36-3.99 (m, 2H), 3.73 (s, 3H), 3.22-2.93 (m, 1H), 2.77-2.44 (m, 1H), 2.24 (dt, J = 25.8, 6.7 Hz, 2H), 1.76 (d, J = 42.9 Hz, 3H), 1.57 (dd, J = 15.8, 6.4 Hz, 3H), 1.31 (s, 2H). | 100% |
| 136 | 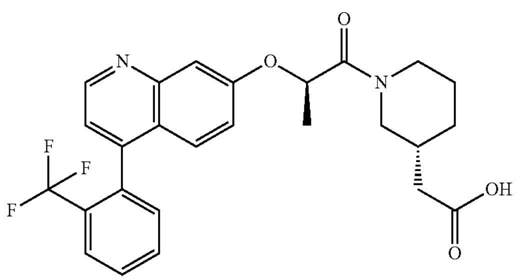 [SMILES: C[C@@H](Oc1ccc2c(-c3ccccc3C(F)(F)F)ccnc2c1)C(=O)N1CCC[C@H](CC(=O)O)C1] | (R,R)-2K$_{1x}$ | (300 MHz, DMSO-d$_6$) δ 12.29 (s, 1H), 8.91 (dd, J = 7.6, 4.4 Hz, 1H), 8.07-7.97 (m, 1H), 7.94-7.76 (m, 2H), 7.52 (t, J = 7.2 Hz, 1H), 7.38-7.16 (m, 4H), 5.65-5.46 (m, 1H), 4.29 (d, J = 12.9 Hz, 1H), 4.12 (dd, J = 35.2, 13.4 Hz, 1H), 3.09 (dt, J = 39.3, 11.4 Hz, 1H), 2.80-2.45 (m, 1H), 2.35-2.09 (m, 2H), 1.96-1.64 (m, 2H), 1.57 (dd, J = 15.9, 6.4 Hz, 3H), 1.38-1.24 (m, 2H). | 99% |
| 137 | 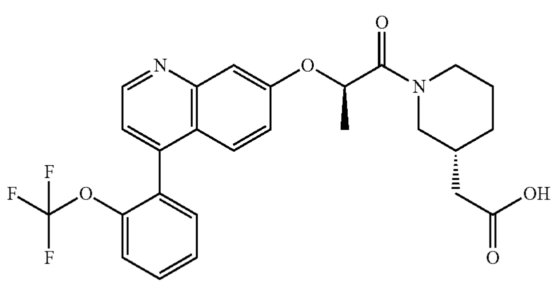 [SMILES: C[C@@H](Oc1ccc2c(-c3ccccc3OC(F)(F)F)ccnc2c1)C(=O)N1CCC[C@H](CC(=O)O)C1] | (R,R)-2K$_{1x}$ | (300 MHz, DMSO-d$_6$) δ 12.29 (s, 1H), 8.95 (dd, J = 7.5, 4.4 Hz, 1H), 7.83-7.55 (m, 4H), 7.48-7.25 (m, 4H), 5.69-5.48 (m, 1H), 4.37-3.98 (m, 2H), 3.24-2.95 (m, 1H), 2.80-2.46 (m, 1H), 2.34-2.09 (m, 2H), 1.96-1.65 (m, 3H), 1.58 (dd, J = 16.2, 6.4 Hz, 3H), 1.38-1.24 (m, 2H). | 100% |
| 138 | 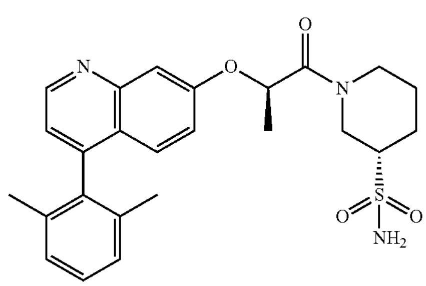 [SMILES: Cc1cccc(C)c1-c1ccnc2cc(O[C@H](C)C(=O)N3CCC[C@H](S(N)(=O)=O)C3)ccc12] | (R)-6G$_1$ | (400 MHz, DMSO-d$_6$) δ 9.05 (d, J = 4.9 Hz, 1H), 7.44 (s, 1H), 7.39-7.21 (m, 6H), 7.08-6.87 (m, 2H), 5.65-5.42 (m, 1H), 4.87-3.97 (m, 2H), 3.59-2.60 (m, 3H), 2.29-2.08 (m, 1H), 2.02-1.65 (m, 9H), 1.61-1.47 (m, 3H). | 100% |
| 139 | 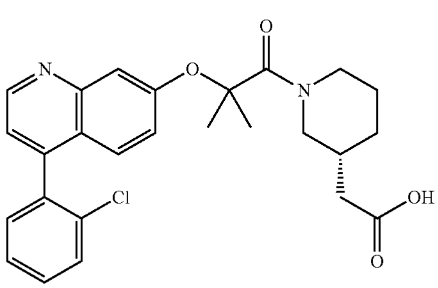 [SMILES: CC(C)(Oc1ccc2c(-c3ccccc3Cl)ccnc2c1)C(=O)N1CCC[C@H](CC(=O)O)C1] | (gem)-2G$_1$ | (400 MHz, DMSO-d$_6$) δ 12.08 (s, 1H), 8.87 (d, J = 4.4 Hz, 1H), 7.67 (dt, J = 7.8, 1.5 Hz, 1H), 7.60-7.43 (m, 3H), 7.35-7.25 (m, 3H), 7.21-7.11 (m, 1H), 4.66-4.44 (m, 1H), 4.41-4.19 (m, 1H), 3.12-2.33 (m, 2H), 2.18-1.94 (m, 2H), 1.74-1.54 (m, 8H), 1.25-1.21 (m, 1H), 1.17 (d, J = 4.7 Hz, 2H). | 93% |

TABLE 6-continued

Compounds of formula (I) of the invention

| Ex | Structure | BB | ¹H-NMR | LC purity % ee |
|---|---|---|---|---|
| 140 | 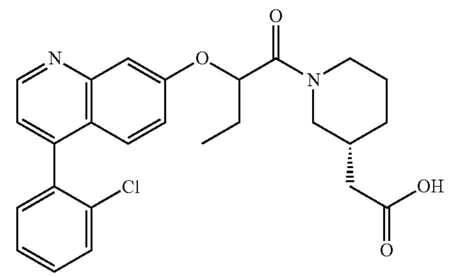 [SMILES: CCC(Oc1ccc2c(-c3ccccc3Cl)ccnc2c1)C(=O)N1CCC[C@H](CC(=O)O)C1] | (R)-Et-2G₁ | (400 MHz, DMSO-d₆) δ 9.02 (dd, J = 6.9, 4.8 Hz, 1H), 7.78-7.27 (m, 8H), 5.42-5.20 (m, 1H), 4.34-3.94 (m, 2H), 3.33-2.71 (m, 1H), 2.65-2.37 (m, 1H), 2.36-1.60 (m, 7H), 1.43-1.17 (m, 2H), 1.12-0.98 (m, 3H). | 100% |
| 141 | 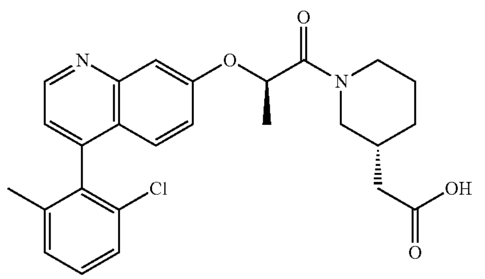 [SMILES: Cc1cccc(Cl)c1-c1ccnc2cc(O[C@H](C)C(=O)N3CCC[C@H](CC(=O)O)C3)ccc12] | (R,R)-2K₁ₓ | (400 MHz, DMSO-d₆) δ 8.94 (d, J = 4.4 Hz, 1H), 8.09 (d, J = 7.7 Hz, 1H), 7.90 (dd, J = 7.7, 7.5 Hz, 1H), 7.75 (dd, J = 7.7, 7.6 Hz, 1H), 7.66 (d, J = 7.4 Hz, 1H), 7.44-7.23 (m, 4H), 5.63-5.43 (m, 1H), 4.29-3.95 (m, 2H), 3.14-2.86 (m, 1H), 2.70-2.37 (m, 1H), 2.22-2.01 (m, 2H), 1.91-1.44 (m, 6H), 1.32-1.14 (m, 2H). | 91% |
| 142 | 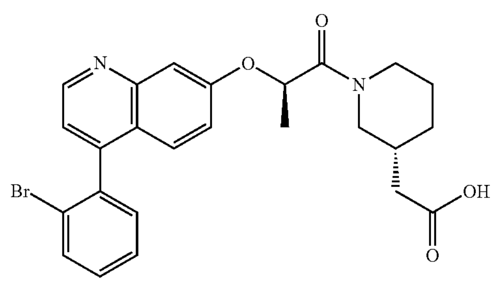 [SMILES: C[C@@H](Oc1ccc2c(-c3ccccc3Br)ccnc2c1)C(=O)N1CCC[C@H](CC(=O)O)C1] | (R,R)-2K₁ₓ | (300 MHz, DMSO-d₆) δ 8.88 (dd, J = 7.7, 4.5 Hz, 1H), 7.84 (d, J = 7.9 Hz, 1H), 7.63-7.38 (m, 3H), 7.35-7.18 (m, 4H), 5.62-5.41 (m, 1H), 4.24 (d, J = 12.7 Hz, 1H), 4.18-3.94 (m, 1H), 3.16-2.87 (m, 1H), 2.75-2.40 (m, 1H), 2.33-2.04 (m, 1H), 1.92-1.60 (m, 4H), 1.52 (dd, J = 16.2, 6.4 Hz, 3H), 1.35-1.17 (m, 2H). | 96% |
| 143 | 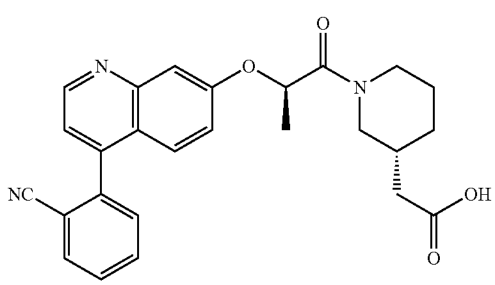 [SMILES: C[C@@H](Oc1ccc2c(-c3ccccc3C#N)ccnc2c1)C(=O)N1CCC[C@H](CC(=O)O)C1] | (R,R)-2K₁ₓ | (300 MHz, DMSO-d₆) δ 8.98-8.88 (m, 1H), 8.08 (d, J = 7.7 Hz, 1H), 7.90 (dd, J = 7.7, 7.5 Hz, 1H), 7.75 (dd, J = 7.7, 7.6 Hz, 1H), 7.66 (d, J = 7.4 Hz, 1H), 7.44-7.23 (m, 4H), 5.63-5.43 (m, 1H), 4.30-3.95 (m, 2H), 3.13-2.88 (m, 1H), 2.71-2.37 (m, 1H), 2.22-2.00 (m, 2H), 1.93-1.43 (m, 6H), 1.32-1.14 (m, 2H). | 91% |
| 144 | 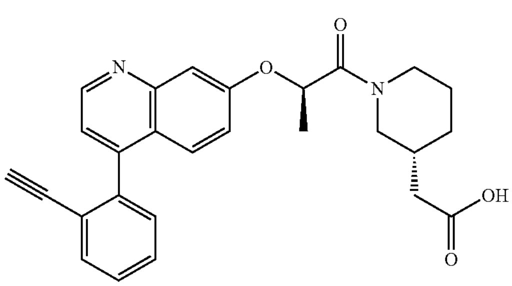 [SMILES: C#Cc1ccccc1-c1ccnc2cc(O[C@H](C)C(=O)N3CCC[C@H](CC(=O)O)C3)ccc12] | (R,R)-2K₁ₓ | (300 MHz, DMSO-d₆) δ 8.86 (dd, J = 7.6, 4.5 Hz, 1H), 7.75-7.66 (m, 1H), 7.65-7.49 (m, 2H), 7.46-7.32 (m, 2H), 7.31-7.16 (m, 3H), 5.60-5.38 (m, 1H), 4.32-3.95 (m, 2H), 3.92 (d, J = 3.3 Hz, 1H), 3.16-2.89 (m, 1H), 2.70-2.41 (m, 1H), 2.27-2.06 (m, 1H), 1.70 (d, J = 42.7 Hz, 4H), 1.52 (dd, J = 15.5, 6.3 Hz, 3H), 1.25 (s, 2H). | 93% |

TABLE 6-continued

Compounds of formula (I) of the invention

| Ex | Structure | BB | ¹H-NMR | LC purity % ee |
|---|---|---|---|---|
| 145 | 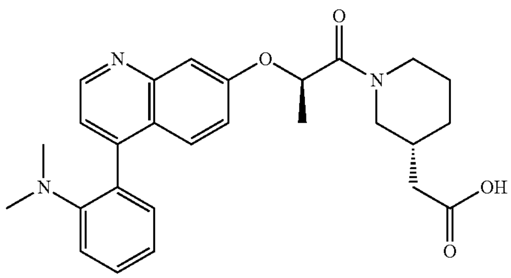 [SMILES: C[C@@H](Oc1ccc2c(-c3ccccc3N(C)C)ccnc2c1)C(=O)N1CCC[C@H](CC(=O)O)C1] | (R,R)-2K₁ₓ | (300 MHz, DMSO-d₆) δ 8.66 (dd, J =8.2, 4.5 Hz, 1H), 7.35-7.20 (m, 2H), 7.19-6.86 (m, 6H), 5.37-5.21 (m, 1H), 3.98 (dd, J = 51.5, 22.6 Hz, 2H), 3.00-2.39 (m, 2H), 2.31-2.17 (m, 6H), 2.07-1.89 (m, 1H), 1.52 (d, J = 44.9 Hz, 4H), 1.35 (dd, J = 17.7, 6.4 Hz, 3H), 1.08 (s, 2H). | 97% |
| 146 | 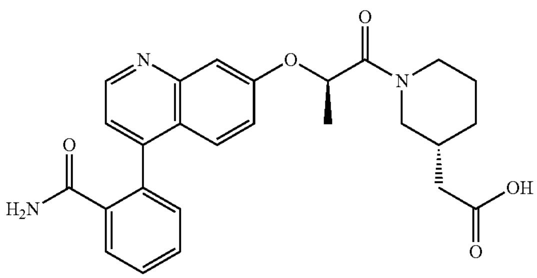 [SMILES: C[C@@H](Oc1ccc2c(-c3ccccc3C(N)=O)ccnc2c1)C(=O)N1CCC[C@H](CC(=O)O)C1] | | | |
| 147 | 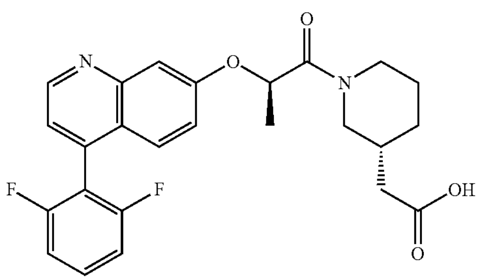 [SMILES: C[C@@H](Oc1ccc2c(-c3c(F)cccc3F)ccnc2c1)C(=O)N1CCC[C@H](CC(=O)O)C1] | | | |
| 148 | 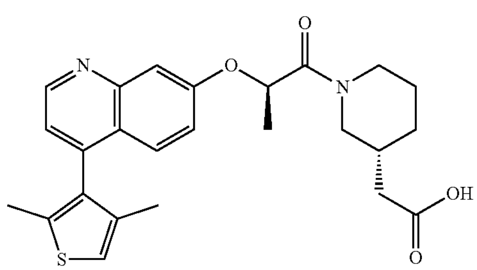 [SMILES: Cc1csc(C)c1-c1ccnc2cc(O[C@H](C)C(=O)N3CCC[C@H](CC(=O)O)C3)ccc12] | | | |
| 149 | 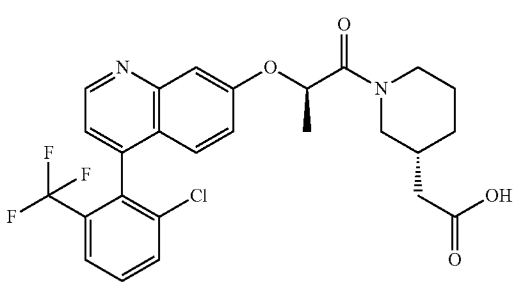 [SMILES: C[C@@H](Oc1ccc2c(-c3c(Cl)cccc3C(F)(F)F)ccnc2c1)C(=O)N1CCC[C@H](CC(=O)O)C1] | | | |

TABLE 6-continued

Compounds of formula (I) of the invention

| Ex | Structure | BB | ¹H-NMR | LC purity % ee |
|---|---|---|---|---|
| 150 | 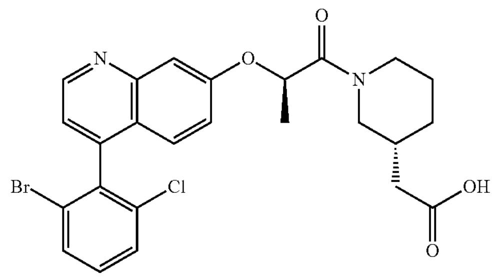 | | | |
| 151 | 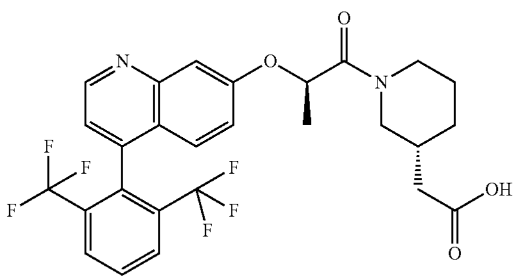 [SMILES: C[C@@H](Oc1ccc2c(-c3c(C(F)(F)F)cccc3C(F)(F)F)ccnc2c1)C(=O)N1CCC[C@H](CC(=O)O)C1] | (R,R)-2K₁ₓ | (300 MHz, DMSO-d₆) δ 8.92-8.85 (m, 1H), 8.28 (s, 1H), 8.22 (d, J = 8.0 Hz, 1H), 7.77-7.72 (m, 1H), 7.35-7.14 (m, 4H), 5.61-5.40 (m, 1H), 4.30-3.94 (m, 2H), 3.15-2.89 (m, 1H), 2.70-2.38 (m, 1H), 2.28-2.00 (m, 2H), 1.94-1.42 (m, 7H), 1.34-1.11 (m, 2H). | 97% |
| 152 | 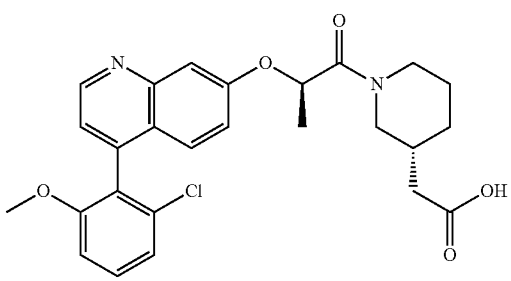 [SMILES: COc1cccc(Cl)c1-c1ccnc2cc(O[C@H](C)C(=O)N3CCC[C@H](CC(=O)O)C3)ccc12] | (R,R)-2K₁ₓ | (300 MHz, DMSO-d₆) δ 8.89-8.82 (m, 1H), 7.53 (t, J = 8.3 Hz, 1H), 7.28-7.14 (m, 6H), 5.59-5.40 (m, 1H), 4.30-3.95 (m, 2H), 3.63 (s, 3H), 3.15-2.54 (m, 2H), 2.33-2.05 (m, 2H), 1.94-1.43 (m, 6H), 1.36-1.15 (m, 2H). | 95% |
| 153 | 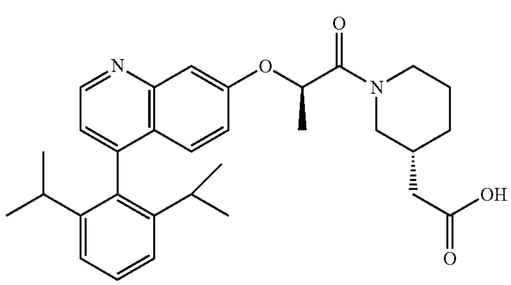 [SMILES: CC(C)c1cccc(C(C)C)c1-c1ccnc2cc(O[C@H](C)C(=O)N3CCC[C@H](CC(=O)O)C3)ccc12] | | | |
| 154 | 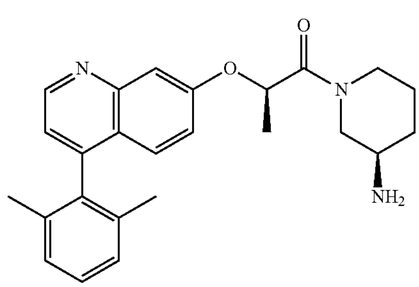 [SMILES: Cc1cccc(C)c1-c1ccnc2cc(O[C@H](C)C(=O)N3CCC[C@@H](N)C3)ccc12] | | | |

TABLE 6-continued

Compounds of formula (I) of the invention

| Ex | Structure | BB | ¹H-NMR | LC purity % ee |
|---|---|---|---|---|
| 155 | 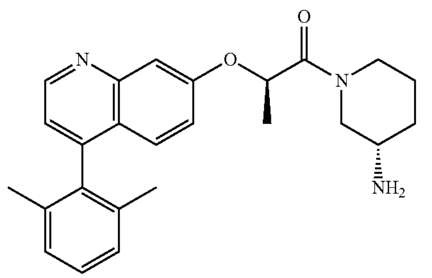 [SMILES: Cc1cccc(C)c1-c1ccnc2cc(O[C@H](C)C(=O)N3CCC[C@H](N)C3)ccc12] | | | |
| 156 | 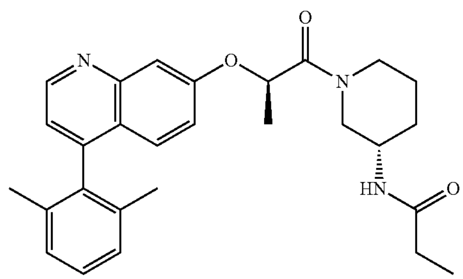 [SMILES: CCC(=O)N[C@H]1CCCN(C(=O)[C@@H](C)Oc2ccc3c(-c4c(C)cccc4C)ccnc3c2)C1] | | | |
| 157 | 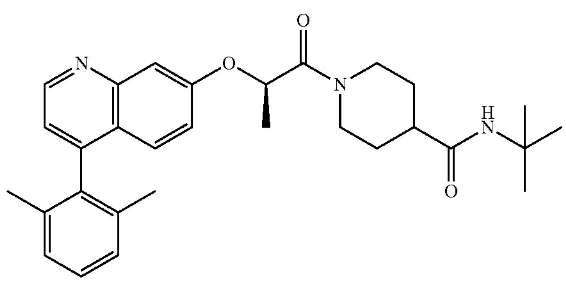 [SMILES: Cc1cccc(C)c1-c1ccnc2cc(O[C@H](C)C(=O)N3CCC(C(=O)NC(C)(C)C)CC3)ccc12] | | | |
| 158 | 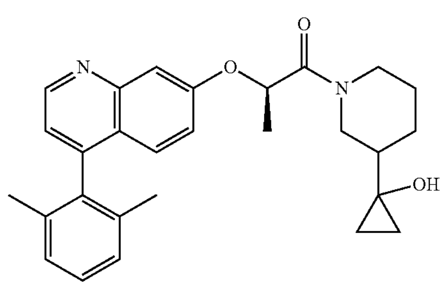 [SMILES: Cc1cccc(C)c1-c1ccnc2cc(O[C@H](C)C(=O)N3CCCC(C4(O)CC4)C3)ccc12] | | | |
| 159 | 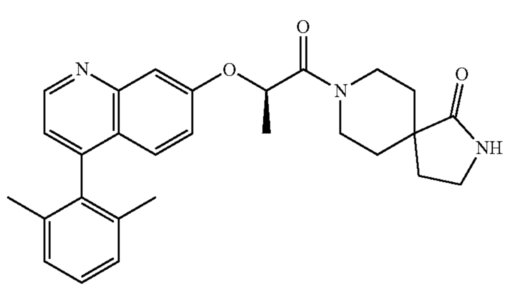 [SMILES: Cc1cccc(C)c1-c1ccnc2cc(O[C@H](C)C(=O)N3CCC4(CCNC4=O)CC3)ccc12] | | | |

TABLE 6-continued

Compounds of formula (I) of the invention

| Ex | Structure | BB | ¹H-NMR | LC purity % ee |
|----|-----------|----|----|----|
| 160 | 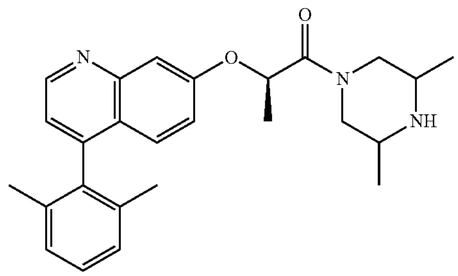 | | | |
| 161 | 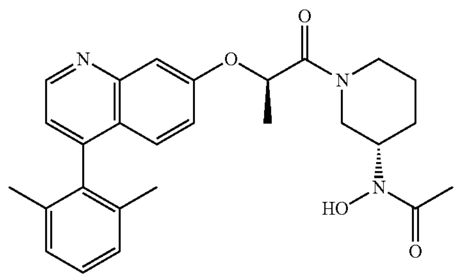 [SMILES: CC(=O)N(O)[C@H]1CCCN(C(=O)[C@@H](C)Oc2ccc3c(-c4c(C)cccc4C)ccnc3c2)C1] | | | |
| 162 | 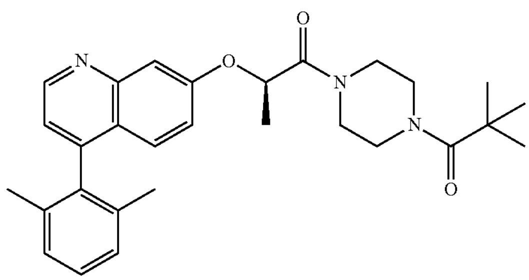 [SMILES: Cc1cccc(C)c1-c1ccnc2cc(O[C@H](C)C(=O)N3CCN(C(=O)C(C)(C)C)CC3)ccc12] | | | |
| 163 | 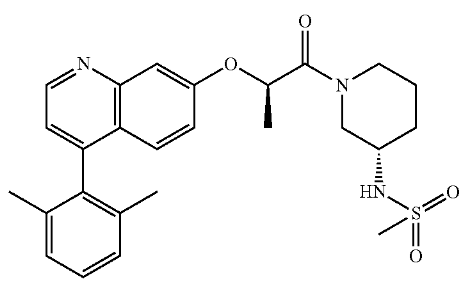 [SMILES: Cc1cccc(C)c1-c1ccnc2cc(O[C@H](C)C(=O)N3CCC[C@H](NS(C)(=O)=O)C3)ccc12] | | | |
| 164 | 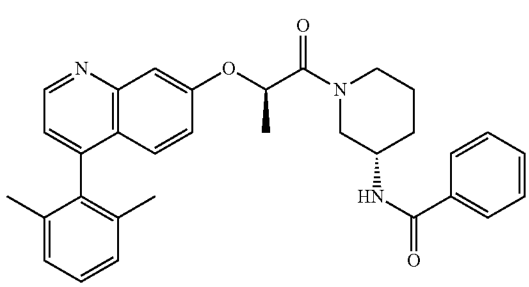 [SMILES: Cc1cccc(C)c1-c1ccnc2cc(O[C@H](C)C(=O)N3CCC[C@H](NC(=O)c4ccccc4)C3)ccc12] | | | |

TABLE 6-continued

Compounds of formula (I) of the invention

| Ex | Structure | BB | ¹H-NMR | LC purity % ee |
|----|-----------|----|--------|----------------|
| 165 | 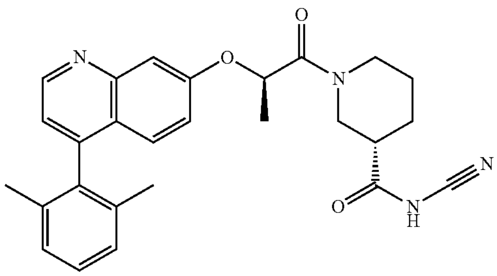 [SMILES: Cc1cccc(C)c1-c1ccnc2cc(O[C@H](C)C(=O)N3CCC[C@H](C(=O)NC#N)C3)ccc12] | | | |
| 166 | 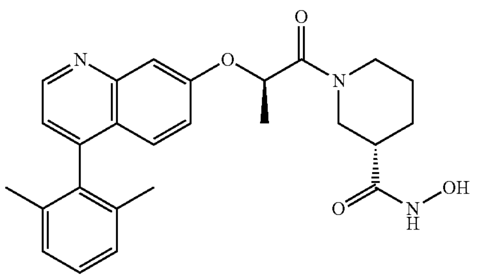 [SMILES: Cc1cccc(C)c1-c1ccnc2cc(O[C@H](C)C(=O)N3CCC[C@H](C(=O)NO)C3)ccc12] | | | |
| 167 | 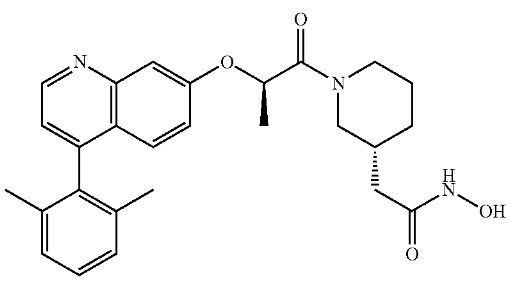 [SMILES: Cc1cccc(C)c1-c1ccnc2cc(O[C@H](C)C(=O)N3CCC[C@H](CC(=O)NO)C3)ccc12] | | | |
| 168 | 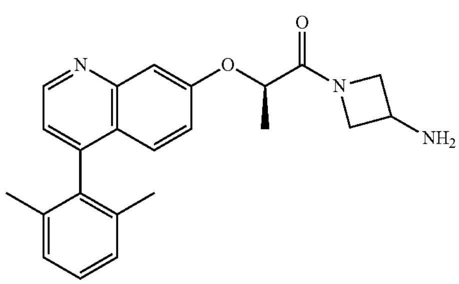 [SMILES: Cc1cccc(C)c1-c1ccnc2cc(O[C@H](C)C(=O)N3CC(N)C3)ccc12] | | | |
| 169 | 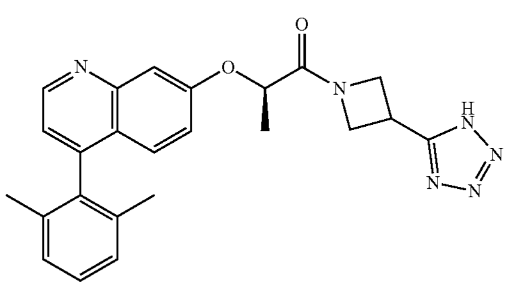 [SMILES: Cc1cccc(C)c1-c1ccnc2cc(O[C@H](C)C(=O)N3CC(c4nnn[nH]4)C3)ccc12] | | | |

TABLE 6-continued

Compounds of formula (I) of the invention

| Ex | Structure | BB | ¹H-NMR | LC purity % ee |
|---|---|---|---|---|
| 170 | 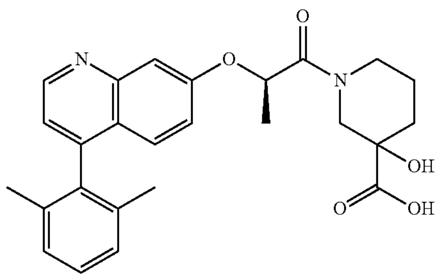 [SMILES: Cc1cccc(C)c1-c1ccnc2cc(O[C@H](C)C(=O)N3CCCC(O)(C(=O)O)C3)ccc12] | | | |
| 171 | 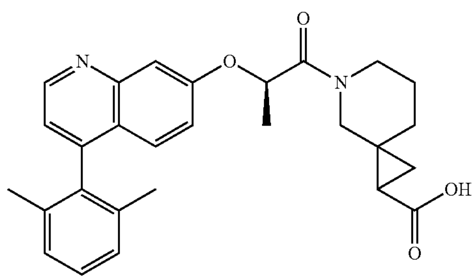 [SMILES: Cc1cccc(C)c1-c1ccnc2cc(O[C@H](C)C(=O)N3CCCC4(CC4C(=O)O)C3)ccc12] | | | |
| 172 | 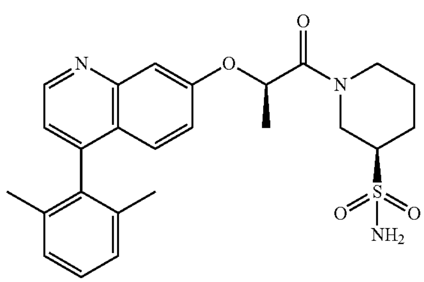 [SMILES: Cc1cccc(C)c1-c1ccnc2cc(O[C@H](C)C(=O)N3CCC[C@@H](S(N)(=O)=O)C3)ccc12] | (R)-6G₁ | (400 MHz, DMSO-d₆) δ 9.04 (d, J = 4.9 Hz, 1H), 7.44 (d, J = 4.9 Hz, 1H), 7.38-7.15 (m, 6H), 7.05-6.85 (m, 2H), 5.60-5.33 (dd, J = 48.4, 6.8 Hz, 1H), 4.88-4.00 (m, 2H), 3.33-3.05 (m, 1H), 2.91-2.77 (m, 1H), 2.72-2.56 (m, 1H), 2.25-2.09 (m, 1H), 1.93-1.60 (m, 8H), 1.58-1.32 (m, 4H). | 97% |
| 173 | 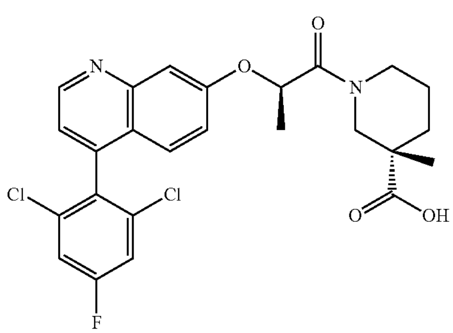 [SMILES: C[C@@H](Oc1ccc2c(-c3c(Cl)cc(F)cc3Cl)ccnc2c1)C(=O)N1CCC[C@](C)(C(=O)O)C1] | (R)-9G₁ | (400 MHz, DMSO-d₆) δ 8.96-8.88 (m, 1H), 7.82-7.20 (m, 6H), 5.81-5.47 (m, 1H), 4.18-3.94 (m, 1H), 3.80-3.06 (m, 3H), 2.95-2.59 (m, 1H), 2.19-1.23 (m, 7H), 1.17-0.91 (m, 2H). | 92% ee98% |
| 174 | 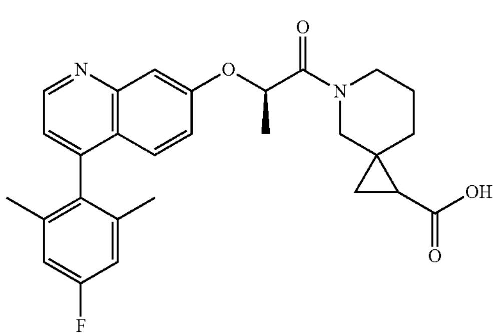 [SMILES: Cc1cc(F)cc(C)c1-c1ccnc2cc(O[C@H](C)C(=O)N3CCCC4(CC4C(=O)O)C3)ccc12] | (R)-8G₁ | (400 MHz, DMSO-d₆) δ 8.91-8.85 (m, 1H), 7.40-7.06 (m, 6H), 5.59-5.40 (m, 1H), 3.78-3.40 (m, 3H), 1.90-1.66 (m, 9H), 1.63-1.40 (m, 5H), 1.26-0.71 (m, 3H). | 98% ee 96% (methyl-group) |

TABLE 6-continued

Compounds of formula (I) of the invention

| Ex | Structure | BB | ¹H-NMR | LC purity % ee |
|---|---|---|---|---|
| 175 | 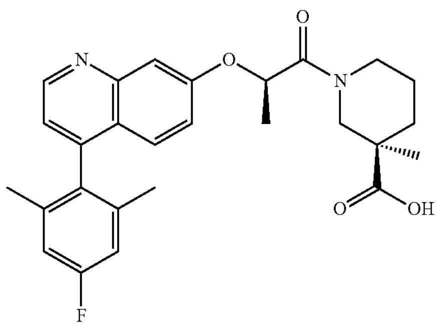 | (R)-8G$_1$ | (400 MHz, DMSO-d$_6$) δ 8.88 (d, J = 3.6 Hz, 1H), 7.29 (d, J = 10.1 Hz, 1H), 7.20-7.14 (m, 3H), 7.10 (d, J = 9.8 Hz, 2H), 5.66-5.42 (m, 1H), 4.01-3.58 (m, 2H), 3.50-3.13 (m, 2H), 2.08-1.77 (m, 7H), 1.69-1.37 (m, 6H), 1.22-0.93 (m, 3H). | 99% ee100% |
| 176 | 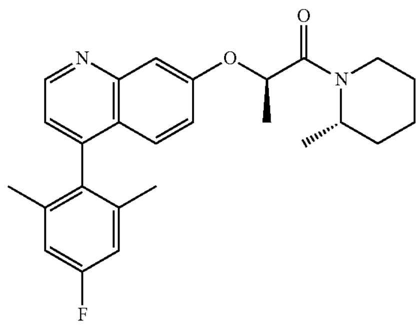 [SMILES: Cc1cc(F)cc(C)c1-c1ccnc2cc(O[C@H](C)C(=O)N3CCCC[C@@H]3C)ccc12] | (R)-8G$_1$ | (300 MHz, DMSO-d$_6$) δ 8.90-8.86 (m, 1H), 7.30-7.06 (m, 6H), 5.49 (q, J = 6.4 Hz, 1H), 4.75-4.33 (m, 1H), 4.31-3.88 (m, 1H), 3.21-2.68 (m, 1H), 1.87-1.80 (m, 6H), 1.76-1.37 (m, 10H), 1.27-1.02 (m, 2H). | 99% |
| 177 | 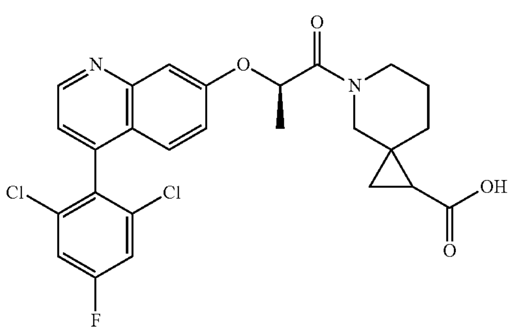 [SMILES: C[C@@H](Oc1ccc2c(-c3c(Cl)cc(F)cc3Cl)ccnc2c1)C(=O)N1CCCC2(CC2C(=O)O)C1] | (R)-9F$_1$_Et | (400 MHz, DMSO-d$_6$) δ 8.97-8.91 (m, 1H), 7.83-7.73 (m, 2H), 7.44-7.19 (m, 4H), 5.63-5.45 (m, 1H), 3.80-3.40 (m, 4H), 1.87-1.40 (m, 8H), 1.27-0.71 (m, 2H). | 96% |
| 178 | 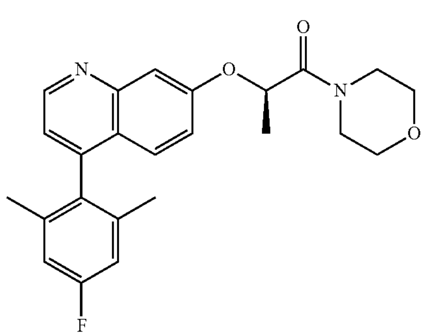 [SMILES: Cc1cc(F)cc(C)c1-c1ccnc2cc(O[C@H](C)C(=O)N3CCOCC3)ccc12] | (R)-8G$_1$ | (400 MHz, DMSO-d$_6$) δ 8.89 (d, J = 4.4 Hz, 1H), 7.32 (d, J = 2.1 Hz, 1H), 7.21-7.14 (m, 3H), 7.10 (d, J = 10.0 Hz, 2H), 5.52 (q, J = 6.5 Hz, 1H), 3.80-3.37 (m, 8H), 1.85 (s, 3H), 1.83 (s, 3H), 1.51 (d, J = 6.5 Hz, 3H). | 98% ee 92% |

TABLE 6-continued

Compounds of formula (I) of the invention

| Ex | Structure | BB | ¹H-NMR | LC purity % ee |
|---|---|---|---|---|
| 179 | 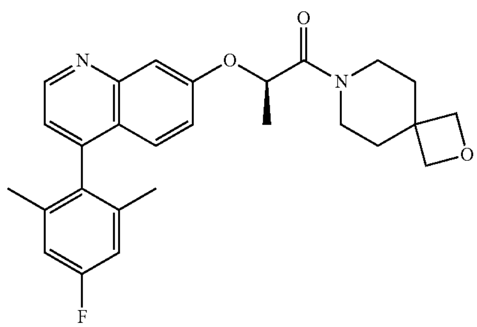 [SMILES: Cc1cc(F)cc(C)c1-c1ccnc2cc(O[C@H](C)C(=O)N3CCC4(CC3)COC4)ccc12] | (R)-8G₁ | (400 MHz, DMSO-d₆) δ 8.87 (d, J = 4.4 Hz, 1H), 7.26 (d, J = 2.0 Hz, 1H), 7.20-7.07 (m, 5H), 5.51 (q, J = 6.5 Hz, 1H), 4.41-4.28 (m, 4H), 3.68-3.34 (m, 4H), 1.94-1.68 (m, 4H), 1.84 (s, 3H), 1.82 (s, 3H), 1.48 (d, J = 6.5 Hz, 3H). | 98% ee92% |
| 180 | 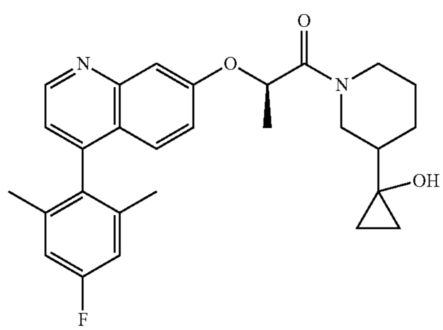 [SMILES: Cc1cc(F)cc(C)c1-c1ccnc2cc(O[C@H](C)C(=O)N3CCCC(C4(O)CC4)C3)ccc12] | (R)-8G₁ | (400 MHz, DMSO-d₆) δ 8.91-8.85 (m, 1H), 7.41-7.06 (m, 6H), 5.56-5.40 (m, 1H), 5.18-5.06 (m, 1H), 4.54-4.34 (m, 1H), 4.22-3.89 (m, 1H), 3.17-2.88 (m, 1H), 1.91-1.64 (m, 8H), 1.60-1.39 (m, 4H), 1.36-0.87 (m, 2H), 0.57-0.19 (m, 4H). | 95% ee92% (methyl group) |
| 181 | 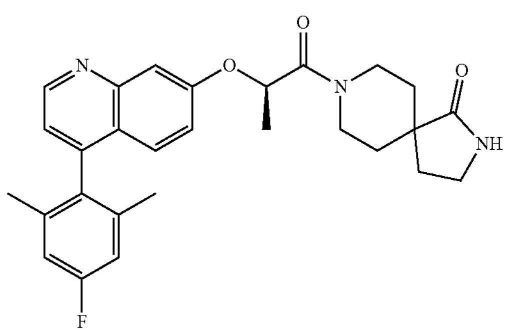 [SMILES: Cc1cc(F)cc(C)c1-c1ccnc2cc(O[C@H](C)C(=O)N3CCC4(CCNC4=O)CC3)ccc12] | (R)-8G₁ | (400 MHz, DMSO-d₆) δ 8.92-8.85 (m, 1H), 7.63 (d, J = 7.2 Hz, 1H), 7.34-7.06 (m, 6H), 5.58-5.47 (m, 1H), 4.21-4.00 (m, 2H), 3.44-3.14 (m, 3H), 3.03-2.87 (m, 1H), 2.08-1.94 (m, 2H), 1.85 (s, 3H), 1.83 (s, 3H), 1.67-1.33 (m, 7H). | 98% |
| 182 | 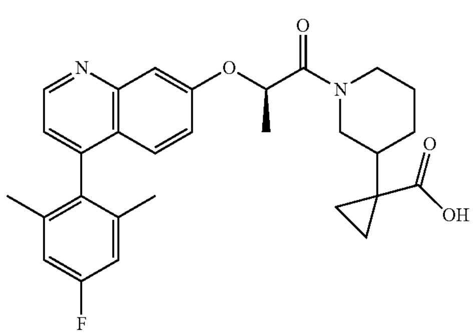 [SMILES: Cc1cc(F)cc(C)c1-c1ccnc2cc(O[C@H](C)C(=O)N3CCCC(C4(C(=O)O)CC4)C3)ccc12] | (R)-8G₁ | (400 MHz, DMSO-d₆) δ 8.91-8.85 (m, 1H), 7.40-7.07 (m, 6H), 5.54-5.45 (m, 1H), 4.39 (d, J = 12.4 Hz, 1H), 4.17-3.98 (m, 1H), 3.25-2.88 (m, 1H), 2.68-2.41 (m, 1H), 1.89-1.81 (m, 6H), 1.79-1.18 (m, 9H), 1.09-0.59 (m, 3H). | 99% |

TABLE 6-continued

Compounds of formula (I) of the invention

| Ex | Structure | BB | ¹H-NMR | LC purity % ee |
|---|---|---|---|---|
| 183 | 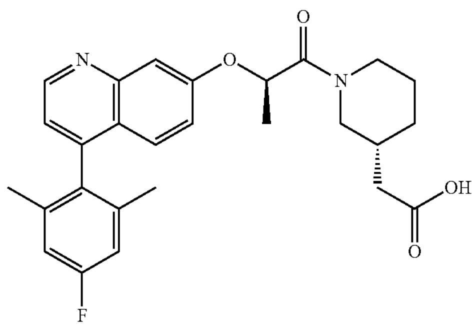 [SMILES: Cc1cc(F)cc(C)c1-c1ccnc2cc(O[C@H](C)C(=O)N3CCC[C@H](CC(=O)O)C3)ccc12] | (R)-8G₁ | (400 MHz, DMSO-d₆) δ 8.90-8.81 (m, 1H), 7.29-7.06 (m, 6H), 5.55-5.40 (m, 1H), 4.29-3.96 (m, 3H), 3.15-2.91 (m, 1H), 2.70-2.43 (m, 1H), 2.24-2.03 (m, 2H), 1.91-1.40 (m, 12H), 1.33-1.17 (m, 1H). | 95% ee 97% |
| 184 | 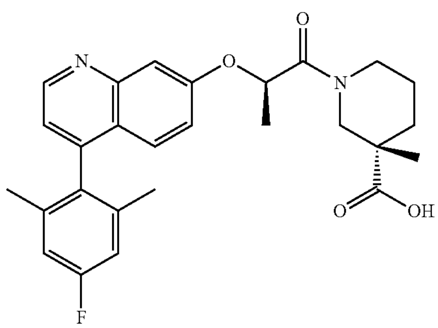 | (R)-8G₁ | (400 MHz, DMSO-d₆) δ 8.91-8.84 (m, 1H), 7.63-7.06 (m, 6H), 5.74-5.43 (m, 1H), 4.17-3.93 (m, 1H), 3.80-3.10 (m, 2H), 2.98-2.65 (m, 1H), 2.18-1.70 (m, 8H), 1.67-1.23 (m, 6H), 1.18-0.90 (m, 2H). | 99% ee96% (methyl group) |
| 185 | 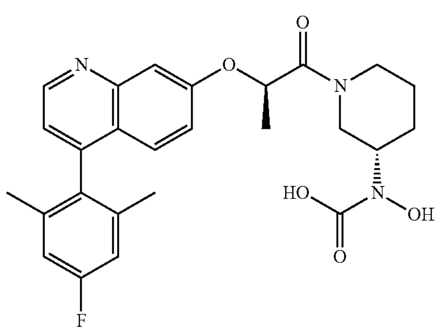 [SMILES: Cc1cc(F)cc(C)c1-c1ccnc2cc(O[C@H](C)C(=O)N3CCC[C@H](N(O)C(=O)O)C3)ccc12] | (R)-8G₁ | (300 MHz, Chloroform-d) δ 8.91-8.71 (m, 1H), 7.62-7.45 (m, 1H), 7.35-7.08 (m, 3H), 6.90 (d, J = 9.4 Hz, 2H), 5.25 (q, J = 6.6 Hz, 1H), 4.59-4.19 (m, 2H), 3.57-3.42 (m, 1H), 3.09-2.90 (m, 1H), 2.56-2.40 (m, 1H), 2.19-1.51 (m, 16H). | 97% |
| 186 | 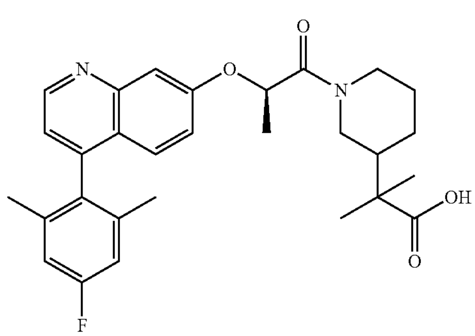 [SMILES: Cc1cc(F)cc(C)c1-c1ccnc2cc(O[C@H](C)C(=O)N3CCCC(C(C)(C)C(=O)O)C3)ccc12] | (R)-8G₁ | (400 MHz, DMSO-d₆) δ 8.91-8.85 (m, 1H), 7.40-7.07 (m, 6H), 5.55-5.34 (m, 1H), 4.49-4.35 (m, 1H), 4.15-3.92 (m, 1H), 2.98-2.65 (m, 1H), 3.13-2.81 (m, 1H), 2.48-2.28 (m, 1H), 1.90-1.44 (m, 12H), 1.38-0.91 (m, 7H). | 97% |

TABLE 6-continued

Compounds of formula (I) of the invention

| Ex | Structure | BB | ¹H-NMR | LC purity % ee |
|---|---|---|---|---|
| 187 | 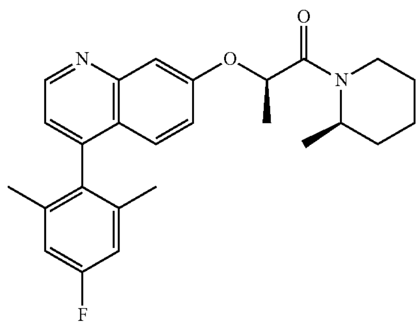 [SMILES: Cc1cc(F)cc(C)c1-c1ccnc2cc(O[C@H](C)C(=O)N3CCCC[C@H]3C)ccc12] | (R)-8G$_1$ | (300 MHz, DMSO-d$_6$) δ 8.90-8.86 (m, 1H), 7.30-7.06 (m, 6H), 5.49 (q, J = 6.4 Hz, 1H), 4.75-4.32 (m, 1H), 4.31-3.88 (m, 1H), 3.20-2.68 (m, 1H), 1.88-1.79 (m, 6H), 1.76-1.36 (m, 10H), 1.27-1.02 (m, 2H). | 99% |
| 188 | 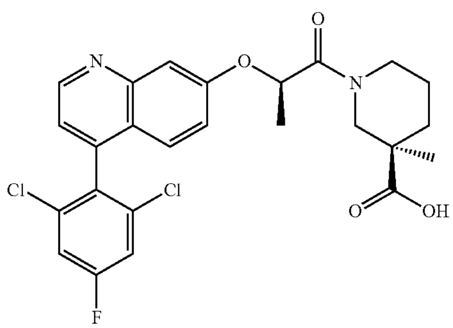 [SMILES: C[C@@H](Oc1ccc2c(-c3c(Cl)cc(F)cc3Cl)ccnc2c1)C(=O)N1CCC[C@@](C)(C(=O)O)C1] | (R)-9G$_1$ | (300 MHz, DMSO-d$_6$) δ 8.96-8.86 (m, 1H), 7.83-7.73 (m, 2H), 7.41-7.19 (m, 4H), 5.73-5.45 (m, 1H), 4.46-4.02 (m, 4H), 2.07-1.80 (m, 1H), 1.68-1.35 (m, 6H), 1.27-0.91 (m, 3H). | 96% ee96% |
| 189 | 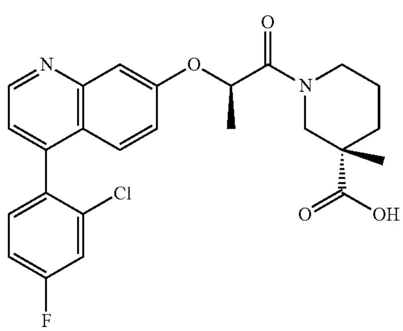 [SMILES: C[C@@H](Oc1ccc2c(-c3ccc(F)cc3Cl)ccnc2c1)C(=O)N1CCC[C@](C)(C(=O)O)C1] | (R)-4G$_1$ | (300 MHz, DMSO-d$_6$) δ 8.90-8.83 (m, 1H), 7.72-7.18 (m, 7H), 5.78-5.42 (m, 1H), 4.24-3.90 (m, 2H), 3.80-3.06 (m, 1H), 2.97-2.58 (m, 1H), 2.19-0.85 (m, 10H). | 95% ee100% |
| 190 | 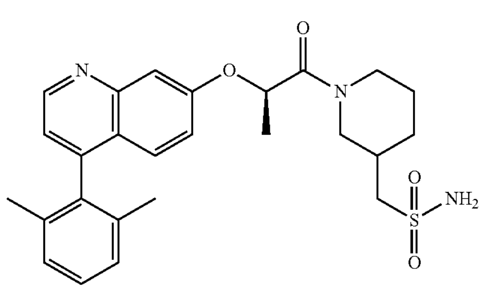 [SMILES: Cc1cccc(C)c1-c1ccnc2cc(O[C@H](C)C(=O)N3CCCC(CS(N)(=O)=O)C3)ccc12] | (R)-6G$_1$ | (300 MHz, DMSO-d$_6$) δ 9.03 (dd, J = 6.9, 4.1 Hz, 1H), 7.49-7.17 (m, 8H), 7.04 (d, J = 6.5 Hz, 1H), 6.85 (d, J = 3.5 Hz, 1H), 5.64-5.35 (m, 1H), 4.36-3.88 (m, 2H), 3.38-2.18 (m, 5H), 2.01 (s, 2H), 1.84 (d, J = 7.6 Hz, 7H), 1.65 (d, J = 19.8 Hz, 1H), 1.58-1.34 (m, 5H). | 91% |

TABLE 6-continued

Compounds of formula (I) of the invention

| Ex | Structure | BB | ¹H-NMR | LC purity % ee |
|---|---|---|---|---|
| 191 | 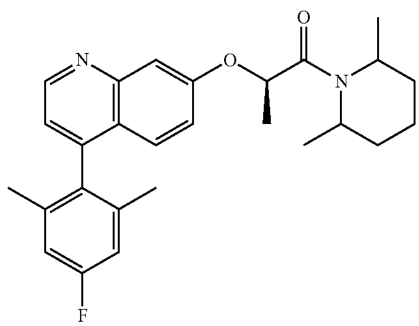 [SMILES: Cc1cc(F)cc(C)c1-c1ccnc2cc(O[C@H](C)C(=O)N3C(C)CCCC3C)ccc12] | (R)-8G₁ | (300 MHz, DMSO-d₆) δ 8.91-8.86 (m, 1H), 7.34-7.07 (m, 6H), 5.56-5.30 (m, 1H), 4.69-4.07 (m, 2H), 2.04-1.76 (m, 7H), 1.69-1.41 (m, 9H), 1.32-1.11 (m, 5H). | 96% |
| 192 | 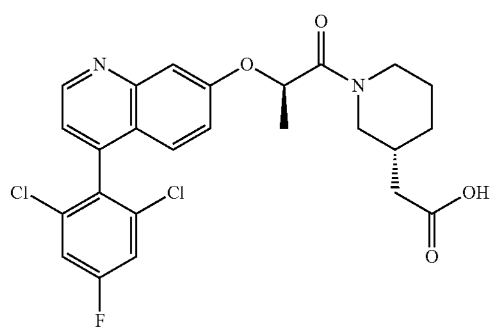 [SMILES: C[C@@H](Oc1ccc2c(-c3c(Cl)cc(F)cc3Cl)ccnc2c1)C(=O)N1CCC[C@H](CC(=O)O)C1] | (R)-9G₁ | (400 MHz, DMSO-d₆) δ 8.95-8.90 (m, 1H), 7.81-7.73 (m, 2H), 7.40-7.22 (m, 4H), 5.59-5.43 (m, 1H), 4.29-3.94 (m, 2H), 3.13-2.90 (m, 1H), 2.69-2.40 (m, 1H), 2.23-2.00 (m, 2H), 1.92-1.46 (m, 6H), 1.33-1.17 (m, 2H). | 98% ee100% |
| 193 | 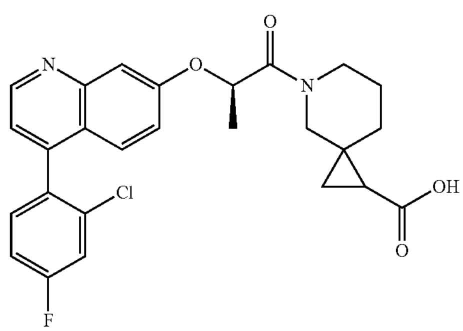 [SMILES: C[C@@H](Oc1ccc2c(-c3ccc(F)cc3Cl)ccnc2c1)C(=O)N1CCCC2(CC2C(=O)O)C1] | (R)-4G₁ | (400 MHz, DMSO-d₆) δ 8.91-8.87 (m, 1H), 7.71-7.19 (m, 7H), 5.60-5.44 (m, 1H), 3.77-3.32 (m, 4H), 1.86-1.40 (m, 8H), 1.30-0.73 (m, 2H). | 99% ee 99% (methyl group) |
| 194 | 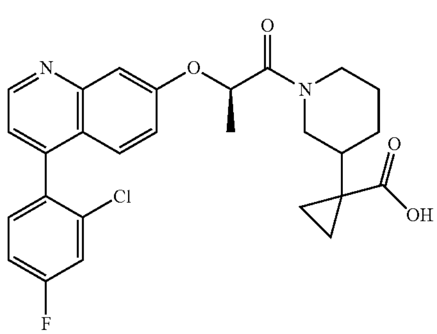 [SMILES: C[C@@H](Oc1ccc2c(-c3ccc(F)cc3Cl)ccnc2c1)C(=O)N1CCCC(C2(C(=O)O)CC2)C1] | (R)-4G₁ | (400 MHz, DMSO-d₆) δ 8.91-8.87 (m, 1H), 7.72-7.20 (m, 7H), 5.57-5.46 (m, 1H), 4.44-4.00 (m, 2H), 3.19-2.56 (m, 2H), 1.84-1.20 (m, 8H), 1.09-0.67 (m, 4H). | 98% |

TABLE 6-continued

Compounds of formula (I) of the invention

| Ex | Structure | BB | ¹H-NMR | LC purity % ee |
|---|---|---|---|---|
| 195 | 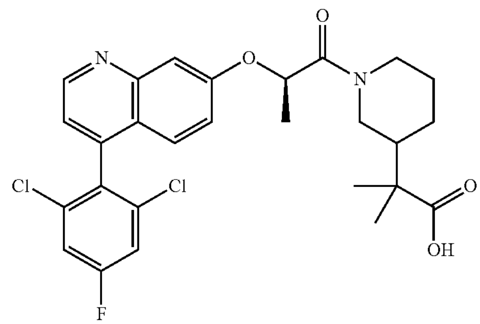 [SMILES: C[C@@H](Oc1ccc2c(-c3c(Cl)cc(F)cc3Cl)ccnc2c1)C(=O)N1CCCC(C(C)(C)C(=O)O)C1] | (R)-9G₁ | (400 MHz, DMSO-d₆) δ 8.96-8.90 (m, 1H), 7.82-7.73 (m, 2H), 7.41-7.20 (m, 4H), 5.59-5.30 (m, 1H), 4.48-3.95 (m, 2H), 3.13-2.81 (m, 1H), 2.53-2.27 (m, 1H), 1.89-1.20 (m, 8H), 1.16-0.80 (m, 6H). | 96% ee100% (methyl group) |
| 196 | 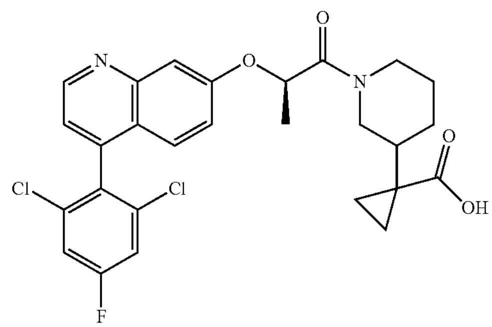 [SMILES: C[C@@H](Oc1ccc2c(-c3c(Cl)cc(F)cc3Cl)ccnc2c1)C(=O)N1CCCC(C2(C(=O)O)CC2)C1] | (R)-9G₁ | (400 MHz, DMSO-d₆) δ 8.95-8.90 (m, 1H), 7.82-7.73 (m, 2H), 7.43-7.21 (m, 4H), 5.58-5.48 (m, 1H), 4.42-4.03 (m, 2H), 3.26-2.88 (m, 1H), 2.69-2.40 (m, 1H), 1.86-1.20 (m, 8H), 1.08-0.67 (m, 4H). | 98% ee100% (methyl group) |
| 197 | 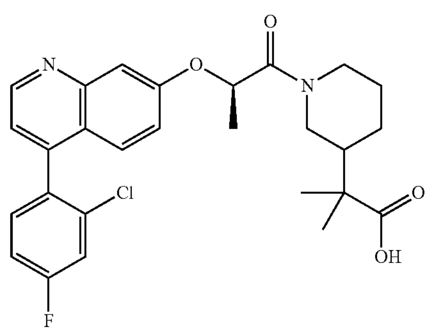 [SMILES: C[C@@H](Oc1ccc2c(-c3ccc(F)cc3Cl)ccnc2c1)C(=O)N1CCCC(C(C)(C)C(=O)O)C1] | (R)-4G₁ | (300 MHz, DMSO-d₆) δ 8.92-8.84 (m, 1H), 7.73-7.66 (m, 1H), 7.56-7.18 (m, 6H), 5.60-5.29 (m, 1H), 4.49-4.32 (m, 1H), 4.17-3.93 (m, 1H), 3.14-2.77 (m, 1H), 2.45-2.24 (m, 1H), 1.89-1.19 (m, 8H), 1.15-0.78 (m, 6H). | 98% ee100% |
| 198 | 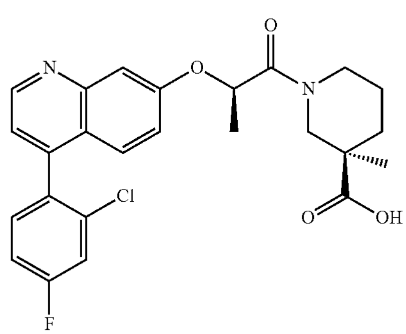 [SMILES: C[C@@H](Oc1ccc2c(-c3ccc(F)cc3Cl)ccnc2c1)C(=O)N1CCC[C@@](C)(C(=O)O)C1] | (R)-4G₁ | (300 MHz, DMSO-d₆) δ 8.88 (d, J = 4.3 Hz, 1H), 7.69 (dd, J = 8.9, 2.2 Hz, 1H), 7.56-7.37 (m, 2H), 7.35-7.18 (m, 4H), 5.77-5.42 (m, 1H), 4.03-3.62 (m, 2H), 3.42-3.03 (m, 2H), 2.05-1.32 (m, 7H), 1.19-0.89 (m, 3H). | 95% ee100% |

TABLE 6-continued
Compounds of formula (I) of the invention
| Ex | Structure | BB | ¹H-NMR | LC purity % ee |
|---|---|---|---|---|
| 199 | 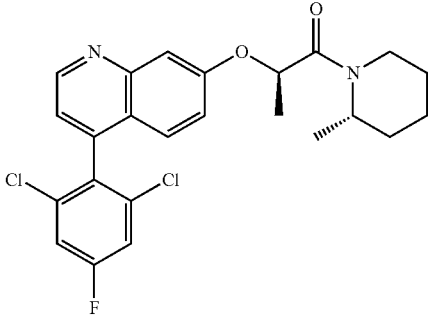 [SMILES: C[C@@H](Oc1ccc2c(-c3c(Cl)cc(F)cc3Cl)ccnc2c1)C(=O)N1CCCC[C@@H]1C] | (R)-9G₁ | (300 MHz, DMSO-d₆) δ 8.93 (d, J = 4.3 Hz, 1H), 7.83-7.73 (m, 2H), 7.41-7.19 (m, 4H), 5.58-5.47 (m, 1H), 4.73-4.32 (m, 1H), 4.30-3.87 (m, 1H), 3.21-2.68 (m, 1H), 1.77-1.33 (m, 10H), 1.27-1.00 (m, 2H). | 99% |
| 200 | 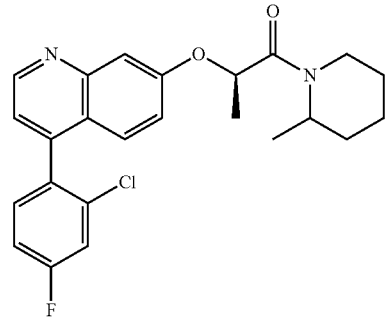 [SMILES: CC1CCCCN1C(=O)[C@@H](C)Oc1ccc2c(-c3ccc(F)cc3Cl)ccnc2c1] | (R)-4G₁ | (300 MHz, DMSO-d₆) δ 8.92-8.85 (m, 1H), 7.69 (dd, J = 9.0, 1.4 Hz, 1H), 7.55-7.38 (m, 2H), 7.35-7.15 (m, 4H), 5.59-5.33 (m, 1H), 4.75-3.91 (m, 2H), 3.21-2.63 (m, 1H), 1.84-1.01 (m, 12H). | 95% |
| 201 | 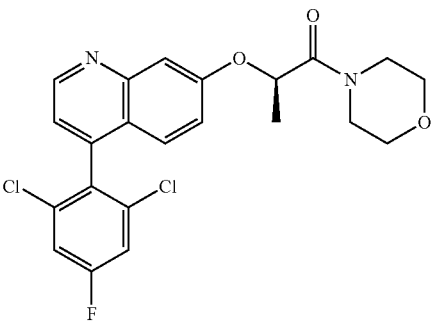 [SMILES: C[C@@H](Oc1ccc2c(-c3c(Cl)cc(F)cc3Cl)ccnc2c1)C(=O)N1CCOCC1] | (R)-9G₁ | (300 MHz, DMSO-d₆) δ 8.94 (d, J = 4.4 Hz, 1H), 7.82-7.75 (m, 2H), 7.41-7.35 (m, 3H), 7.25 (dd, J = 9.1, 2.6 Hz, 1H), 5.60-5.52 (m, 1H), 3.80-3.35 (m, 8H), 1.51 (d, J = 6.5 Hz, 3H). | 99% ee92% |
| 202 | 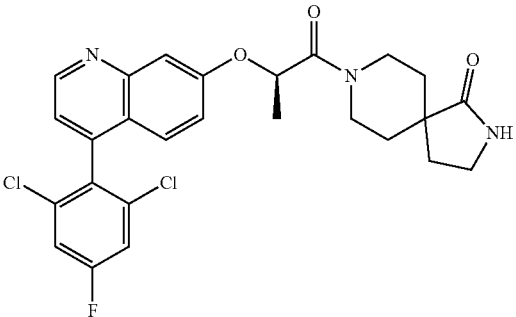 [SMILES: C[C@@H](Oc1ccc2c(-c3c(Cl)cc(F)cc3Cl)ccnc2c1)C(=O)N1CCC2(CCNC2=O)CC1] | (R)-9G₁ | (300 MHz, DMSO-d₆) δ 8.97-8.91 (m, 1H), 7.83-7.60 (m, 3H), 7.41-7.29 (m, 3H), 7.24 (dd, J = 9.1, 2.5 Hz, 1H), 5.62-5.51 (m, 1H), 4.22-3.97 (m, 2H), 3.44-2.84 (m, 4H), 2.08-1.93 (m, 2H), 1.83-1.22 (m, 7H). | 98% ee100% |

TABLE 6-continued

Compounds of formula (I) of the invention

| Ex | Structure | BB | ¹H-NMR | LC purity % ee |
|---|---|---|---|---|
| 203 | 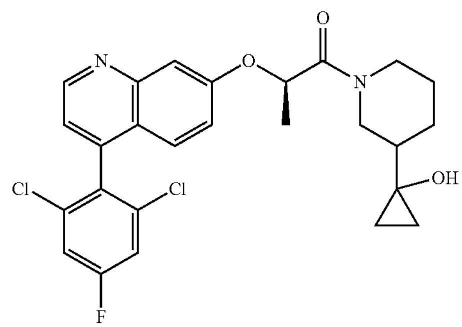 [SMILES: C[C@@H](Oc1ccc2c(-c3c(Cl)cc(F)cc3Cl)ccnc2c1)C(=O)N1CCCC(C2(O)CC2)C1] | (R)-9G$_1$ | (300 MHz, DMSO-d$_6$) δ 8.96-8.89 (m, 1H), 7.84-7.73 (m, 2H), 7.41-7.19 (m, 4H), 5.61-5.43 (m, 1H), 5.18-5.05 (m, 1H), 4.53-3.96 (m, 2H), 3.18-2.88 (m, 1H), 2.55-2.37 (m, 1H), 1.85-1.64 (m, 2H), 1.59-0.85 (m, 6H), 0.58-0.12 (m, 4H). | 99% ee100% (methyl group) |
| 204 | 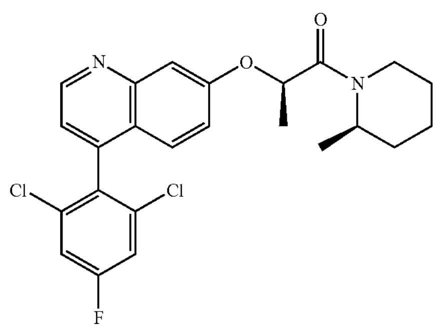 [SMILES: C[C@@H]1CCCCN1C(=O)[C@@H](C)Oc1ccc2c(-c3c(Cl)cc(F)cc3Cl)ccnc2c1] | (R)-9G$_1$ | (300 MHz, DMSO-d$_6$) δ 8.98-8.80 (m, 1H), 7.85-7.73 (m, 2H), 7.43-7.14 (m, 4H), 5.62-5.37(m, 1H), 4.75-4.45 (m, 1H), 4.31-3.96 (m, 1H), 3.31-2.64 (m, 1H), 1.87-1.42 (m, 8H), 1.35-1.02 (m, 4H). | 99% |
| 205 | 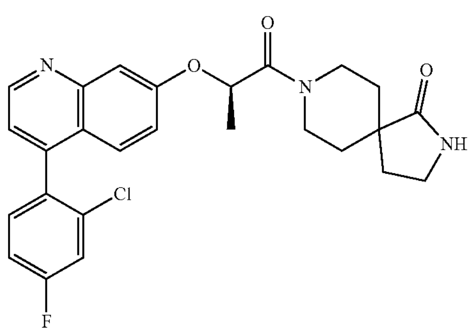 [SMILES: C[C@@H](Oc1ccc2c(-c3ccc(F)cc3Cl)ccnc2c1)C(=O)N1CCC2(CCNC2=O)CC1] | (R)-4G$_1$ | (300 MHz, DMSO-d$_6$) δ 8.92-8.85 (m, 1H), 7.72-7.20 (m, 8H), 5.61-5.48 (m, 1H), 4.21-3.97 (m, 2H), 3.46-3.14 (m, 3H), 3.04-2.83 (m, 1H), 2.08-1.94 (m, 2H), 1.82-1.21 (m, 7H) | 95% ee100% |
| 206 | 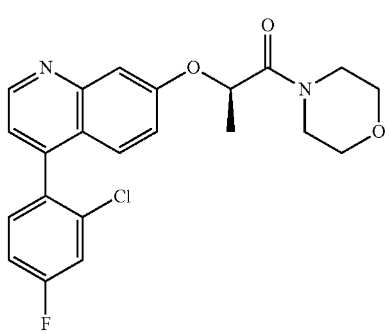 [SMILES: C[C@@H](Oc1ccc2c(-c3ccc(F)cc3Cl)ccnc2c1)C(=O)N1CCOCC1] | (R)-4G$_1$ | (300 MHz, DMSO-d$_6$) δ 8.89 (d, J = 4.4 Hz, 1H), 7.70 (dd, J = 8.9, 1.9 Hz, 1H), 7.56-7.38 (m, 2H), 7.36-7.30 (m, 2H), 7.29 (d, J = 4.4 Hz, 1H), 7.23 (dd, J = 9.2, 2.5 Hz, 1H), 5.60-5.50 (m, 1H), 3.82-3.35 (m, 8H), 1.51 (d, J = 6.5 Hz, 3H). | 95% |

TABLE 6-continued

Compounds of formula (I) of the invention

| Ex | Structure | BB | ¹H-NMR | LC purity % ee |
|---|---|---|---|---|
| 207 | 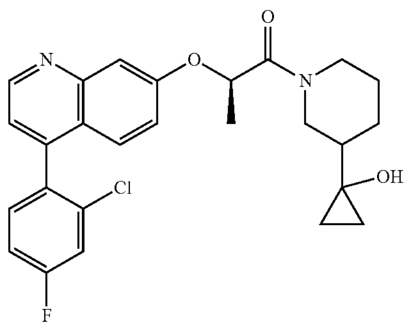 [SMILES: C[C@@H](Oc1ccc2c(-c3ccc(F)cc3Cl)ccnc2c1)C(=O)N1CCCC(C2(O)CC2)C1] | (R)-4G₁ | (300 MHz, DMSO-d₆) δ 8.91-8.85 (m, 1H), 7.69 (dd, J = 8.9, 1.1 Hz, 1H), 7.56-7.38 (m, 2H), 7.37-7.17 (m, 4H), 5.60-5.41 (m, 1H), 5.16-5.04 (m, 1H), 4.54-3.97 (m, 2H), 3.15-2.86 (m, 1H), 2.54-2.37 (m, 1H), 1.86-0.86 (m, 8H), 0.59-0.11 (m, 4H). | 95% |
| 208 | 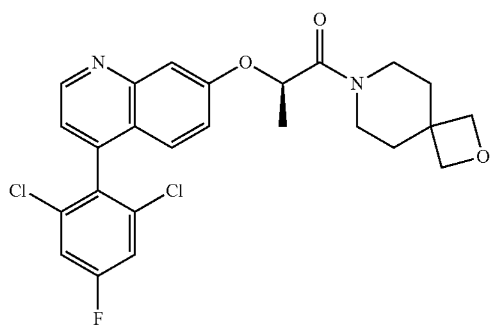 [SMILES: C[C@@H](Oc1ccc2c(-c3c(Cl)cc(F)cc3Cl)ccnc2c1)C(=O)N1CCC2(CC1)COC2] | (R)-9G₁ | (400 MHz, DMSO-d₆) δ 8.92 (d, J = 4.4 Hz, 1H), 7.82-7.73 (m, 2H), 7.40-7.30 (m, 3H), 7.23 (dd, J = 9.1, 2.2 Hz, 1H), 5.58-5.51 (m, 1H), 4.40-4.29 (m, 4H), 3.66-3.32 (m, 4H), 1.93-1.66 (m, 4H), 1.49 (d, J = 6.4 Hz, 3H). | 97% ee92% |
| 209 | 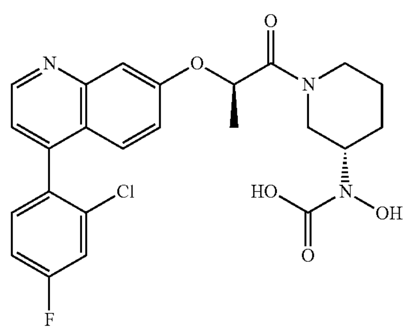 [SMILES: C[C@@H](Oc1ccc2c(-c3ccc(F)cc3Cl)ccnc2c1)C(=O)N1CCC[C@H](N(O)C(=O)O)C1] | (R)-4G₁ | (300 MHz, DMSO-d₆) δ 9.83-9.58 (m, 1H), 8.88 (dd, J = 8.9, 4.4 Hz, 1H), 7.68 (dd, J = 8.8, 2.1 Hz, 1H), 7.57-7.38 (m, 2H), 7.36-7.19 (m, 4H), 5.61-5.46 (m, 1H), 4.36-3.96 (m, 3H), 3.02-2.63 (m, 1H), 2.02-1.97 (m, 3H), 1.87-1.77 (m, 4H), 1.58-1.22 (m, 4H). | 98% |
| 210 | 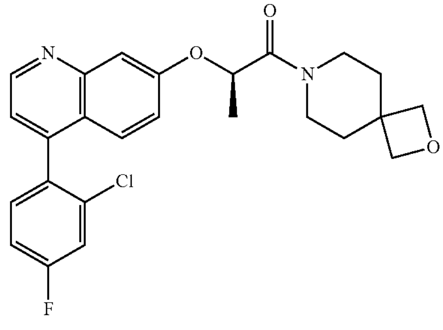 [SMILES: C[C@@H](Oc1ccc2c(-c3ccc(F)cc3Cl)ccnc2c1)C(=O)N1CCC2(CC1)COC2] | (R)-4G₁ | (300 MHz, DMSO-d₆) δ 8.87 (d, J = 4.4 Hz, 1H), 7.70 (dd, J = 8.3, 2.2 Hz, 1H), 7.55-7.37 (m, 2H), 7.34-7.19 (m, 4H), 5.59-5.48 (m, 1H), 4.40-4.28 (m, 4H), 3.69-3.33 (m, 4H), 1.94-1.64 (m, 4H), 1.48 (d, J = 6.4 Hz, 3H). | 95% |

TABLE 6-continued

Compounds of formula (I) of the invention

| Ex | Structure | BB | ¹H-NMR | LC purity % ee |
|---|---|---|---|---|
| 211 | 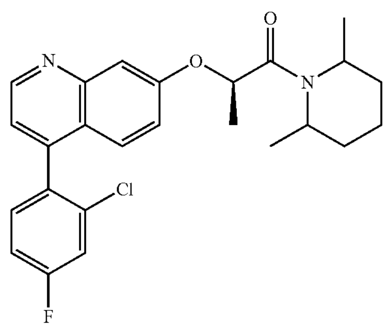 [SMILES: CC1CCCC(C)N1C(=O)[C@@H](C)Oc1ccc2c(-c3ccc(F)cc3Cl)ccnc2c1] | (R)-4G₁ | (300 MHz, DMSO-d₆) δ 8.91-8.85 (m, 1H), 7.72-7.66 (m, 1H), 7.56-7.19 (m, 6H), 5.57-5.34 (m, 1H), 4.69-4.56 (m, 1H), 4.54-4.15 (m, 1H), 2.01-1.40 (m, 10H), 1.33-1.04 (m, 5H). | 94% |
| 212 | 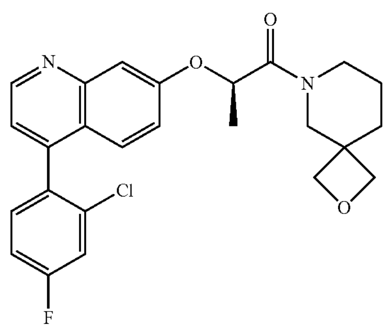 [SMILES: C[C@@H](Oc1ccc2c(-c3ccc(F)cc3Cl)ccnc2c1)C(=O)N1CCCC2(COC2)C1] | (R)-4G₁ | (300 MHz, DMSO-d₆) δ 8.88 (d, J = 4.3 Hz, 1H), 7.72-7.65 (m, 1H), 7.57-7.18 (m, 6H), 5.75-5.44 (m, 1H), 4.56-3.83 (m, 6H), 3.72-3.47 (m, 2H), 2.01-1.70 (m, 2H), 1.67-1.34 (m, 5H). | 95% |
| 213 | 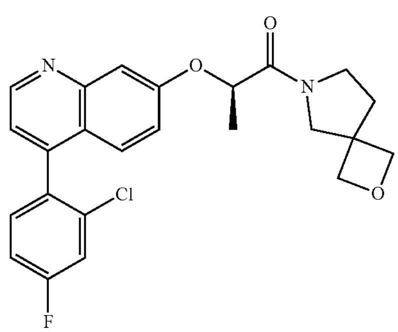 [SMILES: C[C@@H](Oc1ccc2c(-c3ccc(F)cc3Cl)ccnc2c1)C(=O)N1CCC2(COC2)C1] | (R)-4G₁ | (300 MHz, DMSO-d₆) δ 8.90-8.86 (m, 1H), 7.69 (66, J = 8.9, 2.0 Hz, 1H), 7.55-7.38 (m, 2H), 7.35-7.19 (m, 4H), 5.36-5.22 (m, 1H), 4.63-4.40 (m, 4H), 4.04-3.33 (m, 3H), 3.17 (d, J = 5.2 Hz, 1H), 2.30-2.00 (m, 2H), 1.55-1.43 (m, 3H). | 95% |
| 214 | 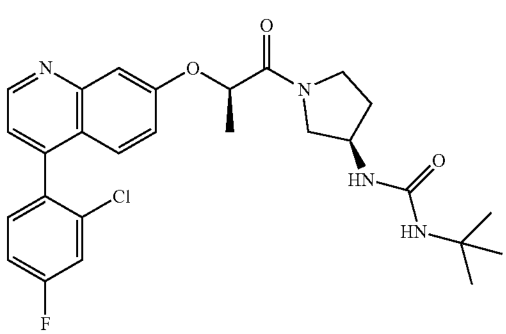 [SMILES: C[C@@H](Oc1ccc2c(-c3ccc(F)cc3Cl)ccnc2c1)C(=O)N1CC[C@@H](NC(=O)NC(C)(C)C)C1] | (R)-4G₁ | (300 MHz, DMSO-d₆) δ 8.90-8.80 (m, 1H), 7.69 (dd, J = 8.7, 1.9 Hz, 1H), 7.54-7.39 (m, 2H), 7.35-7.20 (m, 4H), 5.97-5.94 (m, 1H), 5.59-5.54 (m, 1H), 5.32-5.21 (m, 1H), 4.21-3.98 (m, 1H), 3.93-3.75 (m, 1H), 3.60-3.39 (m, 2H), 3.29-3.06 (m, 1H), 2.16-1.93 (m, 1H), 1.84-1.59 (m, 1H), 1.50-1.48 (m, 3H), 1.21-1.20 (m, 9H). | 95% |

TABLE 6-continued

Compounds of formula (I) of the invention

| Ex | Structure | BB | ¹H-NMR | LC purity % ee |
|---|---|---|---|---|
| 215 | 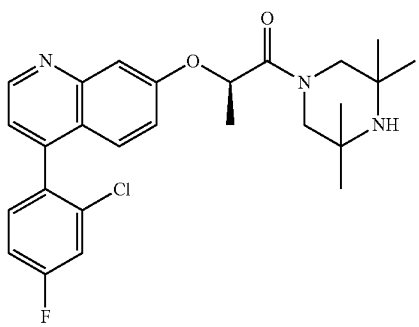 | (R)-4G₁ | (300 MHz, DMSO-d₆) δ 8.88 (d, J = 4.4 Hz, 1H), 7.72-7.66 (m, 1H), 7.55-7.47 (m, 1H), 7.46-7.19 (m, 5H), 5.50 (q, J = 6.3 Hz, 1H), 3.57-3.43 (m, 2H), 3.25-3.15 (m, 1H), 2.91 (d, J = 12.4, 4.4 Hz, 1H), 1.65 (bs, 1H), 1.52 (d, J = 6.3 Hz, 3H), 1.30-1.20 (m, 3H), 1.10-0.95 (m, 9H). | 95% |
| 216 | 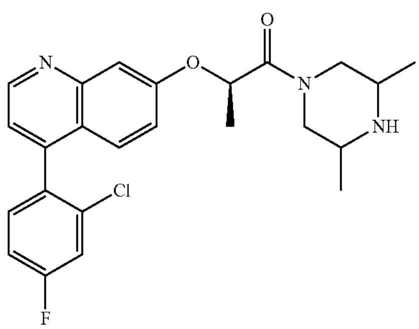 [SMILES: CC1CN(C(=O)[C@@H](C)Oc2ccc3c(-c4ccc(F)cc4Cl)ccnc3c2)CC(C)N1] | (R)-4G₁ | (300 MHz, DMSO-d₆) δ 10.10-9.29 (m, 3H), 9.23-9.12 (m, 1H), 7.84-7.41 (m, 4H), 5.83-5.54 (m, 1H), 4.50-4.00 (m, 3H), 3.66-2.68 (m, 4H), 1.61-1.12 (m, 10H). | 95% |
| 217 | 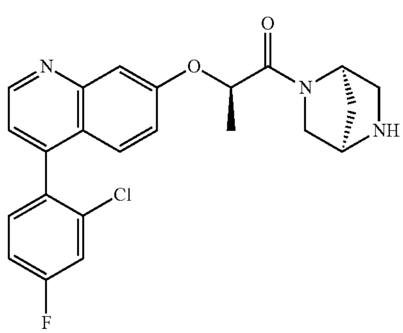 [SMILES: C[C@@H](Oc1ccc2c(-c3ccc(F)cc3Cl)ccnc2c1)C(=O)N1C[C@H]2C[C@@H]1CN2] | (R)-4G₁ | (300 MHz, DMSO-d₆) δ 8.89 (d, J = 4.4 Hz, 1H), 7.69 (dd, J = 8.9, 2.3 Hz, 1H), 7.52 (dd, J = 8.4, 6.4 Hz, 1H), 7.42 (dt, J = 8.5, 2.4 Hz, 1H), 7.35-7.17 (m, 4H), 5.41-5.03 (m, 1H), 4.93-4.50 (m, 1H), 3.71-3.36 (m, 2H), 3.09-2.35 (m, 4H), 1.78-0.89 (m, 5H). | 90% |
| 218 | 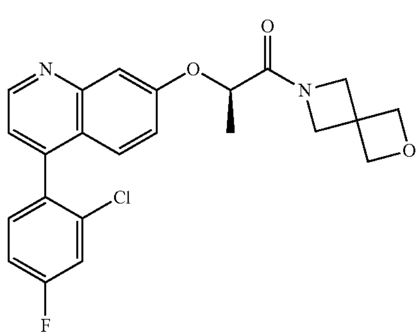 [SMILES: C[C@@H](Oc1ccc2c(-c3ccc(F)cc3Cl)ccnc2c1)C(=O)N1CC2(COC2)C1] | (R)-4G₁ | (300 MHz, Chloroform-d) δ 8.88 (d, J = 4.6 Hz, 1H), 7.57 (bs, 1H), 7.45 (d, J = 9.2 Hz, 1H), 7.36-7.27 (m, 2H), 7.25-7.11 (m, 3H), 4.93 (q, J = 6.7 Hz, 1H), 4.87 (d, J = 7.0 Hz, 1H), 4.82 (d, J = 7.0 Hz, 1H), 4.77-4.69 (m, 1H), 4.73 (d, J = 7.0 Hz, 1H), 4.65 (d, J = 7.0 Hz, 1H), 4.30 (d, J = 10.0 Hz, 1H), 4.29 (d, J = 11.0 Hz, 1H), 4.16 (d, J = 11.0 Hz, 1H), 1.65 (d, J = 6.7 Hz, 3H). | 95% |

TABLE 6-continued

Compounds of formula (I) of the invention

| Ex | Structure | BB | ¹H-NMR | LC purity % ee |
|---|---|---|---|---|
| 219 | 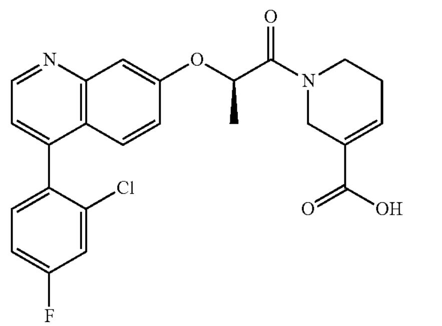 [SMILES: C[C@@H](Oc1ccc2c(-c3ccc(F)cc3Cl)ccnc2c1)C(=O)N1CCC=C(C(=O)O)C1] | (R)-4G₁ | (400 MHz, DMSO-d₆) δ 8.88 (d, J = 4.2 Hz, 1H), 7.69 (ddd, J = 8.9, 2.6, 1.4 Hz, 1H), 7.52 (dd, J = 8.6, 6.2 Hz, 1H), 7.42 (tdd, J = 8.5, 2.6, 1.8 Hz, 1H), 7.37-7.17 (m, 4H), 7.00-6.92 (m, 1H), 5.68-5.48 (m, 1H), 4.45-3.98 (m, 2H), 3.84-3.48 (m, 3H), 2.47-2.18 (m, 2H), 1.59-1.45 (m, 3H). | 100% ee94% |
| 220 | 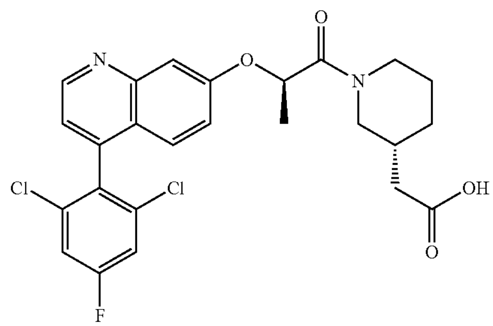 [SMILES: C[C@@H](Oc1ccc2c(-c3c(Cl)cc(F)cc3Cl)ccnc2c1)C(=O)N1CCC[C@H](CC(=O)O)C1] | (R)-9G₄ | (400 MHz, DMSO-d₆) δ 9.05-9.02 (m, 1H), 7.81 (d, J = 8.6 Hz, 2H), 7.71 (d, J = 8.9 Hz, 1H), 7.45-7.42 (m, 1H), 7.16 (d, J = 8.9 Hz, 1H), 5.99-5.86 (m, 1H), 4.24-3.98 (m, 2H), 3.16-2.70 (m, 2H), 2.32-1.63 (m, 6H), 1.55-1.24 (m, 5H). | 95% ee90% |
| 221 | 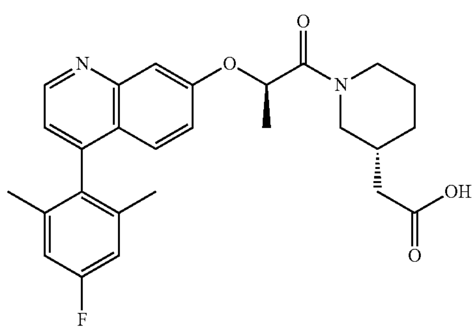 [SMILES: Cc1cc(F)cc(C)c1-c1ccnc2cc(O[C@H](C)C(=O)N3CCC[C@H](CC(=O)O)C3)ccc12] | (R)-8G₄ | (400 MHz, DMSO-d₆) δ 9.00-8.96 (m, 1H), 7.53 (d, J = 8.9 Hz, 1H), 7.31-7.28 (m, 1H), 7.13-7.08 (m, 3H), 5.99-5.86 (m, 1H), 4.24-3.91 (m, 2H), 3.17-2.64 (m, 2H), 2.46-2.07 (m, 3H), 1.93-1.82 (m, 8H), 1.71-1.46 (m, 6H). | 97% ee96% |

The IUPAC chemical names for the compounds shown in Table 6 are provided in Table 7 below.

4. HOMOGENEOUS TR-FRET ASSAY FOR HTS AND ACTIVITY DETERMINATION

The TR-FRET assay was basically conducted as described in WO2016/193231A1, especially as described in example 1 (hereby incorporated by reference). With respect to the back ground of the mitochondrial transcription it is referred to Falkenberg et al. (2002) and Posse et al. (Posse et al., 2015). The method monitors the activity of mitochondrial RNA-polymerase via detection of the formation of its product, a 407 bp long RNA sequence. Detection of the product is facilitated by hybridization of two DNA-oligonucleotide probes to specific and adjacent sequences within the RNA product sequence. Upon annealing of the probes, two fluorophores that are coupled directly to an acceptor nucleotide probe (ATT0647, 5') or introduced via a coupled streptavidin interacting with a biotinylated donor nucleotide probe on the other side (Europium cryptate, 3') are brought into sufficient proximity to serve as a fluorescence-donor-acceptor pair as generally described in Walters and Namchuk (2003). Thus, a FRET signal at 665 nm is generated upon excitation at 340 nm.

Briefly, the protocol described here was applied for screening and activity determination in a low-volume 384-well microtiter plate with non-binding surface. For high-throughput application in the 1536-well microtiter plate format, volumes of the reagent mixes were adjusted, maintaining the volumetric ratio. Proteins POLRMT (NM_172551.3), TFAM (NM_009360.4) and TFB2M (NM_008249.4) were diluted from their stocks to working concentrations of 150 nM, 1.8 µM and 330 nM respectively, in a dilution buffer containing 100 mM Tris-HCl pH 8.0, 200 mM NaCl, 10% (v/v) glycerole, 2 mM glutathione (GSH), 0.5 mM EDTA and 0.1 mg/mL BSA. Protein dilutions and template DNA, comprising a pUC18 plasmid encoding the mitochondrial light strand promoter, restriction linearized proximal to the promoter 3'-end (pUC-LSP), were mixed at the twofold final assay-concentration in a reaction buffer, containing 10 mM Tris-HCl pH 7.5, 10 mM MgCl$_2$, 40 mM NaCl, 2 mM GSH, 0.01% (w/v) Tween-20 and 0.1 mg/mL BSA.

5 µL of this mix were dispensed, depending on the chosen microtiter plate format, using multi-channel pipettes or a Multidrop® dispenser (Thermo Fisher Scientific, Waltham Mass.) into the wells of a microtiter plate and incubated at room temperature (rt) for 10 min. Chemical compounds under scrutiny in the assay were applied using contact-free acoustic droplet-dispensing (Echo520® Labcyte Inc., Sunnyvale Calif.) from 10 mM compound stocks in 100% DMSO, to a final concentration of 10 µM or in serial dilution series of the required concentration range. Equal amounts of DMSO without any compound were added to positive control samples, followed by an incubation step at rt for 10 min.

The enzymatic reaction was started by the addition of 5 µL of a mix of dNTPs in reaction buffer to a final concentration of 500 µM each. No nucleotide mix was added to negative control samples. The content of the wells was mixed using a VarioTeleshaker™ (Thermo Fisher Scientific, Waltham Mass.) at 1500 rpm for 45 sec after which the microtiter plate was centrifuged at 500×g for 1 min. The samples were incubated for 2 h at rt with humidity control to avoid evaporation. The detection reagents were prepared in a buffer that was composed, such that the enzymatic reaction was terminated due to chelating of Mg-ions and increased ionic strength, containing 50 mM Tris-HCl pH 7.5, 700 mM NaCl, 20 mM EDTA, and 0.01% (w/v) Tween-20. Importantly Eu-cryptate-coupled streptavidin had to be preincubated with a 100-fold molar excess of a random sequence oligonucleotide for 10 min at rt in the dark to block unspecific binding of single stranded RNA to the protein. Subsequently, the blocked streptavidin(-Eu) was mixed with the DNA-probes on ice and kept away from light until use.

At the end of the enzymatic reaction time 10 µL detection reagent mix was added, such that the final concentration of fluorescent-donor probe (bio-5'-AACACATCTCT(-bio)GC-CAAACCCCA-bio-3'), fluorescent-acceptor probe (ATTO647N-5'-ACAAAGAACCCTAACACCAG-3') and streptavidin(-Eu) in each assay well was 1 nM, 3 nM, and 1 nM respectively. Assay plates were again mixed and centrifuged as above and stored at rt, protected from light for at least 2 h or until binding of the DNA probes to RNA product and binding of streptavidin(-Eu) to the biotinylated DNA probe led to the development of the maximal FRET signal. The generated signal was measured with an EnVision plate reader, including TRF light unit (Perkin Elmer, Waltham Mass.), using excitation at 320 nm, an integration time of 200 µs and a delay time of 100 µs, prior to detection at 620 nm and 665 nm. The ratio of donor- and acceptor-fluorescence was used to assess the specific FRET signal, as a measure of the generated product content (i.e. enzymatic activity).

5. QUANTITATIVE REAL TIME-PCR TO ASSESS CELLULAR ACTIVITY

Quantitative real-time PCR (qRT-PCR), based on the TaqMan™ (Thermo Fisher Scientific, Waltham Mass.) technology, was carried out essentially as described in Held et al. (1996). HeLa cells were plated one day before compound treatment in RPMI medium supplemented with 10% Fetal Calf Serum and 2 mM L-glutamine. Cells were incubated with dilution series of compounds or vehicle (DMSO) for 4 h, prior to harvest and extraction of the RNA using the RNeasy Mini Kit (Qiagen, Hilden D), according to the manufacturer's instructions. RNA concentrations were measured spectroscopically, using a NanoDrop-2000 (Thermo Fisher Scientific, Waltham Mass.) and normalized prior to cDNA synthesis, using a 'High-Capacity cDNA Reverse Transcription Kit' (Thermo Fisher Scientific, Waltham Mass.). qRT-PCR was carried out using the 'TaqMan Fast Advance Master Mix' (Thermo Fisher Scientific, Waltham Mass.) on a 7500 Fast Real-Time PCR machine (Applied Biosystems, Foster City Calif.)

For these measurements, three genes were used to compare the effect of the scrutinized compounds in relation to their concentration. The POLRMT-gene was used to detect potential influences on nuclear transcription. Mitochondrial transcription in vivo was monitored by measurements 7S RNA. The TBP (TATA-box binding protein) gene was employed as the control (housekeeping gene) during qRT-PCR. The short-lived mitochondrial 7S RNA, which is not post-transcriptionally stabilized, allowed us to monitor rapid changes in mitochondrial transcription activity following compound addition. Biological triplicates were analyzed using the comparative CT Method (ΔΔCt) method (Bubner and Baldwin, 2004) and reported as Rq % values (Rq=Relative quantification=2−ΔΔCt).

6. BIOLOGICAL ACTIVITIES OF COMPOUNDS

Activities of compounds are listed in Table 7 together with compound number and IUPAC names as determined by the homogeneous TR-FRET assay for mitochondrial transcription activity according to Example 4 and the quantitative real time-PCR assay of inhibition of mitochondrial transcription according to Example 5 were grouped according to the following scheme:

| | <20 nM | 20 nM ≤ x < 100 nM | 100 nM ≤ x < 1 µM | 1µM ≤ x < 10 µM |
|---|---|---|---|---|
| mitochondrial transcription activity (IC-50) | +++ | ++ | + | (+) |
| | <10 nM | 10 nM ≤ x < 50 nM | 50 nM ≤ x < 500 nM | 500 nM ≤ x < 5 µM |
| cellular qPCR assay IMT (IC-50) | +++ | ++ | + | (+) |

Table 7—IUPAC Chemical Names and Biological Activities

| Ex | IUPAC Name | mitochondrial transcription activity | cellular qPCR assay |
|---|---|---|---|
| 1 | (3S)-1-[(2R)-2-[[4-(o-tolyl)-7-quinolyl]oxy]propanoyl]piperidine-3-carboxylic acid | +++ | +++ |
| 2 | (3S)-1-[(2R)-2-[[4-(2,6-dimethylphenyl)-7-quinolyl]oxy]propanoyl]piperidine-3-carboxylic acid | +++ | +++ |
| 3 | 2-[(3R)-1-[(2R)-2-[[4-(2,6-dimethylphenyl)-7-quinolyl]oxy]propanoyl]-3-piperidyl]acetic acid | +++ | +++ |

| Ex | IUPAC Name | mitochondrial transcription activity | cellular qPCR assay |
|---|---|---|---|
| 4 | ethyl (3S)-1-[(2R)-2[[4-(2,6-dimethylphenyl)-7-quinolyl]oxy]propanoyl]piperidine-3-carboxylate | +++ | +++ |
| 5 | 2-[(3S)-1-[(2R)-2-[[4-(2,6-dimethylphenyl)-7-quinolyl]oxy]propanoyl]-3-piperidyl]acetic acid | +++ | +++ |
| 6 | ethyl 2-[(3R)-1-[(2R)-2-[[4-(2,6-dimethylphenyl)-7-quinolyl]oxy]propanoyl]-3-piperidyl]acetate | +++ | |
| 7 | (3R)-1-[(2R)-2-[[4-(2-chlorophenyl)-7-quinolyl]oxy]propanoyl]piperidine-3-carboxylic acid (formic acid salt) | +++ | +++ |
| 8 | ethyl 2-[(3R)-1-[(2R)-2-[[4-(o-tolyl)-7-quinolyl]oxy]propanoyl]-3-piperidyl]acetate | +++ | + |
| 9 | (3S)-1-[(2R)-2-[[4-(2-chlorophenyl)-7-quinolyl]oxy]propanoyl]piperidine-3-carboxylic acid (formic acid salt) | +++ | +++ |
| 10 | (3S)-1-[(2R)-2-[[4-(2-chloro-4-fluoro-phenyl)-7-quinolyl]oxy]propanoyl]piperidine-3-carboxylic acid (formic acid salt) | +++ | ++ |
| 11 | (2R)-2[[4-(2-chloro-4-fluoro-phenyl)-7-quinolyl]oxy]-1-[(3S)-3-(2H-tetrazol-5-yl)-1-piperidyl]propan-1-one | +++ | + |
| 12 | (3S)-1-[(2R)-2-[[4-(2-chlorophenyl)-2-fluoro-7-quinolyl]oxy]propanoyl]piperidine-3-carboxylic acid (trifluoroacetic acid salt) | +++ | +++ |
| 13 | 2-[(3R)-1-[(2R)-2-[[4-(o-tolyl)-7-quinolyl]oxy]propanoyl]-3-piperidyl]acetic acid (formic acid salt) | ++ | ++ |
| 14 | ethyl (3S)-1-[(2R)-2-[[4-(o-tolyl)-7-quinolyl]oxy]propanoyl]piperidine-3-carboxylate | ++ | + |
| 15 | ethyl 2-[(3R)-1-[(2R)-2-[[4-(2-chloro-4-fluoro-phenyl)-7-quinolyl]oxy]propanoyl]-3-piperidyl]acetate | ++ | + |
| 16 | 2-[(3R)-1-[(2R)-2-[[4-(2-chlorophenyl)-7-quinolyl]oxy]propanoyl]-3-piperidyl]acetic acid (formic acid salt) | ++ | + |
| 17 | (3R)-1-[(2R)-2-[[4-(2-chloro-4-fluoro-phenyl)-7-quinolyl]oxy]propanoyl]piperidine-3-carboxylic acid | ++ | + |
| 18 | 2-[(3R)-1-[(2R)-2-[[4-(2-chloro-4-fluoro-phenyl)-7-quinolyl]oxy]propanoyl]-3-piperidyl]acetic acid (formic acid salt) | ++ | + |
| 19 | (3S)-1-[(2R)-2[[4-(2-chloro-4-fluoro-phenyl)-7-quinolyl]oxy]propanoyl]pyrrolidine-3-carboxylic acid | ++ | + |
| 20 | (2R)-2[[4-(2-chloro-4-fluoro-phenyl)-7-quinolyl]oxy]-1-(1-piperidyl)propan-1-one (formic acid salt) | ++ | ++ |
| 21 | 2-[(3R)-1-[(2R)-2-[[2-chloro-4-(o-tolyl)-7-quinolyl]oxy]propanoyl]-3-piperidyl]acetic acid | ++ | (+) |
| 22 | 2-[(3S)-1-[(2R)-2-[[4-(2-chloro-4-fluoro-phenyl)-7-quinolyl]oxy]propanoyl]-3-piperidyl]acetic acid | ++ | + |
| 23 | rac-(3S)-1-[2-[[4-(2-chlorophenyl)-7-quinolyl]oxy]propanoyl]piperidine-3-carboxylic acid | ++ | |
| 24 | 1-[(2R)-2-[[4-(2-chloro-4-fluoro-phenyl)-7-quinolyl]oxy]propanoyl]piperidine-4-carboxylic acid | ++ | + |
| 25 | (3S)-1-[(2R)-2-[[2-chloro-4-(o-tolyl)-7-quinolyl]oxy]propanoyl]piperidine-3-carboxylic acid | ++ | ++ |
| 26 | 3-[[(2R)-2-[[4-(2-chloro-4-fluoro-phenyl)-7-quinolyl]oxy]propanoyl]amino]benzoic acid | ++ | + |
| 27 | ethyl (3S)-1-[(2R)-2-[[4-(2-chloro-4-fluoro-phenyl)-7-quinolyl]oxy]propanoyl]piperidine-3-carboxylate | ++ | (+) |
| 28 | (2R)-2-[[4-(2-chloro-4-fluoro-phenyl)-7-quinolyl]oxy]-1-(4-propanoylpiperazin-1-yl)propan-1-one | + | ++ |
| 29 | tert-butyl (2R)-2-[[4-(2-chlorophenyl)-7-quinolyl]oxy]propanoate | + | +++ |
| 30 | (3S)-1-[(2R)-2-[[4-(2-chloro-4-fluoro-phenyl)-7-quinolyl]oxy]propanoyl]piperidine-3-carbonitrile | + | ++ |
| 31 | (3S)-1-[(2R)-2-[[2-methyl-4-(o-tolyl)-7-quinolyl]oxy]propanoyl]piperidine-3-carboxylic acid (trifluoroacetic acid salt) | + | +++ |
| 32 | (2R)-2-[[4-(2-chloro-4-fluoro-phenyl)-7-quinolyl]oxy]-N-isopropyl-N-methyl-propanamide | + | ++ |
| 33 | 1-[rac-(2R)-2-[[4-(2-chloro-4-fluoro-phenyl)-7-quinolyl]oxy]propanoyl]piperidine-3-sulfonamide | + | +++ |
| 34 | (3S)-1-[(2R)-2-[[2-chloro-4-(2-chlorophenyl)-7-quinolyl]oxy]propanoyl]piperidine-3-carboxylic acid | + | ++ |
| 35 | (3S)-1-[(2R)-2-[[2-chloro-4-(4-fluoro-2-methyl-phenyl)-7-quinolyl]oxy]propanoyl]piperidine-3-carboxylic acid | + | +++ |
| 36 | isopropyl (2R)-2-[[4-(2-chlorophenyl)-7-quinolyl]oxy]propanoate (formic acid salt) | + | + |
| 37 | methyl 2-[(3R)-1-[(2R)-2-[[4-(2-chloro-4-fluoro-phenyl)-7-quinolyl]oxy]propanoyl]pyrrolidin-3-yl]acetate | + | |
| 38 | (3S)-1-[(2R)-2-[[4-(2-chloro-4-fluoro-phenyl)-7-quinolyl]oxy]propanoyl]-N-methyl-piperidine-3-carboxamide | + | ++ |
| 39 | 2-[(3S)-1-[(2R)-2-[[4-(2-chloro-4-fluoro-phenyl)-7-quinolyl]oxy]propanoyl]pyrrolidin-3-yl]acetic acid | + | + |
| 40 | 2-[(3R)-1-[(2R)-2-[[4-(2-chloro-4-fluoro-phenyl)-7-quinolyl]oxy]propanoyl]pyrrolidin-3-yl]acetic acid | + | + |
| 41 | ethyl (3S)-1-[(2R)-2-[[4-(2-chlorophenyl)-2-fluoro-7-quinolyl]oxy]propanoyl]piperidine-3-carboxylate | + | (+) |
| 42 | (2R)-2-[[4-(2-chloro-4-fluoro-phenyl)-7-quinolyl]oxy]-1-pyrrolidin-1-yl-propan-1-one | + | + |
| 43 | (2R)-2-[[2-chloro-4-(o-tolyl)-7-quinolyl]oxy]propanoic acid | + | |
| 44 | (2R)-2-[[4-(2-chloro-4-fluoro-phenyl)-7-quinolyl]oxy]propanoic acid | + | |
| 45 | (2R)-2-[[4-(2-chloro-4-fluoro-phenyl)-7-quinolyl]oxy]-N,N-dimethyl-propanamide (formic acid salt) | + | + |
| 46 | (3S)-1-[2-[[4-(2-chlorophenyl)-7-quinolyl]oxy]acetyl]piperidine-3-carboxylic acid (formic acid salt) | + | + |
| 47 | (2R)-N-tert-butyl-2-[[4-(2-chloro-4-fluoro-phenyl)-7-quinolyl]oxy]propanamide | + | ++ |
| 48 | (2R)-2-[[4-(2-chlorophenyl)-7-quinolyl]oxy]-N-isopropyl-propanamide (formic acid salt) | + | + |
| 49 | ethyl 2-[(3R)-1-[(2R)-2-[[2-methyl-4-(o-tolyl)-7-quinolyl]oxy]propanoyl]-3-piperidyl]acetate | + | ++ |
| 50 | ethyl (2R)-2-[[4-(2-chlorophenyl)-7-quinolyl]oxy]propanoate | + | ++ |
| 51 | ethyl 4-[[(2R)-2-[[4-(2-chloro-4-fluoro-phenyl)-7-quinolyl]oxy]propanoyl]amino]benzoate | + | |
| 52 | (3S)-1-[(2R)-2-[[2-chloro-4-(o-tolyl)-7-quinolyl]oxy]propanoyl]piperidine-3-carboxamide | + | ++ |
| 53 | (2R)-2-[[4-(2-chlorophenyl)-7-quinolyl]oxy]-1-(1-piperidyl)propan-1-one | + | ++ |
| 54 | methyl 3-[[[(2R)-2-[[4-(2-chloro-4-fluoro-phenyl)-7-quinolyl]oxy]propanoyl]amino]cyclobutane-carboxylate | + | |
| 55 | (2R)-2-[[4-(2-chloro-4-fluoro-phenyl)-7-quinolyl]oxy]-1-piperazin-1-yl-propan-1-one (trifluoroacetic acid salt) | + | + |
| 56 | 2-[(3R)-1-[(2R)-2-[[2-chloro-4-(2-chloro-4-fluoro-phenyl)-7-quinolyl]oxy]propanoyl]-3-piperidyl]acetic acid | + | + |
| 57 | 2-[(3R)-1-[(2R)-2-[[2-chloro-4-(4-fluoro-2-methyl-phenyl)-7-quinolyl]oxy]propanoyl]-3-piperidyl]acetic acid | + | + |
| 58 | ethyl 1-[(2R)-2-[[4-(2-chloro-4-fluoro-phenyl)-7-quinolyl]oxy]propanoyl]piperidine-4-carboxylate | + | |

| Ex | IUPAC Name | mitochondrial transcription activity | cellular qPCR assay |
|---|---|---|---|
| 59 | (3S)-1-[(2R)-2-[[4-(2-chloro-4-fluoro-phenyl)-2-methyl-7-quinolyl]oxy]propanoyl]piperidine-3-carboxylic acid | + | ++ |
| 60 | 4-[[(2R)-2-[[4-(2-chloro-4-fluoro-phenyl)-7-quinolyl]oxy]propanoyl]amino]benzoic acid (trifluoroacetic acid salt) | + | + |
| 61 | (2R)-2-[[4-(2-chloro-4-fluoro-phenyl)-7-quinolyl]oxy]-N-isopropyl-propanamide | + | + |
| 62 | (3S)-1-[2-[[5-(2-chloro-4-fluoro-phenyl)-1,8-naphthyridin-2-yl]oxy]propanoyl]piperidine-3-carboxylic acid | + | ++ |
| 63 | 4-[(2R)-2-[[4-(2-chloro-4-fluoro-phenyl)-7-quinolyl]oxy]propanoyl]piperazin-2-one | + | + |
| 64 | (3S)-1-[(2R)-2-[[2-chloro-4-(2-chloro-4-fluoro-phenyl)-7-quinolyl]oxy]propanoyl]piperidine-3-carboxylic acid | + | + |
| 65 | 2-[(3R)-1-[(2R)-2-[[4-(2-chloro-3-fluoro-phenyl)-7-quinolyl]oxy]propanoyl]-3-piperidyl]acetic acid | ++ | |
| 66 | (3S)-1-[(2R)-2-[(4-phenyl-7-quinolyl)oxy]propanoyl]piperidine-3-carboxylic acid | + | ++ |
| 67 | methyl 2-[(3S)-1-[(2R)-2-[[4-(2-chloro-4-fluoro-phenyl)-7-quinolyl]oxy]propanoyl]pyrrolidin-3-yl]acetate | + | |
| 68 | 2-[(3R)-1-[(2R)-2-[[2-chloro-4-(2-chlorophenyl)-7-quinolyl]oxy]propanoyl]-3-piperidyl]-N-methyl-acetamide | + | + |
| 69 | 2-[(3R)-1-[(2R)-2-[[2-methyl-4-(o-tolyl)-7-quinolyl]oxy]propanoyl]-3-piperidyl]acetic acid (trifluoroacetic acid salt) | + | ++ |
| 70 | (2R)-2-[[2-chloro-4-(2-chlorophenyl)-7-quinolyl]oxy]-1-[4-(cyclopropanecarbonyl)piperazin-1-yl]propan-1-one | + | (+) |
| 71 | methyl (3R)-1-[(2R)-2-[[4-(2-chloro-4-fluoro-phenyl)-7-quinolyl]oxy]propanoyl]piperidine-3-carboxylate | + | |
| 72 | (2R)-2-[[2-chloro-4-(2-chlorophenyl)-7-quinolyl]oxy]-1-(4-propanoylpiperazin-1-yl)propan-1-one | + | |
| 73 | tert-butyl (2R)-2-[[2-chloro-4-(o-tolyl)-7-quinolyl]oxy]propanoate | + | + |
| 74 | ethyl 2-[(3R)-1-[(2R)-2-[[4-(2-chloro-4-fluoro-phenyl)-2-methyl-7-quinolyl]oxy]propanoyl]-3-piperidyl]acetate | + | + |
| 75 | ethyl (3S)-1-[(2R)-2-[[4-(2-chloro-4-fluoro-phenyl)-7-quinolyl]oxy]propanoyl]pyrrolidine-3-carboxylate | + | |
| 76 | (3S)-1-[(2R)-2-[[2-chloro-4-(2-chlorophenyl)-7-quinolyl]oxy]propanoyl]piperidine-3-carboxamide | + | ++ |
| 77 | (2R)-2-[[4-(2-chloro-4-fluoro-phenyl)-7-quinolyl]oxy]-N-cyclopropyl-propanamide | + | + |
| 78 | (3S)-1-[(2S)-2-[[4-(2-chlorophenyl)-7-quinolyl]oxy]propanoyl]piperidine-3-carboxylic acid (formic acid salt) | + | (+) |
| 79 | 2-[(3R)-1-[(2R)-2-[[4-(2-methyl-3-thienyl)-7-quinolyl]oxy]propanoyl]-3-piperidyl]acetic acid | + | + |
| 80 | 2-[rac-(3R)-1-[(2R)-2-[[5-(2-chloro-4-fluoro-phenyl)-1,8-naphthyridin-2-yl]oxy]propanoyl]-3-piperidyl]acetic acid | (+) | + |
| 81 | (3S)-1-[(2R)-2-[[2-chloro-4-(2-chloro-4-fluoro-phenyl)-7-quinolyl]oxy]propanoyl]piperidine-3-carboxamide | (+) | + |
| 82 | isopropyl 2-[[4-(2-chlorophenyl)-7-quinolyl]oxy]acetate (formic acid salt) | (+) | |
| 83 | 2-[(3R)-1-[(2R)-2-[[2-chloro-4-(2-chlorophenyl)-7-quinolyl]oxy]propanoyl]-3-piperidyl]acetic acid | (+) | (+) |
| 84 | (3S)-1-[(2R)-2-[[4-(4-fluoro-2,6-dimethyl-phenyl)-7-quinolyl]oxy]propanoyl]piperidine-3-carboxylic acid | +++ | |
| 85 | (2R)-1-[4-(2-aminoacetyl)piperazin-1-yl]-2-[[2-chloro-4-(2-chlorophenyl)-7-quinolyl]oxy]propan-1-one (trifluoroacetic acid salt) | (+) | |
| 86 | 2-[[4-(2-chlorophenyl)-7-quinolyl]oxy]-N,N-dimethyl-propanamide | (+) | + |
| 87 | ethyl (3S)-1-[2-[[4-(2-chlorophenyl)-7-quinolyl]oxy]acetyl]piperidine-3-carboxylate | (+) | |
| 88 | (2R)-2-[[4-(2-chlorophenyl)-7-quinolyl]oxy]-N,N-dimethyl-propanamide (formic acid salt) | (+) | + |
| 89 | ethyl 2-[(3S)-1-[(2R)-2-[[4-(2-chloro-4-fluoro-phenyl)-7-quinolyl]oxy]propanoyl]-3-piperidyl]acetate | (+) | |
| 90 | (2R)-2-[[4-(2-chlorophenyl)-2-fluoro-7-quinolyl]oxy]propanoic acid (trifluoroacetic acid salt) | (+) | |
| 91 | (2R)-2-[[2-chloro-4-(2-chloro-4-fluoro-phenyl)-7-quinolyl]oxy]propanoic acid | (+) | |
| 92 | ethyl 2-[(3R)-1-[(2R)-2-[[2-chloro-4-(2-chlorophenyl)-7-quinolyl]oxy]propanoyl]-3-piperidyl]acetate | (+) | |
| 93 | ethyl 2-[(3R)-1-[(2R)-2-[[2-chloro-4-(2-chloro-4-fluoro-phenyl)-7-quinolyl]oxy]propanoyl]-3-piperidyl]acetate | (+) | |
| 94 | ethyl (3S)-1-[(2R)-2-[[2-chloro-4-(4-fluoro-2-methyl-phenyl)-7-quinolyl]oxy]propanoyl]piperidine-3-carboxylate | (+) | |
| 95 | (2R)-2-[[4-(2-chloro-4-fluoro-phenyl)-7-quinolyl]oxy]-N-(4-pyridyl)-propanamide (trifluoroacetic acid salt) | + | + |
| 96 | (3S)-1-[(2R)-2-[[2-chloro-4-(2-chlorophenyl)-7-quinolyl]oxy]propanoyl]-N-methyl-piperidine-3-carboxamide | (+) | |
| 97 | methyl 3-[[(2R)-2-[[2-chloro-4-(2-chlorophenyl)-7-quinolyl]oxy]propanoyl]amino]cyclobutanecarboxylate | (+) | |
| 98 | 2-[(3R)-1-[(2R)-2-[[2-chloro-4-(2-chloro-4-fluoro-phenyl)-7-quinolyl]oxy]propanoyl]-3-piperidyl]-N-methyl-acetamide | (+) | |
| 99 | (2R)-2-[[2-chloro-4-(2-chlorophenyl)-7-quinolyl]oxy]-1-(1-piperidyl)propan-1-one | (+) | (+) |
| 100 | (3S)-1-[(2R)-2-[[2-chloro-4-(2-chlorophenyl)-7-quinolyl]oxy]propanoyl]-N,N-dimethyl-piperidine-3-carboxamide | (+) | |
| 101 | 2-[(3R)-1-[(2R)-2-[[4-(2-chloro-4-fluoro-phenyl)-2-methyl-7-quinolyl]oxy]propanoyl]-3-piperidyl]acetic acid (trifluoroacetic acid salt) | (+) | (+) |
| 102 | (3R)-1-[(2S)-2-[[4-(2-chlorophenyl)-7-quinolyl]oxy]propanoyl]piperidine-3-carboxylic acid (formic acid salt) | (+) | |
| 103 | (2R)-2-[[4-(2-chlorophenyl)-7-quinolyl]oxy]propanoic acid | (+) | |
| 104 | (2R)-2-[[2-chloro-4-(2-chlorophenyl)-7-quinolyl]oxy]-1-piperazin-1-yl-propan-1-one (trifluoroacetic acid salt) | (+) | + |
| 105 | (3S)-N-methyl-1-[(2R)-2-[[2-chloro-4-(2-chloro-4-fluoro-phenyl)-7-quinolyl]oxy]propanoyl]piperidine-3-carboxamide | (+) | |
| 106 | 2-[[4-(o-tolyl)-7-quinolyl]oxy]acetamide | (+) | |
| 107 | (2R)-2-[[2-chloro-4-(2-chloro-4-fluoro-phenyl)-7-quinolyl]oxy]-1-(1-piperidyl)propan-1-one | (+) | |
| 108 | ethyl 3-[[(2R)-2-[[4-(2-chloro-4-fluoro-phenyl)-7-quinolyl]oxy]propanoyl]amino]benzoate | (+) | |
| 109 | 2-[[5-(2-chloro-4-fluoro-phenyl)-1,8-naphthyridin-2-yl]oxy]-N-isopropyl-propanamide | (+) | |
| 110 | 2-[(3R)-1-[(2R)-2-[[4-(2-fluorophenyl)-7-quinolyl]oxy]propanoyl]-3-piperidyl]acetic acid | (+) | |
| 111 | tert-butyl (3S)-1-[(2R)-2-[2-methyl-4-(o-tolyl)-7-quinolyl]oxy]propanoyl]piperidine-3-carboxylate | (+) | |
| 112 | 2-[1-[(2R)-2-[[4-(2-chlorophenyl)-7-quinolyl]oxy]propanoyl]-4-piperidyl]acetic acid | ++ | ++ |

| Ex | IUPAC Name | mitochondrial transcription activity | cellular qPCR assay |
|---|---|---|---|
| 113 | (3S)-1-[(2R)-2-[[4-(2,6-dimethylphenyl)-2-methyl-7-quinolyl]oxy]propanoyl]piperidine-3-sulfonamide (trifluoroacetic acid salt) | + | + |
| 114 | (3R)-1-[(2R)-2-[[4-(2,6-dimethylphenyl)-2-methyl-7-quinolyl]oxy]propanoyl]piperidine-3-sulfonamide (trifluoroacetic acid salt) | + | ++ |
| 115 | (3R)-1-[(2R)-2-[[4-(2-chloro-4-fluoro-phenyl)-2-methyl-7-quinolyl]oxy]propanoyl]piperidine-3-sulfonamide (trifluoroacetic acid salt) | (+) | + |
| 116 | (3S)-1-[(2R)-2-[[4-(2-chloro-4-fluoro-phenyl)-7-quinolyl]oxy]propanoyl]piperidine-3-sulfonamide (trifluoroacetic acid salt) | + | +++ |
| 117 | (3R)-1-[(2R)-2-[[4-(2-chloro-4-fluoro-phenyl)-7-quinolyl]oxy]propanoyl]piperidine-3-sulfonamide (trifluoroacetic acid salt) | + | ++ |
| 118 | 3-[1-[(2R)-2-[[4-(2-chlorophenyl)-7-quinolyl]oxy]propanoyl]-4-piperidyl]propanoic acid | +++ | ++ |
| 119 | 1-[rac-(2R)-2-[[4-(2,6-dimethylphenyl)-7-quinolyl]oxy]propanoyl]piperidine-3-sulfonamide | +++ | +++ |
| 120 | 2-[(3R)-1-[(2R)-2-[[4-(2,6-dichlorophenyl)-7-quinolyl]oxy]propanoyl]-3-piperidyl]acetic acid | +++ | ++ |
| 121 | 2-[(3R)-1-[(2R)-2-[[4-(2-ethylphenyl)-7-quinolyl]oxy]propanoyl]-3-piperidyl]acetic acid | ++ | ++ |
| 122 | 2-[(3R)-1-[(2R)-2-[[4-(2-isopropylphenyl)-7-quinolyl]oxy]propanoyl]-3-piperidyl]acetic acid | (+) | |
| 123 | [1-[rac-(2R)-2-[[4-(2-chloro-4-fluoro-phenyl)-7-quinolyl]oxy]propanoyl]-3-piperidyl] methanesulfonamide (trifluoroacetic acid salt) | + | + |
| 124 | 2-[(3R)-1-[(2R)-2-[[4-(2,6-dimethylphenyl)-2-methyl-7-quinolyl]oxy]propanoyl]-3-piperidyl]acetic acid | + | + |
| 125 | (2R)-2-[[4-(2-chloro-4-fluoro-phenyl)-7-quinolyl]oxy-N-[4-(2-hydroxyethyl)phenyl]propanamide(trifluoroacetic acid salt) | (+) | |
| 126 | (3S)-1-[(2R)-2-[[5-(2-chloro-4-fluoro-phenyl)-1,8-naphthyridin-2-yl]oxy]propanoyl]piperidine-3-carboxylic acid (formic acid salt) | + | ++ |
| 127 | (3S)-1-[(2S)-2-[[5-(2-chloro-4-fluoro-phenyl)-1,8-naphthyridin-2-yl]oxy]propanoyl]piperidine-3-carboxylic acid | (+) | |
| 128 | 2-[(3R)-1-[(2R)-2-[[5-(2-chloro-4-fluoro-phenyl)-1,8-naphthyridin-2-yl]oxy]propanoyl]-3-piperidyl]acetic acid (formic acid salt) | + | + |
| 129 | (3S)-1-[(2R)-2-[[4-(2,6-dichlorophenyl)-7-quinolyl]oxy]propanoyl]piperidine-3-carboxylic acid | +++ | +++ |
| 130 | (2R)-2-[[4-(2-chloro-4-fluoro-phenyl)-7-quinolyl]oxy]-N-(2-pyridyl)propanamide (trifluoroacetic acid salt) | + | (+) |
| 131 | (2R)-2-[[4-(2-chloro-4-fluoro-phenyl)-7-quinolyl]oxy]-N-ethyl-propanamide (trifluoroacetic acid salt) | (+) | + |
| 132 | (3S)-1-[(2R)-2-[[4-(2,6-dichloro-4-fluoro-phenyl)-7-quinolyl]oxy]propanoyl]piperidine-3-carboxylic acid | +++ | +++ |
| 133 | 2-[(3R)-1-[(2R)-2-[[4-(4-methyl-3-thienyl)-7-quinolyl]oxy]propanoyl]-3-piperidyl]acetic acid | + | + |
| 134 | 2-[(3R)-1-[(2R)-2-[[4-(3-methyl-2-thienyl)-7-quinolyl]oxy]propanoyl]-3-piperidyl]acetic acid | (+) | |
| 135 | 2-[(3R)-1-[(2R)-2-[[4-(2-methoxyphenyl)-7-quinolyl]oxy]propanoyl]-3-piperidyl]acetic acid | (+) | |
| 136 | 2-[(3R)-1-[(2R)-2-[[4-[2-(trifluoromethyl)phenyl]-7-quinolyl]oxy]propanoyl]-3-piperidyl]acetic acid | + | |
| 137 | 2-[(3R)-1-[(2R)-2-[[4-[2-(trifluoromethoxy)phenyl]-7-quinolyl]oxy]propanoyl]-3-piperidyl]acetic acid | (+) | |
| 138 | (3S)-1-[(2R)-2-[[4-(2,6-dimethylphenyl)-7-quinolyl]oxy]propanoyl]piperidine-3-sulfonamide | +++ | |
| 139 | 2-[(3R)-1-[2-[[4-(2-chlorophenyl)-7-quinolyl]oxy]-2-methyl-propanoyl]-3-piperidyl]acetic acid | (+) | |
| 140 | 2-[rac-(3R)-1-[2-[[4-(2-chlorophenyl)-7-quinolyl]oxy]butanoyl]-3-piperidyl]acetic acid | ++ | |
| 141 | 2-[(3R)-1-[(2R)-2-[[4-(2-chloro-6-methyl-phenyl)-7-quinolyl]oxy]propanoyl]-3-piperidyl]acetic acid | +++ | |
| 142 | 2-[(3R)-1-[(2R)-2-[[4-(2-bromophenyl)-7-quinolyl]oxy]propanoyl]-3-piperidyl]acetic acid | +++ | |
| 143 | 2-[(3R)-1-[(2R)-2-[[4-(2-cyanophenyl)-7-quinolyl]oxy]propanoyl]-3-piperidyl]acetic acid | + | |
| 144 | 2-[(3R)-1-[(2R)-2-[[4-(2-ethynylphenyl)-7-quinolyl]oxy]propanoyl]-3-piperidyl]acetic acid | ++ | |
| 145 | 2-[(3R)-1-[(2R)-2-[[4-[2-(dimethylamino)phenyl]-7-quinolyl]oxy]propanoyl]-3-piperidyl]acetic acid | + | |
| 146 | 2-[(3R)-1-[(2R)-2-[[4-(2-carbamoylphenyl)-7-quinolyl]oxy]propanoyl]-3-piperidyl]acetic acid | | |
| 147 | 2-[(3R)-1-[(2R)-2-[[4-(2,6-difluorophenyl)-7-quinolyl]oxy]propanoyl]-3-piperidyl]acetic acid | | |
| 148 | 2-[(3R)-1-[(2R)-2-[[4-(2,4-dimethyl-3-thienyl)-7-quinolyl]oxy]propanoyl]-3-piperidyl]acetic acid | | |
| 149 | 2-[(3R)-1-[(2R)-2-[[4-[2-chloro-6-(trifluoromethyl)phenyl]-7-quinolyl]oxy]propanoyl]-3-piperidyl]acetic acid | | |
| 150 | 2-[(3R)-1-[(2R)-2-[[4-(2-bromo-6-chloro-phenyl)-7-quinolyl]oxy]propanoyl]-3-piperidyl]acetic acid | | |
| 151 | 2-[(3R)-1-[(2R)-2-[[4-[2,6-bis(trifluoromethyl)phenyl]-7-quinolyl]oxy]propanoyl]-3-piperidyl]acetic acid | (+) | |
| 152 | 2-[(3R)-1-[(2R)-2-[[4-(2-chloro-6-methoxy-phenyl)-7-quinolyl]oxy]propanoyl]-3-piperidyl]acetic acid | (+) | |
| 153 | 2-[(3R)-1-[(2R)-2-[[4-(2,6-diisopropylphenyl)-7-quinolyl]oxy]propanoyl]-3-piperidyl]acetic acid | | |
| 154 | (2R)-1-[(3R)-3-amino-1-piperidyl]-2-[[4-(2,6-dimethylphenyl)-7-quinolyl]oxy]propan-1-one | | |
| 155 | (2R)-1-[(3S)-3-amino-1-piperidyl]-2-[[4-(2,6-dimethylphenyl)-7-quinolyl]oxy]propan-1-one | | |
| 156 | N-[(3S)-1-[(2R)-2-[[4-(2,6-dimethylphenyl)-7-quinolyl]oxy]propanoyl]-3-piperidyl]propanamide | | |
| 157 | N-tert-butyl-4-[(2R)-2-[[4-(2,6-dimethylphenyl)-7-quinolyl]oxy]propanoyl]piperazine-1-carboxamide | | |
| 158 | (2R)-2-[[4-(2,6-dimethylphenyl)-7-quinolyl]oxy]-1-[3-(1-hydroxycyclopropyl)-1-piperidyl]propan-1-one | | |
| 169 | 8-[(2R)-2-[[4-(2,6-dimethylphenyl)-7-quinolyl]oxy]propanoyl]-2,8-diazaspiro[4.5]decan-1-one | | |
| 160 | (2R)-2-[[4-(2,6-dimethylphenyl)-7-quinolyl]oxy]-1-(3,5-dimethylpiperazin-1-yl)propan-1-one | | |
| 161 | N-[(3S)-1-[(2R)-2-[[4-(2,6-dimethylphenyl)-7-quinolyl]oxy]propanoyl]-3-piperidyl]-N-hydroxy-acetamide | | |
| 162 | 1-[4-[(2R)-2-[[4-(2,6-dimethylphenyl)-7-quinolyl]oxy]propanoyl]piperazin-1-yl]-2,2-dimethyl-propan-1-one | | |
| 163 | N-[(3S)-1-[(2R)-2-[[4-(2,6-dimethylphenyl)-7-quinolyl]oxy]propanoyl]-3-piperidyl]methanesulfonamide | | |
| 164 | N-[(3S)-1-[(2R)-2-[[4-(2,6-dimethylphenyl)-7-quinolyl]oxy]propanoyl]-3-piperidyl]benzamide | | |
| 165 | (3S)-N-cyano-1-[(2R)-2-[[4-(2,6-dimethylphenyl)-7-quinolyl]oxy]propanoyl]piperidine-3-carboxamide | | |
| 166 | (3S)-1-[(2R)-2-[[4-(2,6-dimethylphenyl)-7-quinolyl]oxy]propanoyl]piperidine-3-carbohydroxamic acid | | |
| 167 | 2-[(3R)-1-[(2R)-2-[[4-(2,6-dimethylphenyl)-7-quinolyl]oxy]propanoyl]-3-piperidyl]ethanehydroxamic acid | | |

| Ex | IUPAC Name | mitochondrial transcription activity | cellular qPCR assay |
|---|---|---|---|
| 168 | (2R)-1-(3-aminoazetidin-1-yl)-2-[[4-(2,6-dimethylphenyl)-7-quinolyl]oxy]propan-1-one | | |
| 169 | (2R)-2-[[4-(2,6-dimethylphenyl)-7-quinolyl]oxy]-1-[3-(1H-tetrazol-5-yl)azetidin-1-yl]propan-1-one | | |
| 170 | 3-hydroxy-1-[(2R)-2-[[4-(2,6-dimethylphenyl)-7-quinolyl]oxy]propanoyl]piperidine-3-carboxylic acid | | |
| 171 | 5-[(2R)-2-[[4-(2,6-dimethylphenyl)-7-quinolyl]oxy]propanoyl]-5-azaspiro[2.5]octane-2-carboxylic acid | | |
| 172 | (3R)-1-[(2R)-2-[[4-(2,6-dimethylphenyl)-7-quinolyl]oxy]propanoyl]piperidine-3-sulfonamide | +++ | |
| 173 | (3S)-1-[(2R)-2-[[4-(2,6-dichloro-4-fluoro-phenyl)-7-quinolyl]oxy]propanoyl]-3-methyl-piperidine-3-carboxylic acid | +++ | +++ |
| 174 | 5-[rac-(2R)-2-[[4-(4-fluoro-2,6-dimethyl-phenyl)-7-quinolyl]oxy]propanoyl]-5-azaspiro[2.5]octane-2-carboxylic acid | +++ | +++ |
| 175 | (3R)-1-[(2R)-2-[[4-(4-fluoro-2,6-dimethyl-phenyl)-7-quinolyl]oxy]propanoyl]-3-methyl-piperidine-3-carboxylic acid | +++ | +++ |
| 176 | (2R)-2-[[4-(4-fluoro-2,6-dimethyl-phenyl)-7-quinolyl]oxy]-1-[(2S)-2-methyl-1-piperidyl]propan-1-one | +++ | ++ |
| 177 | 5-[rac-(2R)-2-[[4-(2,6-dichloro-4-fluoro-phenyl)-7-quinolyl]oxy]propanoyl]-5-azaspiro[2.5]octane-2-carboxylic acid | +++ | +++ |
| 178 | (2R)-2-[[4-(4-fluoro-2,6-dimethyl-phenyl)-7-quinolyl]oxy]-1-morpholino-propan-1-one | +++ | ++ |
| 179 | (2R)-2-[[4-(4-fluoro-2,6-dimethyl-phenyl)-7-quinolyl]oxy]-1-(2-oxa-7-azaspiro[3.5]nonan-7-yl)propan-1-one | +++ | +++ |
| 180 | rac-(2R)-2-[[4-(4-fluoro-2,6-dimethyl-phenyl)-7-quinolyl]oxy]-1-[3-(1-hydroxycyclopropyl)-1-piperidyl]propan-1-one | +++ | +++ |
| 181 | 8-[(2R)-2-[[4-(4-fluoro-2,6-dimethyl-phenyl)-7-quinolyl]oxy]propanoyl]-2,8-diazaspiro[4.5]decan-1-one | +++ | +++ |
| 182 | 1-[1-[rac-(2R)-2-[[4-(4-fluoro-2,6-dimethyl-phenyl)-7-quinolyl]oxy]propanoyl]-3-piperidyl]cyclopropanecarboxylic acid | +++ | +++ |
| 183 | 2-[(3R)-1-[(2R)-2-[[4-(4-fluoro-2,6-dimethyl-phenyl)-7-quinolyl]oxy]propanoyl]-3-piperidyl]acetic acid | +++ | +++ |
| 184 | (3S)-1-[(2R)-2-[[4-(4-fluoro-2,6-dimethyl-phenyl)-7-quinolyl]oxy]propanoyl]-3-methyl-piperidine-3-carboxylic acid | +++ | +++ |
| 185 | N-[(3S)-1-[(2R)-2-[[4-(4-fluoro-2,6-dimethyl-phenyl)-7-quinolyl]oxy]propanoyl]-3-piperidyl]-N-hydroxy-acetamide | +++ | +++ |
| 186 | 2-methyl-2-[1-[rac-(2R)-2-[[4-(4-fluoro-2,6-dimethyl-phenyl)-7-quinolyl]oxy]propanoyl]-3-piperidyl]propanoic acid | +++ | +++ |
| 187 | (2R)-2-[[4-(4-fluoro-2,6-dimethyl-phenyl)-7-quinolyl]oxy]-1-[(2R)-2-methyl-1-piperidyl]propan-1-one | +++ | +++ |
| 188 | (3R)-1-[(2R)-2-[[4-(2,6-dichloro-4-fluoro-phenyl)-7-quinolyl]oxy]propanoyl]-3-methyl-piperidine-3-carboxylic acid | +++ | ++ |
| 189 | (3S)-1-[(2R)-2-[[4-(2-chloro-4-fluoro-phenyl)-7-quinolyl]oxy]propanoyl]-3-methyl-piperidine-3-carboxylic acid | +++ | +++ |
| 190 | [1-[rac-(2R)-2-[[4-(2,6-dimethylphenyl)-7-quinolyl]oxy]propanoyl]-3-piperidyl]methanesulfonamide | +++ | |
| 191 | rac-(2R)-1-(2,6-dimethyl-1-piperidyl)-2-[[4-(4-fluoro-2,6-dimethyl-phenyl)-7-quinolyl]oxy]propan-1-one | +++ | |
| 192 | 2-[(3R)-1-[(2R)-2-[[4-(2,6-dichloro-4-fluoro-phenyl)-7-quinolyl]oxy]propanoyl]-3-piperidyl]acetic acid | ++ | +++ |
| 193 | 5-[rac-(2R)-2-[[4-(2-chloro-4-fluoro-phenyl)-7-quinolyl]oxy]propanoyl]-5-azaspiro[2.5]octane-2-carboxylic acid | ++ | ++ |
| 194 | 1-[1-[rac-(2R)-2-[[4-(2-chloro-4-fluoro-phenyl)-7-quinolyl]oxy]propanoyl]-3-piperidyl]cyclopropanecarboxylic acid | ++ | ++ |
| 195 | 2-methyl-2-[1-[rac-(2R)-2-[[4-(2,6-dichloro-4-fluoro-phenyl)-7-quinolyl]oxy]propanoyl]-3-piperidyl]propanoic acid | ++ | ++ |
| 196 | 1-[1-[rac-(2R)-2-[[4-(2,6-dichloro-4-fluoro-phenyl)-7-quinolyl]oxy]propanoyl]-3-piperidyl]cyclopropanecarboxylic acid | ++ | ++ |
| 197 | 2-methyl-2-[1-[rac-(2R)-2-[[4-(2-chloro-4-fluoro-phenyl)-7-quinolyl]oxy]propanoyl]-3-piperidyl]propanoic acid | ++ | ++ |
| 198 | (3R)-1-[(2R)-2-[[4-(2-chloro-4-fluoro-phenyl)-7-quinolyl]oxy]propanoyl]-3-methyl-piperidine-3-carboxylic acid | ++ | +++ |
| 199 | (2R)-2-[[4-(2,6-dichloro-4-fluoro-phenyl)-7-quinolyl]oxy]-1-[(2S)-2-methyl-1-piperidyl]propan-1-one | ++ | +++ |
| 200 | rac-(2R)-2-[[4-(2-chloro-4-fluoro-phenyl)-7-quinolyl]oxy]-1-(2-methyl-1-piperidyl)propan-1-one | ++ | +++ |
| 201 | (2R)-2-[[4-(2,6-dichloro-4-fluoro-phenyl)-7-quinolyl]oxy]-1-morpholino-propan-1-one | + | ++ |
| 202 | 8-[(2R)-2-[[4-(2,6-dichloro-4-fluoro-phenyl)-7-quinolyl]oxy]propanoyl]-2,8-diazaspiro[4.5]decan-1-one | + | ++ |
| 203 | rac-(2R)-2-[[4-(2,6-dichloro-4-fluoro-phenyl)-7-quinolyl]oxy]-143-(1-hydroxycyclopropyl)-1-piperidyl]propan-1-one | + | ++ |
| 204 | (2R)-2-[[4-(2,6-dichloro-4-fluoro-phenyl)-7-quinolyl]oxy]-1-[(2R)-2-methyl-1-piperidyl]propan-1-one | + | ++ |
| 205 | 8-[(2R)-2-[[4-(2-chloro-4-fluoro-phenyl)-7-quinolyl]oxy]propanoyl]-2,8-diazaspiro[4.5]decan-1-one | + | ++ |
| 206 | (2R)-2-[[4-(2-chloro-4-fluoro-phenyl)-7-quinolyl]oxy]-1-morpholino-propan-1-one | + | ++ |
| 207 | (2R)-2-[[4-(2-chloro-4-fluoro-phenyl)-7-quinolyl]oxy]-1-[3-(1-hydroxycyclopropyl)-1-piperidyl]propan-1-one | + | +++ |
| 208 | (2R)-2-[[4-(2,6-dichloro-4-fluoro-phenyl)-7-quinolyl]oxy]-1-(2-oxa-7-azaspiro[3.5]nonan-7-yl)propan-1-one | + | ++ |
| 209 | N-hydroxy-N-[rac-(3S)-1-[rac-(2R)-2-[[4-(2-chloro-4-fluoro-phenyl)-7-quinolyl]oxy]propanoyl]-3-piperidyl]acetamide | + | ++ |
| 210 | (2R)-2-[[4-(2-chloro-4-fluoro-phenyl)-7-quinolyl]oxy]-1-(2-oxa-7-azaspiro[3.5]nonan-7-yl)propan-1-one | + | ++ |
| 211 | (2R)-2-[[4-(2-chloro-4-fluoro-phenyl)-7-quinolyl]oxy]-1-(2,6-dimethyl-1-piperidyl)propan-1-one | + | ++ |
| 212 | (2R)-2-[[4-(2-chloro-4-fluoro-phenyl)-7-quinolyl]oxy]-1-(2-oxa-8-azaspiro[3.5]nonan-8-yl)propan-1-one | + | +++ |
| 213 | (2R)-2-[[4-(2-chloro-4-fluoro-phenyl)-7-quinolyl]oxy]-1-(2-oxa-7-azaspiro[3.4]octan-7-yl)propan-1-one | + | + |
| 214 | 1-tert-butyl-3-[(3R)-1-[(2R)-2-[[4-(2-chloro-4-fluoro-phenyl)-7-quinolyl]oxy]propanoyl]pyrrolidin-3-yl]urea | + | + |
| 215 | (2R)-2-[[4-(2-chloro-4-fluoro-phenyl)-7-quinolyl]oxy]-1-(3,3,5,5-tetramethylpiperazin-1-yl)propan-1-one | + | + |
| 216 | (2R)-2-[[4-(2-chloro-4-fluoro-phenyl)-7-quinolyl]oxy]-1-(3,5-dimethylpiperazin-1-yl)propan-1-one | + | + |
| 217 | (2R)-2-[[4-(2-chloro-4-fluoro-phenyl)-7-quinolyl]oxy]-1-[(1R)-2,5-diazabicyclo[2.2.1]heptan-2-yl]propan-1-one | (+) | |

-continued

| Ex | IUPAC Name | mitochondrial transcription activity | cellular qPCR assay |
|---|---|---|---|
| 218 | (2R)-2-[[4-(2-chloro-4-fluoro-phenyl)-7-quinolyl]oxy]-1-(2-oxa-6-azaspiro[3.3]heptan-6-yl)propan-1-one | (+) | |
| 219 | 1-[(2R)-2-[[4-(2-chloro-4-fluoro-phenyl)-7-quinolyl]oxy]propanoyl]-3,6-dihydro-2H-pyridine-5-carboxylic acid | ++ | + |
| 220 | 2-[(3R)-1-[(2R)-2-[[5-(2,6-dichloro-4-fluoro-phenyl)-1,8-naphthyridin-2-yl]oxy]propanoyl]-3-piperidyl]acetic acid | ++ | +++ |
| 221 | 2-[(3R)-1-[(2R)-2-[[5-(4-fluoro-2,6-dimethyl-phenyl)-1,8-naphthyridin-2-yl]oxy]propanoyl]-3-piperidyl]acetic acid | +++ | +++ |

7. INHIBITION OF VARIOUS CANCER CELL LINES IN VITRO

The CellTiter-Glo Luminescent Cell Viability Assay (Promega) is a homogeneous method of determining the number of viable cells in culture. It is based on quantification of ATP, indicating the presence of metabolically active cells. The assay can be used to determine the inhibitory activity of the compounds of the invention on the growth of cancer cells in vitro.

Cells are seeded on day 1 at cell numbers that assure assay linearity and optimal signal intensity. After incubation for 3 h in humidified chambers at 37° C./5% $CO_2$ compounds/DMSO are added at different concentrations. Cells are further incubated for 72 h at 37° C. and 5% $CO_2$. Cells treated with the compound vehicle DMSO are used as positive controls and cells treated with 10 µM Staurosporine served as negative controls. At day 4 the CellTiter Glo Reagent is prepared according to the instructions of the kit (Promega Inc.): Reagent is mixed 1:1 with cell culture medium. Thereon, mixture and assay plates are equilibrated at room temperature for 20 min. Equal volumes of the reagent-medium-mixture are added to the volume of culture medium present in each well.

The plates are mixed at ~200 rpm for 2 minutes on an orbital shaker. The microplates are then incubated at room temperature for 10 minutes for stabilization of the luminescent signal. Following incubation the luminescence is recorded on a Victor microplate reader (Perkin Elmer) using 200 ms integration time. The data are then analyzed with Excel using the XLFIT Plugin (dose response Fit 205) for $IC_{50}$-determination. As quality control, the Z'-factor is calculated from 16 positive and negative control values. Only assay results showing a Z'-factor ≥0.5 are used for further analysis.

A suitable cell line panel for the CellTiter GLO viability assay is CA-46 (lymphoma), HEC-59 (endometrial), HRT-18 (colon), NCI-H1299 (lung), NCI-H23 (lung), NCI-H596 (lung), SW403 (colon), SW48 (colon), SW948 (colon)

LITERATURE

ARIAANS, G., JALVING, M., VRIES, E. G. & JONG, S. 2017. Anti-tumor effects of everolimus and metformin are complementary and glucose-dependent in breast cancer cells. BMC Cancer, 17, 232.

ARNOLD, J. J., SMIDANSKY, E. D., MOUSTAFA, I. M. & CAMERON, C. E. 2012. Human mitochondrial RNA polymerase: structure-function, mechanism and inhibition. Biochim Biophys Acta, 1819, 948-60.

BEHERA, M. A., DAI, Q., GARDE, R., SANER, C., JUNGHEIM, E. & PRICE, T. M. 2009. Progesterone stimulates mitochondrial activity with subsequent inhibition of apoptosis in MCF-10A benign breast epithelial cells. Am J Physiol Endocrinol Metab, 297, E1089-96.

BHAT, M., SONENBERG, N. & GORES, G. J. 2013. The mTOR pathway in hepatic malignancies. Hepatology, 58, 810-8.

BISSEMBER, A. C. & BANWELL, M. G. 2009. Microwave-assisted trans-halogenation reactions of various chloro-, bromo-, trifluoromethanesulfonyloxy- and nonafluorobutanesulfonyloxy-substituted quinolines, isoquinolines, and pyridines leading to the corresponding iodinated heterocycles. J Org Chem, 74, 4893-5.

BRALHA, F. N., LIYANAGE, S. U., HURREN, R., WANG, X., SON, M. H., FUNG, T. A., CHINGCUANCO, F. B., TUNG, A. Y., ANDREAZZA, A. C., PSARIANOS, P., SCHIMMER, A. D., SALMENA, L. & LAPOSA, R. R. 2015. Targeting mitochondrial RNA polymerase in acute myeloid leukemia. Oncotarget, 6, 37216-28.

BRECHT, K., RIEBEL, V., COUTTET, P., PAECH, F., WOLF, A., CHIBOUT, S. D., POGNAN, F., KRAHENBUHL, S. & UTENG, M. 2017. Mechanistic insights into selective killing of OXPHOS-dependent cancer cells by arctigenin. Toxicol In Vito, 40, 55-65.

BUBNER, B. & BALDWIN, I. T. 2004. Use of real-time PCR for determining copy number and zygosity in transgenic plants. Plant Cell Rep, 23, 263-71.

CARO, P., KISHAN, A. U., NORBERG, E., STANLEY, I. A., CHAPUY, B., FICARRO, S. B., POLAK, K., TONDERA, D., GOUNARIDES, J., YIN, H., ZHOU, F., GREEN, M. R., CHEN, L., MONTI, S., MARTO, J. A., SHIPP, M. A. & DANIAL, N. N. 2012. Metabolic signatures uncover distinct targets in molecular subsets of diffuse large B cell lymphoma. Cancer Cell, 22, 547-60.

CARROLL, S. S., TOMASSINI, J. E., BOSSERMAN, M., GETTY, K., STAHLHUT, M. W., ELDRUP, A. B., BHAT, B., HALL, D., SIMCOE, A. L., LAFEMINA, R., RUTKOWSKI, C. A., WOLANSKI, B., YANG, Z., MIGLIACCIO, G., DE FRANCESCO, R., KUO, L. C., MACCOSS, M. & OLSEN, D. B. 2003. Inhibition of hepatitis C virus RNA replication by 2'-modified nucleoside analogs. J Biol Chem, 278, 11979-84.

CHEN, Y. F., LIN, Y. C., MORRIS-NATSCHKE, S. L., WEI, C. F., SHEN, T. C., LIN, H. Y., HSU, M. H., CHOU, L. C., ZHAO, Y., KUO, S. C., LEE, K. H. & HUANG, L. J. 2015. Synthesis and SAR studies of novel 6,7,8-substituted 4-substituted benzyloxyquinolin-2(1H)-one derivatives for anticancer activity. Br J Pharmacol, 172, 1195-221.

DENISE, C., PAOLI, P., CALVANI, M., TADDEI, M. L., GIANNONI, E., KOPETZ, S., KAZMI, S. M., PIA, M. M., PETTAZZONI, P., SACCO, E., CASELLI, A., VANONI, M., LANDRISCINA, M., CIRRI, P. & CHIARUGI, P. 2015. 5-fluorouracil resistant colon cancer cells are addicted to OXPHOS to survive and enhance stem-like traits. Oncotarget, 6, 41706-21.

DÖRR, J. R., YU, Y., MILANOVIC, M., BEUSTER, G., ZASADA, C., DABRITZ, J. H., LISEC, J., LENZE, D., GERHARDT, A., SCHLEICHER, K., KRATZAT, S., PURFURST, B., WALENTA, S., MUELLER-KLIESER, W., GRALER, M., HUMMEL, M., KELLER, U., BUCK, A. K., DORKEN, B., WILLMITZER, L., REIMANN, M., KEMPA, S., LEE, S. & SCHMITT, C. A. 2013.

Synthetic lethal metabolic targeting of cellular senescence in cancer therapy. *Nature,* 501, 421-5.

FALKENBERG, M., GASPARI, M., RANTANEN, A., TRIFUNOVIC, A., LARSSON, N. G. & GUSTAFSSON, C. M. 2002. Mitochondrial transcription factors B1 and B2 activate transcription of human mtDNA. *Nat Genet,* 31, 289-94.

FIER, P. S. & HARTWIG, J. F. 2013. Selective C—H fluorination of pyridines and diazines inspired by a classic amination reaction. *Science,* 342, 956-60.

FULDA, S., GALLUZZI, L. & KROEMER, G. 2010. Targeting mitochondria for cancer therapy. *Nat Rev Drug Discov,* 9, 447-64.

GOSSELIN, F., BRITTON, R. A., DAVIES, I. W., DOLMAN, S. J., GAUVREAU, D., HOERRNER, R. S., HUGHES, G., JANEY, J., LAU, S., MOLINARO, C., NADEAU, C., O'SHEA, P. D., PALUCKI, M. & SIDLER, R. 2010. A practical synthesis of 5-lipoxygenase inhibitor MK-0633. *J Org Chem,* 75, 4154-60.

HAQ, R., SHOAG, J., ANDREU-PEREZ, P., YOKOYAMA, S., EDELMAN, H., ROWE, G. C., FREDERICK, D. T., HURLEY, A. D., NELLORE, A., KUNG, A. L., WARGO, J. A., SONG, J. S., FISHER, D. E., ARANY, Z. & WIDLUND, H. R. 2013. Oncogenic BRAF regulates oxidative metabolism via PGC1alpha and MITF. *Cancer Cell,* 23, 302-15.

HAYNES, D. A., JONES, W. & MOTHERWELL, W. D. S. 2005. Occurrence of pharmaceutically acceptable anions and cations in the Cambridge Structural Database. *Journal of Pharmaceutical Sciences,* 94, 2111-2120.

HEID, C. A., STEVENS, J., LIVAK, K. J. & WILLIAMS, P. M. 1996. Real time quantitative PCR. *Genome Res,* 6, 986-94.

HSU, P. P. & SABATINI, D. M. 2008. Cancer cell metabolism: Warburg and beyond. *Cell,* 134, 703-7.

KLOMP, J. A., PETILLO, D., NIEMI, N. M., DYKEMA, K. J., CHEN, J., YANG, X. J., SAAF, A., ZICKERT, P., ALY, M., BERGERHEIM, U., NORDENSKJOLD, M., GAD, S., GIRAUD, S., DENOUX, Y., YONNEAU, L., MEJEAN, A., VASILIU, V., RICHARD, S., MACKEIGAN, J. P., TEH, B. T. & FURGE, K. A. 2010. Birt-Hogg-Dube renal tumors are genetically distinct from other renal neoplasias and are associated with upregulation of mitochondrial gene expression. *BMC Med Genomics,* 3, 59.

LEONETTI, F., FAVIA, A., RAO, A., ALIANO, R, PALUSZCAK, A., HARTMANN, R. W. & CAROTTI, A. 2004. Design, synthesis, and 3D QSAR of novel potent and selective aromatase inhibitors. *J Med Chem,* 47, 6792-803.

LING, S., SONG, L., FAN, N., FENG, T., LIU, L., YANG, X., WANG, M., LI, Y., TIAN, Y., ZHAO, F., LIU, Y., HUANG, Q., HOU, Z., XU, F., SHI, L. & LI, Y. 2017. Combination of metformin and sorafenib suppresses proliferation and induces autophagy of hepatocellular carcinoma via targeting the mTOR pathway. *Int J Oncol,* 50, 297-309.

MITSUNOBU, O. & YAMADA, M. 1967. Preparation of Esters of Carboxylic and Phosphoric Acid via Quaternary Phosphonium Salts. *Bulletin of the Chemical Society of Japan,* 40, 2380-2382.

NADJI, M., GOMEZ-FERNANDEZ, C., GANJEI-AZAR, P. & MORALES, A. R. 2005. Immunohistochemistry of estrogen and progesterone receptors reconsidered: experience with 5,993 breast cancers. *Am J Clin Pathol,* 123, 21-7.

NICOLETI, C. R., GARCIA, D. N., DA SILVA, L. E., BEGNINI, I. M., REBELO, R. A., JOUSSEF, A. C. & MACHADO, V. G. 2012. Synthesis of 1,8-naphthyridines and their application in the development of anionic fluorogenic chemosensors. *J Fluoresc,* 22, 1033-46.

PELICANO, H., MARTIN, D. S., XU, R. H. & HUANG, P. 2006. Glycolysis inhibition for anticancer treatment. *Oncogene,* 25, 4633-46

PELICANO, H., ZHANG, W., LIU, J., HAMMOUDI, N., DAI, J., XU, R. H., PUSZTAI, L. & HUANG, P. 2014. Mitochondrial dysfunction in some triple-negative breast cancer cell lines: role of mTOR pathway and therapeutic potential. *Breast Cancer Res,* 16, 434.

POSSE, V., SHAHZAD, S., FALKENBERG, M., HALLBERG, B. M. & GUSTAFSSON, C. M. 2015. TEFM is a potent stimulator of mitochondrial transcription elongation in vitro. *Nucleic Acids Res,* 43, 2615-24.

RODRIGUES, M. F., OBRE, E., DE MELO, F. H., SANTOS, G. C., JR., GALINA, A., JASIULIONIS, M. G., ROSSIGNOL, R., RUMJANEK, F. D. & AMOEDO, N. D. 2016. Enhanced OXPHOS, glutaminolysis and beta-oxidation constitute the metastatic phenotype of melanoma cells. *Biochem J,* 473, 703-15.

RODRIGUEZ-ENRIQUEZ, S., HERNANDEZ-ESQUIVEL, L., MARIN-HERNANDEZ, A., E L HAFIDI, M., GALLARDO-PEREZ, J. C., HERNANDEZ-RESENDIZ, I., RODRIGUEZ-ZAVALA, J. S., PACHECO-VELAZQUEZ, S. C. & MORENO-SANCHEZ, R. 2015. Mitochondrial free fatty acid beta-oxidation supports oxidative phosphorylation and proliferation in cancer cells. *Int J Biochem Cell Biol,* 65, 209-21.

ROESCH, A., VULTUR, A., BOGESKI, I., WANG, H., ZIMMERMANN, K. M., SPEICHER, D., KORBEL, C., LASCHKE, M. W., GIMOTTY, P. A., PHILIPP, S. E., KRAUSE, E., PATZOLD, S., VILLANUEVA, J., KREPLER, C., FUKUNAGA-KALABIS, M., HOTH, M., BASTIAN, B. C., VOGT, T. & HERLYN, M. 2013. Overcoming intrinsic multidrug resistance in melanoma by blocking the mitochondrial respiratory chain of slow-cycling JARID1B(high) cells. *Cancer Cell,* 23, 811-25.

SALEM, A. F., WHITAKER-MENEZES, D., LIN, Z., MARTINEZ-OUTSCHOORN, U. E., TANOWITZ, H. B., AL-ZOUBI, M. S., HOWELL, A., PESTELL, R. G., SOTGIA, F. & LISANTI, M. P. 2012. Two-compartment tumor metabolism: autophagy in the tumor microenvironment and oxidative mitochondrial metabolism (OXPHOS) in cancer cells. *Cell Cycle,* 11, 2545-56.

SANCHEZ-ALVAREZ, R., MARTINEZ-OUTSCHOORN, U. E., LAMB, R., HULIT, J., HOWELL, A., GANDARA, R., SARTINI, M., RUBIN, E., LISANTI, M. P. & SOTGIA, F. 2013. Mitochondrial dysfunction in breast cancer cells prevents tumor growth: understanding chemoprevention with metformin. *Cell Cycle,* 12, 172-82.

SCARPULLA, R. C. 2008. Transcriptional paradigms in mammalian mitochondrial biogenesis and function. *Physiol Rev,* 88, 611-38.

SCATENA, R., BOTTONI, P., PONTOGLIO, A., MASTROTOTARO, L. & GIARDINA, B. 2008. Glycolytic enzyme inhibitors in cancer treatment. *Expert Opin Investig Drugs,* 17, 1533-45.

SCHÖCKEL, L., GLASAUER, A., BASIT, F., BITSCHAR, K., TRUONG, H., ERDMANN, G., ALGIRE, C., HAGEBARTH, A., WILLEMS, P. H., KOPITZ, C., KOOPMAN, W. J. & HEROULT, M. 2015. Targeting mitochondrial complex I using BAY 87-2243 reduces melanoma tumor growth. *Cancer Metab*, 3, 11.

SHARMA, D., REDDY, C. B., SHIL, A. K., SAROACH, R. P. & DAS, P. 2013. Cyclohexyl iodide promoted approach for coumarin analog synthesis using small scaffold. *Mol Divers*, 17, 651-9.

SIEGEL, R. L., MILLER, K. D. & JEMAL, A. 2016. Cancer statistics, 2016. *CA Cancer J Clin*, 66, 7-30.

TISDALE, M. J. 2002. Cachexia in cancer patients. *Nat Rev Cancer*, 2, 862-71.

UPTON, C. 1986. Cyclic amidines. Part 26. The reported syntheses of 7-anilino-6-aryl-5,12-diazabenz[a]anthracenes are reinvestigated and their correct structures identified. *Journal of the Chemical Society, Perkin Transactions 1*, 1225-1229.

VANDER HEIDEN, M. G., CANTLEY, L. C. & THOMPSON, C. B. 2009. Understanding the Warburg effect: the metabolic requirements of cell proliferation. *Science*, 324, 1029-33.

WALTERS, W. P. & NAMCHUK, M. 2003. Designing screens: how to make your hits a hit. *Nat Rev Drug Discov*, 2, 259-66.

WANROOIJ, S. & FALKENBERG, M. 2010. The human mitochondrial replication fork in health and disease. *Biochim Biophys Acta*, 1797, 1378-88.

WEINBERG, S. E. & CHANDEL, N. S. 2015. Targeting mitochondria metabolism for cancer therapy. *Nat Chem Biol*, 11, 9-15.

WHITAKER-MENEZES, D., MARTINEZ-OUTSCHOORN, U. E., LIN, Z., ERTEL, A., FLOMENBERG, N., WITKIEWICZ, A. K., BIRBE, R. C., HOWELL, A., PAVLIDES, S., GANDARA, R., PESTELL, R. G., SOTGIA, F., PHILP, N. J. & LISANTI, M. P. 2011. Evidence for a stromal-epithelial "lactate shuttle" in human tumors: MCT4 is a marker of oxidative stress in cancer-associated fibroblasts. *Cell Cycle*, 10, 1772-83.

YEUNG, K. Y., DICKINSON, A., DONOGHUE, J. F., POLEKHINA, G., WHITE, S. J., GRAMMATOPOULOS, D. K., MCKENZIE, M., JOHNS, T. G. & ST JOHN, J. C. 2014. The identification of mitochondrial DNA variants in glioblastoma multiforme. *Acta Neuropathol Commun*, 2, 1.

WO 2016/146583 A1
WO 2016/193231 A1

---

---

The invention claimed is:

1. A compound of the general formula (I)

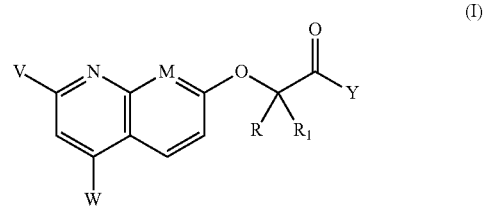

wherein
R is —H, or —C$_1$-C$_4$-alkyl;
R$_1$ is —H, or -methyl;
M is CH or N;
V is —H, —OH, —Cl, —F, or —C$_1$-C$_4$-alkyl;
W is

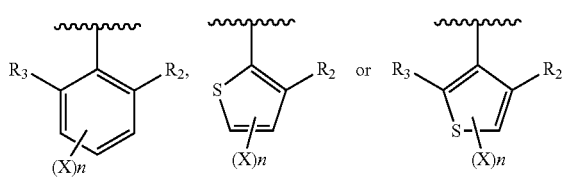

$R_2$ and $R_3$ are identical or different and are
—H, —$C_1$-$C_4$-alkyl, halogen-$C_1$-$C_4$-alkyl, —$C_1$-$C_4$-alkoxy, —$C_1$-$C_4$-dialkylamino, —$C_2$-$C_6$-alkenyl, —$C_2$-$C_6$-alkynyl, -halogen, —CN or —CO—$NH_2$;

X is -halogen, or —CN;

n=0, 1, or 2;

m=0 or 1;

Y is —$NR_4R_5$ wherein
  $R_4$ is —H, or —$C_1$-$C_4$-alkyl, and
  $R_5$ is —H, —$C_1$-$C_4$-alkyl, an unsubstituted or substituted —$C_3$-$C_6$-cycloalkyl; or
    an unsubstituted or substituted pyridine residue; or
    an unsubstituted or substituted phenyl residue; or Y is —$NR_4R_5$ wherein N, $R_4$ and $R_5$ form an unsubstituted or substituted 4-, 5- or 6-membered saturated heterocycle; or Y is —$OR_6$, wherein $R_6$ is —H or —$C_1$-$C_4$-alkyl;

or a pharmaceutically or veterinary acceptable salt, hydrate or solvate thereof.

2. The compound of claim 1, wherein
W is

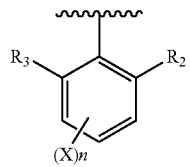

$R_3$ is —H, —$C_1$-$C_4$-alkyl, —$CF_3$, —$OCH_3$, —$N(CH_3)_2$, acetylenyl, —F, —Cl, —Br, —CN, or —CO—$NH_2$;

$R_2$ is —H, -methyl, -ethyl, isopropyl, —$CF_3$, —F, or —Cl; and

X is —F with n=1; or n=0.

3. The compound of claim 1, wherein
W is

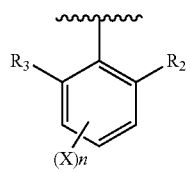

$R_2$ is —H, -methyl, -ethyl, isopropyl, —Cl;

$R_3$ is —H, -methyl or —Cl; and n=0.

4. The compound of claim 1, wherein
Y is —$NR_4R_5$ wherein
  $R_4$ is —H, or —$C_1$-$C_4$-alkyl, and
  $R_5$ is —H, —$C_1$-$C_4$-alkyl, unsubstituted —$C_3$-$C_4$-cycloalkyl, —$C_4$-cycloalkyl substituted with —COO—$CH_3$.

5. The compound of claim 1, wherein
Y is —$NR_4R_5$ wherein
  $R_4$ is —H, or —$C_1$-$C_4$-alkyl, and
  $R_5$ is an unsubstituted pyridine residue; or
    an unsubstituted or substituted phenyl residue;
      wherein the substituents are selected from the group consisting of:
      —$C_1$-$C_4$-alkyl, —$C_1$-$C_4$-alkoxy, —$(CH_2)_2$—OH, —COOH, or —CO—O—($C_1$-$C_4$-alkyl).

6. The compound of claim 1, wherein
Y is —$NR_4R_5$ wherein
  N, $R_4$ and $R_5$ form an unsubstituted or substituted azetidine residue, an unsubstituted or substituted piperidine residue, an unsubstituted or substituted piperazine residue, an unsubstituted or substituted pyrrolidine residue, an unsubstituted or substituted morpholine residue, or an unsubstituted or substituted tetrahydropyridine residue, each optionally and independently substituted with one or more, preferably with one of the following residues:
  —$C_1$-$C_4$-alkyl;
  —C(OH)-cyclopropyl); —C(COOH)-cyclopropyl;
  unsubstituted or substituted —$C_3$-$C_6$-cycloalkyl;
  —$(CH_2)_o$—$COOR_7$ wherein
    $R_7$ is —H, —$C_1$-$C_8$-alkyl,
    and
    o=0, 1 or 2;

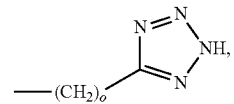

and o is as defined above;
  —$(CH_2)_p$$CONR_8R_9$ wherein
    $R_8$ and $R_9$ independently are —H, —OH, —CN or —$C_1$-$C_4$-alkyl, and
    p=0, 1 or 2;
  —$C(CH_3)_2$—COOH;
  =O or —OH;
  —CO-cyclopropyl;
  —CO—($C_1$-$C_4$-alkyl);
  —CO—$(CH_2)_q$—$NR_{12}R_{13}$ wherein $R_{12}$ and $R_{13}$ independently are —H, —$C_1$-$C_4$-alkyl or —CN, and
    q=0, 1 or 2;
  —$NH_2$, —NH—CO-cyclopropyl, —NH—CO—$CH_2$—Cl, —NH—CO—$CH_2$—$CH_3$, —NH—CO—NH—$C(CH_3)_3$, —NH—$SO_2CH_3$, —NH—CO-phenyl, —NOH—CO—$CH_3$;
  —F; —CN;
  $R_{14}$ and $R_{15}$ form a pyrrolidinone ring, a cyclopropanecarboxlic acid ring, an oxetane ring, or a —$CH_2$— group; or
  —$(CH_2)_r$$SO_2NR_{10}R_{11}$ wherein $R_{10}$ and $R_{11}$ independently are —H, or —$C_1$-$C_4$-alkyl and
    r=0, 1 or 2.

7. The compound of claim 1, wherein
Y is —$NR_4R_5$ wherein
  N, $R_4$ and $R_5$ form an unsubstituted or substituted piperidine reside, an unsubstituted or substituted piperazine residue, an unsubstituted or substituted pyrrolidine residue, or an unsubstituted or substituted morpholine residue, each optionally and independently substituted with one or more the following residues:
  —$C_1$-$C_4$-alkyl;
  —C(OH)cyclopropyl;
  hydroxycyclopropyl or carboxycyclopropyl;
  —$(CH_2)_o$—$COOR_7$ wherein
    $R_7$ is —H, —$C_1$-$C_8$-alkyl, and
    o=0, 1 or 2;

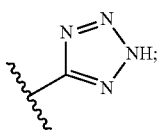 [SMILES: *c1nn[nH]n1]

—(CH$_2$)$_p$CONR$_8$R$_9$ wherein
R$_8$ and R$_9$ independently are —H, —OH, —CN, -methyl, or -tert-butyl and p=0;
—C(CH$_3$)$_2$—COOH;
=O or —OH;
—CO-cyclopropyl;
—CO—CH$_2$—CH$_3$;
—CO-tert-butyl;
—NH$_2$,
—CO—CH$_2$—NH$_2$;
—NH—CO—CH$_2$—CH$_3$, —NH—CO—NH—C(CH$_3$)$_3$, —NH—SO$_2$CH$_3$, —NH—CO-phenyl, —NOH—CO—CH$_3$;
—CN;
R$_{14}$ and R$_{15}$ form a pyrrolidinone ring, a cyclopropanecarboxlic acid ring, an oxetane ring; or a —CH$_2$— group;
—SO$_2$NR$_{10}$R$_{11}$ wherein R$_{10}$ and R$_{11}$ independently are —H or -methyl; or
—CH$_2$SO$_2$NH$_2$.

8. The compound of claim 1, wherein
Y is —NR$_4$R$_5$ wherein
N, R$_4$ and R$_5$ form an unsubstituted or substituted piperidine residue, optionally and independently substituted with one or more of the following residues:
—COOH, —COOCH3, —COOC2H5, —CH$_2$COOH, —C(CH$_3$)$_2$—COOH,
—CH2COOCH3, —CH2COOCH2CH3, —CONH2, —CONHCH3, —CON(CH3)2, —SO$_2$NH$_2$ or —CH$_2$SO$_2$NH$_2$.

9. The compound of claim 1, wherein
Y is —OR$_6$, wherein R$_6$ is —H, -methyl, -ethyl, -isopropyl, or -tert-butyl.

10. The compound of claim 1, wherein
V is —H, —Cl, —F, or -methyl.

11. The compound of claim 1, wherein
R is -methyl; and
R$_1$ is —H.

12. The compound of formula (I) according to claim 1, selected from
(3S)-1-[(2R)-2-[[4-(o-tolyl)-7-quinolyl]oxy]propanoyl]piperidine-3-carboxylic acid,
(3S)-1-[(2R)-2-[[4-(2,6-dimethylphenyl)-7-quinolyl]oxy]propanoyl]piperidine-3-carboxylic acid,
2-[(3R)-1-[(2R)-2-[[4-(2,6-dimethylphenyl)-7-quinolyl]oxy]propanoyl]-3-piperidyl]acetic acid,
ethyl (3S)-1-[(2R)-2-[[4-(2,6-dimethylphenyl)-7-quinolyl]oxy]propanoyl]piperidine-3-carboxylate,
2-[(3S)-1-[(2R)-2-[[4-(2,6-dimethylphenyl)-7-quinolyl]oxy]propanoyl]-3-piperidyl]acetic acid,
ethyl 2-[(3R)-1-[(2R)-2-[[4-(2,6-dimethylphenyl)-7-quinolyl]oxy]propanoyl]-3-piperidyl]acetate,
(3R)-1-[(2R)-2-[[4-(2-chlorophenyl)-7-quinolyl]oxy]propanoyl]piperidine-3-carboxylic acid,
ethyl 2-[(3R)-1-[(2R)-2-[[4-(o-tolyl)-7-quinolyl]oxy]propanoyl]-3-piperidyl]acetate,
(3S)-1-[(2R)-2-[[4-(2-chlorophenyl)-7-quinolyl]oxy]propanoyl]piperidine-3-carboxylic acid,
(3S)-1-[(2R)-2-[[4-(2-chloro-4-fluoro-phenyl)-7-quinolyl]oxy]propanoyl]piperidine-3-carboxylic acid,
(2R)-2-[[4-(2-chloro-4-fluoro-phenyl)-7-quinolyl]oxy]-1-[(3S)-3-(2H-tetrazol-5-yl)-1-piperidyl]propan-1-one,
(3S)-1-[(2R)-2-[[4-(2-chlorophenyl)-2-fluoro-7-quinolyl]oxy]propanoyl]piperidine-3-carboxylic acid,
2-[(3R)-1-[(2R)-2-[[4-(o-tolyl)-7-quinolyl]oxy]propanoyl]-3-piperidyl]acetic acid,
ethyl (3S)-1-[(2R)-2-[[4-(o-tolyl)-7-quinolyl]oxy]propanoyl]piperidine-3-carboxylate,
ethyl 2-[(3R)-1-[(2R)-2-[[4-(2-chloro-4-fluoro-phenyl)-7-quinolyl]oxy]propanoyl]-3-piperidyl]acetate,
2-[(3R)-1-[(2R)-2-[[4-(2-chlorophenyl)-7-quinolyl]oxy]propanoyl]-3-piperidyl]acetic acid
(3R)-1-[(2R)-2-[[4-(2-chloro-4-fluoro-phenyl)-7-quinolyl]oxy]propanoyl]piperidine-3-carboxylic acid,
2-[(3R)-1-[(2R)-2-[[4-(2-chloro-4-fluoro-phenyl)-7-quinolyl]oxy]propanoyl]-3-piperidyl]acetic acid,
(3S)-1-[(2R)-2-[[4-(2-chloro-4-fluoro-phenyl)-7-quinolyl]oxy]propanoyl]pyrrolidine-3-carboxylic acid,
(2R)-2-[[4-(2-chloro-4-fluoro-phenyl)-7-quinolyl]oxy]-1-(1-piperidyl)propan-1-one,
2-[(3R)-1-[(2R)-2-[[2-chloro-4-(o-tolyl)-7-quinolyl]oxy]propanoyl]-3-piperidyl]acetic acid,
2-[(3S)-1-[(2R)-2-[[4-(2-chloro-4-fluoro-phenyl)-7-quinolyl]oxy]propanoyl]-3-piperidyl]acetic acid,
rac-(3S)-1-[2-[[4-(2-chlorophenyl)-7-quinolyl]oxy]propanoyl]piperidine-3-carboxylic acid,
1-[(2R)-2-[[4-(2-chloro-4-fluoro-phenyl)-7-quinolyl]oxy]propanoyl]piperidine-4-carboxylic acid,
(3S)-1-[rac-(2R)-2-[[2-chloro-4-(o-tolyl)-7-quinolyl]oxy]propanoyl]piperidine-3-carboxylic acid,
3-[[(2R)-2-[[4-(2-chloro-4-fluoro-phenyl)-7-quinolyl]oxy]propanoyl]amino]benzoic acid ethyl (3S)-1-[(2R)-2-[[4-(2-chloro-4-fluoro-phenyl)-7-quinolyl]oxy]propanoyl]piperidine-3-carboxylate,
(2R)-2-[[4-(2-chlorophenyl)-7-quinolyl]oxy]-1-(4-propanoylpiperazin-1-yl)propan-1-one,
tert-butyl (2R)-2-[[4-(2-chlorophenyl)-7-quinolyl]oxy]propanoate,
(3S)-1-[(2R)-2-[[4-(2-chloro-4-fluoro-phenyl)-7-quinolyl]oxy]propanoyl]piperidine-3-carbonitrile,
(3S)-1-[(2R)-2-[[2-methyl-4-(o-tolyl)-7-quinolyl]oxy]propanoyl]piperidine-3-carboxylic acid,
(2R)-2-[[4-(2-chloro-4-fluoro-phenyl)-7-quinolyl]oxy]-N-isopropyl-N-methyl-propanamide,
1-[rac-(2R)-2-[[4-(2-chloro-4-fluoro-phenyl)-7-quinolyl]oxy]propanoyl]piperidine-3-sulfonamide,
(3S)-1-[(2R)-2-[[2-chloro-4-(2-chlorophenyl)-7-quinolyl]oxy]propanoyl]piperidine-3-carboxylic acid,
(3S)-1-[(2R)-2-[[2-chloro-4-(4-fluoro-2-methyl-phenyl)-7-quinolyl]oxy]propanoyl]piperidine-3-carboxylic acid,
isopropyl (2R)-2-[[4-(2-chlorophenyl)-7-quinolyl]oxy]propanoate,
methyl 2-[(3R)-1-[(2R)-2-[[4-(2-chloro-4-fluoro-phenyl)-7-quinolyl]oxy]propanoyl]pyrrolidin-3-yl]acetate,
(3S)-1-[(2R)-2-[[4-(2-chloro-4-fluoro-phenyl)-7-quinolyl]oxy]propanoyl]-N-methyl-piperidine-3-carboxamide,
2-[(3S)-1-[(2R)-2-[[4-(2-chloro-4-fluoro-phenyl)-7-quinolyl]oxy]propanoyl]pyrrolidin-3-yl]acetic acid,
2-[(3R)-1-[(2R)-2-[[4-(2-chloro-4-fluoro-phenyl)-7-quinolyl]oxy]propanoyl]pyrrolidin-3-yl]acetic acid,
ethyl (3S)-1-[(2R)-2-[[4-(2-chlorophenyl)-2-fluoro-7-quinolyl]oxy]propanoyl]piperidine-3-carboxylate, (2R)-2-[[4-(2-chloro-4-fluoro-phenyl)-7-quinolyl]oxy]-1-pyrrolidin-1-yl-propan-1-one,
(2R)-2-[[2-chloro-4-(o-tolyl)-7-quinolyl]oxy]propanoic acid,
(2R)-2-[[4-(2-chloro-4-fluoro-phenyl)-7-quinolyl]oxy]propanoic acid,
(2R)-2-[[4-(2-chloro-4-fluoro-phenyl)-7-quinolyl]oxy]-N,N-dimethyl-propanamide,
rac-(3S)-1-[2-[[4-(2-chlorophenyl)-7-quinolyl]oxy]acetyl]piperidine-3-carboxylic acid,
(2R)—N-tert-butyl-2-[[4-(2-chloro-4-fluoro-phenyl)-7-quinolyl]oxy]propanamide,
(2R)-2-[[4-(2-chlorophenyl)-7-quinolyl]oxy]-N-isopropyl-propanamide,
ethyl 2-[(3R)-1-[(2R)-2-[[2-methyl-4-(o-tolyl)-7-quinolyl]oxy]propanoyl]-3-piperidyl]acetate,
ethyl (2R)-2-[[4-(2-chlorophenyl)-7-quinolyl]oxy]propanoate,
ethyl 4-[[(2R)-2-[[4-(2-chloro-4-fluoro-phenyl)-7-quinolyl]oxy]propanoyl]amino]benzoate,
(3S)-1-[(2R)-2-[[2-chloro-4-(o-tolyl)-7-quinolyl]oxy]propanoyl]piperidine-3-carboxamide,
(2R)-2-[[4-(2-chlorophenyl)-7-quinolyl]oxy]-1-(1-piperidyl)propan-1-one,
methyl 3-[[(2R)-2-[[4-(2-chloro-4-fluoro-phenyl)-7-quinolyl]oxy]propanoyl]amino]cyclobutanecarboxylate,
(2R)-2-[[4-(2-chloro-4-fluoro-phenyl)-7-quinolyl]oxy]-1-piperazin-1-yl-propan-1-one,
2-[(3R)-1-[(2R)-2-[[2-chloro-4-(2-chloro-4-fluoro-phenyl)-7-quinolyl]oxy]propanoyl]-3-piperidyl]acetic acid,
2-[(3R)-1-[(2R)-2-[[2-chloro-4-(4-fluoro-2-methyl-phenyl)-7-quinolyl]oxy]propanoyl]-3-piperidyl]acetic acid,
ethyl 1-[(2R)-2-[[4-(2-chloro-4-fluoro-phenyl)-7-quinolyl]oxy]propanoyl]piperidine-4-carboxylate,
(3S)-1-[(2R)-2-[[4-(2-chloro-4-fluoro-phenyl)-2-methyl-7-quinolyl]oxy]propanoyl]piperidine-3-carboxylic acid,
4-[[(2R)-2-[[4-(2-chloro-4-fluoro-phenyl)-7-quinolyl]oxy]propanoyl]amino]benzoic acid,
(2R)-2-[[4-(2-chloro-4-fluoro-phenyl)-7-quinolyl]oxy]-N-isopropyl-propanamide,
(3S)-1-[2-[[5-(2-chloro-4-fluoro-phenyl)-1,8-naphthyridin-2-yl]oxy]propanoyl]piperidine-3-carboxylic acid,
4-[(2R)-2-[[4-(2-chloro-4-fluoro-phenyl)-7-quinolyl]oxy]propanoyl]piperazin-2-one,
(3S)-1-[(2R)-2-[[2-chloro-4-(2-chloro-4-fluoro-phenyl)-7-quinolyl]oxy]propanoyl]piperidine-3-carboxylic acid,
2-[(3R)-1-[(2R)-2-[[4-(2-chloro-3-fluoro-phenyl)-7-quinolyl]oxy]propanoyl]-3-piperidyl]acetic acid,
(3S)-1-[(2R)-2-[(4-phenyl-7-quinolyl)oxy]propanoyl]piperidine-3-carboxylic acid,
methyl 2-[(3S)-1-[(2R)-2-[[4-(2-chloro-4-fluoro-phenyl)-7-quinolyl]oxy]propanoyl]pyrrolidin-3-yl]acetate,
2-[(3R)-1-[(2R)-2-[[2-chloro-4-(2-chlorophenyl)-7-quinolyl]oxy]propanoyl]-3-piperidyl]-N-methyl-acetamide,
2-[(3R)-1-[(2R)-2-[[2-methyl-4-(o-tolyl)-7-quinolyl]oxy]propanoyl]-3-piperidyl]acetic acid,
(2R)-2-[[2-chloro-4-(2-chlorophenyl)-7-quinolyl]oxy]-1-[4-(cyclopropanecarbonyl)piperazin-1-yl]propan-1-one,
methyl (3R)-1-[(2R)-2-[[4-(2-chloro-4-fluoro-phenyl)-7-quinolyl]oxy]propanoyl]piperidine-3-carboxylate,
(2R)-2-[[2-chloro-4-(2-chlorophenyl)-7-quinolyl]oxy]-1-(4-propanoylpiperazin-1-yl)propan-1-one,
tert-butyl (2R)-2-[[2-chloro-4-(o-tolyl)-7-quinolyl]oxy]propanoate,
ethyl 2-[(3R)-1-[(2R)-2-[[4-(2-chloro-4-fluoro-phenyl)-2-methyl-7-quinolyl]oxy]propanoyl]-3-piperidyl]acetate,
ethyl (3S)-1-[(2R)-2-[[4-(2-chloro-4-fluoro-phenyl)-7-quinolyl]oxy]propanoyl]pyrrolidine-3-carboxylate,
(3S)-1-[(2R)-2-[[2-chloro-4-(2-chlorophenyl)-7-quinolyl]oxy]propanoyl]piperidine-3-carboxamide,
(2R)-2-[[4-(2-chloro-4-fluoro-phenyl)-7-quinolyl]oxy]-N-cyclopropyl-propanamide,
(3S)-1-[(2S)-2-[[4-(2-chlorophenyl)-7-quinolyl]oxy]propanoyl]piperidine-3-carboxylic acid,
2-[(3R)-1-[(2R)-2-[[4-(2-methyl-3-thienyl)-7-quinolyl]oxy]propanoyl]-3-piperidyl]acetic acid,
2-[rac-(3R)-1-[2-[[5-(2-chloro-4-fluoro-phenyl)-1,8-naphthyridin-2-yl]oxy]propanoyl]-3-piperidyl]acetic acid,
(3S)-1-[(2R)-2-[[2-chloro-4-(2-chloro-4-fluoro-phenyl)-7-quinolyl]oxy]propanoyl]piperidine-3-carboxamide,
isopropyl 2-[[4-(2-chlorophenyl)-7-quinolyl]oxy]acetate,
(3S)-1-[(2R)-2-[[4-(4-fluoro-2,6-dimethyl-phenyl)-7-quinolyl]oxy]propanoyl]piperidine-3-carboxylic acid,
(2R)-1-[4-(2-aminoacetyl)piperazin-1-yl]-2-[[2-chloro-4-(2-chlorophenyl)-7-quinolyl]oxy]propan-1-one,
2-[[4-(2-chlorophenyl)-7-quinolyl]oxy]-N,N-dimethyl-propanamide,
ethyl (3S)-1-[2-[[4-(2-chlorophenyl)-7-quinolyl]oxy]acetyl]piperidine-3-carboxylate,
(2R)-2-[[4-(2-chlorophenyl)-7-quinolyl]oxy]-N,N-dimethyl-propanamide,
ethyl 2-[(3S)-1-[(2R)-2-[[4-(2-chloro-4-fluoro-phenyl)-7-quinolyl]oxy]propanoyl]-3-piperidyl]acetate,
(2R)-2-[[4-(2-chlorophenyl)-2-fluoro-7-quinolyl]oxy]propanoic acid,
(2R)-2-[[2-chloro-4-(2-chloro-4-fluoro-phenyl)-7-quinolyl]oxy]propanoic acid,
ethyl 2-[(3R)-1-[(2R)-2-[[2-chloro-4-(2-chlorophenyl)-7-quinolyl]oxy]propanoyl]-3-piperidyl]acetate,
ethyl 2-[(3R)-1-[(2R)-2-[[2-chloro-4-(2-chloro-4-fluoro-phenyl)-7-quinolyl]oxy]propanoyl]-3-piperidyl]acetate,
ethyl (3S)-1-[(2R)-2-[[2-chloro-4-(4-fluoro-2-methyl-phenyl)-7-quinolyl]oxy]propanoyl]piperidine-3-carboxylate,
(2R)-2-[[4-(2-chloro-4-fluoro-phenyl)-7-quinolyl]oxy]-N-(4-pyridyl)propanamide,
(3S)-1-[(2R)-2-[[2-chloro-4-(2-chlorophenyl)-7-quinolyl]oxy]propanoyl]-N-methyl-piperidine-3-carboxamide,
methyl 3-[[(2R)-2-[[2-chloro-4-(2-chlorophenyl)-7-quinolyl]oxy]propanoyl]amino]cyclobutanecarboxylate,
2-[(3R)-1-[(2R)-2-[[2-chloro-4-(2-chloro-4-fluoro-phenyl)-7-quinolyl]oxy]propanoyl]-3-piperidyl]-N-methyl-acetamide,
(2R)-2-[[2-chloro-4-(2-chlorophenyl)-7-quinolyl]oxy]-1-(1-piperidyl)propan-1-one,
(3S)-1-[(2R)-2-[[2-chloro-4-(2-chlorophenyl)-7-quinolyl]oxy]propanoyl]-N,N-dimethyl-piperidine-3-carboxamide,
2-[(3R)-1-[(2R)-2-[[4-(2-chloro-4-fluoro-phenyl)-2-methyl-7-quinolyl]oxy]propanoyl]-3-piperidyl]acetic acid,
(3R)-1-[(2S)-2-[[4-(2-chlorophenyl)-7-quinolyl]oxy]propanoyl]piperidine-3-carboxylic acid, (2R)-2-[[4-(2-chlorophenyl)-7-quinolyl]oxy]propanoic acid,
(2R)-2-[[2-chloro-4-(2-chlorophenyl)-7-quinolyl]oxy]-1-piperazin-1-yl-propan-1-one,
(3S)—N-methyl-1-[(2R)-2-[[2-chloro-4-(2-chloro-4-fluoro-phenyl)-7-quinolyl]oxy]propanoyl]piperidine-3-carboxamide,
2-[[4-(o-tolyl)-7-quinolyl]oxy]acetamide,
(2R)-2-[[2-chloro-4-(2-chloro-4-fluoro-phenyl)-7-quinolyl]oxy]-1-(1-piperidyl)propan-1-one,
ethyl 3-[[(2R)-2-[[4-(2-chloro-4-fluoro-phenyl)-7-quinolyl]oxy]propanoyl]amino]benzoate,
2-[[5-(2-chloro-4-fluoro-phenyl)-1,8-naphthyridin-2-yl]oxy]-N-isopropyl-propanamide,
2-[(3R)-1-[(2R)-2-[[4-(2-fluorophenyl)-7-quinolyl]oxy]propanoyl]-3-piperidyl]acetic acid,
tert-butyl (3S)-1-[(2R)-2-[[2-methyl-4-(o-tolyl)-7-quinolyl]oxy]propanoyl]piperidine-3-carboxylate,
2-[1-[(2R)-2-[[4-(2-chlorophenyl)-7-quinolyl]oxy]propanoyl]-4-piperidyl]acetic acid,
(3S)-1-[rac-(2R)-2-[[4-(2,6-dimethylphenyl)-2-methyl-7-quinolyl]oxy]propanoyl]piperidine-3-sulfonamide,
(3R)-1-[rac-(2R)-2-[[4-(2,6-dimethylphenyl)-2-methyl-7-quinolyl]oxy]propanoyl]piperidine-3-sulfonamide,
(3R)-1-[rac-(2R)-2-[[4-(2,6-dimethylphenyl)-2-methyl-7-quinolyl]oxy]propanoyl]piperidine-3-sulfonamide,
(3R)-1-[(2R)-2-[[4-(2-chloro-4-fluoro-phenyl)-2-methyl-7-quinolyl]oxy]propanoyl]piperidine-3-sulfonamide,
(3S)-1-[(2R)-2-[[4-(2-chloro-4-fluoro-phenyl)-7-quinolyl]oxy]propanoyl]piperidine-3-sulfonamide,
(3R)-1-[(2R)-2-[[4-(2-chloro-4-fluoro-phenyl)-7-quinolyl]oxy]propanoyl]piperidine-3-sulfonamide,
3-[1-[(2R)-2-[[4-(2-chlorophenyl)-7-quinolyl]oxy]propanoyl]-4-piperidyl]propanoic acid,
1-[rac-(2R)-2-[[4-(2,6-dimethylphenyl)-7-quinolyl]oxy]propanoyl]piperidine-3-sulfonamide,
2-[(3R)-1-[(2R)-2-[[4-(2,6-dichlorophenyl)-7-quinolyl]oxy]propanoyl]-3-piperidyl]acetic acid,
2-[(3R)-1-[(2R)-2-[[4-(2-ethylphenyl)-7-quinolyl]oxy]propanoyl]-3-piperidyl]acetic acid,
2-[(3R)-1-[(2R)-2-[[4-(2-isopropylphenyl)-7-quinolyl]oxy]propanoyl]-3-piperidyl]acetic acid,
[1-[rac-(2R)-2-[[4-(2-chloro-4-fluoro-phenyl)-7-quinolyl]oxy]propanoyl]-3-piperidyl]methanesulfonamide,
2-[(3R)-1-[(2R)-2-[[4-(2,6-dimethylphenyl)-2-methyl-7-quinolyl]oxy]propanoyl]-3-piperidyl]acetic acid,
(2R)-2-[[4-(2-chloro-4-fluoro-phenyl)-7-quinolyl]oxy]-N-[4-(2-hydroxyethyl)phenyl]propanamide,
(3S)-1-[(2R)-2-[[5-(2-chloro-4-fluoro-phenyl)-1,8-naphthyridin-2-yl]oxy]propanoyl]piperidine-3-carboxylic acid,
(3S)-1-[(2S)-2-[[5-(2-chloro-4-fluoro-phenyl)-1,8-naphthyridin-2-yl]oxy]propanoyl]piperidine-3-carboxylic acid,
(3S)-1-[(2S)-2-[[5-(2-chloro-4-fluoro-phenyl)-1,8-naphthyridin-2-yl]oxy]propanoyl]piperidine-3-carboxylic acid,
2-[(3R)-1-[(2R)-2-[[5-(2-chloro-4-fluoro-phenyl)-1,8-naphthyridin-2-yl]oxy]propanoyl]-3-piperidyl]acetic acid,
2-[(3R)-1-[(2S)-2-[[5-(2-chloro-4-fluoro-phenyl)-1,8-naphthyridin-2-yl]oxy]propanoyl]-3-piperidyl]acetic acid,
(3S)-1-[(2R)-2-[[4-(2,6-dichlorophenyl)-7-quinolyl]oxy]propanoyl]piperidine-3-carboxylic acid,
(2R)-2-[[4-(2-chloro-4-fluoro-phenyl)-7-quinolyl]oxy]-N-(2-pyridyl)propanamide,
(2R)-2-[[4-(2-chloro-4-fluoro-phenyl)-7-quinolyl]oxy]-N-ethyl-propanamide,
(3S)-1-[(2R)-2-[[4-(2,6-dichloro-4-fluoro-phenyl)-7-quinolyl]oxy]propanoyl]piperidine-3-carboxylic acid,
2-[(3R)-1-[(2R)-2-[[4-(4-methyl-3-thienyl)-7-quinolyl]oxy]propanoyl]-3-piperidyl]acetic acid,
2-[(3R)-1-[(2R)-2-[[4-(3-methyl-2-thienyl)-7-quinolyl]oxy]propanoyl]-3-piperidyl]acetic acid,
2-[(3R)-1-[(2R)-2-[[4-(2-methoxyphenyl)-7-quinolyl]oxy]propanoyl]-3-piperidyl]acetic acid,
2-[(3R)-1-[(2R)-2-[[4-[2-(trifluoromethyl)phenyl]-7-quinolyl]oxy]propanoyl]-3-piperidyl]acetic acid,
2-[(3R)-1-[(2R)-2-[[4-[2-(trifluoromethoxy)phenyl]-7-quinolyl]oxy]propanoyl]-3-piperidyl]acetic acid,
(3S)-1-[(2R)-2-[[4-(2,6-dimethylphenyl)-7-quinolyl]oxy]propanoyl]piperidine-3-sulfonamide,
2-[(3R)-1-[2-[[4-(2-chlorophenyl)-7-quinolyl]oxy]-2-methyl-propanoyl]-3-piperidyl]acetic acid,
2-[rac-(3R)-1-[2-[[4-(2-chlorophenyl)-7-quinolyl]oxy]butanoyl]-3-piperidyl]acetic acid,
2-[(3R)-1-[(2R)-2-[[4-(2-chloro-6-methyl-phenyl)-7-quinolyl]oxy]propanoyl]-3-piperidyl]acetic acid,
2-[(3R)-1-[(2R)-2-[[4-(2-bromophenyl)-7-quinolyl]oxy]propanoyl]-3-piperidyl]acetic acid,
2-[(3R)-1-[(2R)-2-[[4-(2-cyanophenyl)-7-quinolyl]oxy]propanoyl]-3-piperidyl]acetic acid,
2-[(3R)-1-[(2R)-2-[[4-(2-ethynylphenyl)-7-quinolyl]oxy]propanoyl]-3-piperidyl]acetic acid,
2-[(3R)-1-[(2R)-2-[[4-[2-(dimethylamino)phenyl]-7-quinolyl]oxy]propanoyl]-3-piperidyl]acetic acid,
2-[(3R)-1-[(2R)-2-[[4-(2-carbamoylphenyl)-7-quinolyl]oxy]propanoyl]-3-piperidyl]acetic acid,
2-[(3R)-1-[(2R)-2-[[4-(2,6-difluorophenyl)-7-quinolyl]oxy]propanoyl]-3-piperidyl]acetic acid,
2-[(3R)-1-[(2R)-2-[[4-(2,4-dimethyl-3-thienyl)-7-quinolyl]oxy]propanoyl]-3-piperidyl]acetic acid,
2-[(3R)-1-[(2R)-2-[[4-[2-chloro-6-(trifluoromethyl)phenyl]-7-quinolyl]oxy]propanoyl]-3-piperidyl]acetic acid,
2-[(3R)-1-[(2R)-2-[[4-(2-bromo-6-chloro-phenyl)-7-quinolyl]oxy]propanoyl]-3-piperidyl]acetic acid,
2-[(3R)-1-[(2R)-2-[[4-[2,6-bis(trifluoromethyl)phenyl]-7-quinolyl]oxy]propanoyl]-3-piperidyl]acetic acid,
2-[(3R)-1-[(2R)-2-[[4-(2-chloro-6-methoxy-phenyl)-7-quinolyl]oxy]propanoyl]-3-piperidyl]acetic acid,
2-[(3R)-1-[(2R)-2-[[4-(2,6-diisopropylphenyl)-7-quinolyl]oxy]propanoyl]-3-piperidyl]acetic acid,
(2R)-1-[(3R)-3-amino-1-piperidyl]-2-[[4-(2,6-dimethylphenyl)-7-quinolyl]oxy]propan-1-one,
(2R)-1-[(3S)-3-amino-1-piperidyl]-2-[[4-(2,6-dimethylphenyl)-7-quinolyl]oxy]propan-1-one,
N-[(3S)-1-[(2R)-2-[[4-(2,6-dimethylphenyl)-7-quinolyl]oxy]propanoyl]-3-piperidyl]propanamide,
N-tert-butyl-4-[(2R)-2-[[4-(2,6-dimethylphenyl)-7-quinolyl]oxy]propanoyl]piperazine-1-carboxamide,
(2R)-2-[[4-(2,6-dimethylphenyl)-7-quinolyl]oxy]-1-[3-(1-hydroxycyclopropyl)-1-piperidyl]propan-1-one,
8-[(2R)-2-[[4-(2,6-dimethylphenyl)-7-quinolyl]oxy]propanoyl]-2,8-diazaspiro[4.5]decan-1-one,
(2R)-2-[[4-(2,6-dimethylphenyl)-7-quinolyl]oxy]-1-(3,5-dimethylpiperazin-1-yl)propan-1-one,
N-[(3S)-1-[(2R)-2-[[4-(2,6-dimethylphenyl)-7-quinolyl]oxy]propanoyl]-3-piperidyl]-N-hydroxy-acetamide,
1-[4-[(2R)-2-[[4-(2,6-dimethylphenyl)-7-quinolyl]oxy]propanoyl]piperazin-1-yl]-2,2-dimethyl-propan-1-one, N-[(3S)-1-[(2R)-2-[[4-(2,6-dimethylphenyl)-7-quinolyl]oxy]propanoyl]-3-piperidyl]methanesulfonamide,
N-[(3S)-1-[(2R)-2-[[4-(2,6-dimethylphenyl)-7-quinolyl]oxy]propanoyl]-3-piperidyl]benzamide,
(3S)—N-cyano-1-[(2R)-2-[[4-(2,6-dimethylphenyl)-7-quinolyl]oxy]propanoyl]piperidine-3-carboxamide,
(3S)-1-[(2R)-2-[[4-(2,6-dimethylphenyl)-7-quinolyl]oxy]propanoyl]piperidine-3-carbohydroxamic acid,
2-[(3R)-1-[(2R)-2-[[4-(2,6-dimethylphenyl)-7-quinolyl]oxy]propanoyl]-3-piperidyl]ethanehydroxamic acid,
(2R)-1-(3-aminoazetidin-1-yl)-2-[[4-(2,6-dimethylphenyl)-7-quinolyl]oxy]propan-1-one,
(2R)-2-[[4-(2,6-dimethylphenyl)-7-quinolyl]oxy]-1-[3-(1H-tetrazol-5-yl)azetidin-1-yl]propan-1-one,
3-hydroxy-1-[(2R)-2-[[4-(2,6-dimethylphenyl)-7-quinolyl]oxy]propanoyl]piperidine-3-carboxylic acid,
5-[(2R)-2-[[4-(2,6-dimethylphenyl)-7-quinolyl]oxy]propanoyl]-5-azaspiro[2.5]octane-2-carboxylic acid,
(3R)-1-[(2R)-2-[[4-(2,6-dimethylphenyl)-7-quinolyl]oxy]propanoyl]piperidine-3-sulfonamide,
(3S)-1-[(2R)-2-[[4-(2,6-dichloro-4-fluoro-phenyl)-7-quinolyl]oxy]propanoyl]-3-methyl-piperidine-3-carboxylic acid,
5-[rac-(2R)-2-[[4-(4-fluoro-2,6-dimethyl-phenyl)-7-quinolyl]oxy]propanoyl]-5-azaspiro[2.5]octane-2-carboxylic acid,
(3R)-1-[(2R)-2-[[4-(4-fluoro-2,6-dimethyl-phenyl)-7-quinolyl]oxy]propanoyl]-3-methyl-piperidine-3-carboxylic acid,
(2R)-2-[[4-(4-fluoro-2,6-dimethyl-phenyl)-7-quinolyl]oxy]-1-[(2S)-2-methyl-1-piperidyl]propan-1-one,
5-[rac-(2R)-2-[[4-(2,6-dichloro-4-fluoro-phenyl)-7-quinolyl]oxy]propanoyl]-5-azaspiro[2.5]octane-2-carboxylic acid,
(2R)-2-[[4-(4-fluoro-2,6-dimethyl-phenyl)-7-quinolyl]oxy]-1-morpholino-propan-1-one,
(2R)-2-[[4-(4-fluoro-2,6-dimethyl-phenyl)-7-quinolyl]oxy]-1-(2-oxa-7-azaspiro[3.5]nonan-7-yl)propan-1-one,
rac-(2R)-2-[[4-(4-fluoro-2,6-dimethyl-phenyl)-7-quinolyl]oxy]-1-[3-(1-hydroxycyclopropyl)-1-piperidyl]propan-1-one,
8-[(2R)-2-[[4-(4-fluoro-2,6-dimethyl-phenyl)-7-quinolyl]oxy]propanoyl]-2,8-diazaspiro[4.5]decan-1-one,
1-[1-[rac-(2R)-2-[[4-(4-fluoro-2,6-dimethyl-phenyl)-7-quinolyl]oxy]propanoyl]-3-piperidyl]cyclopropanecarboxylic acid,
2-[(3R)-1-[(2R)-2-[[4-(4-fluoro-2,6-dimethyl-phenyl)-7-quinolyl]oxy]propanoyl]-3-piperidyl]acetic acid,
(3S)-1-[(2R)-2-[[4-(4-fluoro-2,6-dimethyl-phenyl)-7-quinolyl]oxy]propanoyl]-3-methyl-piperidine-3-carboxylic acid,
N-[(3S)-1-[(2R)-2-[[4-(4-fluoro-2,6-dimethyl-phenyl)-7-quinolyl]oxy]propanoyl]-3-piperidyl]-N-hydroxy-acetamide,
2-methyl-2-[1-[rac-(2R)-2-[[4-(4-fluoro-2,6-dimethyl-phenyl)-7-quinolyl]oxy]propanoyl]-3-piperidyl]propanoic acid,
(2R)-2-[[4-(4-fluoro-2,6-dimethyl-phenyl)-7-quinolyl]oxy]-1-[(2R)-2-methyl-1-piperidyl]propan-1-one,
(3R)-1-[(2R)-2-[[4-(2,6-dichloro-4-fluoro-phenyl)-7-quinolyl]oxy]propanoyl]-3-methyl-piperidine-3-carboxylic acid,
(3S)-1-[(2R)-2-[[4-(2-chloro-4-fluoro-phenyl)-7-quinolyl]oxy]propanoyl]-3-methyl-piperidine-3-carboxylic acid,
[1-[rac-(2R)-2-[[4-(2,6-dimethylphenyl)-7-quinolyl]oxy]propanoyl]-3-piperidyl]methanesulfonamide,
rac-(2R)-1-(2,6-dimethyl-1-piperidyl)-2-[[4-(4-fluoro-2,6-dimethyl-phenyl)-7-quinolyl]oxy]propan-1-one,
2-[(3R)-1-[(2R)-2-[[4-(2,6-dichloro-4-fluoro-phenyl)-7-quinolyl]oxy]propanoyl]-3-piperidyl]acetic acid,
5-[rac-(2R)-2-[[4-(2-chloro-4-fluoro-phenyl)-7-quinolyl]oxy]propanoyl]-5-azaspiro[2.5]octane-2-carboxylic acid,
1-[1-[rac-(2R)-2-[[4-(2-chloro-4-fluoro-phenyl)-7-quinolyl]oxy]propanoyl]-3-piperidyl]cyclopropanecarboxylic acid,
2-methyl-2-[1-[rac-(2R)-2-[[4-(2,6-dichloro-4-fluoro-phenyl)-7-quinolyl]oxy]propanoyl]-3-piperidyl]propanoic acid,
1-[1-[rac-(2R)-2-[[4-(2,6-dichloro-4-fluoro-phenyl)-7-quinolyl]oxy]propanoyl]-3-piperidyl]cyclopropanecarboxylic acid,
2-methyl-2-[1-[rac-(2R)-2-[[4-(2-chloro-4-fluoro-phenyl)-7-quinolyl]oxy]propanoyl]-3-piperidyl]propanoic acid,
(3R)-1-[(2R)-2-[[4-(2-chloro-4-fluoro-phenyl)-7-quinolyl]oxy]propanoyl]-3-methyl-piperidine-3-carboxylic acid,
(2R)-2-[[4-(2,6-dichloro-4-fluoro-phenyl)-7-quinolyl]oxy]-1-[(2S)-2-methyl-1-piperidyl]propan-1-one,
rac-(2R)-2-[[4-(2-chloro-4-fluoro-phenyl)-7-quinolyl]oxy]-1-(2-methyl-1-piperidyl)propan-1-one,
(2R)-2-[[4-(2,6-dichloro-4-fluoro-phenyl)-7-quinolyl]oxy]-1-morpholino-propan-1-one,
8-[(2R)-2-[[4-(2,6-dichloro-4-fluoro-phenyl)-7-quinolyl]oxy]propanoyl]-2,8-diazaspiro[4.5]decan-1-one,
rac-(2R)-2-[[4-(2,6-dichloro-4-fluoro-phenyl)-7-quinolyl]oxy]-1-[3-(1-hydroxycyclopropyl)-1-piperidyl]propan-1-one,
(2R)-2-[[4-(2,6-dichloro-4-fluoro-phenyl)-7-quinolyl]oxy]-1-[(2R)-2-methyl-1-piperidyl]propan-1-one,
8-[(2R)-2-[[4-(2-chloro-4-fluoro-phenyl)-7-quinolyl]oxy]propanoyl]-2,8-diazaspiro[4.5]decan-1-one,
(2R)-2-[[4-(2-chloro-4-fluoro-phenyl)-7-quinolyl]oxy]-1-morpholino-propan-1-one,
(2R)-2-[[4-(2-chloro-4-fluoro-phenyl)-7-quinolyl]oxy]-1-[3-(1-hydroxycyclopropyl)-1-piperidyl]propan-1-one,
(2R)-2-[[4-(2,6-dichloro-4-fluoro-phenyl)-7-quinolyl]oxy]-1-(2-oxa-7-azaspiro[3.5]nonan-7-yl)propan-1-one,
N-hydroxy-N-[rac-(3S)-1-[rac-(2R)-2-[[4-(2-chloro-4-fluoro-phenyl)-7-quinolyl]oxy]propanoyl]-3-piperidyl]acetamide,
(2R)-2-[[4-(2-chloro-4-fluoro-phenyl)-7-quinolyl]oxy]-1-(2-oxa-7-azaspiro[3.5]nonan-7-yl)propan-1-one,
(2R)-2-[[4-(2-chloro-4-fluoro-phenyl)-7-quinolyl]oxy]-1-(2,6-dimethyl-1-piperidyl)propan-1-one,
(2R)-2-[[4-(2-chloro-4-fluoro-phenyl)-7-quinolyl]oxy]-1-(2-oxa-8-azaspiro[3.5]nonan-8-yl)propan-1-one,
(2R)-2-[[4-(2-chloro-4-fluoro-phenyl)-7-quinolyl]oxy]-1-(2-oxa-7-azaspiro[3.4]octan-7-yl)propan-1-one,
1-tert-butyl-3-[(3R)-1-[(2R)-2-[[4-(2-chloro-4-fluoro-phenyl)-7-quinolyl]oxy]propanoyl]pyrrolidin-3-yl]urea,
(2R)-2-[[4-(2-chloro-4-fluoro-phenyl)-7-quinolyl]oxy]-1-(3,3,5,5-tetramethylpiperazin-1-yl)propan-1-one,
(2R)-2-[[4-(2-chloro-4-fluoro-phenyl)-7-quinolyl]oxy]-1-(3,5-dimethylpiperazin-1-yl)propan-1-one, (2R)-2-[[4-(2-chloro-4-fluoro-phenyl)-7-quinolyl]oxy]-1-[(1R)-2,5-diazabicyclo[2.2.1]heptan-2-yl]propan-1-one, (2R)-2-[[4-(2-chloro-4-fluoro-phenyl)-7-quinolyl]oxy]-1-(2-oxa-6-azaspiro[3.3]heptan-6-yl)propan-1-one, 1-[(2R)-2-[[4-(2-chloro-4-fluoro-phenyl)-7-quinolyl]oxy]propanoyl]-3,6-dihydro-2H-pyridine-5-carboxylic acid, 2-[(3R)-1-[(2R)-2-[[5-(2,6-dichloro-4-fluoro-phenyl)-1,8-naphthyridin-2-yl]oxy]propanoyl]-3-piperidyl]acetic acid, and 2-[(3R)-1-[(2R)-2-[[5-(4-fluoro-2,6-dimethyl-phenyl)-1,8-naphthyridin-2-yl]oxy]propanoyl]-3-piperidyl]acetic acid, or a pharmaceutically or veterinary acceptable salt, hydrate or solvate thereof.

13. A pharmaceutical composition comprising a compound of claim 1 and pharmaceutically or veterinary acceptable carriers and/or excipients.

14. The compound of claim 1, wherein
R is —H, -methyl, -or ethyl;
$R_1$ is —H;
M is —CH;
V is —H, —Cl, —F, or -methyl;
$R_2$ and $R_3$ are identical or different and are —H, —$C_1$-$C_4$-alkyl, —$CF_3$, —$OCH_3$, —$NHCH_3$, —$N(CH_3)_2$, —F, or —Cl;
n is 0 or 1; and
m=0,
Y is —$NR_4R_5$ wherein
$R_4$ is —H or -methyl, and
$R_5$ is -methyl, -ethyl, -isopropyl, or -cyclopropyl; or substituted phenyl residue, substituted at the para position; or
Y is —$NR_4R_5$ wherein N, $R_4$ and $R_5$ form an unsubstituted or substituted azetidine residue, an unsubstituted or substituted piperidine residue, an unsubstituted or substituted pyrrolidine residue, an unsubstituted or substituted piperazine residue, an unsubstituted or substituted morpholine residue, or an unsubstituted or substituted tetrahydropyridine residue; or Y is —$OR_6$, wherein $R_6$ is —H, -methyl, -ethyl, -isopropyl, or -tert-butyl;
or a pharmaceutically or veterinary acceptable salt, hydrate or solvate thereof.

15. The compound of claim 1, wherein X is —F; with n=1 or 2 or with m=1.

16. The compound of claim 2, wherein X is at the para position of the phenyl ring.

17. The compound of claim 3, wherein
$R_2$ is -methyl or —Cl.

18. The compound of claim 3, wherein
$R_2$ is -methyl; and $R_3$ is -methyl; or
Wherein $R_2$ is —Cl and $R_3$ is —Cl.

19. The compound of claim 1, wherein
Y is —$NR_4R_5$ wherein
$R_4$ is —H or -methyl; and
$R_5$ is -methyl, -ethyl, -isopropyl, -cyclopropyl, or a phenyl residue that is unsubstituted or substituted with one substituent at the para position.

20. The compound of claim 6, wherein
N, $R_4$ and $R_5$ form an unsubstituted or substituted piperidine residue that is optionally and independently substituted with one or more of the following residues:
hydroxycyclopropyl, or carboxycyclopropyl;
—$(CH_2)_o$—$COOR_7$ wherein
$R_7$ is —H, -methyl, -ethyl, -isopropyl, or -tert-butyl; and
o=0 or 1;
—$(CH_2)_p CONR_8R_9$ wherein
$R_8$ and $R_9$ independently are —H or -methyl, and
p=0 or 1;
—CO—$CH_2$—$CH_3$;
—CO—$(CH_2)_q$—$NR_{12}R_{13}$ wherein
$R_{12}$ and $R_{13}$ independently are —CO—$(CH_2)_q$—$NH_2$ or —CO—$CH_2$—$NH_2$, and
q=0 or 1; and
—$(CH_2)_r SO_2 NR_{10}R_{11}$ wherein
$R_{10}$ and $R_{11}$ independently are —H or -methyl, or $CH_2SO_2NH_2$, and
r=0 or 1.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Fluorescent-donor probe biotinylated

<400> SEQUENCE: 1
aacacatctc tgccaaaccc ca        22

<210> SEQ ID NO 2
<211> LENGTH: 20
<212> TYPE: DNA
<213> ORGANISM: Artificial Sequence
<220> FEATURE:
<223> OTHER INFORMATION: Fluorescent-acceptor probe conjugated to
      ATTO647N

<400> SEQUENCE: 2
acaaagaacc ctaacaccag        20